United States Patent
Ashman et al.

(10) Patent No.: US 9,499,612 B2
(45) Date of Patent: Nov. 22, 2016

(54) ANTIGEN BINDING CONSTRUCTS

(75) Inventors: Claire Ashman, Stevenage (GB); Ian Richard Catchpole, Stevenage (GB); Zoe Hughes-Thomas, Stevenage (GB); Alan Peter Lewis, Stevenage (GB); Michael Steward, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 70 days.

(21) Appl. No.: 14/235,330

(22) PCT Filed: Jul. 25, 2012

(86) PCT No.: PCT/EP2012/064632
§ 371 (c)(1),
(2), (4) Date: Jan. 27, 2014

(87) PCT Pub. No.: WO2013/014208
PCT Pub. Date: Jan. 31, 2013

(65) Prior Publication Data
US 2014/0205604 A1 Jul. 24, 2014

Related U.S. Application Data

(60) Provisional application No. 61/512,138, filed on Jul. 27, 2011.

(51) Int. Cl.
| C12P 21/08 | (2006.01) |
| C07K 16/00 | (2006.01) |
| C07K 16/22 | (2006.01) |
| A61K 39/00 | (2006.01) |

(52) U.S. Cl.
CPC ......... *C07K 16/22* (2013.01); *A61K 2039/505* (2013.01); *C07K 2317/31* (2013.01); *C07K 2317/52* (2013.01); *C07K 2317/569* (2013.01); *C07K 2317/60* (2013.01); *C07K 2317/64* (2013.01); *C07K 2317/76* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| 2013/0236467 A1* | 9/2013 | Griggs | C07K 16/22 424/139.1 |
| 2013/0310281 A1* | 11/2013 | Harding | C07K 16/22 506/18 |

FOREIGN PATENT DOCUMENTS

| GB | WO 2008149146 A2 * | 12/2008 | ........... C07K 16/005 |
| WO | WO 00/29004 A1 | 5/2000 | |
| WO | WO 2006/003388 A2 | 1/2006 | |
| WO | WO 2006/030220 A1 | 3/2006 | |
| WO | WO 2008/143954 A2 | 11/2008 | |
| WO | WO 2008/149150 A2 | 12/2008 | |
| WO | WO 2009/074634 A2 | 6/2009 | |
| WO | WO 2010097385 A1 * | 9/2010 | ........... C07K 16/241 |

OTHER PUBLICATIONS

Raina et al., 2011, Am. J. Physiol Renal Physiol. vol. 301: F773-F783.*
Saint-Geniez et al., 2009, PNAS, vol. 106: 18751-18756.*
Holliger et al., 2005, Nat. Biotech. vol. 23: 1126-1136.*
Hua Yang, "Author Response: Bevaizumab suppression of establishment of micrometastases in experimental ocular melanoma" Investigative Ophthalmology & Visual Science, vol. 51, No. 12, Dec. 1, 2010, pp. 6906-6907.
Holt, L. J., et al., "Domain Antibodies: proteins for therapy" Trends in Biotechnology, vol. 21, No. 11, Nov. 1, 2003, pp. 484-490.
Ward, et al., "Binding Activities of a Repertoire of Single Immunoglobulin variable Domains Secreted from *Escherichia coli*" Nature, Jan. 1, 1989, pp. 544-548.

* cited by examiner

*Primary Examiner* — Amy Juedes
(74) *Attorney, Agent, or Firm* — Leah M. Octavio; Andrea V. Lockenour

(57) ABSTRACT

The present invention is directed to antigen binding constructs comprising one or two epitope binding domains separated by a single chain Fc region of an antibody, wherein each epitope binding domain in capable of binding to VEGF, to dimers comprising two antigen binding constructs of the invention, pharmaceutical compositions comprising said dimers and their use in the treatment of diseases associated with VEGF signalling, such as diabetic macular edema (DME), wet age-related macular degeneration (Wet AMD), diabetic retinopathy, retinal vein occlusion (RVO), and corneal neovascularization, and polynucleotide sequences encoding said antigen binding constructs.

17 Claims, 3 Drawing Sheets

Figure 1: ELISA, with EC50 values, showing comparison of DMS1529, DMS1576 and Bevacizumab (Avastin) binding to human $VEGF_{165}$.
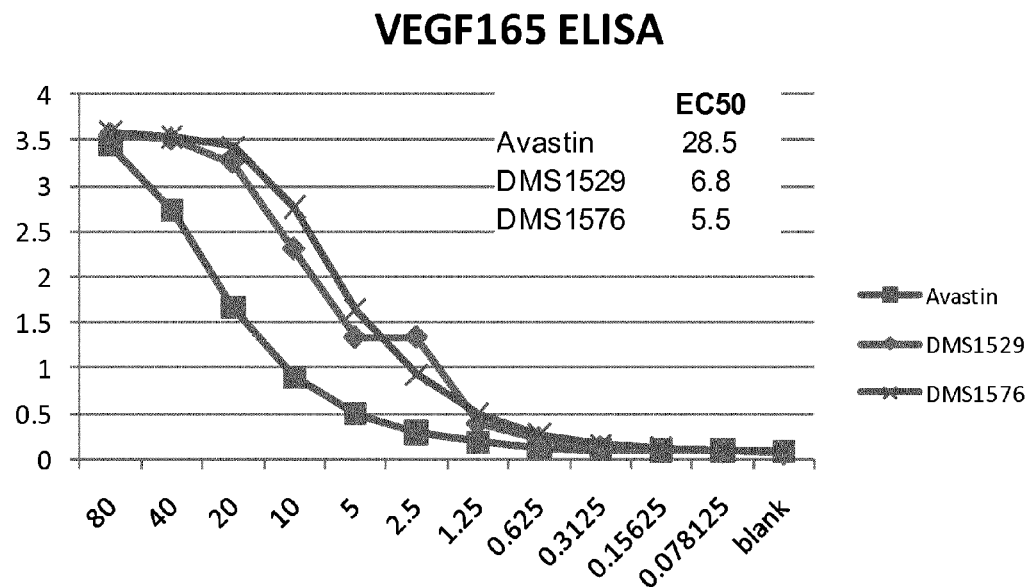
Figure 2A: Binding of Vh dAb-Fc DMS1576 to VEGF after pre-saturation with Vk Fc-dAb DMS30000 3ug/mL by MSD
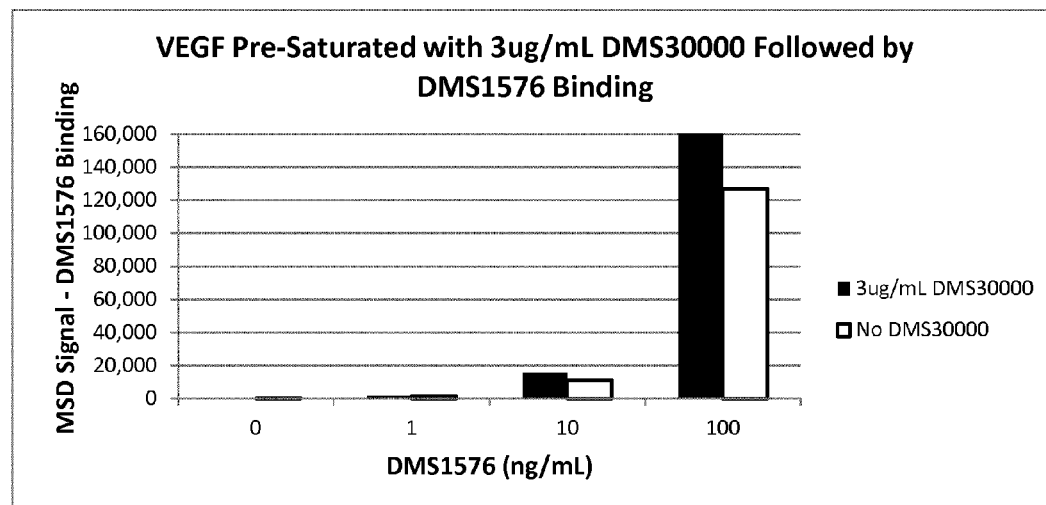
■ : DMS1576 full binding of VEGF pre-saturated with DMS30000
☐ : DMS1576 binding VEGF in the absence of DMS30000

Figure 2B: Binding of Vk Fc-dAb DMS30000 to VEGF after pre-saturation with Vh dAb-Fc DMS1576 3ug/mL by MSD ■ : DMS30000 full binding of VEGF pre-saturated with DMS1576
☐ : DMS30000 binding VEGF in the absence of DMS1576

Figure 3: Weighted analysis of variance on maximum inhibition of VEGF induced Human Umbilical Cord Endothelial Cell (HUVEC) proliferation assay from anti-VEGF Vh dAb-Fc, Vk Fc-dAb and dAb-Fc-dAb molecules compared to Bevacizumab (Avastin).

Figure 4: Binding of DMS1529 and DMS30000 to mouse $VEGF_{164}$ by MSD.
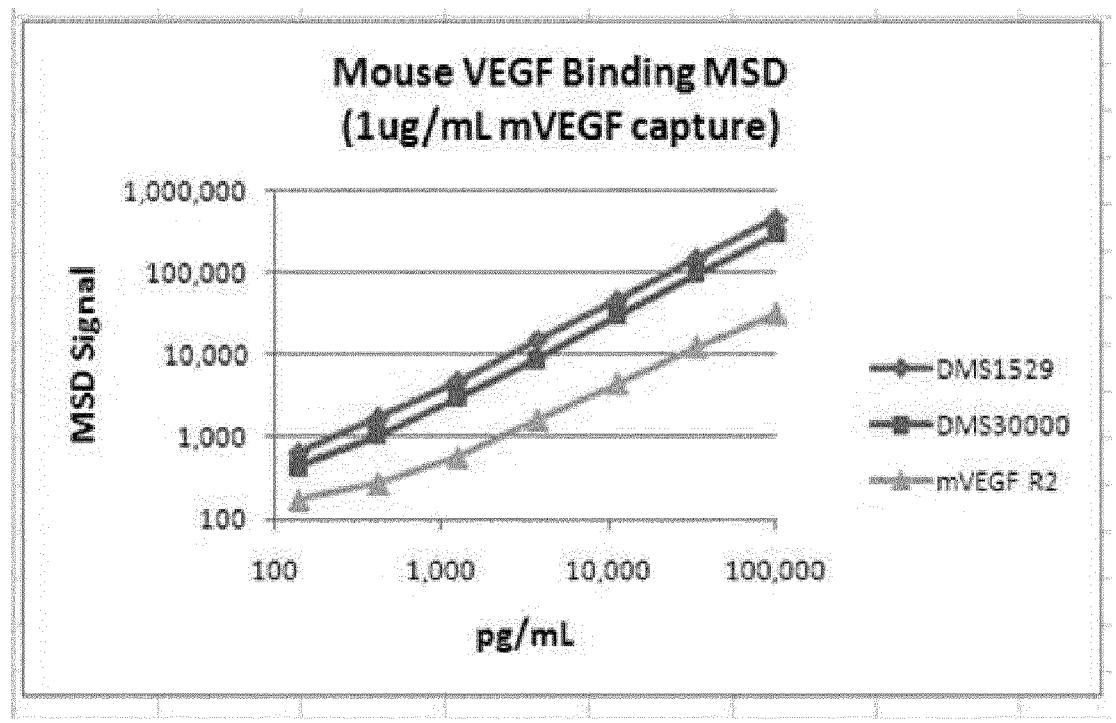

ANTIGEN BINDING CONSTRUCTS

This application is a US National Stage Application under 35 USC §371 of International Application No. PCT/EP2012/064632 filed Jul. 25, 2012 which claims the benefit of U.S. Provisional Patent Application No. 61/512,138 filed on Jul. 27, 2011. The entire teachings of the above identified applications are incorporated herein by reference.

BACKGROUND

The Vascular Endothelial Growth Factor (VEGF) family of growth factors and their receptors are essential regulators of angiogenesis and vascular permeability. The VEGF family comprises VEGF-A, PlGF (placenta growth factor), VEGF-B, VEGF-C, VEGF-E and snake venom VEGF and each is thought to have a distinct role in vascular patterning and vessel development. Due to alternative splicing of mRNA transcribed from a single 8-exon gene, VEGF-A has at least 9 subtypes (isoforms) identified by the number of amino acids remaining after signal peptide cleavage. For example, in humans the most prominent isoform is $VEGF_{165}$, which exists in equilibrium between a soluble and cell associated form. Longer isoforms ($VEGF_{183}$, $VEGF_{189}$ & $VEGF_{206}$) possess C-terminal regions that are highly positively charged and mediate association with cell surface glycans and heparin that modulates their bioavailability. All VEGF-A isoforms form homodimers with the association occurring via a core of approximately 110 N-terminal residues that constitutes the receptor-binding VEGF fragment. Under normal circumstances, and in the centre of solid tumours, expression of VEGF is principally mediated by hypoxic conditions, signifying a shortage of vascular supply. The hypoxia causes dimerization of the hypoxia inducible factor HIF-1α with the constitutively expressed HIF-1α, forming a transcription factor that binds to hypoxic response elements in the promoter region of the VEGF gene. Under normoxia, the HIF-1α protein undergoes ubiquitin-mediated degradation as a consequence of multiple proline hydroxylation events. Other tumour-associated VEGF up-regulation occurs due to activation via oncogene pathways (i.e. ras) via inflammatory cytokines & growth factors as well as by mechanical forces.

The active VEGF homodimer is bound at the cell surface by receptors of the VEGFR family. The principal vascular endothelium associated receptors for VEGF-A are VEGFR1 (Flt1) and VEGFR2 (Flk-2; KDR). Both receptors are members of the tyrosine kinase family and require ligand-mediated dimerization for activation. Upon dimerization the kinase domains undergo autophosphorylation, although the extent of the kinase activity in VEGFR2 is greater than that in VEGFR1. It has been demonstrated that the angiogenic signalling of VEGF is mediated largely through VEGFR2, although the affinity of VEGF is approximately 3-fold greater for VEGFR1 (KD~30 pM compared with 100 pM for VEGFR2). This has led to the proposal that VEGFR1 principally acts as a decoy receptor to sequester VEGF and moderate the extent of VEGFR2 activation. Although VEGFR1 expression is associated with some tumours, its principal role appears to be during embryonic development & organogenesis. $VEGF-A_{165}$ is also bound by the neuropilin receptors NRP1 & NRP2. Although these receptors lack TK domains, they are believed to acts as co-receptors for VEGFR2 and augment signalling by transferring the VEGF to the VEGFR2.

Numerous studies have helped confirm VEGF-A as a key factor in tumour angiogenesis. For example VEGF-A is expressed in most tumours and in tumour associated stroma. In the absence of a well developed and expanding vasculature system to support growth, tumour cells become necrotic and apoptotic thereby imposing a limit to the increase in tumour volume (of the order 1 mm3) that can result from continuous cell proliferation. The expression of VEGF-A is highest in hypoxic tumour cells adjacent to necrotic areas indicating that the induction of VEGF-A by hypoxia in growing tumours can change the balance of activators and inhibitors of angiogenesis, leading to the growth of new blood vessels in the tumour. Consistent with this hypothesis, a number of approaches, including small-molecular weight tyrosine kinase inhibitors, monoclonal antibodies, antisense oligonucleotides etc., that inhibit or capture either VEGF-A or block its signalling receptor, VEGFR-2, have been developed as therapeutic agents.

VEGF-A has also been implicated in a number of ocular diseases, such as age-related macular degeneration (AMD), wet AMD, geographic atrophy, diabetic retinopathy, retinal vein-occlusive diseases, diabetic macular oedema and corneal vascularisation. VEGF-A is produced by various ocular cell types in response to hypoxia and has a number of functions, including promoting vascular permeability and stimulating endothelial cell growth.

AMD is defined as an abnormality of the retinal pigment epithelium, which leads to degeneration of the overlying photoreceptor in the macula and results in loss of central vision. AMD represents a major public health burden and it is estimated that over 9 million people in the US have intermediate or advanced forms of AMD. Early AMD is characterised by drusen and hyper or hypopigmentation of the retinal pigment epithelium without loss of vision. Advanced AMD, where loss of vision occurs, can present as geographic atrophy or choriodal neovascularisation (CNV). CNV, which is also referred to as wet AMD, is a result of the abnormal growth of blood vessels.

Ranibizumab (LUCENTIS™), bevacizumab (AVASTIN™) and aflibercept (EYLEA™) are examples of anti-VEGF therapies, which are commonly administered for neovascular AMD. Despite the presence of such therapies, there exists a need for further therapies for the treatment of AMD and other ocular diseases.

SUMMARY OF THE INVENTION

The present invention is directed to antigen binding constructs comprising one or two epitope binding domains separated by a single chain Fc region of an antibody, wherein each epitope binding domain is capable of binding to VEGF.

In one aspect, each epitope binding domain of an antigen binding construct of the present invention is a domain antibody, also referred to as a DAB™.

In a further aspect, the present invention is directed to the following antigen binding construct:
  a) DOM 15-26-597-AS-Fc (SEQ ID No. 110)-Fibronectinx4-DT02-K-044-085; or
  b) DOM 15-26-597-IgG1 hinge-Fc (SEQ ID No. 110)-Fibronectinx4-DT02-K-044-085; or
  c) A variant of (a) or (b) having at least 97% amino acid identity across the whole sequence; or
  d) A variant of (a) or (b), wherein each DAB™ sequence has at least 97% sequence identity to the sequence of the specific DAB™.

The present invention is further directed to dimers comprising two antigen binding constructs of the invention, pharmaceutical compositions comprising said dimers and their use in the treatment of diseases associated with VEGF signalling, such as diabetic macular edema (DME), wet age-related macular degeneration (Wet AMD), diabetic retinopathy, retinal vein occlusion (RVO), and corneal neovascularisation, and polynucleotide sequences encoding said antigen binding constructs.

FIGURES

FIG. 1: ELISA, with EC50 values, showing comparison of DMS1529, DMS1576 and Bevacizumab (AVASTIN™) binding to human VEGF$_{165}$.

FIG. 2A: Binding of Vh dAb-Fc DMS1576 to VEGF after pre-saturation with Vk Fc-dAb DMS30000 3 ug/mL by MSD™.

FIG. 2B: Binding of Vk Fc-dAb DMS30000 to VEGF after pre-saturation with Vh dAb-Fc DMS1576 3 ug/mL by MSD™.

FIG. 3: Weighted analysis of variance on maximum inhibition of VEGF induced Human Umbilical Cord Endothelial Cell (HUVEC) proliferation assay from anti-VEGF Vh dAb-Fc, Vk Fc-dAb and dAb-Fc-dAb molecules compared to Bevacizumab (AVASTIN™).

FIG. 4: Binding of DMS1529 and DMS30000 to mouse VEGF$_{165}$ by MSD™.

DETAILED DESCRIPTION OF THE INVENTION

The present invention is directed to antigen binding constructs comprising two epitope binding domains separated by a single chain Fc region of an antibody, wherein each epitope binding domain in capable of binding to VEGF.

In one aspect, each epitope binding domain of an antigen binding construct of the present invention is a domain antibody, also referred to as a DAB™.

As used herein, the term "epitope binding domain" refers to a domain that specifically binds an antigen or epitope independently of a different variable region or domain. This may be a domain antibody (DAB™) or it may be a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEI and GroES; transferrin (trans-body); ankyrin repeat protein (DARPin); peptide aptamer; C-type lectin domain (Tetranectin); human γ-crystallin and human ubiquitin (affilins); PDZ domains; scorpion toxin (charybdotoxin); kunitz type domains of human protease inhibitors; PDZ-domains of the Ras-binding protein AF-6; and fibronectin (adnectin); which has been subjected to protein engineering in order to obtain binding to a ligand other than the natural ligand.

As used herein, the term "domain" is a folded protein structure which has tertiary structure independent of the rest of the protein. Generally, domains are responsible for discrete functional properties of proteins and in many cases may be added, removed or transferred to other proteins without loss of function of the remainder of the protein and/or of the domain.

As used herein, the term "domain antibody" refers to a folded polypeptide domain comprising sequences characteristic of antibody variable domains. It therefore includes complete antibody variable domains such as VH, VHH and VL and modified antibody variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A single variable domain is capable of binding an antigen or epitope independently of a different variable region or domain. A "domain antibody" or "DAB™" may also be referred to as a "single variable domain". A domain antibody may be a human domain antibody, but also includes single domain antibodies from other species such as rodent (for example, as disclosed in WO 00/29004), nurse shark and Camelid VHH DAB™s. Camelid VHH are immunoglobulin single variable domain polypeptides that are derived from species including camel, llama, alpaca, dromedary, and guanaco, which produce heavy chain antibodies naturally devoid of light chains. Such VHH domains may be humanised according to standard techniques available in the art, and such domains are considered to be "domain antibodies". As used herein VH includes camelid VHH domains. NARV are another type of immunoglobulin domain antibody, which were identified in cartilaginous fish including the nurse shark (Mol. Immunol. 44, 656-665 (2006). These domains are also known as Novel Antigen Receptor variable region (commonly abbreviated to V(NAR) or NARV).

As used herein, the term "single chain Fc region of an antibody" refers to a single heavy chain Fc region of an IgG, such as an IgG1, IgG2, IgG3, IgG4 or IgG4PE, or an IgA antibody. A single heavy chain Fc region may comprise one or more of the CH1, CH2 and CH3 constant region antibody domains, for example all three constant region antibody domains or just the CH2 and CH3 domains. In addition to comprising one or more of the CH1, CH2 and CH3 constant region antibody domains, the single heavy chain FC region of an antibody may further comprise a hinge region of an antibody (such a region normally found between the CH1 and CH2 domains).

In one aspect, the single chain Fc region of an antibody is a single IgG1 heavy chain, for example a single IgG1 heavy chain comprising the CH2 and CH3 antibody constant domains.

In a further aspect, the single chain Fc region of an antibody is the IgG1 sequence of SEQ ID No. 110.

In a further aspect, the single chain Fc region of an antibody is the following sequence:

```
                                              (SEQ ID NO: 193)
QASSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGK
```

In one aspect the N terminus of the Fc sequence starts "AS" or no N-terminal amino acid at start of Fc (Fc sequence starts ASTHTCPPC (SEQ ID NO: 194) or THTCPPC (SEQ ID NO: 195)).

In another aspect the Fc region comprises a mutation within the N-terminus of the Fc, for example THTCPPC is replaced by TATCPPC (SEQ ID NO: 196). For example THTCPPC is replaced by THPCPPC (eg SEQ ID 83 and 84). Such mutations may be present in any sequence disclosed herein, and are variant sequences of those specific sequences disclosed herein.

The Fc region of an antibody may be selected for its degree of effector function.

The term "Effector Function" as used herein is meant to refer to one or more of Antibody Dependant Cell-mediated Cytotoxic (ADCC), Complement-Dependant Cytotoxic (CDC) mediated responses, Fc-mediated phagocytosis and antibody recycling via the FcRn receptor. For IgG antibodies, effector functionalities including ADCC and ADCP are mediated by the interaction of the heavy chain constant region with a family of Fcγ receptors present on the surface of immune cells. In humans these include FcγRI (CD64), FcγRII (CD32) and FcγRIII (CD16). Interaction between the antigen binding protein bound to antigen and the formation of the Fc/Fcγ complex induces a range of effects including cytotoxicity, immune cell activation, phagocytosis and release of inflammatory cytokines.

The interaction between the constant region of an antigen binding protein and various Fc receptors (FcR) is believed to mediate the effector functions of the antigen binding protein. Significant biological effects can be a consequence of effector functionality, in particular, antibody-dependent cellular cytotoxicity (ADCC), fixation of complement (complement dependent cytotoxicity or CDC), and half-life/clearance of the antigen binding protein. Usually, the ability to mediate effector function requires binding of the antigen binding protein to an antigen and not all antigen binding proteins will mediate every effector function.

Effector function can be measured in a number of ways including for example via binding of the FcγRIII to Natural Killer cells or via FcγRI to monocytes/macrophages to measure for ADCC effector function. For example an antigen binding protein of the present invention can be assessed for ADCC effector function in a Natural Killer cell assay. Examples of such assays can be found in Shields et al, 2001 The Journal of Biological Chemistry, Vol. 276, p 6591-6604; Chappel et al, 1993 The Journal of Biological Chemistry, Vol 268, p 25124-25131; Lazar et al, 2006 PNAS USA, 103; 4005-4010. Examples of assays to determine CDC function include that described in 1995 J Imm Meth 184:29-38.

Some isotypes of human constant regions, in particular IgG4 and IgG2 isotypes, essentially lack the functions of (a) activation of complement by the classical pathway; and (b) antibody-dependent cellular cytotoxicity. Various modifications to the heavy chain constant region of antigen binding proteins may be carried out depending on the desired effector property. IgG1 constant regions containing specific mutations have separately been described to reduce binding to Fc receptors and therefore reduce ADCC and CDC (Duncan et al. Nature 1988, 332; 563-564; Lund et al. J. Immunol. 1991, 147; 2657-2662; Chappel et al. PNAS USA 1991, 88; 9036-9040; Burton and Woof, Adv. Immunol. 1992, 51; 1-84; Morgan et al., Immunology 1995, 86; 319-324; Hezareh et al., J. Virol. 2001, 75 (24); 12161-12168).

Human IgG1 constant regions containing specific mutations or altered glycosylation on residue Asn297 have also been described to enhance binding to Fc receptors. In some cases these mutations have also been shown to enhance ADCC and CDC (Lazar et al. PNAS USA 2006, 103; 4005-4010; Shields et al. J Biol Chem 2001, 276; 6591-6604; Nechansky et al. Mol Immunol, 2007, 44; 1815-1817).

In one embodiment of the present invention, such mutations are in one or more of positions selected from 239, 332 and 330 (IgG1), or the equivalent positions in other IgG isotypes. Examples of suitable mutations are S239D and I332E and A330L. In one embodiment the antigen binding protein of the invention herein described is mutated at positions 239 and 332, for example S239D and I332E or in a further embodiment it is mutated at three or more positions selected from 239 and 332 and 330, for example S239D and I332E and A330L (EU index numbering).

In an alternative embodiment of the present invention, there is provided an antigen binding protein comprising a heavy chain constant region with an altered glycosylation profile such that the antigen binding protein has enhanced effector function. For example, wherein the antigen binding protein has enhanced ADCC or enhanced CDC or wherein it has both enhanced ADCC and CDC effector function. Examples of suitable methodologies to produce antigen binding proteins with an altered glycosylation profile are described in WO2003011878, WO2006014679 and EP1229125, all of which can be applied to the antigen binding proteins of the present invention.

The antigen binding constructs of the present invention comprise epitope binding domains that are capable of binding to VEGF. As used herein, the term "VEGF" is a reference to any VEGF molecule, in particular VEGF-A, for example human VEGF-A, and including any isoform of VEGF-A, such as $VEGF_{165}$.

Antigen binding constructs of the present invention, in one aspect, comprise two epitope binding domains separated by a single chain Fc region of an antibody. By separated it is meant that the epitope binding domains are not directly attached to one another. In one aspect the epitope binding domains are located at opposite ends of the Fc region. One epitope binding domain is attached to the N-terminus and the other it attached to the C-terminus. Each epitope binding domain is independently selected and such domains may bind the same epitope on VEGF or different epitopes.

In one aspect, the epitope binding domain attached to the N-terminus end of the Fc region of an antibody, in an antigen binding construct of the present invention, is a heavy or light chain DAB™, wherein the light chain DAB™ may be a kappa or lambda light chain.

In a further aspect, where antigen binding constructs of the present invention have an epitope binding domain attached to the C-terminus, the epitope binding domain is an light chain DAB™, wherein the light chain DAB™ may be a kappa or lambda light chain.

In a yet further aspect, where antigen binding constructs of the present invention comprise two epitope binding domains, the one attached to the N-terminus of the Fc region is a heavy chain DAB™ and the one attached to the C-terminus of the Fc region is a light chain DAB™.

In a yet further aspect, where antigen binding constructs of the present invention comprise two epitope binding domains, the one attached to the N-terminus of the Fc region is a light chain DAB™ and the one attached to the C-terminus of the Fc region is a light chain DAB™.

Antigen binding constructs of the present invention may be expressed as a fusion protein or the epitope binding domain may be expressed separately and connected by another means, such as chemical conjugation using methods well known in the art.

Epitope binding domains can be attached directly to the Fc region of an antibody or indirectly through a linker. In constructs where the N-terminus of a DAB™ is fused to the C-terminus of a Fc region of an antibody, a peptide linker may enhance antigen binding of the DAB™. Indeed, the N-terminal end of a DAB™ is located closely to the complementarity-determining regions (CDRs) involved in antigen-binding activity.

Thus a peptide linker may act as a spacer between the epitope-binding, and the constant domain of the protein scaffold, which may allow the DAB™ CDRs to more easily reach the antigen, and in some circumstances bind with higher affinity. Furthermore, certain peptide linkers, for examples those greater than 7 amino acids in length, may promote and enable the association of a heavy chain DAB™ attached to the N-terminus of the Fc region of an antibody to a light chain DAB™ attached to the C-terminus of the Fc region of an antibody, in heterodimers and homodimers as described herein. Such association may enhance antigen binding and/or other properties of the antigen binding constructs and dimers of the present invention.

When fused at the C-terminal end of the Fc region of the antibody, each DAB™ may be located in the vicinity of the CH3 domains of the Fc portion. This is not expected to impact on the Fc binding properties to Fc receptors (e.g. FcγRI, II, III and FcRn) as these receptors engage with the $C_{H2}$ domains (for the FcγRI, II and III class of receptors) or with the hinge between the CH2 and CH3 domains (e.g. FcRn receptor). Another feature of such antigen-binding constructs is that both DAB™s are expected to be spatially close to each other and provided that flexibility is provided by provision of appropriate linkers, these DAB™s may even form homodimeric species, hence propagating the 'zipped' quaternary structure of the Fc portion, which may enhance stability of the construct.

Examples of suitable linkers include amino acid sequences which may be from 1 amino acid to 150 amino acids in length, or from 1 amino acid to 140 amino acids, for example, from 1 amino acid to 130 amino acids, or from 1 to 120 amino acids, or from 1 to 80 amino acids, or from 1 to 50 amino acids, or from 1 to 20 amino acids, or from 1 to 10 amino acids, or from 5 to 18 amino acids, or greater than 7 but less than or equal to 10, 20, 30, 40, 50, 60, 70, 80, 90, 100, 110, 120, 130, 140 or 150 amino acids. Such sequences may have their own tertiary structure, for example, a linker of the present invention may comprise a single variable domain. The size of a linker in one embodiment is equivalent to a single variable domain. Suitable linkers may be of a size from 1 to 100 Angstroms, for example may be of a size from 20 to 80 angstroms or for example may be of a size from 20 to 60 angstroms or for example less than 40 angstroms, or less than 20 angstroms, or less than 5 angstroms in length.

In one aspect, the linker is greater than 7 and less than or equal to 150 amino acids in length.

Examples of linkers include, but are not limited to, those outlined as SEQ ID No. 57 to 63 and 66 to 82 In one aspect, the linkers are selected from SEQ ID No.'s 58, 60, 62, 63 and 75.

Where an antigen binding construct of the present invention comprises two epitope binding domains, the epitope binding domains may be attached to the Fc region of an antibody by identical or different linkers.

In one aspect, where a linker is used to attach an epitope binding domain to the N-terminus of the Fc region of an antibody, the linker is selected from the group consisting of SEQ ID No. 58, SEQ ID No. 60 and 62. In a further aspect, the N-terminus linker is SEQ ID no. 58 or SEQ ID No. 60.

In one aspect, where a linker is used to attach an epitope binding domain to the C-terminus of the Fc region of an antibody, the linker is selected from the group consisting of SEQ ID No. 63 and SEQ ID No. 75. A particular preferred linker is SEQ ID No. 63.

In one aspect, linkers of use in the antigen-binding constructs of the present invention may comprise, either alone or in addition to other linkers, one or more sets of GS residues, for example 'GSTVAAPS' (SEQ ID NO: 197) or 'TVAAPSGS' (SEQ ID NO: 198) or 'GSTVAAPSGS' (SEQ ID NO: 199).

In one embodiment the epitope binding domain is linked to the Fc region of an antibody by the linker '$(PAS)_n(GS)_m$', '$(GGGGS$ (SEQ ID NO: 200)$)_n(GS)_m$', '$(TVAAPS$ (SEQ ID NO: 201)$)_n(GS)_m$', '$(GS)_m(TVAAPSGS$ (SEQ ID NO: 202)$)_n$', '$(PAVPPP$ (SEQ ID NO: 203)$)_n(GS)_m$', '$(TVSDVP$ (SEQ ID NO: 204)$)_n(GS)_m$', '$(TGLDSP$ (SEQ ID NO: 205)$)_n(GS)_m$', wherein n=1-10, and m=0-4.

Examples of such linkers include $(PAS)_n(GS)_m$ wherein n=1 and m=11, $(PAS)_n(GS)_m$ wherein n=2 and m=1, $(PAS)_n(GS)_m$ wherein n=3 and m=1, $(PAS)_n(GS)_m$ wherein n=4 and m=1, $(PAS)_n(GS)_m$ wherein n=2 and m=0, $(PAS)_n(GS)_m$ wherein n=3 and m=0, $(PAS)_n(GS)_m$ wherein n=4 and m=0.

Examples of such linkers include (GGGGS (SEQ ID NO: 200)$)_n(GS)_m$ wherein n=1 and m=1, (GGGGS (SEQ ID NO: 200)$)_n(GS)_m$ wherein n=2 and m=1, (GGGGS (SEQ ID NO: 200)$)_n(GS)_m$ wherein n=3 and m=1, (GGGGS (SEQ ID NO: 200)$)_n(GS)_m$ wherein n=4 and m=1, (GGGGS (SEQ ID NO: 200)$)_n(GS)_m$ wherein n=2 and m=0 (SEQ ID NO:49), (GGGGS (SEQ ID NO: 200)$)_n(GS)_m$ wherein n=3 and m=0 (SEQ ID NO:50), (GGGGS (SEQ ID NO: 200)$)_n(GS)_m$ wherein n=4 and m=0.

Examples of such linkers include (TVAAPS (SEQ ID NO: 201)$)_n(GS)_m$ wherein n=1 and m=1, (TVAAPS (SEQ ID NO: 201)$)_n(GS)_m$ wherein n=2 and m=1, (TVAAPS (SEQ ID NO: 201)$)_n(GS)_m$ wherein n=3 and m=1, (TVAAPS (SEQ ID NO: 201)$)_n(GS)_m$ wherein n=4 and m=1, (TVAAPS (SEQ ID NO: 201)$)_n(GS)_m$ wherein n=2 and m=0, $(TVAAPS)_n(GS)_m$ wherein n=3 and m=0, $(TVAAPS)_n(GS)_m$ wherein n=4 and m=0.

Examples of such linkers include $(GS)_m$(TVAAPSGS (SEQ ID NO: 202)$)_n$ wherein n=1 and m=1, $(GS)_m$(TVAAPSGS (SEQ ID NO: 202)$)_n$ wherein n=2 and m=1, $(GS)_m$(TVAAPSGS (SEQ ID NO: 202)$)_n$ wherein n=3 and m=1, or $(GS)_m$(TVAAPSGS (SEQ ID NO: 202)$)_n$ wherein n=4 and m=1, $(GS)_m$(TVAAPSGS (SEQ ID NO: 202)$)_n$ wherein n=5 and m=1, $(GS)_m$(TVAAPSGS (SEQ ID NO: 202)), wherein n=6 and m=1, $(GS)_m$(TVAAPSGS (SEQ ID NO: 202)$)_n$ wherein n=1 and m=0, $(GS)_m$(TVAAPSGS (SEQ ID NO: 202)$)_n$ wherein n=2 and m=10, $(GS)_m$(TVAAPSGS (SEQ ID NO: 202)$)_n$ wherein n=3 and m=0, or $(GS)_m$(TVAAPSGS (SEQ ID NO: 202)$)_n$ wherein n=0.

Examples of such linkers include (PAVPPP (SEQ ID NO: 203)$)_n(GS)_m$ wherein n=1 and m=1, (PAVPPP (SEQ ID NO: 203)$)_n(GS)_m$ wherein n=2 and m=1, (PAVPPP (SEQ ID NO: 203)$)_n(GS)_m$ wherein n=3 and m=1, (PAVPPP (SEQ ID NO: 203)$)_n(GS)_m$ wherein n=4 and m=1, (PAVPPP (SEQ ID NO: 203)$)_n(GS)_m$ wherein n=2 and m=0, (PAVPPP (SEQ ID NO: 203)$)_n(GS)_m$ wherein n=3 and m=0, (PAVPPP (SEQ ID NO: 203)$)_n(GS)_m$ wherein n=4 and m=0.

Examples of such linkers include (TVSDVP (SEQ ID NO: 204)$)_n(GS)_m$ wherein n=1 and m=1, (TVSDVP (SEQ ID NO: 204)$)_n(GS)_m$ wherein n=2 and m=1, (TVSDVP (SEQ ID NO: 204)$)_n(GS)_m$ wherein n=3 and m=1, (TVSDVP (SEQ ID NO: 204)$)_n(GS)_m$ wherein n=4 and m=1, (TVSDVP (SEQ ID NO: 204)$)_n(GS)_m$ wherein n=2 and m=0, (TVSDVP (SEQ ID NO: 204)$)_n(GS)_m$ wherein n=3 and m=0, (TVSDVP (SEQ ID NO: 204)$)_n(GS)_m$ wherein n=4 and m=0.

Examples of such linkers include (TGLDSP (SEQ ID NO: 205)$)_n(GS)_m$ wherein n=1 and m=1, (TGLDSP (SEQ ID NO: 205)$)_n(GS)_m$ wherein n=2 and m=1, (TGLDSP (SEQ ID NO: 205)$)_n(GS)_m$ wherein n=3 and m=1, (TGLDSP (SEQ ID NO: 205)$)_n(GS)_m$ wherein n=4 and m=1, (TGLDSP (SEQ ID NO:

205))$_n$(GS)$_m$ wherein n=2 and m=0, (TGLDSP (SEQ ID NO: 205))$_n$(GS)$_m$ wherein n=3 and m=0, (TGLDSP (SEQ ID NO: 205))$_n$(GS)$_m$ wherein n=4 and m=0.

Further linkers that may be used are disclosed in WO 2009068649.

The antigen binding construct may additionally comprise albumin, or a fragment thereof, as a linker, and derived from human serum albumin, such as DETYVPKEFNAETFGS (SEQ ID NO: 206), DETYVPKEFNAETF (SEQ ID NO: 207), EVDETYVPKEFNAETFTFHADGS (SEQ ID NO: 208), EVDETYVPKEFNAETFTFHAD (SEQ ID NO: 209), DDNPNLPRLVRPE (SEQ ID NO: 210), DEMPADLPSLAADF (SEQ ID NO: 211), HKDDNPNLPRLVRPEVDVM (SEQ ID NO: 212), and ENDEMPADLPSLAADFVESKD (SEQ ID NO: 213). The linkers may further comprise some additional residues, for example, they may comprise additional glycine and serine residues or may have amino acids removed from either end of the linker for example in one aspect 5 amino acids are removed. These additional residues may be at the beginning or end of the albumin-derived sequence, or may be within the albumin-derived sequence.

In one aspect, the present invention is directed to antigen binding constructs comprising two epitope binding domains wherein each epitope binding domains is an independently selected DAB™ and comprises an amino acid sequence which is at least 97% identical to the sequence of DOM 15-26-593, DOM 15-26-597, DT02-K-044-085, DT02-K-044-251, DT02-K-044-232, DT02-K-044-236 or DT02-K-044-255.

In a further aspect, each epitope binding domain is a DAB™ independently selected from the group consisting of DOM 15-26-593, DOM 15-26-597, DT02-K-044-085, DT02-K-044-251, DT02-K-044-232, DT02-K-044-236 and DT02-K-044-255.

In a further aspect, the DAB™ attached to the N-terminus of the single chain Fc region comprises an amino acid sequence which is at least 97% identical to the sequence of DOM 15-26-597 or DT02-K-044-085.

In a further aspect, the DAB™ attached to the N-terminus of the single chain Fc region is DOM 15-26-597 or DT02-K-044-085.

In a further aspect, the DAB™ attached to the C-terminus of the single chain Fc region comprises an amino acid sequence which is at least 97% identical to the sequence of DT02-K-044-085, DT02-K-044-251, DT02-K-044-232, DT02-K-044-236 or DT02-K-044-255.

In a further aspect, the DAB™ attached to the C-terminus of the single chain Fc region is DT02-K-044-085, DT02-K-044-251, DT02-K-044-232, DT02-K-044-236 or DT02-K-044-255.

In a further aspect, the antigen binding construct of the present invention is:
(a) DOM 15-26-597-AS-Fc (SEQ ID No. 110)-Fibronectinx4-DT02-K-044-085; or
e) (b) DOM 15-26-597-IgG1 hinge-Fc (SEQ ID No. 110)-Fibronectinx4-DT02-K-044-085; or
f) (c) A variant of (a) or (b) having at least 97% amino acid identity across the whole sequence; or
g) (d) A variant of (a) or (b), wherein each DAB™ sequence has at least 97% sequence identity to the sequence of the specific DAB™.

The present invention is further directed to antigen binding constructs comprising one epitope binding domain attached to a single chain Fc region of an antibody, wherein the epitope binding domain is a DAB™ which comprises an amino acid sequence which is at least 97% identical to the sequence of DT02-K-044-085, DT02-K-044-251, DT02-K-044-232, DT02-K-044-236 or DT02-K-044-255, and further wherein the epitope binding domain is capable of binding to VEGF.

In a yet further aspect, the present invention is directed to antigen binding constructs comprising one epitope binding domain attached to a single chain Fc region of an antibody, wherein the epitope binding domain is a DAB™ selected from DT02-K-044-085, DT02-K-044-251, DT02-K-044-232, DT02-K-044-236 or DT02-K-044-255.

In one aspect, the antigen binding construct has the following structure (N to C terminus):
a. Fc-Linker C-DT02-K-044-085 DAB™;
b. DOM 15-26-593 DAB™-Linker N-Fc-Linker C-DT02-K-044-085 DAB™;
c. DOM 15-26-597 DAB™-Linker N-Fc-Linker C-DT02-K-044-085 DAB™;
d. DT02-K-044-085 DAB™-Linker N-Fc-Linker C-DT02-K-044-085 v;
e. Fc-Linker C-DT02-K-044-251 DAB™;
f. DOM15-26-597 DAB™-Linker N-Fc-Linker C-DT02-K-044-251 DAB™;
g. DT02-K-044-251 DAB™-Linker N-Fc-Linker C-DT02-K-044-251 DAB™;
h. Wherein for a-g, Linker N can be any of those described in: SEQ ID NO:57-63 & SEQ ID NO:76-82;
i. Wherein for a-g, Linker C can be any of those described in: SEQ ID NO:66-75 & SEQ ID NO:85-94;
j. Wherein for a-g, Fc can be any of those described in: SEQ ID NO:64, 65, 102 & SEQ ID NO:83, 84, 110;
k. a variant of any of a-j having at least 97% amino acid identity;
i. a variant of any of a-j wherein the DAB™ sequence has at least 97% identity to the sequence of the specific DAB™;

In a further aspect, the antigen binding construct of the present invention has the following structure:
DAB™ 1-LinkerN-Fc-LinkerC DAB™ 2

Wherein DAB™ 1 can be defined from:

| DAB ™ Sequences | DNA Sequence SEQ ID No. | Amino Acid Sequence SEQ ID No. |
|---|---|---|
| DOM15-26-597 | 96 | 104 |
| DT02-K-044-085 | 97 | 105 |
| DT02-K-044-251 | 100 | 108 |
| DT02-K-044-255 | 101 | 109 |

Wherein LinkerN can be defined from:

| N-terminal Linker Sequences | DNA Sequence SEQ ID No. | Amino Acid Sequence SEQ ID No. |
|---|---|---|
| AAAS Linker | 57 | 76 |
| AS Linker | 58 | 77 |
| TVAAPS tinker | 59 | 78 |
| Hinge IgG1 Linker | 60 | 79 |
| Hinge IgG3 Linker | 61 | 80 |
| Fibronectin x3 Linker | 62 | 81 |
| Fibronectin x4 Linker | 63 | 82 |

Wherein Fc can be defined from:

| | DNA Sequence SEQ ID No. | Amino Acid Sequence SEQ ID No. |
|---|---|---|
| Fc Sequences | | |
| Fc IgG1 | 102 | 110 |
| H2A IgG1 Fc | 64 | 83 |
| T3P IgG1 Fc | 65 | 84 |
| C-terminal Linker Sequences | | |
| ((GS(TVAAPSGS)x3)) Linker | 66 | 85 |
| Fibronectin x3 Linker | 67 | 86 |
| Fibronectin x4 Linker | 68 | 87 |
| Albumin Domain 1 Linker | 69 | 88 |
| Albumin Domain 2 Linker | 70 | 89 |
| Albumin Domain 3 Linker | 71 | 90 |
| Truncated Albumin Domain3 Linker; Alb Dom 3-TFHAD | 72 | 91 |
| Gly4Ser 3x Linker | 73 | 92 |
| Gly4Ser 4x Linker | 74 | 93 |
| Helical Linker | 75 | 94 |

Wherein DAB™ can be defined from:

| DAB ™ Sequences | DNA Sequence SEQ ID No. | Amino Acid Sequence SEQ ID No. |
|---|---|---|
| DT02-K-044-085 | 97 | 105 |
| DT02-K-044-251 | 100 | 108 |
| DT02-K-044-255 | 101 | 109 |

Naturally occurring autoantibodies exist in humans that can bind to proteins. Autoantibodies can thus bind to endogenous proteins (present in naïve subjects) as well as to proteins or peptides which are administered to a subject for treatment. Therapeutic protein-binding autoantibodies and antibodies that are newly formed in response to drug treatment are collectively termed anti-drug antibodies (ADAs). Pre-existing antibodies against molecules such as therapeutic proteins and peptides, administered to a subject can affect their efficacy and could result in administration reactions, hypersensitivity, altered clinical response in treated patients and altered bioavailability by sustaining, eliminating or neutralizing the molecule. It could be advantageous to provide molecules for therapy which comprise human immunoglobulin (antibody) single variable domains or DAB™s which have reduced immunogenicity (i.e. reduced ability to bind to pre-existing ADAs when administered to a subject, in particular a human subject.

Thus in one aspect of the present invention there is provided a modified DAB™ or antigen binding construct or dimer comprising such a modified DAB™, which has reduced ability to bind to pre-existing antibodies (ADAs) as compared to the equivalent unmodified molecule. By reduced ability to bind it is meant that the modified molecule binds with a reduced affinity or reduced avidity to a pre-existing ADA. Said modified DAB™ comprise one or more modifications selected from: (a) a C-terminal addition, extension, deletion or tag, and/or (b) one or more amino acid framework substitutions.

In one aspect the modified DAB™ or antigen binding construct or dimer comprising such a modified DAB™ comprises:
a) a C-terminal sequence consisting of the sequence VTVS(S)nX as shown in SEQ ID NO: 219 [for a VH DAB™] or VEIKpRqX as shown in SEQ ID NO: 220 [for a VL DAB™]; and also optionally b) one or more amino acid substitutions at positions 14, 41, 108, 110, or 112 compared to a human germline framework sequence
wherein:
n represents an integer independently selected from 0 or 1;
p and q each represent 0 or 1 such that when p represents 1 q may be 0 or 1 and such that when p represents 0, q also represents 0;
X may be present or absent, and if present represents an amino acid extension of 1 to 8 amino acid residues.

In one aspect, the C-terminal sequence of the DAB™ is VEIKpRqX as shown in SEQ ID NO: 220, wherein p is 1 and q is 0 and X is absent.

In a further aspect, said modified DAB™ with reduced binding to pre-existing ADAs has one or more amino acid substitutions wherein said one or more amino acid substitutions are selected from the group consisting of a P14A substitution, a P41A substitution, a L108A substitution, a T110A substitution, a S112A substitution, a P14K substitution, a P14Q substitution, and a P14T substitution.

In a further aspect, X is present, and is an extension of 1 to 8 amino acids, in particular an extension of 1 to 8 amino acids which comprises an alanine residue, for example a single alanine extension, or an AS, AST, ASTK (SEQ ID NO: 214), ASTKG (SEQ ID NO: 215), ASTKGP (SEQ ID NO: 216) extension.

In a further aspect, X is present, and is an extension of 1 to 8 amino acids, in particular an extension of 1 to 8 amino acids which comprises an A, AAA or T extension.

In one aspect, the modified DAB™ can comprise a tag present at the C terminus. The tag can be any tag known in the art for example affinity tags such as myc-tags, FLAG tags, his-tags, chemical modification such as PEG, or protein domains such as the antibody Fc domain The C terminal addition or extension or tag can be present as a direct fusion or conjugate with the C terminus of the molecule.

Immunoassays well known to those skilled in the art can be used to confirm that the modified DAB™s have the desired reduced binding to ADAs.

In a further aspect, the present invention is directed to dimers of the antigen binding constructs disclosed herein. As used herein, the term "dimer" means a polypeptide complex which comprises two antigen binding constructs, i.e two chains that associate with one another to form a dimer. A dimer may be a homodimer, comprising two identical antigen binding constructs of the invention or a heterodimer comprising two different antigen binding constructs of the invention. Homodimers and heterodimers of the present invention may have improved properties, such as affinity, for the target VEGF molecule.

In one aspect, homodimers and heterodimers of the present invention may bind VEGF with a Kd of at least 1 mM, for example a Kd of at least 10 nM, in M, 500 pM, 200 pM, 100 pM, <100 pM, 10 pM, 5 pM, 1 pM to antigen as measured by BIACORE™, such as the BIACORE™ method as described in methods herein.

The in-vivo half life of the antigen binding constructs and dimers of the present invention may be increased by modification of the immunoglobulin constant domain or FcRn (Fc receptor neonate) binding domain.

In adult mammals, FcRn, also known as the neonatal Fc receptor, plays a key role in maintaining serum antibody levels by acting as a protective receptor that binds and salvages antibodies of the IgG isotype from degradation. IgG molecules are endocytosed by endothelial cells, and if they bind to FcRn, are recycled out into circulation. In contrast, IgG molecules that do not bind to FcRn enter the cells and are targeted to the lysosomal pathway where they are degraded.

The neonatal FcRn receptor is believed to be involved in both antibody clearance and the transcytosis across tissues (see Junghans R. P (1997) Immunol. Res 16. 29-57 and Ghetie et al (2000) Annu. Rev. Immunol. 18, 739-766). Human IgG1 residues determined to interact directly with human FcRn includes Ile253, Ser254, Lys288, Thr307, Gln311, Asn434 and His435. Switches at any of these positions described in this section may enable increased serum half-life and/or altered effector properties of antigen binding proteins of the invention.

Antigen binding proteins of the present invention may have amino acid modifications that increase the affinity of the constant domain or fragment thereof for FcRn. Increasing the half-life of therapeutic and diagnostic IgG's and other bioactive molecules has many benefits including reducing the amount and/or frequency of dosing of these molecules. In one embodiment there is therefore provided an antigen binding according to the invention provided herein or a fusion protein comprising all or a portion (an FcRn binding portion) of an IgG constant domain having one or more of these amino acid modifications and a non-IgG protein or non-protein molecule conjugated to such a modified IgG constant domain, wherein the presence of the modified IgG constant domain increases the in vivo half life of the antigen binding protein.

PCT Publication No. WO 00/42072 discloses a polypeptide comprising a variant Fc region with altered FcRn binding affinity, which polypeptide comprises an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 386, 388, 400, 413, 415, 424, 433, 434, 435, 436, 439, and 447 of the Fc region, wherein the numbering of the residues in the Fc region is that of the EU index (Kabat et al).

PCT Publication No. WO 02/060919 A2 discloses a modified IgG comprising an IgG constant domain comprising one or more amino acid modifications relative to a wild-type IgG constant domain, wherein the modified IgG has an increased half-life compared to the half-life of an IgG having the wild-type IgG constant domain, and wherein the one or more amino acid modifications are at one or more of positions 251, 253, 255, 285-290, 308-314, 385-389, and 428-435. Shields et al. (2001, J Biol Chem; 276:6591-604) used alanine scanning mutagenesis to alter residues in the Fc region of a human IgG1 antibody and then assessed the binding to human FcRn. Positions that effectively abrogated binding to FcRn when changed to alanine include I253, S254, H435, and Y436. Other positions showed a less pronounced reduction in binding as follows: E233-G236, R255, K288, L309, S415, and H433. Several amino acid positions exhibited an improvement in FcRn binding when changed to alanine; notable among these are P238, T256, E272, V305, T307, Q311, D312, K317, D376, E380, E382, S424, and N434. Many other amino acid positions exhibited a slight improvement (D265, N286, V303, K360, Q362, and A378) or no change (S239, K246, K248, D249, M252, E258, T260, S267, H268, S269, D270, K274, N276, Y278, D280, V282, E283, H285, T289, K290, R292, E293, E294, Q295, Y296, N297, S298, R301, N315, E318, K320, K322, S324, K326, A327, P329, P331, E333, K334, T335, S337, K338, K340, Q342, R344, E345, Q345, Q347, R356, M358, T359, K360, N361, Y373, S375, S383, N384, Q386, E388, N389, N390, K392, L398, S400, D401, K414, R416, Q418, Q419, N421, V422, E430, T437, K439, S440, S442, S444, and K447) in FcRn binding.

The most pronounced effect was found for combination variants with improved binding to FcRn. At pH 6.0, the E380A/N434A variant showed over 8-fold better binding to FcRn, relative to native IgG1, compared with 2-fold for E380A and 3.5-fold for N434A. Adding T307A to this effected a 12-fold improvement in binding relative to native IgG1. In one embodiment the antigen binding protein of the invention comprises the E380A/N434A mutations and has increased binding to FcRn.

Dall'Acqua et al. (2002, J. Immunol. 169: 5171-80) described random mutagenesis and screening of human IgG1 hinge-Fc fragment phage display libraries against mouse FcRn. They disclosed random mutagenesis of positions 251, 252, 254-256, 308, 309, 311, 312, 314, 385-387, 389, 428, 433, 434, and 436. The major improvements in IgG1-human FcRn complex stability occur in substituting residues located in a band across the Fc-FcRn interface (M252, S254, T256, H433, N434, and Y436) and to lesser extend substitutions of residues at the periphery like V308, L309, Q311, G385, Q386, P387, and N389. The variant with the highest affinity to human FcRn was obtained by combining the M252Y/S254T/T256E and H433K/N434F/Y436H mutations and exhibited a 57-fold increase in affinity relative to the wild-type IgG1. The in vivo behaviour of such a mutated human IgG1 exhibited a nearly 4-fold increase in serum half-life in cynomolgus monkey as compared to wild-type IgG1.

The present invention therefore provides a variant of an antigen binding protein with optimized binding to FcRn. In a preferred embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat.

In a further aspect of the invention the modifications are M252Y/S254T/T256E.

Additionally, various publications describe methods for obtaining physiologically active molecules whose half-lives are modified either by introducing an FcRn-binding polypeptide into the molecules (WO 97/43316; U.S. Pat. No. 5,869,046; U.S. Pat. No. 5,747,035; WO 96/32478; WO 91/14438) or by fusing the molecules with antibodies whose FcRn-binding affinities are preserved but affinities for other Fc receptors have been greatly reduced (WO 99/43713) or fusing with FcRn binding domains of antibodies (WO 00/09560; U.S. Pat. No. 4,703,039).

Additionally, methods of producing an antigen binding protein with a decreased biological half-life are also provided. A variant IgG in which His435 is mutated to alanine results in the selective loss of FcRn binding and a significantly reduced serum half-life (Firan et al. 2001, International immunology 13:993). U.S. Pat. No. 6,165,745 discloses a method of producing an antigen binding protein with a decreased biological half-life by introducing a mutation into the DNA segment encoding the antigen binding protein. The mutation includes an amino acid substitution at position 253, 310, 311, 433, or 434 of the Fc-hinge domain.

The invention also relates to a variant of any specific antigen binding construct sequence disclosed herein, such as epitope binding domain sequence, e.g. a DAB™ sequence, or the sequence of the whole antigen binding construct. Suitably the variant comprises an amino acid sequence that has at least 70%, or at least 75%, or at least 80% or at least 85% or at least 90% or at least 95%, at least 96%, at least 97%, at least 98% or at least 99% sequence identity to the specified sequence, suitably whilst substantially retaining the binding properties of the parent sequence, or at least one binding property where the parent is multi-specific, such as some binding affinity for a VEGF, such as VEGF A. Generally any variant will have at least 30% of the binding affinity of the parent, suitably at least 40%, 50%, 60%, 70, 80%, 90% or more, and suitably 100% of the parent sequence (or more).

In one aspect the antigen binding construct may be varied by 1, 2, 3, or 4 amino acids, as long as the antigen binding construct is capable of binding to a VEGF, such as VEGF A.

In one aspect the epitope binding domain sequence comprises a CDR or CDRs from a domain antibody (DAB™). CDRs of any sequence identified or referred to herein may be varied by 1, 2, 3, or 4 amino acids, as long as the antigen binding construct is capable of binding to a VEGF such as VEGF-A.

CDRs are defined as the complementarity determining region amino acid sequences of an antigen binding protein. These are the hypervariable regions of immunoglobulin heavy and light chains.

Throughout this specification, amino acid residues in variable domain sequences are numbered according to the Kabat numbering convention, unless otherwise specified. For further information, see Kabat et al., Sequences of Proteins of Immunological Interest, 4th Ed., U.S. Department of Health and Human Services, National Institutes of Health (1987).

The table below, (Table 1), represents one definition using each numbering convention for each CDR or binding unit. The Kabat numbering scheme is used in Table 1 to number the variable domain amino acid sequence. It should be noted that some of the CDR definitions may vary depending on the individual publication used.

TABLE 1

Numbering Convention for CDRs

| | Kabat CDR | Chothia CDR | AbM CDR | Contact CDR | Minimum binding unit |
|---|---|---|---|---|---|
| H1 | 31-35/35A/35B | 26-32/33/34 | 26-35/35A/35B | 30-35/35A/35B | 31-32 |
| H2 | 50-65 | 52-56 | 50-58 | 47-58 | 52-56 |
| H3 | | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

In one aspect, the present invention provides antigen binding constructs comprising two DAB™s, wherein each DAB™ is independently selected and comprises:
  i) one or more of CDR sequences SEQ ID No. 111, 112 and 113;
  ii) one or more of CDR sequences SEQ ID No. 114, 115 and 116;
  iii) one or more of CDR sequences SEQ ID No. 117, 118 and 119;
  iv) one or more of CDR sequences SEQ ID No. 120, 121 and 122;
  v) one or more of CDR sequences SEQ ID No. 123, 124 and 125;
  vi) one or more of CDR sequences SEQ ID No. 126, 127 and 128; or
  vii) one or more of CDR sequences SEQ ID No. 129, 130 and 131.

In a further aspect, the present invention provides antigen binding constructs comprising two DAB™s, wherein the DAB™ attached to the N-terminus of the Fc region of an antibody comprises one or more CDR sequences SEQ ID No. 114, 115 and 116, and the DAB™ attached to the C-terminus of the Fc region of an antibody comprises one or more CDR sequences SEQ ID No. 117, 118 and 119.

In a yet further aspect, the present invention provides antigen binding constructs comprising one DAB™, which comprises:
  i) one or more of CDR sequences SEQ ID No. 117, 118 and 119;
  ii) one or more of CDR sequences SEQ ID No. 120, 121 and 122;
  iii) one or more of CDR sequences SEQ ID No. 123, 124 and 125;
  iv) one or more of CDR sequences SEQ ID No. 126, 127 and 128; or
  v) one or more of CDR sequences SEQ ID No. 129, 130 and 131.

In one aspect there is provided an antigen binding construct or dimer which competes with an antigen binding construct or dimer herein described, for example, for binding to a VEGF, such as VEGF A.

In one aspect an antigen binding construct and dimers as described herein are able to compete with AVASTIN™ for binding to VEGF-A.

It will be understood that any of the antigen-binding constructs and dimers described herein will be capable of neutralising one or more antigens.

The term "neutralises" and grammatical variations thereof as used throughout the present specification in relation to antigen binding constructs of the invention means that a biological activity of the target is reduced, either totally or partially, in the presence of the antigen binding constructs of the present invention in comparison to the activity of the target in the absence of such antigen binding constructs. Neutralisation may be due to but not limited to one or more of blocking ligand binding, preventing the ligand activating the receptor, down regulating the receptor or affecting effector functionality.

Methods of assessing neutralisation, for example, by assessing the decreased binding between the ligand and its receptor in the presence of neutralising antigen binding construct are known in the art, and include receptor binding assays (see Examples 7, 17, 26, 41 and 50 herein) and rabbit retinal leakage model (see Examples 9 and 42 herein).

The invention also relates to a polynucleotide sequence encoding an antigen binding construct of the invention, or encoding a part of such a construct such as an epitope binding domain sequence. Suitably the polynucleotide encodes a polypeptide able to bind to a VEGF, such as VEGF-A. The invention also relates to a polynucleotide sequence encoding an antigen having at least 70% sequence identity to that antigen binding construct or portion thereof, such as at least 75%, at least 80%, at least 85%, at least 90%, at least 91%, at least 92%, at least 93%, at least 94%, at least 95%, at least 96%, at least 97%, at least 98%, at least 99%. In one aspect the antigen binding construct or portion thereof is able to bind to a VEGF, such as VEGF-A and prevent or treat in whole or in part disease associated with a VEGF, such as VEGF-A signalling.

The invention also relates to a polynucleotide sequences having at least 70% sequence identity to specific polynucleotide sequences disclosed herein, such as at least 75%, at least 80%, at least 85%, at least 90%, at least 91%, at least 92%, at least 93%, at least 94%, at least 95%, at least 96%, at least 971%, at least 98%, at least 99% identity.

The antigen binding constructs of the present invention may be produced by transfection of a host cell with an expression vector comprising the coding sequence for the antigen binding construct of the invention. An expression vector or recombinant plasmid is produced by placing these coding sequences for the antigen binding construct in operative association with conventional regulatory control sequences capable of controlling the replication and expression in, and/or secretion from, a host cell. Regulatory sequences include promoter sequences, e.g., CMV promoter, and signal sequences which can be derived from other known antibodies. Similarly, a second expression vector can be produced having a DNA sequence which encodes a complementary antigen binding construct. In certain embodiments this second expression vector is identical to the first except insofar as the coding sequences and selectable markers are concerned, so to ensure as far as possible that each polypeptide chain is functionally expressed. Alternatively, the coding sequences for the two antigen binding constructs that form a homodimer or heterodimer may reside on a single vector, for example in two expression cassettes in the same vector.

In one aspect, the present invention relates to a recombinant transformed or transfected host cell comprising one or more polynucleotide sequences encoding an antigen binding construct, homodimer or heterodimer as herein described.

A selected host cell can be co-transfected by conventional techniques with both the first and second vectors (or simply transfected by a single vector) to create the transfected host cell of the invention. The transfected cell is then cultured by conventional techniques to produce the engineered antigen binding construct of the invention, homodimer or heterodimer. The antigen binding construct, homodimer or heterodimer is screened from culture by appropriate assay, such as ELISA or RIA. Similar conventional techniques may be employed to construct other antigen binding construct, homodimers or heterodimers as disclosed herein.

Suitable vectors for the cloning and subcloning steps employed in the methods and construction of the compositions of this invention may be selected by one of skill in the art. For example, the conventional pUC series of cloning vectors may be used, such as pUC19. Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

The expression vectors may also be characterized by genes suitable for amplifying expression of the heterologous DNA sequences, e.g., the mammalian dihydrofolate reductase gene (DHFR). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antigen binding constructs, homodimers or heterodimers of the present invention. Host cells useful for the cloning and other manipulations of these cloning vectors are also conventional. However, cells from various strains of *E. coli* may be used for replication of the cloning vectors and other steps in the construction of antigen binding constructs, homodimers or heterodimers of this invention.

Suitable host cells or cell lines for the expression of the antigen binding constructs, heterodimers, or homodimers of the invention include mammalian cells such as NS0, Sp2/0, CHO (e.g. DG44), COS, HEK, a fibroblast cell (e.g., 3T3), and myeloma cells, for example it may be expressed in a CHO or a myeloma cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook, J., Fritsch, E., Maniatis, T. 1989: Cold Spring harbour Press, Molecular Cloning Laboratory Manual.

Bacterial cells and where desired strains of yeast cells known to those skilled in the art are also available as host cells, as well as insect cells, e.g. *Drosophila* and Lepidoptera and viral expression systems. See, e.g. Miller et al., Genetic Engineering, 8:277-298, Plenum Press (1986) and references cited therein.

In another aspect, the invention relates to a method for the production of an antigen binding construct, homodimer or heterodimer as herein described, which method comprises the step of culturing a host cell and isolating the antigen binding construct, homodimer or heterodimer.

The present invention also provides a method for the production of an antigen binding construct, homodimer or heterodimer as described herein comprising the steps of:
a) culturing a recombinant host cell comprising an expression vector comprising the isolated nucleic acid as described herein, wherein the FUT8 gene encoding alpha-1,6-fucosyltransferase has been inactivated in the recombinant host cell; and b) recovering the antigen binding protein.

Such methods for the production of antigen binding constructs, heterodimers and homodimers can be performed, for example, using the POTELLIGENT™ technology system available from BioWa, Inc. (Princeton, N.J.) which may produce antigen binding constructs, homodimers and heterodimers having enhanced antibody dependent cell mediated cytotoxicity (ADCC) activity that is increased relative to an identical protein produced in a cell with a functional FUT8 gene. Aspects of the POTELLIGENT™ technology system are described in U.S. Pat. No. 7,214,775, U.S. Pat. No. 6,946,292, WO0061739 and WO0231240 all of which are incorporated herein by reference. Those of ordinary skill in the art will also recognize other appropriate systems.

The present invention also provides a method of producing an antigen binding construct, homodimer or heterodimer as described herein comprising the steps of:

a) culturing a recombinant host cell comprising an expression vector comprising an isolated nucleic acid as described herein wherein the expression vector comprises a nucleic acid sequence encoding an Fc domain having both IgG1 and IgG3 Fc domain amino acid residues; and
b) recovering the antigen binding protein.

Such methods for the production of antigen binding constructs, heterodimers and homodimers can be performed, for example, using the COMPLEGENT™ technology system available from BioWa, Inc. (Princeton, N.J.) and Kyowa Hakko Kogyo (now, Kyowa Hakko Kirin Co., Ltd.) Co., Ltd. in which a recombinant host cell comprising an expression vector in which a nucleic acid sequence encoding a chimeric Fc domain having both IgG1 and IgG3 Fc domain amino acid residues is expressed to produce an antigen binding construct, heterodimer or homodimer having enhanced complement dependent cytotoxicity (CDC) activity that is increased relative to an otherwise identical protein lacking such a chimeric Fc domain. Aspects of the COMPLEGENT™ technology system are described in WO2007011041 and US20070148165 each of which are incorporated herein by reference. In an alternative embodiment CDC activity may be increased by introducing sequence specific mutations into the Fc region of an IgG chain. Those of ordinary skill in the art will also recognize other appropriate systems.

It will be apparent to those skilled in the art that such modifications may not only be used alone but may be used in combination with each other in order to further enhance effector function.

In one aspect of the present invention there is provided an antigen binding construct, heterodimer or homodimer comprising a heavy chain constant region which comprises a mutated and chimaeric heavy chain constant region, comprising at least one CH2 domain from IgG3 and one CH2 domain from IgG1, wherein the IgG1 CH2 domain has one or more mutations at positions selected from 239 and 332 and 330 (for example the mutations may be selected from S239D and I332E and A330L) such that the antigen binding protein has enhanced effector function, for example wherein it has one or more of the following functions, enhanced ADCC or enhanced CDC, for example wherein it has enhanced ADCC and enhanced CDC. In one aspect the IgG1 CH2 domain has the mutations S239D and I332E.

In an alternative aspect of the present invention there is provided an antigen binding construct, heterodimer or homdimer, comprising a chimaeric heavy chain constant region and which has an altered glycosylation profile. In one such aspect, the heavy chain constant region comprises at least one CH2 domain from IgG3 and one CH2 domain from IgG1 and has an altered glycosylation profile such that the ratio of fucose to mannose is 0.8:3 or less, for example wherein the antigen binding protein is defucosylated so that said antigen binding protein has an enhanced effector function in comparison with an equivalent antigen binding protein with an immunoglobulin heavy chain constant region lacking said mutations and altered glycosylation profile, for example wherein it has one or more of the following functions, enhanced ADCC or enhanced CDC, for example wherein it has enhanced ADCC and enhanced CDC In one aspect of the invention, there is provided a method of producing an antigen binding construct, heterodimer or homdimer as described herein which uses the ACCRETAMAB™ technology system available from BioWa, Inc. (Princeton, N.J.) which combines the POTELLIGENT™ and COMPLEGENT™ technology systems to produce an antigen binding protein having both ADCC and CDC enhanced activity that is increased relative to an otherwise identical monoclonal antibody lacking a chimeric Fc domain and which has fucose on the oligosaccharide.

Another method of expression of the antigen binding constructs may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

The invention also relates to a method for producing an antigen binding construct as disclosed herein wherein the amino acid sequence of an antigen binding construct or a nucleic acid encoding it, or a part thereof, is designed using a computer and wherein the construct exists in silico on the computer.

The invention also provides antigen-binding constructs disclosed herein for use in medicine, for example for use in the manufacture of a medicament for treating diseases associated with a VEGF signalling, such as VEGF-A signalling, such as cancer and ocular diseases such as Diabetic Macular Edema (DME), Wet AMD (Age-related macular degeneration), Diabetic retinopathy, RVO, (retinal vein occlusion), and corneal neovascularisation.

The invention also relates to a method of treating a patient suffering from ocular vascular diseases caused by a VEGF signalling, such as VEGF-A, such as cancer and ocular diseases such as Diabetic Macular Edema (DME), Wet AMD, Diabetic retinopathy, RVO, and corneal neovascularisation, comprising administering a therapeutic amount of an antigen-binding construct of the invention.

The invention also relates to an antigen-binding construct of the invention for the treatment of cancer and ocular diseases such as Diabetic Macular Edema (DME), Wet AMD, Diabetic retinopathy, RVO, and corneal neovascularisation.

The dose and duration of treatment relates to the relative duration of the molecules of the present invention in the human circulation, and can be adjusted by one of skill in the art depending upon the condition being treated and the general health of the patient. It is envisaged that repeated dosing (e.g. once a week or once every two weeks) over an extended time period (e.g. four to six months) maybe required to achieve maximal therapeutic efficacy.

The mode of administration of the therapeutic agent of the invention may be any suitable route which delivers the agent to the host. The antigen binding constructs, and pharmaceutical compositions of the invention are particularly useful for parenteral administration, i.e., subcutaneously (s.c.), intrathecally, intraperitoneally, intramuscularly (i.m.), intravenously (i.v.), or intranasally.

In one aspect the administration is for an ocular indication and the administration is by local ocular delivery such as intravitreal, (direct injection into the vitreous of the eye) or is periocular, such as for example is trans-scleral, subconjunctival, sub-tenon, peribulbar, topical, retrobulbar or is delivered to the inferior, superior or lateral rectus muscle. In one aspect the administration is by trans-scleral or topical ocular delivery.

For local administration to the eye, for example by intravitreal injection, the pharmaceutical preparation could be administered in a total volume of up to 100 μL, for example, 50-100 μL, administered by a single injection by a standard syringe with a needle gauge of 25-30 g, such as a 50 μl volume administered with a 30 g needle. Such formulations if prepared for infrequent administration may contain up to 15% of solid suspension within the liquid volume. The dose of active pharmaceutical in such a formulation would vary but in a preferred aspect could include up to 25-30% of the solid suspension. In a preferred aspect 0.5-2.5 mg of active pharmaceutical is administered perocular administration.

In one aspect the administration uses a sustained or slow-release delivery system such as microparticles or a gel-based system, or a liposome based system or any other system known to those skilled in the art that would allow administration locally to the eye, suitably at frequency reduced when compared to a monthly injection regime. Such regimes may allow delivery less frequently than once a week or once every two weeks, and for example could be once every 4 weeks, once every 2 months or 8 weeks, every 3 months or 12 weeks, every 4 months or 16 weeks, every 5 months or 20 weeks, every 6 months or 24 weeks, every 9 months or 36 weeks, or every 12 months or 52 weeks. A preferred delivery frequency for the antigen binding constructs, heterodimers and homodimers of the present invention is once every 6 months or 24 weeks.

Therapeutic agents of the invention may be prepared as pharmaceutical compositions containing an effective amount of an antigen binding construct, homodimer or heterodimer of the invention as an active ingredient in a pharmaceutically acceptable carrier. In the prophylactic agent of the invention, an aqueous suspension or solution containing the antigen binding construct, preferably buffered at physiological pH, in a form ready for injection is preferred. The compositions for parenteral administration will commonly comprise a solution of the antigen binding construct of the invention or a cocktail thereof dissolved in a pharmaceutically acceptable carrier, preferably an aqueous carrier. A variety of aqueous carriers may be employed, e.g., 0.9% saline, 0.3% glycine, and the like. These solutions may be made sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antigen binding construct of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an antigen binding construct of the invention. Similarly, a pharmaceutical composition of the invention for intravenous infusion could be made up to contain about 250 ml of sterile Ringer's solution, and about 1 to about 30 and preferably 5 mg to about 25 mg of an antigen binding construct of the invention per ml of Ringer's solution. Actual methods for preparing parenterally administrable compositions are well known or will be apparent to those skilled in the art and are described in more detail in, for example, Remington's Pharmaceutical Science, 15th ed., Mack Publishing Company, Easton, Pa. For the preparation of intravenously administrable antigen binding construct formulations of the invention see Lasmar U and Parkins D "The formulation of Biopharmaceutical products", Pharma. Sci. Tech. today, page 129-137, Vol. 3 (3 Apr. 2000), Wang, W "Instability, stabilisation and formulation of liquid protein pharmaceuticals", Int. J. Pharm 185 (1999) 129-188, Stability of Protein Pharmaceuticals Part A and B ed Ahern T J., Manning M. C., New York, N.Y.: Plenum Press (1992), Akers, M. J. "Excipient-Drug interactions in Parenteral Formulations", J. Pharm Sci 91 (2002) 2283-2300, Imamura, K et al "Effects of types of sugar on stabilization of Protein in the dried state", J Pharm Sci 92 (2003) 266-274, Izutsu, Kkojima, S. "Excipient crystallinity and its protein-structure-stabilizing effect during freeze-drying", J. Pharm. Pharmacol, 54 (2002) 1033-1039, Johnson, R, "Mannitol-sucrose mixtures-versatile formulations for protein lyophilization", J. Pharm. Sci, 91 (2002) 914-922. Ha, E Wang W, Wang Y. J. "Peroxide formation in polysorbate 80 and protein stability", J. Pharm Sci, 91, 2252-2264, (2002) the entire contents of which are incorporated herein by reference and to which the reader is specifically referred.

It is preferred that the therapeutic agent of the invention, when in a pharmaceutical preparation, be present in unit dose forms. The appropriate therapeutically effective dose will be determined readily by those of skill in the art. Suitable doses may be calculated for patients according to their weight, for example suitable doses may be in the range of 0.01 to 20 mg/kg, for example 0.1 to 20 mg/kg, for example 1 to 20 mg/kg, for example 10 to 20 mg/kg or for example 1 to 15 mg/kg, for example 10 to 15 mg/kg. To effectively treat conditions of use in the present invention in a human, suitable doses may be within the range of 0.01 to 1000 mg, for example 0.1 to 1000 mg, for example 0.1 to 500 mg, for example 500 mg, for example 0.1 to 100 mg, or 0.1 to 80 mg, or 0.1 to 60 mg, or 0.1 to 40 mg, or for example 1 to 100 mg, or 1 to 50 mg, of an antigen binding construct of this invention, which may be administered parenterally, for example subcutaneously, intravenously or intramuscularly. Such dose may, if necessary, be repeated at appropriate time intervals selected as appropriate by a physician.

The antigen binding constructs described herein can be lyophilized for storage and reconstituted in a suitable carrier prior to use. This technique has been shown to be effective with conventional immunoglobulins and art-known lyophilization and reconstitution techniques can be employed.

There are several methods known in the art which can be used to generate epitope-binding domains of use in the present invention.

In one example, the methods employ a display system that links the coding function of a nucleic acid and physical, chemical and/or functional characteristics of the polypeptide encoded by the nucleic acid. Such a display system can comprise a plurality of replicable genetic packages, such as bacteriophage or cells (bacteria). The display system may comprise a library, such as a bacteriophage display library. Bacteriophage display is an example of a display system.

The term "library" refers to a mixture of heterogeneous polypeptides or nucleic acids. The library is composed of members, each of which has a single polypeptide or nucleic acid sequence. To this extent, "library" is synonymous with "repertoire." Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. In one example, each individual organism or cell contains only one or a limited number of library members. Advantageously, the nucleic acids are incorporated into expression vectors, in order to allow expression of the polypeptides encoded by the nucleic acids. In a one aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of diverse polypeptides.

A number of suitable bacteriophage display systems (e.g., monovalent display and multivalent display systems) have been described. (See, e.g., Griffiths et al., U.S. Pat. No. 6,555,313 B1 (incorporated herein by reference); Johnson et al., U.S. Pat. No. 5,733,743 (incorporated herein by reference); McCafferty et al., U.S. Pat. No. 5,969,108 (incorporated herein by reference); Mulligan-Kehoe, U.S. Pat. No. 5,702,892 (Incorporated herein by reference); Winter, G. et al., *Annu. Rev. Immunol.* 12:433-455 (1994); Soumillion, P. et al., *Appl. Biochem. Biotechnol.* 47(2-3):175-189 (1994); Castagnoli, L. et al., *Comb. Chem. High Throughput Screen*, 4(2):121-133 (2001).) The peptides or polypeptides displayed in a bacteriophage display system can be displayed on any suitable bacteriophage, such as a filamentous phage (e.g., fd, M13, F1), a lytic phage (e.g., T4, T7, lambda), or an RNA phage (e.g., MS2), for example.

When a display system (e.g., a system that links coding function of a nucleic acid and functional characteristics of the peptide or polypeptide encoded by the nucleic acid), such as phage display, is used in the methods described herein, eg in the selection of a DAB™ or other epitope binding domain, it is frequently advantageous to amplify or increase the copy number of the nucleic acids that encode the selected peptides or polypeptides. This provides an efficient way of obtaining sufficient quantities of nucleic acids and/or peptides or polypeptides for additional rounds of selection, using the methods described herein or other suitable methods, or for preparing additional repertoires (e.g., affinity maturation repertoires). Nucleic acids can be amplified using any suitable methods, such as by phage amplification, cell growth or polymerase chain reaction.

Generally, a library of phage that displays a repertoire of peptides or phage polypeptides, as fusion proteins with a suitable phage coat protein (e.g., fd pill protein), is produced or provided. The fusion protein can display the peptides or polypeptides at the tip of the phage coat protein, or if desired at an internal position. For example, the displayed peptide or polypeptide can be present at a position that is amino-terminal to domain 1 of pIII. (Domain 1 of pIII is also referred to as N1.) The displayed polypeptide can be directly fused to pill (e.g., the N-terminus of domain 1 of pIII) or fused to pIII using a linker. If desired, the fusion can further comprise a tag (e.g., myc epitope, His tag). Libraries that comprise a repertoire of peptides or polypeptides that are displayed as fusion proteins with a phage coat protein, can be produced using any suitable methods, such as by introducing a library of phage vectors or phagemid vectors encoding the displayed peptides or polypeptides into suitable host bacteria, and culturing the resulting bacteria to produce phage (e.g., using a suitable helper phage or complementing plasmid if desired). The library of phage can be recovered from the culture using any suitable method, such as precipitation and centrifugation.

The display system can comprise a repertoire of peptides or polypeptides that contains any desired amount of diversity. For example, the repertoire can contain peptides or polypeptides that have amino acid sequences that correspond to naturally occurring polypeptides expressed by an organism, group of organisms, desired tissue or desired cell type, or can contain peptides or polypeptides that have random or randomized amino acid sequences. If desired, the polypeptides can share a common core or scaffold. For example, all polypeptides in the repertoire or library can be based on a scaffold selected from protein A, protein L, protein G, a fibronectin domain, an anticalin, CTLA4, a desired enzyme (e.g., a polymerase, a cellulase), or a polypeptide from the immunoglobulin superfamily, such as an antibody or antibody fragment (e.g., an antibody variable domain). The polypeptides in such a repertoire or library can comprise defined regions of random or randomized amino acid sequence and regions of common amino acid sequence. In certain embodiments, all or substantially all polypeptides in a repertoire are of a desired type, such as a desired enzyme (e.g., a polymerase) or a desired antigen-binding fragment of an antibody (e.g., human $V_H$ or human $V_L$). In some embodiments, the polypeptide display system comprises a repertoire of polypeptides wherein each polypeptide comprises an antibody variable domain. For example, each polypeptide in the repertoire can contain a $V_H$, a $V_L$ or an Fv (e.g., a single chain Fv).

Amino acid sequence diversity can be introduced into any desired region of a peptide or polypeptide or scaffold using any suitable method. For example, amino acid sequence diversity can be introduced into a target region, such as a complementarity determining region of an antibody variable domain or a hydrophobic domain, by preparing a library of nucleic acids that encode the diversified polypeptides using any suitable mutagenesis methods (e.g., low fidelity PCR, oligonucleotide-mediated or site directed mutagenesis, diversification using NNK codons) or any other suitable method. If desired, a region of a polypeptide to be diversified can be randomized.

The size of the polypeptides that make up the repertoire is largely a matter of choice and uniform polypeptide size is not required. The polypeptides in the repertoire may have at least tertiary structure (form at least one domain).

An epitope binding domain or population of domains can be selected, isolated and/or recovered from a repertoire or library (e.g., in a display system) using any suitable method. For example, a domain is selected or isolated based on a selectable characteristic (e.g., physical characteristic, chemical characteristic, functional characteristic). Suitable selectable functional characteristics include biological activities of the peptides or polypeptides in the repertoire, for example, binding to a generic ligand (e.g., a superantigen), binding to a target ligand (e.g., an antigen, an epitope, a substrate), binding to an antibody (e.g., through an epitope expressed on a peptide or polypeptide), and catalytic activity. (See, e.g., Tomlinson et al., WO 99/20749; WO 01/57065; WO 99/58655.)

The members of the immunoglobulin superfamily all share a similar fold for their polypeptide chain. For example, although antibodies are highly diverse in terms of their primary sequence, comparison of sequences and crystallographic structures has revealed that, contrary to expectation, five of the six antigen binding loops of antibodies (H1, H2, L1, L2, L3) adopt a limited number of main-chain conformations, or canonical structures (Chothia and Lesk (1987) *J. Mol. Biol.*, 196: 901; Chothia et al. (1989) *Nature*, 342: 877). Analysis of loop lengths and key residues has therefore enabled prediction of the main-chain conformations of H1, H2, L1, L2 and L3 found in the majority of human antibodies (Chothia et al. (1992) *J. Mol. Biol.*, 227: 799; Tomlinson et al. (1995) *EMBO J.*, 14: 4628; Williams et al. (1996) *J. Mol. Biol.*, 264: 220). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) *J. Mol. Biol.*, 263: 800; Shirai et al. (1996) *FEBS Letters*, 399: 1).

The DAB™s are advantageously assembled from libraries of domains, such as libraries of $V_H$ domains and/or libraries of $V_L$ domains. In one aspect, libraries of domains are designed in which certain loop lengths and key residues have been chosen to ensure that the main-chain conformation of the members is known. Advantageously, these are real conformations of immunoglobulin superfamily molecules found in nature, to minimise the chances that they are non-functional, as discussed above. Variations may occur at a low frequency, such that a small number of functional members may possess an altered main-chain conformation, which does not affect its function.

Where several known main-chain conformations or a single known main-chain conformation has been selected, DAB™s may be constructed by varying the binding site of the molecule in order to generate a repertoire with structural and/or functional diversity. This means that variants are generated such that they possess sufficient diversity in their structure and/or in their function so that they are capable of providing a range of activities.

In one aspect, the present invention include sequences which are substantially identical, for example sequences which are at least 90% identical, for example which are at least 91%, or at least 92%, or at least 93%, or at least 94% or at least 95%, or at least 96%, or at least 97% or at least 98%, or at least 99% identical to the sequences described herein.

For nucleic acids, the term "substantial identity" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial identity exists when the segments will hybridize under selective hybridization conditions, to the complement of the strand.

For nucleotide and amino acid sequences, the term "identical" indicates the degree of identity between two nucleic acid or amino acid sequences when optimally aligned and compared with appropriate insertions or deletions. Alternatively, substantial identity exists when the DNA segments will hybridize under selective hybridization conditions, to the complement of the strand.

The percent identity between two sequences is a function of the number of identical positions shared by the sequences (i.e., % identity=no. of identical positions/total no. of positions times 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

By way of example, a polynucleotide sequence of the present invention may be identical to a reference sequence, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference sequence by the numerical percent of the respective percent identity (divided by 100) and subtracting that product from said total number of nucleotides in the reference sequence, or:

nn≤xn−(xn·y), wherein nn is the number of nucleotide alterations, xn is the total number of nucleotides in the reference sequence, and y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100% identity, and wherein any non-integer product of xn and y is rounded down to the nearest integer prior to subtracting it from xn. Alterations of the polynucleotide sequence of the reference sequence may create nonsense, missense or frameshift mutations in this coding sequence and thereby alter the polypeptide encoded by the polynucleotide following such alterations.

Similarly, in another example, a polypeptide sequence of the present invention may be identical to a reference sequence, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the polypeptide sequence encoded by the reference sequence by the numerical percent of the respective percent identity (divided by 100) and then subtracting that product from said total number of amino acids in the polypeptide reference sequence or:

$$na \leq xa-(xa \cdot y),$$

wherein na is the number of amino acid alterations, xa is the total number of amino acids in the polypeptide sequence and y is, for instance, 0.70 for 70%, 0.80 for 80%, 0.85 for 85% etc., and wherein any non-integer product of xa and y is rounded down to the nearest integer prior to subtracting it from xa.

The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB.

EXAMPLES

It will be understood that particular embodiments described herein are shown by way of illustration and not as limitations of the invention.

Throughout the examples references are made to dAb-Fc, Fc-dAb and dAb-Fc-dAb molecules. The terms "dAb-Fc" and "Fc-dAb" are simple references to dimers comprising two antigen binding constructs wherein each antigen binding construct has a DAB™ attached to either the N-terminus (dAb-Fc) or C-terminus (Fc-dAb), directly or indirectly through a linker.

Similarly, the term "dAb-Fc-dAb" refers to dimers comprising two antigen binding constructs wherein each antigen binding construct has a DAB™ attached to the N-terminus and a DAB™ attached to the C-terminus; directly or indirectly through a linker.

Example 1

Expression of Vh dAb-Fc Molecules

DMS1529, (SEQ ID NO:1 & 29), has been described in WO2008/149150/A20. DMS1576, (SEQ ID NO:2 & 30), was generated by site directed mutagenesis from DMS1529 converting amino acid 56 from Y to N. DMS1529 and DMS1576 were manufactured from either CHROMOS pooled (or bulk) transfections or stable polyclonal or monoclonal CHO cell lines using GlaxoSmithKline's generic monoclonal antibody production process platform using a combination of shake flask and stirred tank suspension culture. Bioreactors are monitored and maintained at controlled conditions for agitation speed, dissolved oxygen concentration, pH and temperature. Dissolved oxygen is maintained through the addition of 40% $O_2$ in $N_2$ while pH is controlled via automated addition of sodium carbonate and $CO_2$. The production culture duration is determined from a combination of cell viability and minimum antibody titre. At the end of the production period, the culture in the bioreactor is clarified by depth filtration and sterile filtration to generate a batch of clarified unprocessed bulk (CUB).

Example 2

Purification of Vh dAb-Fc Molecules

DMS1529 and DMS1576 were captured from clarified cell culture supernatant (CUB, Example 1) using affinity chromatography and an automated FPLC purification system. Once loaded, the bound product was washed using a combination of pH neutral aqueous buffers to remove non-specifically bound impurities followed by a low pH elution. Over 90% of bound product was recovered and the pH of the elution pool then adjusted to pH 3.5 for 30 minutes to achieve virus neutralisation after which time the pH was adjusted to pH 4.5. If further purification was required, a further pH adjustment was performed in order to achieve binding on the second column. Following binding, the product was washed in a low conductivity buffer at equivalent pH to further remove non-specifically bound impurities. The purified dAb-Fc was then eluted using a pH and salt shift and collected as a pool before 0.2 um filtration and storage. Unless otherwise stated, protein prepared using only the first, affinity column was analysed for VEGF binding in the in vitro assays described in the following examples, however reference will be made when the test material was further purified, i.e. using the $2^{nd}$ column.

Example 3

Molecular Analysis by SDS-PAGE and Size-Exclusion Chromatography (SEC)

The molecular integrity, homogeneity and percentage (%) purity of DMS1529 and DMS1576 were analysed by SDS-PAGE, under both reducing and non-reducing conditions, and analytical size-exclusion chromatography (SEC). SDS-PAGE analysis was carried out according to the manufacturer's instructions using the Novex "NuPAGE" system and gels were stained with Instant Blue Protein Stain Solution (Triple Red Ltd). The gels showed band sizes consistent with the predicted molecular mass of the intact mature proteins (~76-79 kDa) allowing for the presence of the predicted glycan chains per monomer chain. SEC was carried out using a TSK gel G2000SWXL column (TOSOH, BioScience). A sodium phosphate/sodium chloride based mobile phase at neutral pH was used at a flow rate of 0.5 ml/min. The standard sample injection volume of purified protein (at approximately 1 mg/ml) was 10 ul. The UV absorbance of the column effluent was monitored at 214 & 280 nm. The area of all protein related peaks were integrated to determine the purity of the peak relating to the molecules. The proteins were confirmed to be >95% pure target protein by SDS-PAGE and SEC prior to further analysis in biology assays, (data not shown).

Example 4

VEGF Binding ELISA

The ability of DMS1529 and DMS1576 to bind specifically to $VEGF_{165}$ was determined and compared to that of Bevacizumab (AVASTIN™, clinical drug product sourced from Phillip Chapper & Co. Ltd., UK) by ELISA. An F96 MAXISORP 96™ well flat bottom immunoplate (Nunc, Cat No: 439454) was coated with 100 ul of 25 ug/ml of hVEGF165 (GSK 'in house' source of VEGF made from HEK293 mammalian cells) and incubated at 4° C. overnight. The plate was washed six times with PBS containing 0.05% of TWEEN™-20, 200 μl of blocking solution (1% BSA in PBS) was added to each well and the plate was incubated for 1 h at room temperature. The plate was then washed with 0.05% TWEEN™-20/PBS. 90 μl of assay diluents (0.1% BSA, 0.05% TWEEN™-20 in PBS) was added to each well, 10 μl of each sample or control (successively diluted, two-fold over a concentration range from 80-0.08 ng/ml) were then added across the plate in blocking solution and incubated for 1 hr at room temperature. The plate was then washed 0.05% TWEEN™-20/PBS. 100 μl of anti-human IgG (Fc specific) HRP (Sigma, Cat No: A0170) diluted at 1:10,000 in 0.1% BSA, 0.05% TWEEN™-20 in PBS was added to appropriate wells. The plate was incubated for 1 hr at room temperature and washed with 0.05% TWEEN™-20/PBS. 100 μl of 3,3',5,5'-Tetramethylbenzidine (TMB) liquid substrate system (Sigma T0440) was added to each well. Once sufficient blue colour has developed (expected OD450 of >2.0), the reaction was stopped 15 minutes later by addition of 100 μL of 0.25M sulphuric acid (Fisher Scientific J/8410/17). Absorbance was read at 450 nm using the SPECTRAMAXPLUS384 MICROPLATE READER™ (Molecular Devices) using a basic endpoint protocol.

Both DMS1529 and DMS1576 were found to bind specifically in a similar manner to $VEGF_{165}$, and both molecules were shown to be more potent than Bevacizumab (AVASTIN™) as shown by a reduced IC50 value, (FIG. 1).

Example 5

VEGF Binding MSD™

The ability of DMS1529 and DMS1576 to bind specifically to $VEGF_{165}$ was determined by MSD™ (Meso Scale Discovery) assay. The MSD™ data show equivalent binding of DMS1529 and DMS1576 to hVEGF165 after detection with either anti-Vh or anti-Fc reagents.

Example 6

Binding of DMS1529 and DMS1576 to VEGF Using Surface Plasmon Resonance

The binding affinity of the DMS1529 and DMS1576 molecules for $VEGF_{165}$ was determined by surface Plasmon resonance (SPR) using a BIACORE™ T100 (GE Healthcare), Example 6A, and PROTEON™ XPR36 protein interaction array system (BioRad) (data not shown).

Example 6A

Binding of DMS1529 and DMS1576 to VEGF Using BIACORE™

Protein A was immobilised on a C1 chip by primary amine coupling and this surface was then used to capture the anti-VEGF constructs. Human recombinant VEGF (sourced 'in house' from transient transfection of HEK293 cells) was used as the analyte at 256 nM, 64 nM, 16 nM, 4 nM, 1 nM, 0.25 nM and 0.0625 nM. All binding curves were double referenced with a buffer injection (i.e. 0 nM) and the data was fitted both to the 1:1 model (and to the bivalent model (inherent to the T100. Regeneration was carried out using 100 mM $H_3PO_4$. The run was carried out at room temperature, using HBS-EP as the running buffer. For the DMS1529 and DMS1576 reliable kinetics could not be obtained due to the poor fitting of the analysis model to the experimental data, (but estimates could be made for association and dissociation constants and these are summarized in Table 2A.

Both BIACORE™ and PROTEON™ data show that DMS1529 and DMS1576 have comparable binding kinetics to $VEGF_{165}$ using Surface Plasmon Resonance.

TABLE 2A

BIACORE ™ analysis of the binding kinetics of DMS1529 and DMS1576 to human $VEGF_{165}$ to determine ka, kd and KD

| | 1:1 binding model | | | Bivalent analyte model | | |
| --- | --- | --- | --- | --- | --- | --- |
| | Ka (M−1 · s−1) | Kd (s−1) | KD (M) | Ka (M−1 · s−1) | Kd (s−1) | KD (M) |
| DMS1529 | 5.23E+05 | 3.13E−04 | 5.99E−10 | 4.89E+05 | 1.94E−04 | 1.01E−09 |
| DMS1576 | 4.60E+05 | 3.82E−04 | 8.30E−10 | 7.95E+05 | 6.50E−04 | 8.17E−10 |

Example 7

VEGF R1 & R2 Receptor Binding Assay

The potencies of DMS1529 and DMS1576 were analysed in the VEGF receptor binding assay in comparison to that of Bevacizumab (AVASTIN™). This assay measures the binding of VEGF165 to either VEGF R1 or VEGF R2 and the ability of the test molecules to block this interaction. A MSD™ standard bind 96 well plate (L11XA-3) was coated with 0.25 µg/ml VEGF R1 (R&D Systems 321-FL) or VEGF R2 (R&D 357-KD) in bicarbonate buffer (50 µl/well), covered with a plate sealer and incubated overnight at 4° C. The next day the MSD™ plate was washed 3×300 µl/well with Tris wash buffer and blotted over a pad of tissue to remove excess wash buffer from the wells. The MSD™ plate was then blocked with 3% BSA in PBS (250 µl/well) and incubated shaking (750 RPM) at room temperature for 1 hour. The MSD™ plate was washed again before the addition of a 2× concentration of anti-VEGF molecule (25 µl/well) and incubated with shaking (750 RPM) at room temperature for 10 minutes before the addition of a 2× concentration of rhVEGF, 25 µl/well, R&D Systems (293-VE/CF, made in insect cells using Baculovirus) or a GSK 'in house' source of VEGF (made from HEK293 mammalian cells, latter data not shown except Table 3A). The anti-VEGF molecules and the VEGF were prepared using 0.1% BSA in PBS. The initial assay was performed with a step in which the anti-VEGF molecule was pre-incubated with VEGF. The pre-incubations were prepared by adding an equal volume of a 2× concentration of anti-VEGF molecule to an equal volume of a 2× concentration of VEGF (R&D, 293-VE/CF) for 30 minutes at room temperature. The final VEGF concentration used was 10 ng/ml. No VEGF and VEGF alone controls were also included. The MSD™ plate was incubated with shaking (750 RPM) at room temperature for 2 hours after which it was washed again before the addition of the detection reagent (50 µL/well, goat anti-human VEGF biotinylated antibody—R&D Systems BAF293) at 0.25 µg/ml in 1% BSA in PBS and incubated with shaking (750 RPM) at room temperature for 1 hour. The MSD™ plate was washed again before the addition of the streptavidin SULFO-TAG™ (50 µl/well, MSD™ R32AD-1) at 2 µg/ml in 1% BSA in PBS and incubated with shaking (750 RPM) at room temperature for 30 minutes. Prior to measurement of the electrochemiluminescence in a MSD™ Sector Imager 6000, the MSD™ plate was washed and 150l/well of 2× Read Buffer T (MSD™ R92TC-1) was added. Curve fitting and EC50 calculations were performed using GRAPHPAD PRISM™. The ability of DMS1529, DMS1576 and Bevacizumab (AVASTIN™) to inhibit VEGF binding to VEGFR1 and VEGFR2 was determined as described. The EC50 values are listed in Table 3A.

A second assay was performed whereby the anti-VEGF agent and the VEGF were not pre-incubated prior to the addition to the VEGF Receptor coated MSD™ plate. This assay was carried out just comparing DMS1576 and Bevacizumab (AVASTIN™) and only used VEGF sourced from R&D Systems, (293-VE/CF). The ability of DMS1576 and Bevacizumab (AVASTIN™) to inhibit VEGF binding to VEGFR1 and VEGFR2 was determined as described above but without the pre-incubation step. The EC50 values are listed in Table 3B.

From the data in Table 3A, both DMS1529 and DMS1576 appear to have similar EC50 values and these are almost ten-fold lower (i.e. greater potency) than the EC50 values for Bevacizumab (AVASTIN™) against both VEGF binding to VEGFR1 and VEGFR2. All anti-VEGF molecules are more potent at binding R&D Systems VEGF compared to 'in-house' HEK293 produced VEGF for both VEGFR1 and VEGFR2 binding assays and are more potent in the assays where pre-incubation with VEGF occurs. Since DMS1576 maintained the relative EC50 value compared to that for Bevacizumab (AVASTIN™) against both VEGFR1 and VEGFR2 in the absence of pre-incubation with VEGF, this simplified assay type was taken forward for the analysis of new molecules. Note that in all RBA assays although both DMS1529 and DMS1576 appear more potent than Bevacizumab (AVASTIN™), unlike Bevacizumab (AVASTIN™) neither DMS1529 nor DMS1576 seem to quite reach 100% inhibition in these assays, (data not shown).

Table 3 EC50 Values from VEGFR RBAs (A) RBA with Pre-Incubation of Anti-VEGF & VEGF Reagent In-House VEGF and VEGF Sourced from R&D Systems (Baculovirus Produced)

| Receptor | VEGF Source | EC50s (g/mL) | | | EC50s (nM) | | |
|---|---|---|---|---|---|---|---|
| | | AVASTIN ™ | DMS1529 Lead | DMS1576 NTY | AVASTIN ™ | DMS1529 Lead | DMS1576 NTY |
| VEGFR1 | R&D | 1.12E−07 | 5.09E−09 | 7.01E−09 | 0.747 | 0.068 | 0.093 |
| VEGFR1 | GSK | 3.07E−07 | 4.97E−08 | 5.91E−08 | 2.048 | 0.663 | 0.789 |
| VEGFR2 | R&D | 1.06E−07 | 4.65E−09 | 5.70E−09 | 0.706 | 0.062 | 0.076 |
| VEGFR2 | GSK | 2.35E−07 | 3.64E−08 | 4.38E−08 | 1.569 | 0.486 | 0.583 |

(B) Modified RBA (without Pre-Incubation with Anti-VEGF Agent)

VEGF Sourced from R&D Systems (Baculovirus Produced).

| | | EC50 (nM) |
|---|---|---|
| VEGF R1 | AVASTIN ™ | 3.173 |
| | DMS1576 | 0.389 |
| VEGF R2 | AVASTIN ™ | 5.607 |
| | DMS1576 | 0.263 |

Example 8

Human Umbilical Cord Endothelial Cell (HUVEC) Proliferation Assay

DMS1529 and DMS1576 were assayed for their ability to suppress proliferation of human umbilical vein endothelial cells compared to that of Bevacizumab (AVASTIN™). The assay measures the extent of endothelial cell proliferation induced by a defined concentration of $VEGF_{165}$ and the ability of VEGF antagonists to block this effect. HUVECs were seeded at 5000 cells per well in 96-well gelatine-coated plates, leaving outer wells free of cells, and incubated for several hours to permit adherence. Test molecules were assayed at equimolar concentrations (max $3.33 \times 10^{-08}$ M) with a 2-fold serial dilution, each in triplicate. The $VEGF_{165}$ was prepared in basal medium to achieve 75 ng/ml final concentration. Medium was removed manually from the cell monolayers and 50 µl basal media was added to prevent the cells from drying out. 25 µl $VEGF_{165}$-containing medium and 25 μl basal medium or test antibody-containing medium was added as appropriate. Cells were incubated for 72 hrs, after which time the total number of cells was determined using Cell Titre Glo. Treatment of HUVECs with $VEGF_{165}$ resulted in the expected increase in the total number of cells after 72 hrs, when compared with $VEGF_{165}$-untreated cells (data not shown). This VEGF-mediated increase is interpreted as representing the cumulative effects of VEGF on both HUVEC proliferation and prevention of HUVEC cell death. The test compounds were independently assessed on individual plates against the comparator molecule, Bevacizumab (AVASTIN™).

DMS1529 was evaluated in a two separate assays. The data suggest that DMS1529 is only able to inhibit HUVEC proliferation by ~50%, cf ~100% for Bevacizumab (AVASTIN™) and the best fit curve suggests that DMS1529 has a higher IC50 (i.e. is less potent) than Bevacizumab (AVASTIN™) in this assay. DMS1576 has been evaluated on several occasions in the HUVEC assay. In one sample data set, the data suggest that similar to DMS1529, DMS1576 is only able to inhibit HUVEC proliferation by ~50%, cf ~100% for Bevacizumab (AVASTIN™); and the best fit curve suggests that DMS1576 has a higher IC50 (i.e. is less potent) than Bevacizumab (AVASTIN™) in this assay. However, two other data sets suggest a smaller shortfall in % maximum inhibition and IC50 of DMS1576 cf Bevacizumab (AVASTIN™), (data not shown).

Example 9

Performance in VEGF Induced Blood-Retinal Breakdown: Rabbit Retinal Leakage Model DMS1529 and DMS1576 were tested in a human $VEGF_{165}$ (R&D Systems), induced blood-retinal breakdown, (BRB), model in the rabbit eye and compared against Bevacizumab (AVASTIN™), Ranibizumab (LUCENTIS™), and KENACORT™ (Tramcinalone). All sources of Bevacizumab, Ranibizumab and KENACORT™ were obtained from clinical sources as described previously, Phillip Chapper & Co. Ltd, UK. The model has been described in some detail in the literature and is also known as the 'Edelman model' (Edelman J L, Lutz D, Castro M R, Corticosteroids inhibit VEGF-induced vascular leakage in a rabbit model of blood-retinal and blood-aqueous barrier breakdown, Exp Eye Res. 2005 February; 80(2):249-58).

The aim of this study was to evaluate the potency of DMS1529 and DMS1576, at two doses: High, (H), and Low, (L), in reducing the retinal vascular leakage in a recombinant humanVEGF165-induced blood retinal barrier breakdown model in rabbits. The high (H) and low (L) doses were based upon a molar equivalent dosing to Ranibizumab (LUCENTIS™). The low dose, (L), was one third of the high dose. Bevacizumab (AVASTIN™) was also dosed at a scaled down dose from the dose used in the clinic for ocular indications. The dosing and injection schedule is shown in Table 4A.

In brief, all molecules were buffer exchanged using PD-10 Desalting Columns (GE Healthcare) into 10 mM Histidine HCl, 10% α-αtrehalose dehydrate, 0.01% PolySorbate 80, pH 5.5, and concentrated to the desired concentration using VIVASPIN™ 20, molecular weight cut off 5000 Da, spin concentrations (Sartorius Stedim Biotech), both were used according to manufacturer's instructions. Samples were frozen at −80° C., and shipped on dry ice, after testing to confirm stability, functional activity and uniformity after this process as described in the aforementioned examples (data not shown).

Ninety-eight (98) GD79B pigmented rabbits were randomly divided into nine (9) groups of ten (10) animals and one (1) group of eight (8) animals (used for KENACORT™ control). Each group was subdivided into 2 groups corresponding to 2 experimental sets. Test items, reference or control items were administered by intravitreal injection (IVT, 50 μL) into the right eyes on Day-7. Left eyes remained untreated and served as a negative control. On Day 0, right eyes were induced for blood retinal barrier (BRB) breakdown with a single intravitreal injection of 500 ng $rhVEGF_{165}$ (vascular permeability inducer). Sodium fluorescein was intravenously injected to all groups 47 h after the VEGF challenge (Day 2). Within 10 min after the injection of the tracer a retinal angiography was performed on right eye and pictures were taken. Ocular fluorescein contents in the vitreoretinal compartment were measured 1 h later using non-invasive scanning ocular fluorophotometry. A right eye/left eye fluorescein content (AUC) Rt ratio was determined for retinal permeability evaluation. At the end of the evaluation period (Day 2), animals were euthanized and right eyes of all animals were enucleated. Snap-frozen eyeballs and aqueous humor samples were stored at −80° C. until shipment to the sponsor, GSK. Fluorescein angiograms were collected for qualitative assessment. The compounds remained masked upon GSK's request. The administration schedule for this is summarised in Table 4A.

Intravitreally injected VEGF induced a breakdown of the BRB, which was blocked by treatment with compounds masked labelled E: Bevacizumab (AVASTIN™), H: Ranibizumab (LUCENTIS™, high dose) and I: Ranibizumab (LUCENTIS™, low dose), 9 days post injection, with an efficacy similar to that of the marketed reference (KENACORT™). Low values of Rt ratio of vitreoretinal fluorescein contents between right-induced and left eyes were observed (Rt=1.39±0.77 (n=9) for compound E, Rt=1.05±0.52 (n=10) for compound H and Rt=1.81±1.76 (n=10) for compound I. KENACORT™-treated group showed a mean Rt ratio close to that of non-induced animals (Rt=1.15±0.61).

In the masked study, an important retinal vascular leakage was noted in right induced eyes after treatment with compounds A: DMS1576 (high dose), B: DMS1576 (high dose), C: Vehicle, negative control group D: DMS1576 (low dose), F: DMS1529 (low dose) and G: DMS1529 (high dose). Without unmasking of the compounds and comparison to vehicle control compounds A, B, C, D, F and G were clearly less effective than compounds E, H and I.

Unmasked data and statistical analysis demonstrating the inhibition of VEGF induced rabbit retinal leakage is shown in Table 4B. For this analysis the masked groups corresponding to the same molecule and dose were pooled. For the data in Table 4B: P values are shown with and without multiple comparison adjustment, labelled: 'Dunnett' and 'unadjusted' p value respectively. Confidence intervals correspond to unadjusted p value (CI includes ratio of 1 at p>0.05). From the data analysis in Table 4B: DMS1529 (46%) and DMS1576 (41%) at high dose only partially reduced the degree of VEGF induced retinal leakage and at low doses the reduction was even less: DMS1529 (19%) and DMS1576 (25%). Under the same conditions, compounds E: Bevacizumab (AVASTIN™, 75%), H: Ranibizumab (LUCENTIS™, high dose, 82%) and I: Ranibizumab (LUCENTIS™, low dose, 78%), suppressed the VEGF-induced retinal vascular leakage, with an effect similar to the marketed corticoid reference (KENACORT™ retard, 85%).

TABLE 4A

Dosing and injection schedule for inhibition of VEGF induced rabbit retinal leakage by DMS1529, DMS1576 compared to Bevacizumab (AVASTIN ™), Ranibizumab (LUCENTIS ™) and KENACORT ™ (Triamcinalone).

| Group No. | Treatment/compound dosed (right eye) | Dose | Treatment Protocol | Numbers of animals Set 1 | Set 2 | Induction | Measurements |
|---|---|---|---|---|---|---|---|
| 1 | Vehicle | — | 50-µL | 5 | 5 | Day 0, | On Day 2: |
| 2 | LUCENTIS ™ high dose | H | IVT | 5 | 5 | 500 ng/ | * Fluorescein |
| 3 | LUCENTIS ™ low dose | L | Day −7 | 5 | 5 | 50 µL | leakage quantification |
| 4 | AVASTIN ™ | H | | 5 | 5 | rhVEGF, | in vitreous/retina |
| 5 | DMS1529 high dose | H | | 5 | 5 | (R&D Systems | segment (Fluorotron ® |
| 6 | DMS1529 low dose | L | | 5 | 5 | (delivered by | Master). |
| 7 | DMS1576 high dose | H | | 5 | 5 | intravitreal | * Retinal angiography |
| 8 | DMS1576 low dose | H | | 5 | 5 | injection, | assessment using |
| 9 | DMS1576 high dose | H | | 5 | 5 | IVT) | Heidelberg's Retinal |
| 10 | KENACORT ™ Retard | 2 000 µg/eye | | 4 | 4 | | Angiograph * Eyeballs sampling (except for KENACORT ™ group) |

TABLE 4B

Inhibition of VEGF induced rabbit retinal leakage by DMS1529, DMS1576 compared to Bevacizumab (AVASTIN ™), Ranibizumab, (LUCENTIS ™) and KENACORT ™ (Triamcinalone)

| % reduction vs vehicle | treatment | Ratio vs Vehicle | Lower 95% CI | Upper 95% CI | Unadjusted p value | Dunnett p value |
|---|---|---|---|---|---|---|
| 46% | DMS1529H | 0.54021 | 0.29596 | 0.98606 | 0.0450 | 0.2234 |
| 19% | DMS1529L | 0.80759 | 0.44463 | 1.46685 | 0.4786 | 0.9788 |
| 41% | DMS1576H | 0.58638 | 0.34873 | 0.98597 | 0.0442 | 0.2201 |
| 25% | DMS1576L | 0.75355 | 0.41376 | 1.37237 | 0.3508 | 0.9103 |
| 75% | AVASTIN ™ | 0.25446 | 0.13782 | 0.46984 | <.0001 | 0.0002 |
| 85% | KENACORT ™ | 0.14853 | 0.07769 | 0.28395 | <.0001 | <.0001 |
| 82% | LUCENTIS ™ H | 0.18258 | 0.10048 | 0.33175 | <.0001 | <.0001 |
| 78% | LUCENTIS ™ L | 0.21876 | 0.12005 | 0.39865 | <.0001 | <.0001 |

Example 10

Cloning of Anti-VEGF Vk dAb-Fc and Fc-dAb Molecules

The DAB™ sequences (SEQ ID NO:97-101, 105-109) were cloned onto the N- or C-terminus of a generic Fc of the human IgG1 isotype in a mammalian expression vector. The DAB™s were linked to the Fc using a linker sequence: the N-terminal linker was either AAAS (SEQ ID NO:57 & 76), or TVAAPS (SEQ ID NO:59 & 78) and the C-terminal linker was either ((GS(TVAAPSGS)×3) (SEQ ID NO:66 & 85), or Albumin Domain 3 (SEQ ID NO:71 & 90).

Example 11

Expression of Anti-VEGF Vk dAb-Fc and Fc-dAb Molecules

Expression plasmids encoding the relevant Vk anti-VEGF dAb-Fc and Fc-dAb molecules (listed in SEQ ID NO:3-9, 16-24, 31-37 & 44-52, Table 19) were transiently transfected into HEK293 6E cells and expressed at 500 ml scale to produce the antibody fragment molecules. 500 ug of plasmid DNA was added to 18 ml of OPTIMEM™(Invitrogen) and separately 666 ul of 293FECTIN™ was added to 18 ml OPTIMEM™. Both tubes were incubated at room temperature for 5 minutes. The DNA/OPTIMEM™ solution was added slowly to the 293FECTIN™/OPTIMEM™ tube with gentle swirling. The DNA/293FECTIN™ transfection complex was then allowed to form for 25 minutes at room temperature. A HEK293E suspension cell culture was diluted to give $0.5 \times 10^6$ cells per ml and the above transfection complex were added slowly to 500 ml of the diluted cell culture, with gentle swirling of the culture flask. The flask was then returned to the 37° C., 5% $CO_2$ incubator, with shaking at 135 rpm. 24 hrs post-transfection 12.5 ml of 20% w/v casein-tryptone was added to the cell culture and incubation was continued as above. 6 days post-transfection, the culture was centrifuged at 5,500×g for 20 minutes to pellet the cells; the supernatant was filtered (0.22 um) and analysed for secreted protein expression. Expression levels of 50-100 mg/L supernatant were routinely achieved.

Example 12

Purification of Vk Anti-VEGF dAb-Fc and Fc-dAb Molecules

The Vk anti-VEGF dAb-Fc and Fc-dAb molecules were affinity purified from the supernatants (see Example 11). 20 ml of suspended affinity resin in sodium phosphate buffer (50:50 slurry) was added to 500 ml of filtered supernatant; the supernatant/affinity resin mix was rolled gently at +4° C. overnight, for ~3 h at room temperature, to allow binding to take place. After which time, the resin was allowed to settle and the supernatant carefully poured off. The resin was re-suspended in remaining supernatant and poured into an empty drip column. The supernatant was allowed to pass out of the column, and the resin was then washed with 3×10 column volume washes of PBS followed by 4× column washes of Tris buffer. Elution was carried out using 4× column volumes of low pH buffer and the eluate collected into a tube containing 1× column volume of 1M Tris pH 8.0 to neutralize the eluted protein.

Example 13

Molecular Analysis by SDS-PAGE and Size-Exclusion Chromatography (SEC) of Vk Anti-VEGF dAb-Fc and Fc-dAb Molecules The molecular integrity, homogeneity and % purity of the anti-VEGF dAb-Fc and Fc-dAb molecules which had been purified as described in Example 12 were analysed by SDS-PAGE, following Example 3. The gels showed band sizes consistent with the predicted molecular mass of the intact mature protein (from ~76 kDa to ~85 kDa for dAb-Fc and Fc-dAb molecules respectively), allowing for the presence of the predicted glycan chains per monomer chain. The proteins were confirmed to be >95% pure target protein by SDS-PAGE and SEC prior to further analysis in biology assays. If the dAb-Fc or Fc-dAb molecule was <95% pure a further SEC purification was carried out (see Example 14).

Example 14

Purification by Size-Exclusion Chromatography (SEC) of Vk Anti-VEGF dAb-Fc and Fc-dAb Molecules If necessary, preparative size-exclusion chromatography (SEC) was carried out for the Vk dAb-Fc and Fc-dAb molecules using a HiLoad 16/600 Superdex 200 column (GE Healthcare). The mobile phase used was phosphate buffered saline at a flow rate of 0.5 ml/min and 0.5-2 ml fractions were collected. The UV absorbance of the column effluent was monitored at 214 & 280 nm. The fractions collected for the peak corresponding to the elution of the dAb-Fc or Fc-dAb molecule were pooled. The molecular integrity, homogeneity and % purity was again analysed by SDS-PAGE and analytical SEC as described in Example 13. The proteins were confirmed to be >95% pure target protein by SDS-PAGE and SEC prior to further analysis in biology assays.

Example 15

VEGF Binding ELISA of Vk Anti-VEGF dAb-Fc and Fc-dAb Molecules

The ability of the Vk anti-VEGF dAb-Fc and Fc-dAb molecules to bind specifically to $VEGF_{165}$ was determined by ELISA. This was performed in a similar manner to Example 4. All of the anti-VEGF compounds tested were found to bind specifically to $VEGF_{165}$ (data not shown).

Example 16

Binding of Anti-VEGF Vk dAb-Fc and Fc-dAb Molecules to VEGF on BIACORE™

The binding affinity of the anti-VEGF Vk dAb-Fc and Fc-dAb molecules for $VEGF_{165}$ was determined by Surface Plasmon resonance (SPR) using a BIACORE™ T100 in a similar manner to Example 6, but with minor modifications. Protein A was immobilised on a C1 chip by primary amine coupling and this surface was then used to capture the anti-VEGF constructs. Human recombinant $VEGF_{165}$ (sourced 'in house' from transient transfection of HEK293 cells) was used as the analyte at 64 nM, 16 nM, 4 nM, 2 nM, 1 nM, 0.5 nM and 0.25 nM. All binding curves were double referenced with a buffer injection (i.e. 0 nM) and the data was fitted to 1:1 model inherent to the T100. Regeneration was carried out using 50 mM NaOH. The run was carried out at 37° C., using HBS-EP as the running buffer.

The Vk dAb-Fc and Fc-dAb molecules were compared to DMS1576 and Bevacizumab (AVASTIN™). The data shows that the Vk Fc-dAb molecules (DMS30000, DMS30001, DMS30002, DMS30003 and DMS30004) are all improved compared to DMS1576 and the Vk dAb-Fc in terms of binding to VEGF, as determined by BIACORE™, (see Table 5).

TABLE 5

Binding of anti-VEGF dAb-Fc and Fc-dAb molecules and Bevacizumab (AVASTIN ™) to $VEGF_{165}$

| Sample | Temp (° C.) | ka | kd | KD (nM) |
|---|---|---|---|---|
| Bevacizumab (AVASTIN ™) | 37 | Unable to fit data Kinetic constant kd is outside the limits that can be measured by the instrument | | |
| DMS1576 | 37 | Poor fit to 1:1 model | | |
| DMS30005 | 37 | Poor fit to 1:1 model | | |
| DMS30006 | 37 | Poor fit to 1:1 model | | |
| DMS30000 | 37 | 1.44E+07 | 3.34E−05 | 0.002 |
| DMS30001 | 37 | 1.62E+07 | 3.63E−05 | 0.002 |
| DMS30002 | 37 | 1.25E+07 | 3.63E−05 | 0.003 |
| DMS30003 | 37 | 1.27E+07 | 3.84E−05 | 0.003 |
| DMS30004 | 37 | 1.28E+07 | 4.54E−05 | 0.004 |

Example 17

VEGF R1 & R2 Receptor Binding Assay of Anti-VEGF Vk dAb-Fc and Fc-dAb Molecules

The potencies of the anti-VEGF Vk dAb-Fc and Fc-dAb molecules were analysed in the VEGF receptor, (R1 and R2), binding assay using the modified method, i.e. with no pre-incubation, described in Example 7 and were compared to the Vh dAb-Fc, DMS1576 and Bevacizumab (AVASTIN™). The Vk Fc-dAb molecules (DMS30000, DMS30003 and DMS30004) were seen to be more potent (i.e. lower EC50 values, see Tables 6A & 6B), than DMS1576 and Bevacizumab (AVASTIN™) against both VEGFR1 and VEGFR2; whereas the Vk dAb-Fc molecule (DMS30005) was less potent than DMS1576 and similar to Bevacizumab (AVASTIN™) against VEGFR1 and more potent than Bevacizumab (AVASTIN™) against VEGFR2. Against VEGFR1, the data indicate that the inhibition achieved by the Vk Fc-dAb molecules (DMS30000, DMS30003 and DMS30004) are slightly reduced at 87-89% cf the Vh dAb-Fc molecule (DMS1576) and Bevacizumab (AVASTIN™), both 290%. The Vk dAb-Fc molecule (DMS30005) is further reduced, 82%. Against VEGFR2, the data indicate that the inhibition achieved by the Vk Fc-dAb molecules (DMS30000, DMS30003 and DMS30004) match that of the Vh dAb-Fc molecule (DMS1576) and Bevacizumab (AVASTIN™), all 90%. The Vk dAb-Fc molecule (DMS30005) is slightly reduced, 86%.

TABLE 6A

EC$_{50}$ values of anti-VEGF compounds compared to Bevacizumab (AVASTIN ™) in VEGFR1 Receptor Binding Assay. Curve fitting and EC$_{50}$ calculations were performed using GRAPHPAD PRISM ™

| VEGFR1 | Max. % Inhibition | EC50 (g/mL) | EC50 (pM) |
|---|---|---|---|
| AVASTIN ™ | 91.9 | 3.24E−07 | 2,158 |
| DMS1576 | 93.8 | 1.51E−08 | 201 |
| DMS30000 | 86.7 | 3.51E−09 | 47 |
| DMS30003 | 89.1 | 4.42E−09 | 59 |
| DMS30004 | 87.1 | 3.80E−09 | 51 |
| DMS30005 | 82.2 | 2.07E−07 | 2,763 |

TABLE 6B

EC$_{50}$ values of anti-VEGF compounds compared to Bevacizumab (AVASTIN ™) in VEGFR2 Receptor Binding Assay. Curve fitting and EC$_{50}$ calculations were performed using GRAPHPAD PRISM ™.

| VEGFR2 | Max. % Inhibition | EC50 (g/mL) | EC50 (pM) |
|---|---|---|---|
| AVASTIN ™ | 94.6 | 6.29E−07 | 4,192 |
| DMS1576 | 92.9 | 1.80E−08 | 240 |
| DMS30000 | 94.5 | 2.98E−09 | 40 |
| DMS30003 | 97.9 | 2.96E−09 | 40 |
| DMS30004 | 91.0 | 3.12E−09 | 42 |
| DMS30005 | 85.8 | 9.55E−08 | 1,273 |

Example 18

Human Umbilical Cord Endothelial Cell (HUVEC) Proliferation Assay: Inhibition with Anti-VEGF dAb-F and Fc-dAb Molecules The ability of the Vk dAb-Fc and Fc-dAb molecules to suppress the VEGF driven proliferation of human umbilical vein endothelial cells were compared to that of inhibition in this assay from the Vh dAb-Fc (DMS1576) and Bevacizumab (AVASTIN™) as described in Example 8. The Vk dAb-Fc molecules (DMS30005 and DMS30006) were assayed in a single assay, (data not shown). The data indicated that these molecules were less potent (lower IC50) and less able to fully inhibit proliferation, ~70-80%, DMS30005, cf. ~100% for Bevacizumab (AVASTIN™). As previously seen in Example 8, the data suggest that the Vh dAb-Fc molecule (DMS1576) has a higher IC50 (i.e. is less potent) than Bevacizumab (AVASTIN™). The Vk Fc-dAb molecules (DMS30000, DMS30003 & DMS30004) were assayed on several occasions. The data sets indicate that the inhibition achieved by treatment with the Vk Fc-dAb molecules gave levels of VEGF-mediated inhibition that matched that achieved with Bevacizumab (AVASTIN™), i.e ~100%. In fact, all Vk Fc-dAb molecules produced best fit curves that overlayed, or were slightly shifted to the left of the similar Bevacizumab, (AVASTIN™) curve so were potentially more potent molecules in this assay, (data not shown).

Example 19

Demonstration of Differential and Non-Interference of Binding of Anti-VEGF Vh dAb-Fc and Vk Fc-dAb Molecules to Human VEGF The ability of the Vh based dAbFc molecules to bind to VEGF already pre-saturated with Vk based Fc-dAb molecules and, conversely, the ability of Vk based Fc-dAb molecules to bind to VEGF already pre-saturated with Vh based dAbFc molecules was demonstrated in a modified MSD™ assay using DMS30000 as the Vk based Fc-dAb molecule and DMS1576 as the Vh based dAb-Fc molecule.

19.A—Binding of Vh dAb-Fc DMS1576 to VEGF after Pre-Saturation with Vk Fc-dAb DMS30000

A MSD™ high bind 96 well plate (MSD™ L11XB-3) was coated with 3 µg/mL rhVEGF$_{165}$ (sourced 'in house' from transient transfection of HEK293 cells) in PBS (25 µl/well), covered with a plate sealer and incubated overnight at 4° C. The next day the MSD™ plate was washed 3×300 µl/well with Tris wash buffer and blotted over a pad of tissue to remove excess wash buffer from the wells. The MSD™ plate was then blocked with 3% BSA in PBS (250 µl/well) and incubated shaking (750 RPM) at room temperature for 1 hour. After washing the MSD™ plate, saturating DMS30000 concentrations (≥3 µC/ml) were added (25 µl/well) and incubated shaking (750 RPM) at room temperature for 1 hour. The MSD™ plate was washed again before the addition of DMS1576 (25 µl/well, 0-100 ng/ml) and incubated shaking (750 RPM) at room temperature for 1 hour. The DMS30000 and DMS1576 were prepared in 0.1% BSA in PBS. The MSD™ plate was washed again before the addition of a detection reagent specific for the Vh DAB™ contained in DMS1576 (25 µL/well, in-house SULFO-TAG™ labelled anti-Vh mAb) at 1 µg/ml in 1% BSA in PBS and incubated with shaking (750 RPM) at room temperature for 1 hour. Prior to measurement of the electrochemiluminescence in a MSD™ SECTOR IMAGER 6000™ MSD™ plate was washed and 150 µL/well of 2× Read Buffer T (MSD™ R92TC-1) was added. The data in FIG. 2A shows that it is possible for the Vh based dAb-Fc molecule DMS1576 to bind VEGF$_{165}$ which has been pre-saturated with Vk based Fc-dAb molecule DMS30000.

19.B—Binding of Vk Fc-dAb DMS30000 to VEGF after Pre-Saturation with Vh dAb-Fc DMS1576

A MSD™ high bind 96 well plate (MSD™ L11XB-3) was coated with 3 µg/ml VEGF (sourced 'in house' from transient transfection of HEK293 cells) in PBS (25 µl/well), covered with a plate sealer and incubated overnight at 4° C. The next day the MSD™ plate was washed 3×300 µl/well with Tris wash buffer and blotted over a pad of tissue to remove excess wash buffer from the wells. The MSD™ plate was then blocked with 3% BSA in PBS (250 µl/well) and incubated shaking (750 RPM) at room temperature for 1 hour. After washing the MSD™ plate, saturating DMS1576 concentrations (≥3 µg/mL) were added (25 µL/well) and incubated shaking (750 RPM) at room temperature for 1 hour. The MSD™ plate was washed again before the addition of DMS30000 (25 µL/well, 0-100 ng/mL) and incubated shaking (750 RPM) at room temperature for 1 hour. The DMS30000 and DMS1576 were prepared in 0.1% BSA in PBS. The MSD™ plate was washed again before the addition of a detection reagent specific for the Vk DAB™ contained in DMS30000 (25 µL/well, in-house SULFO-TAG™ labelled anti-Vk mAb) at 1 µg/ml in 1% BSA in PBS and incubated with shaking (750 RPM) at room temperature for 1 hour. Prior to measurement of the electrochemiluminescence in a MSD™ Sector Imager 6000, the MSD™ plate was washed and 15011/well of 2× Read Buffer T (MSD™ R92TC-1) was added.

The data in FIG. 2B demonstrates that it is possible for the Vk based Fc-dAb molecule DMS30000 to bind VEGF$_{165}$ which has been pre-saturated with Vh based dAb-Fc molecule DMS1576.

Both sets of data in Example 19 show that it is possible for both the Vk Fc-dAb (DMS30000) and Vh dAb-Fc, (DMS1576) to bind VEGF$_{165}$ in the presence of the other molecule. The experiments described in Example 19 suggest that the two lineages of DAB™, Vk and Vh derived, may bind to different epitopes on the VEGF homodimer.

Example 20

Cloning of Anti-VEGF dAb-Fc-dAb Molecules

The Vh-Vk dAb-Fc-dAbs (SEQ ID NO: 10-11, 25, 38-39 & 53) were engineered by cloning the Vk DAB™ sequences (DT02-K-044-085 (SEQ ID NO: 97 & 105) or DT02-K-044-251 (SEQ ID NO: 100 & 108) onto the C-terminus of the Vh dAb-Fc (DMS1576, SEQ ID NO:2 & 30) in a mammalian expression vector. The C-terminal DAB™s were linked to the C-terminus of Fc using a either the ((GS(TVAAPSGS)×3) (SEQ ID NO:66 & 85), or Albumin Domain 3 (SEQ ID NO:71 & 90) linker sequence. The Vk-Vk dAb-Fc-dAbs (SEQ ID NO:12-15, 26-28, 40-43 & 54-56) were engineered by cloning the Vk DAB™ sequences (DT02-K-044-085 (SEQ ID NO: 97 & 105) or DT02-K-044-251 (SEQ ID NO:100 & 108) onto the C-terminus of the corresponding Vk dAb-Fc (i.e. either DMS30000 (SEQ ID NO:3 & 31) or DMS30003 (SEQ ID NO:6 & 34) or DMS30013 (SEQ ID NO:16 & 44)) in a mammalian expression vector. The N-terminal DAB™s were linked to the N-terminus of Fc using either the AS (SEQ ID NO:58 & 77), or Hinge IgG1 (SEQ ID NO:60 & 79). Site directed mutagenesis was carried out within the Fc region with the following changes for example His 2 Ala or Thr 3 Pro to produce SEQ ID NO: 27 and 28 respectively.

Example 21

Expression of Anti-VEGF dAb-Fc-dAb Molecules

Expression plasmids encoding the relevant anti-VEGF dAb-Fc-dAb molecules (listed in SEQ ID NO:10-15, 25-28, 38-43 & 53-56) were transiently transfected into HEK293 6E cells and expressed at 500 ml scale to produce the antibody fragment molecules using the method described in Example 11. Expression levels of 50-100 mg/L supernatant were routinely achieved.

Example 22

Purification of Anti-VEGF dAb-Fc-dAb Molecules

The dAb-Fc-dAb molecules were affinity purified from the supernatants (Example 21). 2 ml of suspended affinity resin in phosphate buffered saline (50:50 slurry) was added to 500 ml of filtered supernatant; the supernatant/affinity resin mix was rolled gently at +4° C. overnight to allow binding to take place. After which time, the resin was allowed to settle and the supernatant carefully poured off. The resin was re-suspended in remaining supernatant and poured into an empty drip column and the supernatant was allowed to pass out of the column. The bound product was washed using a combination of pH neutral aqueous buffers to remove non-specifically bound impurities followed by a low pH elution. Over 90% of bound product was recovered and the pH of the elution pool then adjusted to pH 3.5 for 30 minutes to achieve virus neutralisation after which time the pH was adjusted to pH4.5.

Example 23

Molecular Analysis by Size-Exclusion Chromatography (SEC) of Anti-VEGF dAb-Fc-dAb Molecules The molecular integrity, homogeneity and % purity of the anti-VEGF dAb-Fc-dAb molecules which had been purified as described in Example 22 were analysed by SDS-PAGE and analytical size-exclusion chromatography (SEC) as described in Example 3. The proteins were confirmed to be >95% pure target protein by SDS-PAGE and SEC prior to further analysis in biology assays.

Example 24

VEGF Binding ELISA of Anti-VEGF dAb-Fc-dAb Molecules

The ability of the anti-VEGF dAb-Fc-dAb molecules to bind specifically to VEGF$_{165}$ was determined by ELISA as described in Examples 4 & 15. All of the anti-VEGF dAb-Fc-dAbs tested were found to bind specifically to VEGF165 (data not shown).

Example 25

Binding of Anti-VEGF dAb-Fc-dAb Molecules to VEGF on BIACORE™

The binding affinity of the anti-VEGF dAb-Fc-dAb molecules for VEGF$_{165}$ was determined by Surface Plasmon resonance (SPR) using a BIACORE™ T100 in a similar manner to Example 6, but with minor modifications. Protein A was immobilised on a C1 chip by primary amine coupling and this surface was then used to capture the anti-VEGF constructs. Human recombinant VEGF$_{165}$ (sourced 'in house' from transient transfection of HEK293 cells) was used as the analyte at 75 nM, 15 nM, 3 nM and 0.6 nM. All binding curves were double referenced with a buffer injection (i.e. 0 nM) and the data was fitted to 1:1 model inherent to the T100. Regeneration was carried out using 50 mM NaOH. The run was carried out at 37° C., using HBS-EP as the running buffer.

The dAb-Fc-dAb molecules were compared to their corresponding Vk Fc-dAb and Vh dAb-Fc molecules. The data for this assay format may suggest that the dAb-Fc-dAb molecules do not appear to be better than the corresponding Vk Fc-dAb. The Vk Fc-dAbs appear to have superior off-rates cf corresponding dAb-Fc-dAbs. However, the traces, (data not shown), may not tell the full story since the dAb-Fc-dAb "affinities" are a mix of two different binding events to VEGF, i.e. the binding of the N-terminal DAB™s and the C-terminal Vk DAB™s. It is to be expected that the Vk DAB™ in the dAb-Fc-dAb, i.e. in the same orientation as in the C-terminal Vk Fc-dAb, will have the same affinity, and this data confirms that previously described in Example 16. Positioning of either the Vh or Vk DAB™ at the N-terminal of the Fc leads to a poorer affinity (see Example 16), therefore making the overall affinity of the combined molecule appear worse. The apparent affinities (see Table 7) show the following potency on the BIACORE™ for these molecules: the Vh-Vk dAb-Fc-dAbs (DMS30007 and DMS30008) have the poorest affinities, the Vk-Vk dAb-Fc-dAbs (DMS30009, DMS30010, DMS30011 and DMS30012) have the best of the dAb-Fc-dAb affinities and appear to be very similar to one another.

TABLE 7

Binding of anti-VEGF dAb-Fc-dAb molecules and corresponding dAb-Fc- and Fc-dAb molecules to VEGF$_{165}$

| Construct | Model | ka | kd | KD (pM) |
|---|---|---|---|---|
| DMS1576 | 1:1 Binding | 3.04E+06 | 4.24E−04 | 139.5 |
| DMS30000 | 1:1 Binding | 2.28E+07 | 1.60E−05 | 0.7 |
| DMS30007 | 1:1 Binding | 2.82E+06 | 1.22E−04 | 43.3 |
| DMS30009 | 1:1 Binding | 2.96E+07 | 6.92E−05 | 2.3 |
| DMS30010 | 1:1 Binding | 2.64E+07 | 8.08E−05 | 3.1 |
| DMS30003 | 1:1 Binding | 1.81E+07 | 1.37E−05 | 0.8 |
| DMS30008 | 1:1 Binding | 2.56E+06 | 1.15E−04 | 44.9 |
| DMS30011 | 1:1 Binding | 1.77E+07 | 8.07E−05 | 4.6 |
| DMS30012 | 1:1 Binding | 1.61E+07 | 7.39E−05 | 4.6 |

Example 26

VEGF R1 & R2 Receptor Binding Assay of Anti-VEGF dAb-Fc-dAb Molecules

The potencies of the anti-VEGF Vh-Vk and Vk-Vk dAb-Fc-dAb molecules were analysed in the VEGF receptor, R1 and R2, binding assay. The potencies (EC50) against both VEGFR1 and VEGFR2 of the dAb-Fc-dAbs was seen to match that of the Vk Fc-dAb molecule (DMS30000) and seen to be more potent (i.e. lower EC50 values) than both the Vh dAb-Fc molecule (DMS1576) and Bevacizumab (AVASTIN™), see Table 8 A and B. Against VEGFR1, the data indicate that the inhibition achieved by both Vh-Vk dAb-Fc-dAbs (DMS30007 and DMS30008) and the Vk-Vk dAb-Fc-dAb (DMS30009) matched that achieved with the Vh dAb-Fc molecule (DMS1576), the Vk Fc-dAb molecule (DMS30000) and Bevacizumab (AVASTIN™) all ≥90%, (Table 8A). Against VEGFR2, the data indicate that the inhibition achieved by the Vh-Vk (DMS30022) dAb-Fc-dAb matched that achieved with the Vh dAb-Fc molecule (DMS1576), the Vk Fc-dAb molecules (DMS30000 and DMS30003) and Bevacizumab (AVASTIN™), all achieved ≥90%; whereas the inhibition achieved by Vh-Vk dAb-Fc-dAbs (DMS30007 and DMS30008) and the Vk-Vk dAb-Fc-dAb molecules (DMS30009, DMS30023 and DMS30025) was lower at 75-87%, (Table 88).

TABLE 8A

EC$_{50}$ values of anti-VEGF dAb-Fc-dAb molecules compared to Bevacizumab (AVASTIN ™) inVEGFR1 Receptor Binding Assay. Curve fitting and EC$_{50}$ calculations were performed using GRAPHPAD PRISM ™.

| VEGFR1 | Max. % Inhibition | EC50 (g/mL) | EC50 (pM) |
|---|---|---|---|
| AVASTIN ™ | 92.0 | 3.45E−07 | 2,297 |
| DMS1576 | 95.8 | 2.15E−08 | 287 |
| DMS30000 | 89.5 | 5.09E−09 | 68 |
| DMS30003 | 92.0 | 5.94E−09 | 79 |
| DMS30007 | 92.8 | 5.90E−09 | 59 |
| DMS30008 | 92.0 | 6.00E−09 | 60 |
| DMS30009 | 92.6 | 4.17E−09 | 42 |

TABLE 8B

EC$_{50}$ values of anti-VEGF dAb-Fc-dAb molecules compared to Bevacizumab, (AVASTIN ™), in VEGFR2 Receptor Binding Assay.

(i) Curve fitting and EC$_{50}$ calculations were performed using GRAPHPAD PRISM ™.

| VEGFR2 | Max. % Inhibition | EC50 (g/mL) | EC50 (pM) |
|---|---|---|---|
| AVASTIN ™ | 94.3 | 5.52E−07 | 3,679 |
| DMS1576 | 96.7 | 3.30E−08 | 439 |
| DMS30000 | 93.6 | 5.01E−09 | 67 |
| DMS30003 | 98.3 | 4.56E−09 | 61 |
| DMS30007 | 81.3 | 8.02E−09 | 80 |
| DMS30008 | 83.0 | 7.20E−09 | 72 |
| DMS30009 | 86.6 | 5.52E−09 | 55 |

(ii)

| VEGFR2 RBA | Max. % Inhibition | EC50 (g/mL) | EC50 (pM) |
|---|---|---|---|
| AVASTIN ™ | 93.6 | 4.67E−07 | 3113 |
| DMS1576 | 95.9 | 6.72E−08 | 896 |
| DMS30000 (Batch 1) | 89.8 | 4.22E−09 | 56 |
| DMS30000 (Batch 2) | 97.7 | 3.30E−09 | 44 |
| DMS30022 | 95.0 | 8.17E−09 | 82 |
| DMS30023 | 74.7 | 5.20E−09 | 52 |
| DMS30025 | 82.4 | 4.86E−09 | 49 |

Example 27

Human Umbilical Cord Endothelial Cell (HUVEC) Proliferation Assay of Anti-VEGF dAb-Fc-dAb Molecules The abilities of the Vh-Vk (DMS30022) and Vk-Vk (DMS30023 and DMS30025) dAb-Fc-dAb molecules to suppress proliferation of human umbilical vein endothelial cells were compared to the Vh dAb-Fc molecule (DMS1576), the Vk Fc-dAb molecule (DMS30000) and Bevacizumab (AVASTIN™) using the method described in Examples 8 & 18 with the following deviations (i) rather than leaving the outer wells free of cells, the whole 96 well plate was used and (ii) the data was analysed using GRAPHPAD PRISM™ using a Sigmodial curve fit, variable slope cf a non-linear regression (variable slope). The data suggest that, as previously seen in Examples 8 and 18, the Vh dAb-Fc molecule (DMS1576) has a higher EC50 (i.e. is less potent) than Bevacizumab (AVASTIN™); on average, it was seen that the Vk Fc-dAb molecule (DMS30000) was similar in terms of EC50 to Bevacizumab (AVASTIN™); whereas all the Vh-Vk and Vk-Vk dAb-Fc-dAb molecules (DMS300022, DMS300023, DMS300024 and DMS300025) were all seen to be improved over Bevacizumab (AVASTIN™) in terms of EC50.

Example 28

Performance of dAb-Fc-dAb and dAb-Fc and Fc-dAb Formats in VEGF Binding Assays Measured in Solution by Isothermal Calorimetry (ITC)

The solution equilibrium binding affinity ($K_D$), stoichiometry (N) and thermodynamics (ΔH, enthalpy and ΔS, entropy) of the anti-VEGF dAb-Fc-dAbs, dAb-Fcs and Fc-dAbs binding to VEGF$_{165}$ was determined by isothermal titration calorimetry (ITC) using a MICROCAL™ VP-ITC and compared to that of the monoclonal antibody Bevacizumab (AVASTIN™). The main aim of the experiment was to compare the relative stoichiometry of binding to VEGF of the different molecular formats. VEGF165 was titrated into antibody solutions at 25° C. until there was greater than 3 fold concentration excess of $VEGF_{165}$ and saturation was achieved. All titrations used the same batch of $VEGF_{165}$ to ensure consistency. The integrated binding isotherms were fitted within the ORIGIN™ software (MICROCAL™ version) using a standard 1:1 binding model as there were no signs of multiphasic behavior. The results are summarised in Table 10.

TABLE 10

Binding of anti-VEGF dAb-Fc-dAb molecules, dAb-Fcs and Fc-dAb molecules to $VEGF_{165}$

| Construct | N (VEGF165 (monomer/ antibody) | $K_A$ $M^{-1}$ | ΔH (cal/mol) | ΔS (cal/mol/ deg) |
|---|---|---|---|---|
| AVASTIN ™ | 1.5 | 4.96E+07 | −1.59E+04 | −18.1 |
| DMS30000 (Fc-dAb) | 1.2 | 8.00E+07 | −1.95E+04 | −29.3 |
| DMS30023 (dAb-Fc-dAb) | 2.1 | 3.78E+07 | −1.93E+04 | −29.9 |
| DMS30022 (dAb-Fc-dAb) | 1.9 | 1.08E+08 | −2.20E+04 | −37.0 |
| DMS30028 (dAb-Fc) | 1.3 | 1.45E+07 | −1.73E+04 | −25.4 |
| DMS51576 (dAb-Fc) | 0.95 | 1.18E+08 | −2.08E+04 | −32.9 |
| AVASTIN ™ | 1.5 | 5.36E+07 | −1.82E+04 | −25.6 |

All antibodies have enthalpically favourable and entropically unfavourable binding at 25° C. There is a clear distinction in the stoichiometry between the dAb-Fc, Fc-dAb and dAb-Fc-dAb DAB™ formats, with a larger capacity on for the dual DAB™ formats. The dAb-Fc-dAb formats also show a higher capacity than AVASTIN™ when $VEGF_{165}$ is present in excess. The affinities measured are in same rank order and consistent with those measured by other methods.

Example 29

Cloning of Anti-VEGF Vh dAb-Fc. Vk dAb-Fc and Vk Fc-dAb Molecules with Various Linker Modifications The DAB™ sequences (SEQ ID NO: 96-97, 104-105, see Table 19) were cloned onto the N- or C-terminus of a generic Fc of the human IgG1 isotype in a mammalian expression vector. The DAB™s were linked to the Fc using a variety of linker sequences (see Table 19, SEQ ID Nos 57-75 & 76-94): For the Vh dAb-Fc the DAB™ was DOM15-26-597; the N-terminal linkers were either AS (SEQ ID NO:58 & 77), or TVAAPS (SEQ ID NO:59 & 78), or Hinge IgG1 linker (SEQ ID NO:60 & 79), or Hinge IgG3 linker (SEQ ID NO:61 & 80) or Fibronectin ×3 linker (SEQ ID NO:62 & 81) or Fibronectin ×4 linker (SEQ ID NO:63 & 82); For the Vk dAb-Fc the DAB™ was DT02-K-044-085; the N-terminal linkers were either AS with a H2A IgG1Fc point mutation (SEQ ID NO:64 & 83), AS with a T3P IgG1Fc point mutation (SEQ ID NO:65 & 84), or TVAAPS (SEQ ID NO:59 & 78), or Hinge IgG1 linker (SEQ ID NO:60 & 79), or Hinge IgG3 linker (SEQ ID NO:61 & 80) or Fibronectin ×3 linker (SEQ ID NO:62 & 81) or Fibronectin ×4 linker (SEQ ID NO:63 & 82); and the Vk Fc-dAb was DT02-K-044-085; the C-terminal linkers were either (GS (TVAAPSGS)×3 (SEQ ID NO:66 & 85), or Fibronectin ×3 linker (SEQ ID NO:67 & 86) or Fibronectin ×4 linker (SEQ ID NO:68 & 87) or Albumin Domain 1 (SEQ ID NO:69 & 88), Albumin Domain 2 (SEQ ID NO:70 & 89), Truncated Albumin Domain 3 linker, (Alb Dom 3-TFHAD, SEQ ID NO:72 & 91) or Gly4Ser 3× Linker, (SEQ ID NO:73 & 92), Gly4Ser 4× Linker, (SEQ ID NO:74 & 93) or Helical Linker, (SEQ ID NO:75 & 94).

Example 30

Expression of Anti-VEGF Vh dAb-Fc. Vk dAb-Fc and Vk Fc-dAb Molecules with Various Linker Modifications Expression plasmids encoding the relevant Vh anti-VEGF dAb-Fc, Vk anti-VEGF dAb-Fc and Vk anti-VEGF Fc-dAb molecules (described in Example 29 SEQ ID NO: 132-134 and 155-176, Table 19) transiently transfected into HEK293 6E cells and expressed at 500 ml scale to produce the antibody fragment molecules, as described in Example 11.

Example 31

Purification of Anti-VEGF Vh dAb-Fc. Vk dAb-Fc and Vk Fc-dAb Molecules with Various Linker Modifications The Vh anti-VEGF dAb-Fc, Vk anti-VEGF dAb-Fc and Vk anti-VEGF Fc-dAb molecules described in Example 30 were affinity purified from the supernatants (see Example 12).

Example 32

Molecular Analysis by SDS-PAGE and Size-Exclusion Chromatography (SEC) of Anti-VEGF Vh dAb-Fc, Vk dAb-Fc and Fc-dAb Molecules with Various Linker Modifications The molecular integrity, homogeneity and % purity of the anti-VEGF Vh dAb-Fc, anti-VEGF Vk dAb-Fc and anti-VEGF Vk Fc-dAb molecules which had been purified as described in Example 31 were analysed by SDS-PAGE, as described in Example 3, The gels showed band sizes consistent with the predicted molecular mass of the intact mature protein (from ~76 kDa to ~85 kDa for dAb-Fc and Fc-dAb molecules), allowing for the presence of the predicted glycan chains per monomer chain. The proteins were confirmed to be >95% pure target protein by SDS-PAGE and SEC prior to further analysis in biology assays. If the dAb-Fc or Fc-dAb molecule was <95% pure a further SEC purification was carried out (see Example 14 & 33).

Example 33

Purification by Size-Exclusion Chromatography (SEC) of Anti-VEGF Vh dAb-Fc. Vk dAb-Fc and Vk Fc-dAb Molecules with Various Linker Modifications If necessary, preparative size-exclusion chromatography (SEC) was carried out for the Vh dAb-Fc, Vk dAb-Fc and Vk Fc-dAb molecules.

Example 34

Binding of Anti-VEGF Vh dAb-Fc, Vk dAb-Fc and Fc-dAb Molecules with Various Linker Modifications to VEGF on BIACORE™

The binding affinity of the anti-VEGF Vh dAb-Fc, Vk dAb-Fc and Fc-dAb molecules for $VEGF_{165}$ was determined by Surface Plasmon resonance (SPR) using a BIACORE™ T100 in a similar manner to Example 16, but with minor modifications. Protein A was immobilised on a C1 chip by primary amine coupling and this surface was then used to capture the anti-VEGF constructs. Human recombinant $VEGF_{165}$ (sourced 'in house' from transient transfection of HEK293 cells) was used as the analyte over a varying range of dilution series detailed below. All binding curves were double referenced with a buffer injection (i.e. 0 nM) and the data was fitted to 1:1 model inherent to the T100. Regeneration was carried out using 50 mM NaOH. The run was carried out at 37° C., using HBS-EP as the running buffer.

The Vk Fc-dAb molecules were compared to DMS30000 and Bevacizumab (AVASTIN™) over a concentration range of 16 nM, 4 nM, 2 nM, 1 nM, 0.5 nM and 0.25 nM. From the data it was concluded that the Vk Fc-dAb molecules with the DT02-K-085 DAB™ linked to the IgG1Fc by C-terminal linkers Albumin domain 2 and Fibronectin ×4 behaved similarly in th BIACORE™ to DMS30000, (Table 11A). Use of the albumin 2 linker was not preferred from biophysical studies, (data not shown), so the Fibronectin 4 (fib4) was the preferred C-terminal linker to replace the (GS(TVAAPSGS (SEQ ID NO: 217))×3 linker in DMS3000, the latter linker contributing many glycosylated isoforms making molecule development problematic, (data not shown). A further anti-VEGF VkFc-dAb data set was generated by similar BIACORE™ experiments, over a concentration range of 128 nM to 0.03125 nM in a 4 fold dilution series, and is shown in Table 11B. The data compares the fib4 linker (DMS30026) with helical linker (DMS30027) as the C-terminal to attach the DT02-K-085 DAB™ to the IgG1Fc. The fib4 linker is preferred.

TABLE 11A

Binding of anti-VEGF Vk dAb-Fc and Fc-dAb molecules to $VEGF_{165}$ and comparison to DMS1576, DMS30000, anti-VEGF dAP-Fc-dAbs and Bevacizumab (AVASTIN ™)

| Sample | Ka (M − 1 · s − 1) | Kd (s − 1) | KD (M) | fit |
|---|---|---|---|---|
| C085 Alb DOM1 | 4.15E+06 | 1.12E−04 | 2.70E−11 | ok |
| C085 Alb DOM2 | 7.52E+06 | Too tight | na | ok |
| C085 Alb DOM3 | 6.17E+06 | 8.12E−05 | 1.32E−11 | ok |
| C085 Fibrx4 | 7.72E+06 | At the limit of Measurement | na | ok |
| C085 G4Sx3 | 6.19E+06 | 1.80E−04 | 2.91E−11 | ok |
| C085 G4Sx4 | 6.11E+06 | 1.41E−04 | 2.31E−11 | ok |
| DMS1576 | 3.48E+06 | 3.05E−04 | 8.77E−11 | Not ideal/doesn't look like 1:1 interaction |
| DMS30000 | 8.96E+06 | Too tight | na | ok |
| DMS30013 | 8.74E+06 | Too tight | na | ok |
| DMS30014 | 8.68E+06 | At the limite of measurement | na | Ok |
| N085 Fibrx4 | 6.76E+06 | 4.83E−06 | 7.15E−12 | Not ideal/doesn't look like 1:1 interaction |
| N085TVAAPS | 8.07E+06 | Too tight | na | Not ideal/doesn't look like 1:1 interaction |
| C085 Alb DOM1 | 4.15E+06 | 1.12E−04 | 2.70E−11 | Ok |
| AVASTIN ™ | Run | Failed | na | bad |

TABLE 11B

Binding of anti-VEGF Vh dAb-Fc, Vk dAb-Fc and Vk Fc-dAb molecules to $VEGF_{165}$ and comparison to DMS1576 and Bevacizumab (AVASTIN ™)

| Sample | Ka (M − 1 · s − 1) | Kd (s − 1) | KD (M) | comment |
|---|---|---|---|---|
| AVASTIN ™ | 3.18E+05 | na | na | Off-rate value outside the range and thus shot reported |
| C085 helical | 1.00E+07 | 6.23E−05 | 6.21E−12 | Good fit to the 1:1 binding model |
| N085 extgl | 1.03E+07 | 6.60E−05 | 6.43E−12 | Biphasic curves |
| C085 Fibr4 | 8.12E+06 | 1.29E−05 | 1.59E−12 | Good fit to the 1:1 binding model Off-rate value approaching the limit of measurement: caution! |
| N597 Fibr3 | 1.88E+06 | 1.31E−05 | 6.96E−12 | Off-rate value approaching the limit of measurement: caution! |
| N085T2P | 9.40E+06 | 7.57E−05 | 8.06E−12 | Biphasic curves |
| DMS1576 | 1.60E+06 | 2.90E−04 | 1.30E−10 | Biphasic curves |

The Vk dAb-Fc molecules were compared to DMS1576 and Bevacizumab (AVASTIN™) over a concentration range of 16 nM, 4 nM, 2 nM, 1 nM, 0.5 nM and 0.25 nMm, where Vk dAbFc molecules with the DT02-K-085 DAB™ linked to the IgG1Fc by N-terminal linkers N085 Fibronectin 4 and 1×TVAAAPS (SEQ ID NO: 201) were compared. The data suggests that the 1×TVAPPS (SEQ ID NO: 201) is the preferred of the two linkers to attach the DT02-K-085 DAB™ to the N-terminus of the IgG1Fc. Further examples of Vk dAb-Fc molecules are shown in Tables 11B and 11C. The data was generated over a concentration range of 128 nM to 0.03125 nM in a 4 fold dilution series and the Vk dAb-Fc proteins with the DT02-K-085 DAB™ attached to the N-terminus of the IgG1Fc by N085 T113P (T2P) or ASTHP linker (DMS30029), N085 extg1 or IgG1 Hinge linker (DMS30028) compared to DMS1576. From the data in Table 11B, the IgG1 Hinge linker, (N085extg1), was taken as the preferred linker for the DT02-K-085 DAB™ attachment to the N-terminus of the IgG1Fc, ahead of the 1×TVAAPS (SEQ ID NO: 201).

The Vh dAb-Fc molecules were compared to DMS1576 and Bevacizumab (AVASTIN™) over a concentration range of 128 nM to 0.03125 nM in a 4 fold dilution series. Data from Table 11B suggest that the preferred linker for attachment of the 15-26-597 Vh DAB™ to the N-terminus of the dAb-Fc is that based upon 3 copies of the Fibronectin repeat. Further data, shown in Table 11C suggest that when other linkers are used to N-terminally attach the 15-26-597 DAB™ to the Fc, the resultant dAb-Fc proteins generated are biphasic nature in anti VEGF BIACORE™. From the shape of the BIACORE™ curves the N597extg1 (IgG1 Hinge) linker was taken to be the next best from this data set.

The overall data set suggested that to build the most optimal anti-VEGF dAb-Fc-dAb using the novel linkers to improve potency but also reduce the number of glycosylated isoforms then for:
(i) the C-terminal addition of the DT-02-K44-085 Vk DAB™ to the Fc; the Fibronectin ×4 and helical linkers were preferred;
(ii) the N-terminal addition of the DT-02-K44-085 Vk DAB™ to the Fc; the IgG1 Hinge, ASTHP (SEQ ID NO: 218) and 1×TVAAPs (SEQ ID NO: 201) linkers were preferred;
(iii) the N-terminal addition of the 15-26-597 Vh DAB™ to the Fc; the Fibronectin 3 linker was preferred, but the IgG1 Hinge and AS linkers were additionally pursued

TABLE 11D

Binding of anti-VEGF VhdAb-Fc molecules with Fibr4 and Fibr3 N-terminal linkers to VEGF$_{165}$ and comparison to DMS1576.

| Ligand | Ka (M − 1 · s − 1) | Kd (s − 1) | KD (M) | Comments |
|---|---|---|---|---|
| N597 Fibr4 | 2.20E+06 | 7.03E−05 | 3.19E−11 | Good fit |
| N597 Fibr3 | 2.13E+06 | 7.83E−05 | 3.67E−11 | Good fit |
| DMS1576 | 1.87E+06 | 1.77E−04 | 9.43E−11 | Decent fit |

Example 35

Cloning of Anti-VEGF Vh/Vk & Vk/Vk dAb-Fc-dAb Molecules with Modified Linkers

The Vk-Vk dAb-Fc-dAbs: DMS30034 and DMS30035 (SEQ ID NO: 135-136, 177-178, Table 19) and the Vh-Vk

TABLE 11C

Binding of anti-VEGF VhdAb-Fc, Vk dAb-Fc molecules to VEGF$_{165}$ and comparison to DMS1576 and Bevacizumab (AVASTIN ™)

| Sample | Ka (M − 1 · s − 1) | Kd (s − 1) | KD (M) | Comment |
|---|---|---|---|---|
| AVASTIN ™ | 3.24E+05 | na | na | Kd is out of the range (run at 60 ul/min) |
| AVASTIN ™ new | 2.85E+05 | 1.92E−05 | 6.74E−11 | Kd is approaching the limit of detection. Caution! |
| AVASTIN ™ new | 3.14E+05 | na | na | Kd out of the range (run at 60 ul/min) |
| DMS1576 | 7.57E+05 | 2.10E−04 | 2.77E−10 | Biphasic curves. Doesn't look like a 1:1 binding |
| N085 TVAAPS | 1.16E+07 | 9.08E−05 | 7.86E−12 | Biphasic curves. Doesn't look like a 1:1 binding Molecule better DMS1576 than mainly due to a better on-rate |
| N597 extg1 | 1.22E+06 | 1.79E−04 | 1.47E−10 | Biphasic curves. Doesn't look like a 1:1 binding Molecule quite similar to DMS1576 |
| N597 extg3 | 1.33E+06 | 1.70E−04 | 1.25E−10 | Biphasic curves. Doesn't look like a 1:1 binding Molecule quite similar to DMS1576 |

The behaviour in anti-VEGF BIACORE™ of the Vh dAb-Fc molecules containing the linkers Fib3 or Fib4 for the N-terminal coupling of the 15-26-597 DAB™ to the Fc with DMS1576 were compared over a concentration range of VEGF 32 nM to 0.03125 nM in a 4 fold dilution series. The data is shown in Table 11D. The data suggest that there is no advantage to using the Fib4 linker over the Fib3 linker but that when the linker is lengthened from the 'AS' present in DMS1576 for the N-terminal attachment of the 15-26-597 DAB™ to the Fc with the sequences of the Fib3 or Fib4 linker the Vh dAb-Fc shows more optimal binding kinetics by anti VEGF BIACORE™.

dAb-Fc-dAbs: DMS30036-DMS30041 (SEQ ID NO: 137-142, 179-184, Table 19 were engineered by cloning the Vk DAB™ sequence (DT02-K-044-085 (SEQ ID NO: 97 & 105) or the Vh DAB™ sequence, DOM15-26-597 (SEQ ID: 96 & 104) from the Vh-dAb-Fc fusion vector (DMS1576, SEQ ID NO: 2 & 30) onto the N-terminus or C-terminus of the Fc IgG1 sequence (SEQ ID: 102 & 110). The Fc IgG1 was linked at the C-terminus to the N-terminus of the Vk DAB™ (DT02-K-044-085 (SEQ ID NO: 97 & 105)) by a Fibronectin ×4 linker (SEQ ID: 63 & 82, see Table 19) in a mammalian expression vector. The N-terminal Vh DAB™s were linked to the N-terminus of Fc using either the AS (SEQ ID NO:58 & 77, Table 19): DMS30038 (SEQ ID NO:139, 181, Table 19), or Hinge IgG1 (SEQ ID NO:60 & 79, Table 19): DMS30037 (SEQ ID NO:138, 180, Table 19) or Fibronectin 3 (SEQ ID NO:67 & 86, Table 19): DMS30036 (SEQ ID NO:137, 179, Table 19) and DMS30040 (SEQ ID NO:141, 183, Table 19) or Fibronectin 4 (SEQ ID NO:60 & 79, Table 19): DMS30039 (SEQ ID NO:140, 182, Table 19) and DMS30041 (SEQ ID NO:142, 184, Table 19-). The N-terminal Vk DAB™s were linked to the N-terminus of Fc using either the Hinge IgG1 (SEQ ID NO:60 & 79, Table 19): DMS30034 (SEQ ID NO:135, 177, Table 19) or ASTHP, (H2A IgG1Fc, SEQ ID NO: 58 & 65; 77 & 84, Table 19): DMS30035 (SEQ ID NO:136, 178, Table 19) or Hinge IgG1 (SEQ ID NO:60 & 79, Table 19-): DMS30043 (SEQ ID NO: 143, 177, Table 19). In sequences DMS 30035, 30040 and 30041 (SEQ IDs 136 & 178; 141 & 183; and 142 & 148 respectively) the Fc contained proline instead of threonine at position 3 of the Fc.

The fibronectin x4 linker sequence and C-terminal Vk DAB™ were codon optimised to raise the overall dAb-Fc-dAb codon adaptation index (human) to >0.95, for stable expression in mammalian cells. This fragment was generated by oligonucleotide assembly and cloned into DMS30034 (SEQ ID 135 & 177), DMS30036 (SEQ ID 137 & 179), DMS30037, (SEQ ID 138 & 180) and DMS30038 (SEQ ID 139 & 181) to generate DMS30043 (SEQ ID 143 & 177), DMS30044 (SEQ ID 144 & 179), DMS30045 (SEQ ID 145 & 180) and DMS30046 (SEQ ID 146 & 181), respectively. For clarification, the protein amino acid sequences remained the same only the DNA sequence was altered.

Example 36

Expression of Anti-VEGF Vh/Vk & Vk/Vk dAb-Fc-dAb Molecules with Modified Linkers Expression plasmids encoding the relevant anti-VEGF dAb-Fc-dAb molecules (listed in SEQ ID NO:135, 137-139 and 177, 179-181) were transiently transfected into HEK293 6E cells and expressed at 500 ml scale to produce the antibody fragment molecules using the method described in Examples 10 and 21. Expression levels of >30 mg/L supernatant were routinely achieved.

Example 37

Purification of Anti-VEGF Vh/Vk & Vk/Vk dAb-Fc-dAb Molecules with Modified Linkers The dAb-Fc-dAb molecules were affinity purified from the supernatants (Example 36). 2 ml of suspended affinity resin in phosphate buffered saline (50:50 slurry) was added to 500 ml of filtered supernatant; the supernatant/affinity resin mix was rolled gently at +4° C. overnight to allow binding to take place. After which time, the resin was allowed to settle and the supernatant carefully poured off. The resin was re-suspended in remaining supernatant and poured into an empty drip column and the supernatant was allowed to pass out of the column. The bound product was washed using a combination of pH neutral aqueous buffers to remove non-specifically bound impurities followed by a low pH elution. Over 90% of bound product was recovered and the pH of the elution pool then adjusted to pH 3.5 for 30 minutes to achieve virus neutralisation after which time the pH was adjusted to pH 4.5.

Example 38

Molecular Analysis by Size-Exclusion Chromatography (SEC) of Anti-VEGF Vh/Vk & Vk/Vk dAb-Fc-dAb Molecules with Modified Linkers The molecular integrity, homogeneity and % purity of the anti-VEGF dAb-Fc-dAb molecules which had been purified as described in Example 38 were analysed by SDS-PAGE and analytical size-exclusion chromatography (SEC) as described in Examples 3, 13 & 24. The proteins were confirmed to be >95% pure target protein by SDS-PAGE and SEC prior to further analysis in biology assays.

Example 39

Binding of Anti-VEGF Vh/Vk & Vk/Vk dAb-Fc-dAb Molecules with Modified Linkers to VEGF and Comparison to Vh and Vk dAb-Fcs and Vk Fc-dAbs on BIACORE™

The binding affinity of the anti-VEGF dAb-Fc-dAb molecules for $VEGF_{165}$ was determined by Surface Plasmon resonance (SPR) using a BIACORE™ T100 in a similar manner to Examples 25 & 34, but with minor modifications. Protein A was immobilised on a C1 chip by primary amine coupling and this surface was then used to capture the anti-VEGF constructs. Human recombinant $VEGF_{165}$ (sourced 'in house' from transient transfection of HEK293 cells) was used as the analyte at 32 nM to 0.03125 nM in a 4 fold dilution series. All binding curves were double referenced with a buffer injection (i.e. 0 nM) and the data was fitted to 1:1 model inherent to the T100. Regeneration was carried out using 50 mM NaOH. The run was carried out at 37° C., using HBS-EP as the running buffer.

The dAb-Fc-dAb molecules were compared to their corresponding Vk Fc-dAb and Vk dAb-Fc and Vh dAb-Fc molecules, the data is shown in Table 12A. Some of these Vh/Vk dAb-Fc-dAbs: DMS30037 and DMS30022, (see Table 12A), performed unexpectedly well in the BIACORE™ and had good on and off rates suggesting highly potent molecules.

TABLE 12A

Binding of anti-VEGF dAb-Fc-dAb molecules and corresponding dAb-Fc- and Fc-dAb molecules to $VEGF_{165}$

| Ligand | Ka (M − 1 · s−1) | Kd (s − 1) | KD (M) |
|---|---|---|---|
| DMS30036 | 4.01E+06 | 1.49E−05 | 3.70E−12 |
| AVASTIN™ | 5.40E+06 | Out of the range | Out of the range |
| DMS30030 | 2.45E+06 | Out of the range | Out of the range |
| DMS30037 | 4.35E+06 | 1.57E−05 | 3.61E−12 |
| DMS30034 | 1.18E+07 | 8.11E−05 | 6.90E−12 |
| DMS30026 | 8.49E+06 | Out of the range | Out of the range |
| DMS30000ITC | 1.31E+07 | 2.29E−05 | 1.74E−12 |
| DMS30028ITC | 1.04E+07 | 2.29E−05 | 1.74E−12 |
| DMS30022ITC | 6.93E+06 | 1.27E−05 | 1.83E−12 |
| DMS30023ITC | 1.33E+07 | 9.13E−05 | 6.85E−12 |
| DMS1576ITC | 2.70E+06 | 1.96E−04 | 7.24E−11 |
| AVASTIN™ITC | 4.60E+05 | Out of the range | Out of the range |

Further BIACORE™ data sets were obtained comparing the most potent looking dAb-Fc-dAbs with DMS1576 and an example of this is shown in Table 12B. The data sets re-affirm that the Vh/Vk dAb-Fc-dAbs: DMS30022, DMS30036, DMS30037 and DMS30038 look similar in potency to AVASTIN™ and that the Vk/Vk dAb-Fc-dAb DMS30034 is overall less potent, (in terms of off-rate Kd s-1 1.04E-04, see Table 12B), though an improvement over DMS1576 in overall KD, (see Table 12B).

In contrast to Example 25 the dAb-Fc-dAb molecule to VEGF binding data which is seen in these results suggests that the BIACORE™ can be a very informative assay format for analysing the bivalent anti-VEGF dAb-Fc DAB™ molecules, when both VEGF binding sites are of similar potency (eg. DMS30036, DMS30037 and DMS30038), and can be used to distinguish from molecules that have one potent and one less potent binding site, eg DMS30034.

TABLE 12B

Binding of anti-VEGF dAb-Fc-dAb molecules molecules to $VEGIF_{165}$ and comparison to DMS1576 and AVASTIN™.

| Ligand | Ka (M − 1 · s − 1) | Kd (s − 1) | KD (M) |
| --- | --- | --- | --- |
| DMS30022 | 1.01E+07 | 5.10E−05 | 5.06E−12 |
| AVASTIN ™ | 5.61E+05 | Out of the range | Out of the range |
| DMS30034 HEK | 2.57E+07 | 1.04E−04 | 4.06E−12 |
| DMS30037 HEK | 8.01E+06 | 4.98E−05 | 6.22E−12 |
| DMS1576 | 3.62E+06 | 2.97E−04 | 8.21E−11 |
| DMS30036 HEK | 6.66E+06 | 4.85E−05 | 7.28E−12 |
| DMS30038 HEK | 7.11E+06 | 4.74E−05 | 6.67E−12 |

Example 40

VEGF R2 Receptor Binding Assay of Anti-VEGF Vh/Vk & Vk/Vk dAb-Fc-dAb Molecules with Modified Linkers Compared to Most Potent Vh dAb-Fc and AVASTIN™

The potencies of some of the anti-VEGF Vh/Vk & Vk/Vk dAb-Fc-dAb molecules with modified linkers were analysed in the VEGF receptor 2, (R2), binding assay using the modified method, i.e. with no pre-incubation, described in Examples 7, 17 & 26 and were compared to the Vh dAb-Fc, DMS30030 and Bevacizumab (AVASTIN™). The data is shown in Tables 13A and 13B. From the data in Table 13A all the tested dAb-Fc-dAb molecules: DMS30022, DMS30023, DMS30034, DMS30036 and DMS30037 appeared to be more potent by lower EC50 values than DMS30030 and considerably more potent than Bevacizumab (AVASTIN™). However, there was some variability in the maximal percentage inhibition achieved by the molecules in the assay with AVASTIN™, DMS30022 and DMS30030 achieving >94% maximal inhibition and DMS30023, DMS30034, DMS30036 and DMS30037 achieving 78-84% maximal inhibition, (data not shown)

Further data was generated comparing the dAb-Fc-dAbs: DMS30022 and DMS30038 with the Vh dAb-Fc, DMS30030 and Bevacizumab (AVASTIN™) and this is shown in Table 13B.

In summary, DMS30022 and DMS30038 appeared to be comparable and more potent by lower EC50 values than DMS30030 and considerably more potent than Bevacizumab (AVASTIN™), Table 13B. Again, there was some variability in the maximal percentage inhibition achieved by the molecules in the assay with AVASTIN™, DMS30022 and DMS30030 achieving >95% maximal inhibition and DMS30038 achieving 91% maximal inhibition, (data not shown).

TABLE 13A $EC_{50}$ values of anti-VEGF dAb-Fc-dAbs compared to DMS30030 and Bevacizumab (AVASTIN ™) in VEGFR2 Receptor Binding Assay. Curve fitting and $EC_{50}$ calculations were performed using GRAPHPAD PRISM ™.

| VEGFR2 RBA | EC50 (g/mL) | EC50 (pM) |
| --- | --- | --- |
| AVASTIN ™ | 2.92E−07 | 1944 |
| DMS30034 (LT111020) | 4.93E−09 | 47 |
| DMS30036 (LT111027) | 3.78E−09 | 36 |
| DMS30037 (LT111020) | 3.86E−09 | 37 |
| DMS30022 (CR290911) | 4.04E−09 | 38 |
| DMS30023 (CR290911) | 3.23E−09 | 31 |
| DMS30030 (MH171011) | 4.93E−09 | 62 |

TABLE 13B $EC_{50}$ values of anti-VEGF dAb-Fc-dAbs: DMS30022 and DMS30038 compared to DMS30030 and Bevacizumab (AVASTINT ™) in VEGFR2 Receptor Binding Assay. Curve fitting and $EC_{50}$ calculations were performed using GRAPHPAD PRISM ™.

| VEGF R2 RBA | EC50 (g/mL) | EC50 (pM) |
| --- | --- | --- |
| AVASTIN ™ | 2.97E−07 | 1933 |
| DMS30022 (CR290911) | 4.67E−09 | 44 |
| DMS30038 (CR291111) | 4.12E−09 | 39 |
| DMS30030 (MH171011) | 1.17E−08 | 146 |

Example 41

Human Umbilical Vein Endothelial Cell (HUVEC) Proliferation Assay: Inhibition with Anti-VEGF Vh/Vk & Vk/Vk dAb-Fc-dAb Molecules Containing Modified Linkers The abilities of the dAb-Fc-dAb molecules with modified linkers: Vh-Vk (DMS30022, DMS30036, DMS30037) and Vk-Vk (DMS30023, DMS30034), to suppress proliferation of human umbilical vein endothelial cells were compared to the Vh dAb-Fc molecule (DMS30030), the Vk Fc-dAb molecule (DMS30026) and Bevacizumab (AVASTIN™) using the method described in Examples 8 & 18 & 27 with the following deviations (i) rather than leaving the outer wells free of cells, the whole 96 well plate was used and (ii) the data was analysed using GRAPHPAD PRISM™ using a Sigmodial curve fit, variable slope cf a non-linear regression (variable slope). The test compounds were independently assessed on individual plates against the comparator molecule, Bevacizumab (AVASTIN™); the assay was carried out on at least four separate occasions, with a total data set per molecule of Bevacizumab (AVASTIN™): 20; DMS30030: 8; DMS30036: 8; DMS30022: 4; DMS30037: 8; DMS30026: 4; DMS30023: 4; DMS30034: 4 (data not shown). The focus was upon analysing both the degree of maximum inhibition and the relative EC50 values in the assay generated by certain molecules compared to that of Bevacizumab (AVASTIN™).

The data was analysed using GRAPHPAD PRISM™ using a Sigmodial curve fit, variable slope cf a non-linear regression (variable slope). Individual curve fits were fitted for each molecule and at each day. Due to some poor fitting, it was decided to introduce constraints for the curve where a plateau was not observed at the lower concentration. This constraint would be equal to the mean of the points at the lowest concentration. Data was manually selected as to whether the minimum was constrained or not, and the curve fit and parameters were automatically updated based upon this criteria selection. Estimates of the curve maxima and the standard error were analysed using a weighted mixed model analysis of variance, using 1/(standard error)$^2$, [SE]$^2$, as a weighting. The analysis adjusted for variability between plates and days using random effects terms. From this analysis, the predicted means were estimated and comparisons were made back to AVASTIN™ (control) (Table 14A). The same analysis was then performed on the log 10 scale for the IC50, and the results back transformed. From this, estimates of the geometric means were generated and comparisons were made back to AVASTIN™ in the form of a ratio to AVASTIN™ (control) i.e. a ratio of 0.5 would indicate a 50% drop from AVASTIN™ (Table 14B).

TABLE 14A

Predicted geometric means of maximum percentage inhibition of anti-VEGF dAb-Fc-dAbs with 95% confidence intervals (CI) compared to DMS30026, DMS30030 and Bevacizumab (AVASTIN ™) in the HUVEC Assay.
Predicted Means for Max % Inhibition

| mAb | Estimate | Lower 95% CI | Upper 95% CI |
|---|---|---|---|
| AVASTIN ™ | 73.5423 | 68.5130 | 78.5717 |
| DMS30022 | 80.3745 | 70.6202 | 90.1287 |
| DMS30023 | 69.7258 | 60.3045 | 79.1471 |
| DMS30026 | 70.5232 | 59.1251 | 81.9213 |
| DMS30030 | 64.7441 | 57.5772 | 79.9110 |
| DMS30034 | 85.1436 | 73.9429 | 96.3444 |
| DMS30036 | 79.0377 | 73.2432 | 84.8323 |
| DMS30037 | 77.8069 | 72.1446 | 83.4691 |

From this analysis molecules DMS30022, DMS30034, DMS30036 and DMS30037 seem to lead to the most maximal inhibition in the HUVEC assay and although they apparently out-performed the AVASTIN™ group, the confidence interval overlapped the zero reference so that there was no statistically significant difference from AVASTIN™, data not shown (Table 14A).

TABLE 14O

Geometric means of IC50 for anti-VEGF dAb-Fc-dAbs with 95% confidence intervals (CI) compared to DMS30026, DMS30030 and Bevacizumab (AVASTIN ™) in the HUVEC Assay.
Predicted Means for IC50

| mAb | Estimate | Lower 95% CI | Upper 95% CI |
|---|---|---|---|
| AVASTIN ™ | 1.773E-9 | 1.504E-9 | 2.09E-9 |
| DMS30022 | 9.03E-10 | 6.53E-10 | 1.25E-9 |
| DMS30023 | 5.98E-10 | 4.27E-10 | 8.36E-10 |
| DMS30026 | 1.675E-9 | 1.201E-9 | 2.336E-9 |
| DMS30030 | 2.405E-9 | 1.82E-9 | 3.18E-9 |
| DMS30034 | 1.216E-9 | 7.77E-10 | 1.902E-9 |

TABLE 14O-continued

Geometric means of IC50 for anti-VEGF dAb-Fc-dAbs with 95% confidence intervals (CI) compared to DMS30026, DMS30030 and Bevacizumab (AVASTIN ™) in the HUVEC Assay.
Predicted Means for IC50

| mAb | Estimate | Lower 95% CI | Upper 95% CI |
|---|---|---|---|
| DMS30036 | 1.052E-9 | 8.4E-10 | 1.316E-9 |
| DMS30037 | 8.04E-10 | 6.42E-10 | 1.007E-9 |

A similar analysis of the geometric means of the IC50 values with 95% confidence intervals, (CI), showed that the molecules DMS30022, DMS30023, DMS30036 and DMS30037 had statistically significantly lower IC50 values than AVASTIN™, data not shown (Table 14B).

A separate set of data was generated from HUVEC assays in a similar format from a different operator. The data focussed upon comparing the behaviour of two dAb-Fc-dAbs in the HUVEC assay: DMS30022 and DMS30037 with that of Bevacizumab (AVASTIN™) and was performed in quadruplicate. The data suggest that both dAb-Fc-dAbs have very similar IC50 values and levels of maximal inhibition in the HUVEC assay and appear more potent, though not statistically so in this particular data set, than Bevacizumab (AVASTIN™), (data not shown).

Example 42

Performance of Anti-VEGF Vh/Vk & Vk/Vk dAb-Fc-dAb Molecules with Modified Linkers in VEGF Induced Blood-Retinal Breakdown: Rabbit Retinal Leakage Model DMS30022, DMS30030, DMS30034, DMS30036 and DMS30037 were tested in a human VEGF165 (R&D Systems), induced blood-retinal breakdown, (BRB), model in the rabbit eye and compared against Bevacizumab (AVASTIN™), and KENACORT™ (Tramcinalone) as described in Example 9.

The aim of this study and method were similar to those outlined for Example 9 above. The dosing and injection schedule is shown in Table 15A.

All molecules were buffer exchanged into 50 mM sodium acetate buffer pH5.5, 104 mM NaCl, 0.02 mM EDTA following the method of Example 9 above.

One hundred and forty (140) HY79B pigmented rabbits were randomly divided into eleven (11) groups of twelve (12) animals and one (1) group of eight animals, each group was sub-divided into 4 experimental sets of 3 animals, bar the KENACORT™ treated group, (4 sets of 2 animals), (see Table 15A).

Mean intravitreal levels of some of the dosed molecules, (DMS30036, DMS30037 and DMS30022), were determined by an MSD™, (Mesoscale Discovery), based functional VEGF binding assay, (data not shown). For the molecules measured, levels were similar to that expected from the injected levels and the likely half life range for the molecules in the rabbit vitreous, (data not shown). Fluorescein angiograms were collected for qualitative assessment.

TABLE 15A

Dosing and injection schedule for inhibition of VEGF induced rabbit retinal leakage by DMS30022, DMS30030, DMS30034, DMS30036 and DMS30037 compared to Bevacizumab (AVASTIN ™) and KENACORT ™ (Triamcinalone).

| Treatment (right eye) | Dose eye | Treatment Protocol | Number of animals | | | | Induction | Measurements |
|---|---|---|---|---|---|---|---|---|
| | | | Set 1 | Set 2 | Set 3 | Set 4 | | |
| Vehicle | — | 50-µL | 3 | 3 | 3 | 3 | Day 0 | On Day 2: |
| AVASTIN ™ | H | IVT | 3 | 3 | 3 | 3 | 500 ng/ | * Retinal angiography |
| AVASTIN ™ | L | Day −7 | 3 | 3 | 3 | 3 | 50 µL | assessment using |
| AVASTIN ™ | L/3 | | 3 | 3 | 3 | 3 | rhVEGF | Heidelberg's Retinal |
| DMS30030 | L | | 3 | 3 | 3 | 3 | (IVT) | Angiograph |
| DMS30030 | L/3 | | 3 | 3 | 3 | 3 | | * Fluorescein |
| DMS30034 | L/3 | | 3 | 3 | 3 | 3 | | leakage quantification |
| DMS30036 | L/3 | | 3 | 3 | 3 | 3 | | in vitreous/retina |
| DMS30037 | L | | 3 | 3 | 3 | 3 | | segment (Fluorotron ® |
| DMS30037 | L/3 | | 3 | 3 | 3 | 3 | | Master) |
| DMS30022 | L/3 | | 3 | 3 | 3 | 3 | | * Eyeballs sampling |
| KENACORT ™ Retard | 2 000 ug/eye | | 2 | 2 | 2 | 2 | | (except for KENACORT ™ group) |

Intravitreally injected VEGF induced a breakdown of the BRB, which was blocked by treatment with the following compounds when un-masked: Bevacizumab (AVASTIN™), at all three doses; DMS30030, (L and L/3 doses); DMS30022 (L/3 dose), DMS30034, (L/3 dose), DMS30036 (L dose), and DMS30037 (L and L/3 dose), 9 days post injection, with an efficacy similar to that of the marketed reference (KENACORT™). In the masked study, an important retinal vascular leakage was noted in right induced eyes after treatment with vehicle, negative control, and DMS30036 at L/3 dose, although the classification was influenced by the presence of a single significant outlying data point, (data not shown). Note than one data point (rabbit 134) was excluded from further analysis from the DMS30037 L/3 dosed group due to a abnormality scoring for fluorescence.

The raw data was subject to further statistical analysis: the masked groups corresponding to the same molecule and dose were pooled and geometric mean values were determined with 95% confidence intervals (CI). The geometric mean data is shown Table 15B (i) and the ratio to vehicle values and variance with 95% CI are shown in Table 15B (ii). From the data analysis in Tables 15B (i) and (ii) the marketed corticoid reference (KENACORT™ retard) reduced the degree of VEGF induced retinal leakage by 80%), the three different doses of Bevacizumab (AVASTIN™), were effective by 71.4-76.4%, with no evidence of a dose response, DMS30022 (L/3) was effective by 74.6%, DMS30037 (L) by 74.2% and (L/3) by 67.4%; DMS30036 L/3 by 63.7%; DMS30034 L/3 by 59.5% and DMS30030 (L) by 65.5% and L/3 by 70.5%. It was concluded that Vh/Vk dAb-Fc-dAbs such as DMS30022 and DMS30037 were the most potent format in this model.

TABLE 15B

Inhibition of VEGF induced rabbit retinal leakage by DMS30022, DMS30030, DMS30034, DMS30036 and DMS30037 compared to Bevacizumab (AVASTIN ™) and KENACORT ™ (Triamcinalone) Analysis of log10 right values (RE) adjusted for log10 left eye values (LE), (excluding rabbit 134 opaque lens in group 5: DMS30037 L/3)

(i) Geometric means

| grpno | group | Geometric mean | lower | upper |
|---|---|---|---|---|
| 1 | DMS30030 L/3 | 15070.42 | 10613.18 | 21399.57 |
| 2 | AVASTIN ™ L3 | 14592.63 | 10277.06 | 20720.39 |
| 3 | AVASTIN ™ H | 12332.94 | 8673.32 | 17536.69 |
| 4 | DMS30036 L/3 | 18539.81 | 13041.82 | 26355.55 |
| 5 | DMS30037 L/3 | 16602.99 | 11620.75 | 23721.32 |
| 6 | Vehicle | 51006.20 | 35920.69 | 72427.12 |
| 7 | DMS30022 L/3 | 12975.83 | 9135.26 | 18431.04 |
| 8 | DMS30037 L | 13159.70 | 9527.22 | 18707.31 |
| 9 | AVASTIN ™ L | 12037.98 | 8470.04 | 17108.87 |
| 10 | DMS30030 L | 17586.48 | 12379.27 | 24984.06 |
| 11 | DMS30034 L/3 | 20632.66 | 14441.37 | 29478.27 |
| 12 | KENACORT ™ | 10205.21 | 6929.09 | 15030.31 |

(ii) Ratio to vehicle and percentage reduction.

| grpno | group | Geometric ratio | lower | upper | P value | % reduction |
|---|---|---|---|---|---|---|
| 1 | DMS30030 L/3 | 0.29546 | 0.20895 | 0.41779 | <.0001 | 70.4537 |
| 2 | AVASTIN ™ L/3 | 0.28609 | 0.20235 | 0.42449 | <.0001 | 71.3905 |
| 3 | AVASTIN ™ H | 0.24179 | 0.17060 | 0.34269 | <.0001 | 75.8207 |
| 4 | DMS30036 L/3 | 0.36348 | 0.25683 | 0.51442 | <.0001 | 63.6519 |
| 5 | DMS30037 L/3 | 0.32551 | 0.22839 | 0.46394 | <.0001 | 67.4491 |
| 7 | DMS30022 L/3 | 0.25440 | 0.17990 | 0.35973 | <.0001 | 74.5603 |
| 8 | DMS30037 L | 0.25800 | 0.18230 | 0.36514 | <.0001 | 74.1998 |
| 9 | AVASTIN ™ L | 0.23601 | 0.16665 | 0.33424 | <.0001 | 76.3990 |
| 10 | DMS30030 L | 0.34479 | 0.24379 | 0.48763 | <.0001 | 65.5209 |
| 11 | DMS30034 L/3 | 0.40451 | 0.28368 | 0.57680 | <.0001 | 59.5487 |
| 12 | KENACORT ™ | 0.20008 | 0.13518 | 0.29612 | <.0001 | 79.9922 |

Example 43

Larger Scale Purification of Vh/Vk dAb-Fc-dAb Molecules from Chinese Hamster Ovary (CHO)

For example, DMS30037 was captured from clarified cell culture supernatant using affinity chromatography and an automated FPLC purification system. Once loaded, the bound product was washed using a combination of pH neutral aqueous buffers to remove non-specifically bound impurities followed by a low pH elution from which over 90% of bound product was recovered. After storage at −40° C. the elution pool was thawed then adjusted to pH 3.6 for 30 minutes to achieve virus neutralisation after which time the pH was adjusted to pH6.0. The pH adjusted pool was further purified on a second column whereby product was loaded under non-product binding conditions that promote removal of process impurities. The purified DMS30037 was then collected as a pool before 0.2 µm filtration and storage. Additionally, DMS30037 affinity column eluates were pH adjusted to 7.5 in low salt buffer, filtered and then concentrated and diafiltered into a suitable formulation buffer using a tangential flow filtration system. Recovered product was 0.2 µm sterile filtered and stored.

Example 44

Cloning of Anti-VEGF Vh/Vk dAb-Fc-dAb Molecules with Modified C-Termini

The Vh-Vk dAb-Fc-dAbs with modifications to the C-terminus of the Vk DAB™: DMS30047-30054 (SEQ ID NO:147-154 & 185-192, Table 19) were engineered by generating the variant Vk dAb sequences by PCR and then by re-cloning into DMS30045 and DMS30046, respectively to generate the modified mammalian expression vectors. From DMS30045: (i) the C-terminal arginine residue was removed to generate DMS30047 (DMS30037-R), (ii) a C-terminal alanine was added to generate DMS30048, (DMS30037+A), (iii) three C-terminal alanines were added to generate DMS30049, (DMS30037+AAA) and a C-terminal threonine was added to generate DMS30050 (DMS30037+T). From DMS30046: (i) the C-terminal arginine residue was removed to generate DMS30051 (DMS30038-R), (ii) a C-terminal alanine was added to generate DMS30052, (DMS30038+A), (iii) three C-terminal alanines were added to generate DMS30053, (DMS30038+AAA) and a C-terminal threonine was added to generate DMS30054 (DMS30038+T).

Example 45

Expression of Anti-VEGF Vh/Vk dAb-Fc-dAb Molecules with Modified C-Termini (DMS30047-30054)

Expression plasmids encoding the relevant anti-VEGF dAb-Fc-dAb molecules (listed in SEQ ID NO:147-154, and 185-192, Table 19) were transiently transfected into HEK293 6E cells and expressed at 500 ml scale to produce the antibody fragment molecules using the method described in Examples 10, 21 and 36. Expression levels of >30 mg/L supernatant were routinely achieved.

Example 46

Purification of Anti-VEGF Vh/Vk dAb-Fc-dAb Molecules with Modified C-Termini

The dAb-Fc-dAb molecules were affinity purified from the supernatants (Example 45), as described for Example 37 above.

Example 47

Molecular Analysis by Size-Exclusion Chromatography (SEC) of Anti-VEGF Vh/Vk dAb-Fc-dAb Molecules with Modified C-Termini The molecular integrity, homogeneity and % purity of the anti-VEGF dAb-Fc-dAb molecules which had been purified as described in Example 46 were analysed by SDS-PAGE and analytical size-exclusion chromatography (SEC) as described in Examples 3 & 13. The proteins were confirmed to be >95% pure target protein by SDS-PAGE and SEC prior to further analysis in biology assays.

Example 48

Binding of Anti-VEGF Vh/Vk dAb-Fc-dAb Molecules with Modified C-Termini to VEGF on BIACORE™

The binding affinity of certain anti-VEGF dAb-Fc-dAb molecules, (with small C-terminal modifications), for $VEGF_{165}$ was determined by Surface Plasmon resonance (SPR) using a BIACORE™ T100 in a similar manner to Examples 34 and 40, but with minor modifications. Protein A was immobilised on a C1 chip by primary amine coupling and this surface was then used to capture the anti-VEGF constructs. Human recombinant $VEGF_{165}$ (sourced 'in house' from transient transfection of HEK293 cells) was used as the analyte at 32 nM to 0.03125 nM in a 4 fold dilution series. All binding curves were double referenced with a buffer injection (i.e. 0 nM) and the data was fitted to 1:1 model inherent to the T100. Regeneration was carried out using 50 mM NaOH. The run was carried out at 37° C., using HBS-EP as the running buffer. The data obtained is shown in Tables 16A, 16B & 16C. From the data in Table 16A, the behaviour of DMS30037 and several variants modified at the C-terminus: DMS30037+A (DMS30048), DMS30037+AAA (DMS30049), and DMS30037+T (DMS30050) seem comparable on BIACORE™ and the C-terminal modifications do not appear to reduce potency over parental.

A further data set is shown in Table 168 where the performance of both DMS30037 and DMS30038 were compared with variants modified at the C-terminus: DMS30037-R, (labelled as +R (DMS30047), DMS30037+T (DMS30050) and DMS30038-R, (labelled as +R (DMS30051) and Bevacizumab (AVASTIN™) in the BIACORE™. In this data set again the behaviour of all the molecules seems comparable on BIACORE™ and the C-terminal modifications do not appear to reduce potency over parental. Meaningful data could not be captured other than to view the curve for AVASTIN™. A further data set is displayed in Table 16C where the molecules DMS30037 and DMS30038 were compared with variants modified at the C-terminus: DMS30037-R, (DMS30047), DMS30037+T (DMS30050), DMS30038-R, (DMS30051) and DMS30038+T (DMS30054) and Bevacizumab (AVASTIN™). Again the behaviour of all the dAb-Fc-dAb molecules seem comparable on BIACORE™ and the C-terminal modifications do not appear to reduce potency over parental. In this data set, see Table 16C, the Bevacizumab (AVASTIN™) data could not be properly measured due to the off-rate being too tight.

TABLE 16A

Binding of the anti-VEGF dAb-Fc-dAb molecule: DMS30037 with C-terminal modifications to $VEGF_{165}$ and comparison to DMS30037.

| Ligand | Ka (M−1 · s−1) | Kd (s−1) | KD (M) |
| --- | --- | --- | --- |
| DMS30037 | 8.18E+06 | 4.34E−05 | 5.30E−12 |
| DMS30037+A | 8.25E+06 | 5.21E−05 | 6.32E−12 |

TABLE 16A-continued

Binding of the anti-VEGF dAb-Fc-dAb molecule:
DMS30037 with C-terminal modifications to
VEGF$_{165}$ and comparison to DMS30037.

| Ligand | Ka (M−1 · s−1) | Kd (s−1) | KD (M) |
| --- | --- | --- | --- |
| DMS30037+AAA | 7.74E+06 | 5.37E−05 | 6.94E−12 |
| DMS30037+T | 8.03E+06 | 4.21E−05 | 5.24E−12 |

TABLE 16B

Binding of the anti-VEGF dAb-Fc-dAb molecules: DM530037
and DM530038 with C-terminal modifications to VEGF$_{165}$ and
comparison to parental dAb-Fc-dAb and Bevacizumab (AVASTIN ™).

| Ligand | Ka (M−1 · s−1) | Kd (s−1) | KD (M) |
| --- | --- | --- | --- |
| DMS30037 | 1.04E+07 | 4.39E−05 | 4.22E−12 |
| DMS30037+R | 1.07E+07 | 4.22E−05 | 3.94E−12 |
| DMS30037+T | 1.10E+07 | 4.27E−05 | 3.90E−12 |
| DMS30038 | 1.03E+07 | 4.79E−05 | 4.64E−12 |
| DMS30038+R | 1.23E+07 | 5.31E−05 | 4.31E−12 |
| AVASTIN ™ | 8.39E+05 | Out of range | Out of range |

TABLE 16C

Binding of the anti-VEGF dAb-Fc-dAb molecules: DMS30037 and
DMS30038 with C-terminal modifications to VEGF$_{165}$ and comparison
to parental dAb-Fc-dAb and Bevacizumab (AVASTIN ™).

| Ligand | Ka (M−1 · s−1) | Kd (s−1) | KD (M) |
| --- | --- | --- | --- |
| DMS30037 | 5.60E+06 | 1.46E−04 | 2.61E−11 |
| DMS30337+T | 5.35E+06 | 1.42E−04 | 2.64E−11 |
| DMS30037−R | 6.97E+06 | 1.55E−04 | 2.22E−11 |
| DMS30038 | 5.69E+06 | 1.55E−04 | 2.73E−11 |
| DMS30038−R | 5.90E+06 | 1.58E−04 | 2.68E−11 |
| DMS30038+T | 8.28E+06 | 1.22E−04 | 1.47E−11 |
| AVASTIN ™ | 1.24E+06 | Out of range | Out of range |

Example 49

VEGF R2 Recentor Binding Assay of Anti-VEGF Vh/Vk dAb-Fc-dAb Molecules with Modified C-Termini The potencies of anti-VEGF Vh/Vk dAb-Fc-dAb molecules based upon DMS30037 and DMS30038, but with C-terminal modifications, were compared both to the wild type molecule and Bevacizumab (AVASTIN™), in the VEGF receptor 2, (R2), binding assay using the modified method, i.e. with no pre-incubation, described in Examples 7, 17 & 26 & 40. The data is shown in Table 17A, all the tested dAb-Fc-dAb molecules: DMS30037, DMS30037+T (DMS30050), DMS30037−R (DMS30047), DMS30038, DMS30038−R (DMS30051), appeared to be of comparable potency and considerably more potent than Bevacizumab (AVASTIN™), Table 17A. There was little variation in the maximal percentage inhibition achieved by the molecules in the assay with all molecules achieving >93-98% maximal inhibition, (data not shown).

Further data was generated comparing the dAb-Fc-dAbs: DMS30038, DMS30038+T, (DMS30050) and DMS30038−R, (DMS30051) with Bevacizumab (AVASTIN™), in the same assay format, the data is displayed in Table 17B. From the data DMS30038 and its C-terminal variants, (Table 17B), have similar potencies judged by EC50 values in the RBA assay and appear to be considerably more potent than Bevacizumab (AVASTIN™) by this criteria. There was little variation in the maximal percentage inhibition achieved by the molecules in the assay with all molecules achieving >94% maximal inhibition, (data not shown)

TABLE 17A

EC$_{50}$ values of anti-VEGF dAb-Fc-dAbs with C-terminal
modifications compared to Bevacizumab (AVASTIN ™)
in VEGFR2 Receptor Binding Assay.
Curve fitting and EC$_{50}$ calculations were performed using
GRAPHPAD_PRISM ™.

| VEGFR2 RBA | EC50 (g/mL) | EC50 (pM) |
| --- | --- | --- |
| AVASTIN ™ | 1.21E−07 | 806 |
| DMS30037 | 2.99E−09 | 28 |
| DMS30037+T | 2.98E−09 | 28 |
| DMS30037−R | 2.66E−09 | 25 |
| DMS30038 | 3.37E−09 | 32 |
| DMS30038−R | 3.84E−09 | 37 |

TABLE 17B

EC$_{50}$ values of anti-VEGF dAb-Fc-dAbs with C-terminal
modifications compared to Bevacizumab
(AVASTIN ™) in VEGFR2 Receptor Binding Assay.
Curve fitting and EC$_{50}$ calculations were performed using
GRAPHPAD PRISM ™.

| VEGFR2 RBA | EC50 (g/mL) | EC50 (pM) |
| --- | --- | --- |
| AVASTIN ™ | 3.4E−07 | 2266 |
| DMS30038 | 5.28E−09 | 50 |
| DMS30038+T | 4.31E−09 | 41 |
| DMS30037−R | 4.53E−09 | 43 |

Example 49

Human Umbilical Vein Endothelial Cell (HUVEC) Proliferation Assay: Inhibition with Anti-VEGF Vh/Vk dAb-Fc-dAb Molecules Containing C-Terminal Modifications The abilities of dAb-Fc-dAb molecules based upon DMS30037 and DMS30038 but with C-terminal modifications: DMS30037−R (DMS30047) & DMS30037+T (DMS30050), DMS30038−R (DMS30051) & DMS30038+T (DMS30054) to suppress proliferation of human umbilical vein endothelial cells were compared to Bevacizumab (AVASTIN™) using the method described in Examples 8, 18, 27 & 41 with the following deviations (i) rather than leaving the outer wells free of cells, the whole 96 well plate was used and (ii) the data was analysed using GRAPHPAD PRISM™ using a Sigmodial curve fit, variable slope cf a non-linear regression (variable slope). The test compounds were independently assessed on individual plates against the comparator molecule, Bevacizumab (AVASTIN™); the assay was carried out on at least three separate occasions, with a total data set per molecule of Bevacizumab (AVASTIN™): 15; DMS30037: 7; DMS30038: 8; DMS30037−R (DMS30047): 3; DMS30037+T (DMS30050): 4; DMS30038−R (DMS30051): 4 & DMS30038+T (DMS30054): 4, (data not shown). The focus was upon analysing both the degree of maximum inhibition and the relative EC50 values in the assay generated by certain molecules compared to that of Bevacizumab (AVASTIN™).

The data was analysed using GRAPHPAD PRISM™ using a Sigmodial curve fit, variable slope cf a non-linear regression (variable slope). Individual curve fits were fitted for each molecule and at each day. Due to some poor fitting, it was decided to introduce constraints for the curve where a plateau was not observed at the lower concentration. One plate was excluded from the analysis due to poor curve fitting despite constraints. This constraint would be equal to the mean of the points at the lowest concentration. Data was manually selected as to whether the minimum was constrained or not, and the curve fit and parameters were automatically updated based upon this criteria selection. Estimates of the curve maxima and the standard error were analysed using a weighted mixed model analysis of variance, using 1/(standard error)$^2$, [SE]$^2$, as a weighting. The analysis adjusted for variability between plates and days using random effects terms. From this analysis, the predicted means were estimated and comparisons were made back to Bevacizumab (AVASTIN™ control) (See Table 18A). The same analysis was then performed on the log 10 scale for the IC50, and the results back transformed. From this, estimates of the geometric means were generated and comparisons were made back to Bevacizumab (AVASTIN™) in the form of a ratio to Bevacizumab (AVASTIN™ control) i.e. a ratio of 0.5 would indicate a 50% drop from Bevacizumab, (AVASTIN™, see Table 18B).

TABLE 18A

Predicted geometric means of maximum percentage inhibition of C-terminally modified anti-VEGF dAb-Fc-dAbs with 95% confidence intervals (CI) compared to parental and Bevacizumab (AVASTIN ™) in the HUVEC Assay. Predicted Means for Max % Inhibition

| mAb | Estimate | Lower 95% CI | Upper 95% CI |
|---|---|---|---|
| AVASTIN ™ | 71.0316 | 61.6741 | 80.3891 |
| DMS30037 | 85.4759 | 74.9164 | 96.0354 |
| DMS30037+T | 89.9852 | 78.2698 | 101.70 |
| DMS30037−R | 82.2693 | 69.9929 | 94.5457 |
| DMS30038 | 73.5602 | 63.7180 | 83.4023 |
| DMS30038+T | 79.0343 | 67.1904 | 90.8782 |
| DMS30038−R | 77.6519 | 65.5487 | 89.7550 |

From this analysis, molecules DMS30037, DMS30037+T and DMS30037−R seem to lead to the most maximal inhibition in the HUVEC assay and they out-performed the AVASTIN™ group, the confidence interval did not overlap the zero reference so the data was statistically significant from that of AVASTIN™, data not shown (see Table 18A).

TABLE 18B

Geometric means of IC50 for C-terminally modified anti-VEGF dAb-Fc-dAbs with 95% confidence intervals (CI) compared to parental and Bevacizumab (AVASTIN ™) in the HUVEC Assay. Geometric Means for IC50

| mAb | Estimate | Lower 95% CI | Upper 95% CI |
|---|---|---|---|
| AVASTIN ™ | 3.829E−9 | 3.119−9 | 4.7E−9 |
| DMS30037 | 1.903E−9 | 1.473E−9 | 2.46E−9 |
| DMS30037+T | 2.332E−9 | 1.758E−9 | 3.092E−9 |
| DMS30037−R | 7.365E−9 | 2.06E−10 | 2.715E−9 |
| DMS30038 | 2.163E−9 | 1.723E−9 | 2.715E−9 |

TABLE 18B-continued

Geometric means of IC50 for C-terminally modified anti-VEGF dAb-Fc-dAbs with 95% confidence intervals (CI) compared to parental and Bevacizumab (AVASTIN ™) in the HUVEC Assay. Geometric Means for IC50

| mAb | Estimate | Lower 95% CI | Upper 95% CI |
|---|---|---|---|
| DMS30038+T | 2.649E−9 | 1.877E−9 | 3.738E−9 |
| DMS30038−R | 2.234E−9 | 1.699E−9 | 2.936E−9 |

A similar analysis of the geometric means of the IC50 values with 95% confidence intervals, (CI), showed that almost all the dAb-Fc-dAb molecules DMS30037, DMS30037+T, DMS30038, DMS30038+T and DMS30038−R had statistically significantly lower IC50 values than Bevacizumab (AVASTIN™), data not shown (see Table 18B). The data set from DMS30037−R was highly variable with a low n number (3).

Overall the data suggest that C-terminal modifications to both dAb-Fc-dAbs: DMS30037 & DMS30038 have very similar IC50 values and levels of maximal inhibition in the HUVEC assay to parental molecules and appear more potent, than Bevacizumab (AVASTIN™), both in terms of maximal percentage inhibition and lower IC50, (see Tables 18A and 18B).

Example 50

Cross-Reactivity of Vh dAb-Fc (DMS1529) and Vk Fc-dAb (DMS30000) to Murine VEGF$_{164}$ AMSD™, (MesoScale Discovery), high bind 96 well plate (MSD™ L11XB-3) was coated with 1 or 2 µg/mL mVEGF$_{164}$ (R&D 493-MV/CF) (25 µL/well), sealed and incubated overnight at 4° C. Next day the MSD™ plate was washed 3×300 µL/well with Tris wash buffer and blocked with 3% BSA in PBS (250 uL/well) and incubated shaking (750 RPM) at room temperature for 1 hour. The MSD™ plate was washed again before the addition of the DMS1529, DMS30000 or mVEGF R2Fc (R&D 443-KD/CF) standard curves (25 µL/well) and incubated shaking (750 RPM) at room temperature for 2 hours. The standards were diluted using 0.1% BSA in PBS. The MSD™ plate was washed again before the addition of the detection reagent (25 µL/well, in-house SULFO-TAG™ labelled goat anti-human IgG, Fc specific—Sigma 12136) at 1 g/mL in 1% BSA in PBS and incubated shaking (750 RPM) at room temperature for 1 hour. Prior to measuring the electrochemical luminescence in a MSD™ Sector Imager 6000, the MSD™ plate was washed again and 150 uL/well of 2× Read Buffer T (MSD™R92TC-1) was added. Excel was used for data analysis and graph plotting.

An example data set is shown in FIG. 4 where the MSD™ signal is plotted against antibody concentration for DMS1529, DMS3000 and a mouse VEGF R2Fc control protein.

There is clear binding of all 3 proteins to mouse VEGF$_{164}$ in a concentration dependent manner indicating that the DAB™s cross-react with mouse VEGF$_{164}$.

TABLE 19

DNA and Amino Acid Sequence ID table

| Molecule ID | Molecule Description | DNA Sequence SEQ ID No. | Amino Acid Sequence SEQ ID No. |
|---|---|---|---|
| Vh dAb-Fc Sequences | | | |
| DMS1529 | DOM15-26-593-Fc dAb-Fc | 1<br>Also see FIG. 52C in WO2008/149150/A2. | 29<br>Also see FIG. 52A in WO2008/149150/A2. SEQ 1D 1 |
| DMS1576 | DOM15-26-597-Fc dAb-Fc | 2 | 30 |
| Vk dAb-Fc and Fc-dAb Sequences | | | |
| DMS30000 | C-terrninal Fc fusion of K-044-085 DAB ™ (GS(TVAARSGS)x3 Linker) Fc-dAb | 3 | 31 |
| DMS30001 | C-terminal Fc fusion of K-044-232 DAB ™ (GS(TVAAPSGS)x3 Linker) Fc-dAb | 4 | 32 |
| DMS30002 | C-terminal Fc fusion of K-044-236 DAB ™ (GS(TVAAPSGS)x3 Linker) Fc-dAb | 5 | 33 |
| DMS30003 | C-terminal Fc fusion of K-044-251 DAB ™ (GS(TVAAPSGS)x3 Linker) Fc-dAb | 6 | 34 |
| DMS30004 | C-terminal Fc fusion of K-044-255 DAB ™ (GS(TVAAPSGS)x3 Linker) Fc-dAb | 7 | 35 |
| DMS30005 | N-terminal Fc fusion of K-044-251 DAB ™ (AAAS Linker) dAb-Fc | 8 | 36 |
| DMS30006 | N-terminal Fc fusion of K-044-255 DAB ™ (AAAS Linker) dAb-Fc | 9 | 37 |
| DMS30013 | C-terrninal Fc fusion of K-044-085 DAB ™ (Albumin Domain 3 Linker) Fc-dAb | 16 | 44 |
| DMS30014 | C-terminal Fc fusion of K-044-085 DAB ™ (Albumin Domain 3 Linker) Fc-dAb | 17 | 45 |
| DMS30015 | C-terminal Fc fusion of K-044-251 DAB ™ (Albumin Domain 3 Linker) Fc-dAb | 18 | 46 |
| DMS30016 | C-terminal Fc fusion of K-044-251 DAB ™ (Albumin Domain 3 Linker) Fc-dAb | 19 | 47 |
| DMS30017 | N-terminal Fc fusion of K-044-085 DAB ™ (TVAAPS Linker) dAb-Fc | 20 | 48 |
| DMS30018 | N-terminal Fc fusion of K-044-232 DAB ™ (TVAAPS Linker) dAb-Fc | 21 | 49 |
| DMS30019 | N-terminal Fc fusion of K-044-236 DAB ™ (TVAAPS Linker) dAb-Fc | 22 | 50 |
| DMS30020 | N-terminal Fc fusion of K-044-251 DAB ™ (TVAAPS Linker) dAb-Fc | 23 | 51 |
| DMS30021 | N-teriminal Fc fusion of K-044-255 DAM ™ (TVAAPS linker) dAb-Fc | 24 | 52 |
| Vh-Vk and Vk-Vk DAb-Fc-DAB ™ Sequences | | | |
| DMS30007 | DOM15-26-597-AS Linker-Fc-Albumin Domain 3 Linker-DT02-K-044-085 Vh-Vk DAb-Fc-dAb | 10 | 38 |
| DMS30008 | DOM15-26-597-AS Linker-Fc-Albumin Domain 3 Linker-DT02-K-044-251 Vh-Vk DAb-Fc-dAb | 11 | 39 |
| DMS30009 | DT02-K-044-085-AS Linker-Fc-Albumin Domain 3 Linker-DT02-K-044-085 Vk-Vk DAb-Fc-dAb | 12 | 40 |
| DMS30010 | DT02-K-044-085-AAAS Linker-Fc-Albumin Domain 3 Linker-DT02-K-044-085 Vk-Vk DAb-Fc-dAb | 13 | 41 |
| DMS30011 | DT02-K-044-251-AS Linker-Fc-Albumin Domain 3 Linker-DT02-K-044-251 Vk-Vk DAb-Fc-dAb | 14 | 42 |
| DMS30012 | DT02-K-044-251-AAAS Linker-Fc-Albumin Domain 3 Linker-DT02-K-044-251 Vk-Vk DAb-Fc-dAb | 15 | 43 |

TABLE 19-continued

DNA and Amino Acid Sequence ID table

| Molecule ID | Molecule Description | DNA Sequence SEQ ID No. | Amino Acid Sequence SEQ ID No. |
|---|---|---|---|
| DMS30022 | DOM15-26-597-AS Linker-Fc-GS(TVAAPSGS)x3 Linker-DT02-K-044-085 Vh-Vk DAb-Fc-dAb | 25 | 53 |
| DMS30023 | DT02-K-044-085-HingeIgG1Linker-Fc-GS(TVAAPSGS)x3 Linker-DT02-K-044-085 Vh-Vk DAb-Fc-dAb | 26 | 54 |
| DMS30024 | DT02-K-044-085-AS-Fc (H112A)-GS(TVAAPSGS)x3 Linker-DT02-K-044-085 Vh-Vk DAb-Fc-dAb | 27 | 55 |
| DMS30025 | DT02-K-044-085-AS-Fc (T113P)-GS(TVAAPSGS)x3 Linker-DT02-K-044-085 Vh-Vk DAb-Fc-dAb | 28 | 56 |
| Linker Sequences | | | |
| AAAS Linker | N-terminal Linker | 57 | 76 |
| AS Linker | N-terminal Linker | 58 | 77 |
| TVAAPS Linker | N-terminal Linker | 59 | 78 |
| Hinge IgG1 Linker | N-terminal Linker | 60 | 79 |
| Hinge IgG3 Linker | N-terminal Linker | 61 | 80 |
| Fibronectin x3 Linker | N-terminal Linker | 62 | 81 |
| Fibronectin x4 Linker | N-terminal Linker | 63 | 82 |
| ((GS(TVAAPSGS)x3)) Linker | C-terminal Linker | 66 | 85 |
| Fibronectin x3 Linker | C-terminal Linker | 67 | 86 |
| Fibronectin x4 Linker | C-terminal Linker | 68 | 87 |
| Albumin Domain 1 Linker | C-terminal Linker | 69 | 88 |
| Albumin Domain 2 Linker | C-terminal Linker | 70 | 89 |
| Albumin Domain 3 Linker | C-terminal Linker | 71 | 90 |
| Truncated Albumin Domain3 Linker; Alb Dom 3-TFHAD | C-terminal Linker | 72 | 91 |
| Gly4Ser 3x Linker | C-terminal Linker | 73 | 92 |
| Gly4Ser 4x Linker | C-terminal Linker | 74 | 93 |
| Helical Linker | C-terminal Linker | 75 | 94 |
| DAB ™ Sequences | | | |
| DOM15-26-593 | | 95 | 103 |
| DOM15-26-597 | | 96 | 104 |
| DT02-K-044-085 | | 97 | 105 |
| DT02-K-044-232 | | 98 | 106 |
| DT02-K-044-236 | | 99 | 107 |
| DT02-K-044-251 | | 100 | 108 |
| DT02-K-044-255 | | 101 | 109 |
| Fc Sequences | | | |
| Fc IgG1 | | 102 | 110 |
| H2A IgG1 Fc | | 64 | 83 |
| T3P IgG1 Fc | | 65 | 84 |
| CDR Sequences (According to Kabat) | | | |
| DOM15-26-593 CDR1 | | | 111 |
| DOM15-26-593 CDR2 | | | 112 |
| DOM15-26-593 CDR3 | | | 113 |
| DOM15-26-597 CDR1 | | | 114 |
| DOM15-26-597 CDR2 | | | 115 |
| DOM15-26-597 CDR3 | | | 116 |
| DT02-K-044-085 CDR1 | | | 117 |
| DT02-K-044-085 CDR2 | | | 118 |
| DT02-K-044-085 CDR3 | | | 119 |
| DT02-K-044-232 CDR1 | | | 120 |
| DT02-K-044-232 CDR2 | | | 121 |
| DT02-K-044-232 CDR3 | | | 122 |
| DT02-K-044-236 CDR1 | | | 123 |
| DT02-K-044-236 CDR2 | | | 124 |
| DT02-K-044-236 CDR3 | | | 125 |
| DT02-K-044-251 CDR1 | | | 126 |
| DT02-K-044-251 CDR2 | | | 127 |
| DT02-K-044-251 CDR3 | | | 128 |
| DT02-K-044-255 CDR1 | | | 129 |
| DT02-K-044-255 CDR2 | | | 130 |
| DT02-K-044-255 CDR3 | | | 131 |

TABLE 19-continued

DNA and Amino Acid Sequence ID table

| Molecule ID | Molecule Description | DNA Sequence SEQ ID No. | Amino Add Sequence SEQ ID No. |
|---|---|---|---|
| Vh dAb-Fc Sequences | | | |
| DMS30030 | N-ferminal Fc fusion of DOM15-26-597 DAB ™ ((TGLDSP)x3) | 132 | 155 |
| DMS30031 | N-terminal Fc fusion of DOM15-26-597 DAB ™ ((TGLDSP)x4) | | 156 |
| DMS30032 | N-terrninal Fc fusion of DOM15-26-597 DAB ™ ((TGLDSP)x3 T113P mutation Fc) | 133 | 157 |
| DMS30033 | N-terminal Fc fusion of DOM15-26-597 DAB ™ ((TGLDSP)x4 T113P mutation Fc) | 134 | 158 |
| DMS30042 | N-terminal Fc fusion of DOM15-26-597 DAB ™ IgG1 Hinge) | | 159 |
| N597 IgG3 | N-terminal Fc fusion of 15-26-597 DAB ™ (IgG3 Hinge) | | 160 |
| N597 TVAAPS | N-terminal Fc fusion of 15-26-597 DAB ™ (TVAAPS) | | 161 |
| Vk dAb-Fc and Fc-dAb Sequences | | | |
| DMS30026 | C-terminal Fc fusion of K-044-085 DAB ™ ((TGLDSP)x4) | | 162 |
| DMS30027 | C-terminal Fc fusion of K-044-085 DAB ™ (Helical Linker) | | 163 |
| DMS30028 | N-terminai Fc fusion of K-044-085 DAB ™ (IgG1 Hinge) | | 164 |
| DMS30029 | N-terminal Fc fusion of K-044-085 DAB ™ (ASTHP linker) | | 165 |
| N085 fib x4 | N-terminal Fc fusion of K-044-085 DAB ™ ((TGLDSP)x4) | | 166 |
| N085 TVAAPS | N-terminal Fc fusion of K-044-085 DAB ™ (TVAAPS) | | 167 |
| N085 fib x3 | N-terminal Fc fusion of K-044-085 DAB ™ ((TGLDSP)x3) | | 168 |
| N085 IgG3 | N-terminal Fc fusion of K-044-085 DAB ™ (IgG3 Hinge) | | 169 |
| N085 H2A | N-terminal Fc fusion of K-044-085-AS-Fc (H112A) | | 170 |
| C085 fib x3 | C-terminal Fc fusion of K-044-085 DAB ™ ((TGLDSP)x3) | | 171 |
| C085 alb d 1 | C-terminal Fc fusion of K-044-085 DAB ™ (Albumin Domain 1) | | 172 |
| C085 alb d 2 | C-terminal Fc fusion of K-044-085 DAB ™ (Albumin Domain 2) | | 173 |
| C085 alb d 3-TFHAD | C-terminal Fc fusion of K-044-085 DAB ™ (Albumin Domain 3-TFHAD) | | 174 |
| C085 G4Sx3 | C-terminal Fc fusion of K-044-085 DAB ™ ((Gly4Ser)x3) | | 175 |
| C085 G4Sx4 | C-terminal Fc fusion of K-044-085 DAB ™ ((Gly4Ser)x4) | | 176 |
| Vh-Vk and Vk-Vk DAb-Fc-dAb Sequences | | | |
| DMS30034 | K-044-085 DAB ™ N-(VEPKSSDK linker) & C-terminal ((TGLDSP)x4) | 135 | 177 |
| DMS30035 | K-044-085 DAB ™ linker) & C-terminal ((TGLDSP)x4) | 136 | 178 |
| DMS30036 | DOM15-26-597 DAB ™ N-((TGLDSP)x3) & C-terminal K-044-085 DAB ™ ((TGLDSP)x4) | 137 | 179 |
| DMS30037 | DOM15-26-597 DAB ™ N-(VEPKSSDK linker) & C-terminal K-044-085 DAB ™ ((TGLDSP)x4) | 138 | 180 |
| DMS30038 | DMS1576 with C-terminal K-044-085 DAB ™ ((TGLDSP)x4) | 139 | 181 |
| DMS30039 | DOM15-26-597 DAB ™ N-((TGLDSP)x4) & C-terminal K-044-085 DAB ™ ((TGLDSP)x4) | 140 | 182 |
| DMS30040 | DOM15-26-597 DAB ™ N-((TGLDSP)x3 T113P mutation Fc) & C-terrninal K-044-085 DAB ™ ((TGLDSP)x4) | 141 | 183 |

TABLE 19-continued

DNA and Amino Acid Sequence ID table

| Molecule ID | Molecule Description | DNA Sequence SEQ ID No. | Amino Add Sequence SEQ ID No. |
|---|---|---|---|
| DMS30041 | DOM15-26-597 DAB ™ N-((TGLDSP)x4 T113P mutation Fc) & C-terminal K-044-085 DAB ™ ((TGLDSP)x4) | 142 | 184 |
| DMS30043 | K-044-085 DAB ™ N-(VEPKSSDK linker) & C-terminal ((TGLDSP)x4) Codon optimised | 143 | 177 |
| DMS30044 | DOM15-26-597 DAB ™ N-((TGLDSP)x3) & C-terminal K-044-085 DAB ™ ((TGLDSP)x4) Codon optimised | 144 | 179 |
| DMS30045 | DOM15-26-597 DAB ™ N-(VEPKSSDK linker) & C-terminal K-044-085 DAB ™ ((TGLDSP)x4) Codon optimised | 145 | 180 |
| DMS30046 | DMS1576 with C-terminal K-044-085 DAB ™ ((TGLDSP)x4) Codon optimised | 146 | 181 |
| DMS30047 | DOM15-26-597 DAB ™ N-(VEPKSSDK linker) & C-terminal K-044-085 DAB ™ minus C-term R ((TGLDSP)x4) Codon optimised | 147 | 185 |
| DMS30048 | DOM15-26-597 DAB ™ N-(VEPKSSDK linker) & C-terminal K-044-085 DAB ™ + A ((TGLDSP)x4) Codon optimised | 148 | 186 |
| DMS30049 | DOM15-26-597 DAB ™ N-(VEPKSSDK linker) & C-terminal K-044-085 DAB ™ + AAA ((TGLDSP)x4) Codon optimised | 149 | 187 |
| DMS30050 | DOM15-26-597 DAB ™ N-(VEPKSSDK linker) & C-terminal K-044-085 DAB ™ + T ((TGLDSP)x4) Codon optimised | 150 | 188 |
| DMS30051 | DMS1576 with C-terminal K-044-085 DAB ™ minus C-term R ((TGLDSP)x4) Codon optimised | 151 | 189 |
| DMS30052 | DMS1576 with C-terrminal K-044-085 DAB ™ + A ((TGLDSP)x4) Codon optimised | 152 | 190 |
| DMS30053 | DM51576 with C-terrninal K-044-085 DAB ™ + AAA (TGLDSP)x4) Codon optimised | 153 | 191 |
| DMS30054 | DMS1576 with C-terminal K-044-085 DAB ™ + T ((TGLDSP)x4) Codon optimised | 154 | 192 |

The material in the ASCII text file named PB64717USNatlSeqList2016rev2.txt, created on May 11, 2016 and having a size of 369,043 bytes is incorporated herein by reference in its entirety.

The invention claimed is:

1. An antigen binding construct comprising two immunoglobulin single variable domains separated by a single heavy chain constant region of an IgG or IgA antibody comprising one or more CH1, CH2, and CH3 constant region antibody domains, wherein each immunoglobulin single variable domain is capable of binding to VEGF and further wherein the first immunoglobulin single variable domain is attached to the N-terminus of the single heavy chain constant region and comprises the CDR sequences of SEQ ID NOs: 114, 115, and 116, and the second immunoglobulin single variable domain is attached to the C-terminus of the single heavy chain constant region and comprises the CDR sequences of SEQ ID NOs: 117, 118, and 119.

2. An antigen binding construct according to claim 1, wherein the first immunoglobulin single variable domain comprises SEQ ID NO: 104.

3. An antigen binding construct according to claim 1, wherein the second immunoglobulin single variable domain comprises SEQ ID NO: 105.

4. An antigen binding construct according to claim 1, wherein the single heavy chain constant region comprises one or more of the CH1, CH2 and CH3 constant region antibody domains, and optionally a hinge region.

5. An antigen binding construct according to claim 4, wherein the single heavy chain constant region comprises the IgG1 sequence of SEQ ID NO: 110.

6. An antigen binding construct according to claim 1, wherein each of the first and second immunoglobulin single variable domains is attached to the single heavy chain constant region through a linker.

7. An antigen binding construct according to claim 6, wherein the linker through which the first immunoglobulin single variable domain attaches to the N-terminus of the single heavy chain constant region comprises SEQ ID NO: 79 or SEQ ID NO: 77.

8. An antigen binding construct according to claim 6, wherein the linker through which the second immunoglobulin single variable domain attaches to the C-terminus of the constant region comprises SEQ ID NO: 87.

9. An antigen binding construct according to claim 1, which comprises SEQ ID NO: 180 or SEQ ID NO: 188.

10. An antigen binding construct according to claim 1, wherein one or more immunoglobulin single variable domains comprise:
a C-terminal sequence consisting of the sequence VTVS(S)nX as shown in SEQ ID NO: 219 for a VH immunoglobulin single variable domain or VEI(K)p(R)qX as shown in SEQ ID NO: 220 for a VL immunoglobulin single variable domain;
wherein:
n represents an integer independently selected from 0 or 1;
p and q each represent 0 or 1 such that when p represents 1 q may be 0 or 1 and such that when p represents 0, q also represents 0;
X may be present or absent, and if present represents an amino acid extension of 1 to 8 amino acids residues.

11. An antigen binding construct according to claim 10, wherein for a VL domain the C-terminal sequence is VEI(K)p(R)X and p is 1, q is 1 and X is A, AAA or T.

12. A dimer comprising two antigen binding constructs according to claim 1, wherein said dimer is a heterodimer or homodimer.

13. A pharmaceutical composition comprising a dimer according to claim 12, and one or more pharmaceutically acceptable carrier(s).

14. A dimer according to claim 12, for use in medicine.

15. A dimer according to claim 12, for use in the treatment of ocular diseases wherein the ocular disease is diabetic macular edema (DME), wet age-related macular degeneration (AMD), diabetic retinopathy, retinal vein occlusion (RVO), or corneal neovascularisation.

16. A dimer according to claim 12, for use in the treatment of cancer.

17. An antigen binding construct produced by a method for the production of an antigen binding construct which method comprises the step of culturing a host cell comprising one or more polynucleotide sequences encoding an antigen binding construct and isolating the antigen binding construct, whereby the antigen binding construct is produced, wherein the antigen binding construct comprises two immunoglobulin single variable domains separated by a single heavy chain constant region of an IgG or IgA antibody comprising one or more CH1, CH2, and CH3 constant region antibody domains, wherein each immunoglobulin single variable domain is capable of binding to VEGF and further wherein the first immunoglobulin single variable domain is attached to the N-terminus of the single heavy chain constant region and comprises the CDR sequences of SEQ ID NOs: 114, 115, and 116, and the second immunoglobulin single variable domain is attached to the C-terminus of the single heavy chain constant region and comprises the CDR sequences of SEQ ID NOs: 117, 118, and 119.

* * * * *

```
                        SEQUENCE LISTING

<160> NUMBER OF SEQ ID NOS: 220

<210> SEQ ID NO 1
<211> LENGTH: 1029
<212> TYPE: DNA
<213> ORGANISM: Artificial Sequence
<220> FEATURE:
<223> OTHER INFORMATION: DOM15-26-593-Fc dAb-Fc nucleic acid
      sequence identified using molecular
      biology techniques.

<400> SEQUENCE: 1
gaggtgcagc tgttggtgtc tgggggaggc ttggtacagc ctggggggtc cctgcgtctc        60
tcctgtgcag cctccggatt caccttaag gcttatccga tgatgtgggt ccgccaggct       120
```

| | |
|---|---|
| ccagggaagg gtctagagtg ggtttcagag atttcgcctt cggggttctta tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaagatcct | 300 |
| cggaagttag actactgggg tcagggaacc ctggtcaccg tctcgagcgc tagcacccac | 360 |
| acctgccccc cctgccctgc ccccgagctg ctgggcggac ctagcgtgtt cctgttcccc | 420 |
| cccaagccta aggacaccct gatgatcagc aggaccccg aagtgacctg cgtggtggtg | 480 |
| gatgtgagcc acgaggaccc tgaagtgaag ttcaactggt acgtggacgg cgtggaagtg | 540 |
| cacaacgcca agaccaagcc cagagaggag cagtacaaca gcacctaccg cgtggtgtct | 600 |
| gtgctgaccg tgctgcacca ggattggctg aacggcaagg agtacaagtg caaagtgagc | 660 |
| aacaaggccc tgcctgcccc tatcgagaaa accatcagca aggccaaggg ccagcctaga | 720 |
| gagccccagg tctacaccct gcctccctcc agagatgagc tgaccaagaa ccaggtgtcc | 780 |
| ctgacctgtc tggtgaaggg cttctacccc agcgacatcg ccgtggagtg ggagagcaac | 840 |
| ggccagcccg agaacaacta caagaccacc cccctgtgc tggacagcga tggcagcttc | 900 |
| ttcctgtact ccaagctgac cgtggacaag agcagatggc agcagggcaa cgtgttcagc | 960 |
| tgcagcgtga tgcacgaggc cctgcacaat cactacaccc agaagagtct gagcctgtcc | 1020 |
| cctggcaag | 1029 |

<210> SEQ ID NO 2
<211> LENGTH: 1029
<212> TYPE: DNA
<213> ORGANISM: Artificial Sequence
<220> FEATURE:
<223> OTHER INFORMATION: DOM15-26-597-Fc dAb-Fc nucleic acid
      sequence identified using molecular
      biology techniques.

<400> SEQUENCE: 2

| | |
|---|---|
| gaggtgcagc tgctggtgtc tggcggcgga ctggtgcagc ctggcggcag cctgagactg | 60 |
| agctgcgccg ccagcggctt caccttcaag gcctacccca tgatgtgggt gcggcaggcc | 120 |
| cctggcaagg gcctggaatg ggtgtccgag atcagcccca gcggcagcaa cacctactac | 180 |
| gccgacagcg tgaagggccg gttcaccatc agccgggaca acagcaagaa caccctgtac | 240 |
| ctgcagatga acagcctgcg ggccgaggac accgccgtgt actactgcgc caaggacccc | 300 |
| cggaagctgg actactgggg ccagggcacc ctggtgaccg tgagcagcgc tagcacccac | 360 |
| acctgccccc cctgccctgc ccctgagctg ctgggcggac cacgtgtt cctgttcccc | 420 |
| cccaagccca aggacaccct gatgatcagc cggaccccg aggtgacctg cgtggtggtg | 480 |
| gacgtgagcc acgaggaccc tgaggtgaag ttcaattggt acgtggacgg cgtggaggtg | 540 |
| cacaacgcca agaccaagcc ccgggaggaa cagtacaaca gcacctaccg ggtggtgtcc | 600 |
| gtgctgaccg tgctgcacca ggactggctg aacggcaaag aatacaagtg caaggtgtcc | 660 |
| aacaaggccc tgcctgcccc catcgagaaa accatcagca aggccaaggg ccagcccagg | 720 |
| gaaccccagg tgtacaccct gccccccagc cgggacgagc tgaccaagaa ccaggtgtcc | 780 |
| ctgacctgcc tggtgaaggg cttctacccc agcgacatcg ccgtggagtg ggagagcaac | 840 |
| ggccagcccg agaacaacta caagaccacc cccctgtgc tggacagcga cggcagcttc | 900 |
| ttcctgtaca gcaagctgac cgtggacaag agcggtggc agcagggcaa cgtgttcagc | 960 |
| tgcagcgtga tgcacgaggc cctgcacaac cactacaccc agaagagcct gagcctgtcc | 1020 |
| cccggcaag | 1029 |

<210> SEQ ID NO 3
<211> LENGTH: 1095
<212> TYPE: DNA
<213> ORGANISM: Artificial Sequence
<220> FEATURE:
<223> OTHER INFORMATION: C-terminal Fc fusion of K-044-085 DAB
      (GS(TVAAPSGS)x3 Linker) Fc-dAb nucleic acid
      sequence identified using molecular biology techniques.

<400> SEQUENCE: 3

```
caggctagct ctgacaagac ccacacctgc cccccctgcc ctgcccccga gctgctggga      60
ggccccagcg tgttcctgtt ccccccaag cctaaggaca ccctgatgat cagcagaacc     120
cccgaggtga cctgtgtggt ggtggatgtg agccacgagg accctgaggt gaagttcaac    180
tggtacgtgg acggcgtgga ggtgcacaat gccaagacca gcccaggga ggagcagtac    240
aacagcacct accgggtggt gtccgtgctg accgtgctgc accaggattg gctgaacggc    300
aaggagtaca gtgtaaggt gtccaacaag gccctgcctg ccctatcga aaaaccatc      360
agcaaggcca agggccagcc cagagagccc caggtgtaca ccctgccccc tagcagagat    420
gagctgacca agaaccaggt gtccctgacc tgcctggtga agggcttcta ccccagcgac    480
atcgccgtgg agtgggagag caacggccag cccgagaaca actacaagac cacccccct    540
gtgctggaca gcgatggcag cttcttcctg tacagcaagc tgaccgtgga caagagcaga    600
tggcagcagg gcaacgtgtt cagctgctcc gtgatgcacg aggccctgca caatcactac    660
acccagaaga gcctgagcct gtcccctggc aagggatcta ccgtggcagc caccaggaa    720
tctaccgtgg cagcaccatc aggttcaaca gtagctgctc cttctggatc cgacatccag    780
atgacccagt ctccatcctc cctgtctgca tctgtaggag accgtgtcac catcacttgc    840
cgggcaagtc agtggattgg tcctgagtta agtggtacc agcagaaacc agggaaagcc    900
cctaagctcc tgatctatca tggttccatt ttgcaaagtg ggggtcccatc acgtttcagt   960
ggcagtggat ctgggacaga cttcactctc accatcagca gtctgcaacc tgaagattt   1020
gctacgtact actgtcaaca gtatatgtat tatcctcata cgttcggcca agggaccaag   1080
gtggaaatca aacgt                                                    1095
```

<210> SEQ ID NO 4
<211> LENGTH: 1095
<212> TYPE: DNA
<213> ORGANISM: Artificial Sequence
<220> FEATURE:
<223> OTHER INFORMATION: C-terminal Fc fusion of K-044-232 DAB
      (GS(TVAAPSGS)x3 Linker) Fc-dAb nucleic acid
      sequence identified using molecular biology techniques.

<400> SEQUENCE: 4

```
caggctagct ctgacaagac ccacacctgc cccccctgcc ctgcccccga gctgctggga      60
ggccccagcg tgttcctgtt ccccccaag cctaaggaca ccctgatgat cagcagaacc     120
cccgaggtga cctgtgtggt ggtggatgtg agccacgagg accctgaggt gaagttcaac    180
tggtacgtgg acggcgtgga ggtgcacaat gccaagacca gcccaggga ggagcagtac    240
aacagcacct accgggtggt gtccgtgctg accgtgctgc accaggattg gctgaacggc    300
aaggagtaca gtgtaaggt gtccaacaag gccctgcctg ccctatcga aaaaccatc      360
agcaaggcca agggccagcc cagagagccc caggtgtaca ccctgccccc tagcagagat    420
gagctgacca agaaccaggt gtccctgacc tgcctggtga agggcttcta ccccagcgac    480
```

```
atcgccgtgg agtgggagag caacggccag cccgagaaca actacaagac caccccccct    540
gtgctggaca gcgatggcag cttcttcctg tacagcaagc tgaccgtgga caagagcaga    600
tggcagcagg gcaacgtgtt cagctgctcc gtgatgcacg aggccctgca caatcactac    660
acccagaaga gcctgagcct gtcccctggc aagggatcta ccgtggcagc accatcagga    720
tctaccgtgg cagcaccatc aggttcaaca gtagctgctc cttctggatc cgacatccag    780
atgacccagt ctccatcctc cctgtctgca tctgtaggag accgtgtcac catcacttgc    840
cgggcaagtc agtggattgg tcctgagtta agttggtacc agcagaaacc agggaaagcc    900
cctaagctcc tgatctatca tggttccatt ttgcaaagtg gggtcccatc acgtttcagt    960
ggcagtggat ctgggacaga cttcactctc accatcagca gtctgcaacc tgaagatttt    1020
gctacgtact actgtcaaca gtatatgtat tatcctgaga cgttcggcca agggaccaag    1080
gtggaaatca aacgt                                                     1095
```

<210> SEQ ID NO 5
<211> LENGTH: 1095
<212> TYPE: DNA
<213> ORGANISM: Artificial Sequence
<220> FEATURE:
<223> OTHER INFORMATION: C-terminal Fc fusion of K-044-236 DAB
    (GS(TVAAPSGS)x3 Linker) Fc-dAb nucleic acid
    sequence identified using molecular biology techniques.

<400> SEQUENCE: 5

```
caggctagct ctgacaagac ccacacctgc cccccctgcc ctgccccccga gctgctggga    60 ggccccagcg tgttcctgtt cccccccaag cctaaggaca ccctgatgat cagcagaacc    120
cccgaggtga cctgtgtggt ggtggatgtg agccacgagg accctgaggt gaagttcaac    180
tggtacgtgg acggcgtgga ggtgcacaat gccaagacca gcccaggga ggagcagtac    240 aacagcacct accgggtggt gtccgtgctg accgtgctgc accaggattg gctgaacggc    300
aaggagtaca gtgtaaggt gtccaacaag gccctgcctg cccctatcga gaaaaccatc    360
agcaaggcca agggccagcc cagagagccc caggtgtaca ccctgccccc tagcagagat    420
gagctgacca gaaccaggt gtccctgacc tgcctggtga agggcttcta ccccagcgac    480
atcgccgtgg agtgggagag caacggccag cccgagaaca actacaagac caccccccct    540
gtgctggaca gcgatggcag cttcttcctg tacagcaagc tgaccgtgga caagagcaga    600
tggcagcagg gcaacgtgtt cagctgctcc gtgatgcacg aggccctgca caatcactac    660
acccagaaga gcctgagcct gtcccctggc aagggatcta ccgtggcagc accatcagga    720
tctaccgtgg cagcaccatc aggttcaaca gtagctgctc cttctggatc cgacatccag    780
atgacccagt ctccatcctc cctgtctgca tctgtaggag accgtgtcac catcacttgc    840
cgggcaagtc agtggattgg tcctgagtta agttggtacc agcagaaacc agggaaagcc    900
cctaagctcc tgatctatca tggttccatt ttgcaaagtg gggtcccatc acgtttcagt    960
ggcagtggat ctgggacaga cttcactctc accatcagca gtctgcaacc tgaagatttt    1020
gctacgtact actgtcaaca gtatatgtat tatcctaaga cgttcggcca agggaccaag    1080
gtggaaatca aacgt                                                     1095
```

<210> SEQ ID NO 6
<211> LENGTH: 1095
<212> TYPE: DNA
<213> ORGANISM: Artificial Sequence
<220> FEATURE:
<223> OTHER INFORMATION: C-terminal Fc fusion of K-044-251 DAB (GS(TVAAPSGS)x3 Linker) Fc-dAb nucleic acid
sequence identified using molecular biology techniques.

<400> SEQUENCE: 6

```
caggctagct ctgacaagac ccacacctgc cccccctgcc ctgccccga gctgctggga      60 ggccccagcg tgttcctgtt ccccccaag cctaaggaca ccctgatgat cagcagaacc     120
cccgaggtga cctgtgtggt ggtggatgtg agccacgagg accctgaggt gaagttcaac     180
tggtacgtgg acggcgtgga ggtgcacaat gccaagacca gcccaggga ggagcagtac     240 aacagcacct accgggtggt gtccgtgctg accgtgctgc accaggattg gctgaacggc     300
aaggagtaca gtgtaaggt gtccaacaag gccctgcctg cccctatcga aaaaccatc     360 agcaaggcca agggccagcc cagagagccc caggtgtaca ccctgccccc tagcagagat     420
gagctgacca agaaccaggt gtccctgacc tgcctggtga agggcttcta ccccagcgac     480
atcgccgtgg agtgggagag caacggccag cccgagaaca actacaagac cacccccct     540 gtgctggaca gcgatggcag cttcttcctg tacagcaagc tgaccgtgga caagagcaga     600
tggcagcagg gcaacgtgtt cagctgctcc gtgatgcacg aggccctgca caatcactac     660
acccagaaga gcctgagcct gtcccctggc aagggatcta ccgtggcagc accatcagga     720
tctaccgtgg cagcaccatc aggttcaaca gtagctgctc cttctggatc cgacatccag     780
atgacccagt ctccatcctc cctgtctgca tctgtaggag accgtgtcac catcacttgc     840
cgggcaagtc agtggattgg tcctgagtta agtggtacc agcagaaacc agggaaagcc     900
cctaagctcc tgatctatca tggttccatt ttgcaaagtg gggtcccatc acgtttcagt     960
ggcagtggat ctgggacaga cttcactctc accatcagca gtctgcaacc tgaagatttt    1020
gctacgtact actgtcaaca gtatatgtat tatcctgaga cgttcggcca agggaccaag    1080
gtggaaatca aacgt                                                     1095
```

<210> SEQ ID NO 7
<211> LENGTH: 1095
<212> TYPE: DNA
<213> ORGANISM: Artificial Sequence
<220> FEATURE:
<223> OTHER INFORMATION: C-terminal Fc fusion of K-044-255 DAB
(GS(TVAAPSGS)x3 Linker) Fc-dAb nucleic acid
sequence identified using molecular biology techniques.

<400> SEQUENCE: 7

```
caggctagct ctgacaagac ccacacctgc cccccctgcc ctgccccga gctgctggga      60 ggccccagcg tgttcctgtt ccccccaag cctaaggaca ccctgatgat cagcagaacc     120
cccgaggtga cctgtgtggt ggtggatgtg agccacgagg accctgaggt gaagttcaac     180
tggtacgtgg acggcgtgga ggtgcacaat gccaagacca gcccaggga ggagcagtac     240 aacagcacct accgggtggt gtccgtgctg accgtgctgc accaggattg gctgaacggc     300
aaggagtaca gtgtaaggt gtccaacaag gccctgcctg cccctatcga aaaaccatc     360 agcaaggcca agggccagcc cagagagccc caggtgtaca ccctgccccc tagcagagat     420
gagctgacca agaaccaggt gtccctgacc tgcctggtga agggcttcta ccccagcgac     480
atcgccgtgg agtgggagag caacggccag cccgagaaca actacaagac cacccccct     540 gtgctggaca gcgatggcag cttcttcctg tacagcaagc tgaccgtgga caagagcaga     600
tggcagcagg gcaacgtgtt cagctgctcc gtgatgcacg aggccctgca caatcactac     660
acccagaaga gcctgagcct gtcccctggc aagggatcta ccgtggcagc accatcagga     720
```

| | |
|---|---|
| tctaccgtgg cagcaccatc aggttcaaca gtagctgctc cttctggatc cgacatccag | 780 |
| atgacccagt ctccatcctc cctgtctgca tctgtaggag accgtgtcac catcacttgc | 840 |
| cgggcaagtc agtggattgg tcctgagtta aagtggtacc agcagaaacc agggaaagcc | 900 |
| cctaagctcc tgatctatca tggttccatt ttgcaaagtg gggtcccatc acgtttcagt | 960 |
| ggcagtggat ctgggacaga cttcactctc accatcagca gtctgcaacc tgaagatttt | 1020 |
| gctacgtact actgtcaaca gtatatgtat tatcctaaga cgttcggcca agggaccaag | 1080 |
| gtggaaatca aacgt | 1095 |

<210> SEQ ID NO 8
<211> LENGTH: 1020
<212> TYPE: DNA
<213> ORGANISM: Artificial Sequence
<220> FEATURE:
<223> OTHER INFORMATION: N-terminal Fc fusion of K-044-251 DAB (AAAS
    Linker) dAb-Fc nucleic acid sequence
    identified using molecular biology techniques.

<400> SEQUENCE: 8

| | |
|---|---|
| gagtcgacgg acatccagat gacccagtct ccatcctccc tgtctgcatc tgtaggagac | 60 |
| cgtgtcacca tcacttgccg ggcaagtcag tggattggtc tgagttaaa gtggtaccag | 120 |
| cagaaaccag ggaaagcccc taagctcctg atctatcatg gttccatttt gcaaagtggg | 180 |
| gtcccatcac gtttcagtgg cagtggatct gggacagact tcactctcac catcagcagt | 240 |
| ctgcaacctg aagattttgc tacgtactac tgtcaacagt atatgtatta tcctgagacg | 300 |
| ttcggccaag gaccaaggt ggaaatcaaa cgggcggccg ctagcaccca cacctgcccc | 360 |
| ccctgccctg ccccgagct gctgggcgga cctagcgtgt tcctgttccc cccaagcct | 420 |
| aaggacaccc tgatgatcag caggaccccc gaagtgacct gcgtggtggt ggatgtgagc | 480 |
| cacgaggacc ctgaagtgaa gttcaactgg tacgtggacg gcgtggaagt gcacaacgcc | 540 |
| aagaccaagc cagagagga gcagtacaac agcacctacc gcgtggtgtc tgtgctgacc | 600 |
| gtgctgcacc aggattggct gaacggcaag gagtacaagt gcaaagtgag caacaaggcc | 660 |
| ctgcctgccc ctatcgagaa aaccatcagc aaggccaagg ccagcctag agagcccag | 720 |
| gtctacaccc tgcctcccc cagagatgag ctgaccaaga accaggtgtc cctgacctgt | 780 |
| ctggtgaagg gcttctaccc cagcgacatc gccgtggagt gggagagcaa cggccagccc | 840 |
| gagaacaact acaagaccac cccccctgtg ctggacagcg atggcagctt cttcctgtac | 900 |
| tccaagctga ccgtggacaa gagcagatgg cagcagggca acgtgttcag ctgcagcgtg | 960 |
| atgcacgagg ccctgcacaa tcactacacc cagaagagtc tgagcctgtc ccctggcaag | 1020 |

<210> SEQ ID NO 9
<211> LENGTH: 1020
<212> TYPE: DNA
<213> ORGANISM: Artificial Sequence
<220> FEATURE:
<223> OTHER INFORMATION: N-terminal Fc fusion of K-044-255 DAB (AAAS
    Linker) dAb-Fc nucleic acid sequence
    identified using molecular biology techniques.

<400> SEQUENCE: 9

| | |
|---|---|
| gagtcgacgg acatccagat gacccagtct ccatcctccc tgtctgcatc tgtaggagac | 60 |
| cgtgtcacca tcacttgccg ggcaagtcag tggattggtc tgagttaaa gtggtaccag | 120 |
| cagaaaccag ggaaagcccc taagctcctg atctatcatg gttccatttt gcaaagtggg | 180 |
| gtcccatcac gtttcagtgg cagtggatct gggacagact tcactctcac catcagcagt | 240 |

```
ctgcaacctg aagatttttgc tacgtactac tgtcaacagt atatgtatta tcctaagacg      300
ttcggccaag ggaccaaggt ggaaatcaaa cgggcggccg ctagcaccca cacctgcccc      360
ccctgccctg cccccgagct gctgggcgga cctagcgtgt tcctgttccc ccccaagcct      420
aaggacaccc tgatgatcag caggaccccc gaagtgacct gcgtggtggt ggatgtgagc      480
cacgaggacc ctgaagtgaa gttcaactgg tacgtggacg gcgtggaagt gcacaacgcc      540
aagaccaagc cagagagga gcagtacaac agcacctacc gcgtggtgtc tgtgctgacc      600
gtgctgcacc aggattggct gaacggcaag gagtacaagt gcaaagtgag caacaaggcc      660
ctgcctgccc ctatcgagaa aaccatcagc aaggccaagg ccagcctag agagccccag      720 gtctacaccc tgcctccctc cagagatgag ctgaccaaga accaggtgtc cctgacctgt      780
ctggtgaagg gcttctaccc cagcgacatc gccgtggagt gggagagcaa cggccagccc      840
gagaacaact acaagaccac ccccctgtg ctggacagcg atggcagctt cttcctgtac      900
tccaagctga ccgtggacaa gagcagatgg cagcagggca cgtgttcag ctgcagcgtg      960 atgcacgagg ccctgcacaa tcactacacc cagaagagtc tgagcctgtc cctggcaag    1020
```

<210> SEQ ID NO 10
<211> LENGTH: 1416
<212> TYPE: DNA
<213> ORGANISM: Artificial Sequence
<220> FEATURE:
<223> OTHER INFORMATION: DOM15-26-597-AS Linker-Fc-Albumin Domain 3
      Linker-DT02-K-044-085 Vh-Vk dAb-Fc-dAb nucleic acid
      sequence identified using molecular biology techniques.

<400> SEQUENCE: 10

```
gaggtgcagc tgctggtgtc tggcggcgga ctggtgcagc ctggcggcag cctgagactg       60
agctgcgccg ccagcggctt caccttcaag gcctacccca tgatgtgggt gcggcaggcc      120
cctggcaagg gcctggaatg ggtgtccgag atcagcccca gcggcagcaa cacctactac      180
gccgacagcg tgaagggccg gttcaccatc agccgggaca cagcaagaa caccctgtac      240 ctgcagatga acagcctgcg ggccgaggac accgccgtgt actactgcgc caaggacccc      300
cggaagctgg actactgggg ccagggcacc ctggtgaccg tgagcagcgc tagcacccac      360 acctgcccc cctgccctgc cccgagctg ctgggaggcc cagcgtgtt cctgttcccc      420 cccaagccta aggacaccct gatgatcagc agaacccccg aggtgacctg tgtggtggtg      480
gatgtgagcc acgaggaccc tgaggtgaag ttcaactggt acgtggacgg cgtggaggtg      540
cacaatgcca agaccaagcc cagggaggag cagtacaaca gcacctaccg ggtggtgtcc      600
gtgctgaccg tgctgcacca ggattggctg aacggcaagg agtacaagtg taaggtgtcc      660
aacaaggccc tgcctgcccc tatcgagaaa accatcagca aggccaaggg ccagcccaga      720
gagccccagg tgtacaccct gcccccctagc agagatgagc tgaccaagaa ccaggtgtcc      780
ctgacctgcc tggtgaaggg cttctacccc agcgacatcg ccgtggagtg ggagagcaac      840
ggccagcccg agaacaacta caagaccacc cccctgtgc tggacagcga tggcagcttc      900
ttcctgtaca gcaagctgac cgtggacaag agcagatggc agcagggcaa cgtgttcagc      960
tgctccgtga tgcacgaggc cctgcacaat cactacaccc agaagagcct gagcctgtcc     1020
cctggcaagg aggtggacga gacctacgtg cccaaggagt caacgccga ccttcacc     1080 ttccacgccg acgacatcca gatgacccag tctccatcct ccctgtctgc atctgtagga     1140
gaccgtgtca ccatcacttg ccgggcaagt cagtggattg tcctgagtt aaagtggtac     1200
```

| cagcagaaac cagggaaagc ccctaagctc ctgatctatc atggttccat tttgcaaagt | 1260 |
| ggggtcccat cacgtttcag tggcagtgga tctgggacag acttcactct caccatcagc | 1320 |
| agtctgcaac tgaagatttt tgctacgtac tactgtcaac agtatatgta ttatcctcat | 1380 |
| acgttcggcc aagggaccaa ggtggaaatc aaacgt | 1416 |

<210> SEQ ID NO 11
<211> LENGTH: 1416
<212> TYPE: DNA
<213> ORGANISM: Artificial Sequence
<220> FEATURE:
<223> OTHER INFORMATION: DOM15-26-597-AS Linker-Fc-Albumin Domain 3
      Linker-DT02-K-044-251 Vh-Vk dAb-Fc-dAb nucleic acid
      sequence identified using molecular biology techniques.

<400> SEQUENCE: 11

| gaggtgcagc tgctggtgtc tggcggcgga ctggtgcagc tggcggcag cctgagactg | 60 |
| agctgcgccg ccagcggctt caccttcaag gcctacccca tgatgtgggt gcggcaggcc | 120 |
| cctggcaagg gcctggaatg ggtgtccgag atcagcccca gcggcagcaa cacctactac | 180 |
| gccgacagcg tgaagggccg gttcaccatc agccgggaca acagcaagaa caccctgtac | 240 |
| ctgcagatga cagcctgcg ggccgaggac accgccgtgt actactgcgc caaggacccc | 300 |
| cggaagctgg actactgggg ccagggcacc ctggtgaccg tgagcagcgc tagcacccac | 360 |
| acctgccccc cctgccctgc ccccgagctg ctggaggcc ccagcgtgtt cctgttcccc | 420 |
| cccaagccta aggacaccct gatgatcagc agaaccccg aggtgacctg tgtggtggtg | 480 |
| gatgtgagcc acgaggaccc tgaggtgaag ttcaactggt acgtggacgg cgtggaggtg | 540 |
| cacaatgcca agaccaagcc cagggaggag cagtacaaca gcacctaccg ggtggtgtcc | 600 |
| gtgctgaccg tgctgcacca ggattggctg aacggcaagg agtacaagtg taaggtgtcc | 660 |
| aacaaggccc tgcctgcccc tatcgagaaa accatcagca aggccaaggg ccagcccaga | 720 |
| gagcccagg tgtacaccct gccccctagc agagatgagc tgaccaagaa ccaggtgtcc | 780 |
| ctgacctgcc tggtgaaggg cttctacccc agcgacatcg ccgtggagtg ggagagcaac | 840 |
| ggccagcccg agaacaacta caagaccacc cccctgtgc tggacagcga tggcagcttc | 900 |
| ttcctgtaca gcaagctgac cgtggacaag agcagatggc agcagggcaa cgtgttcagc | 960 |
| tgctccgtga tgcacgaggc cctgcacaat cactacaccc agaagagcct gagcctgtcc | 1020 |
| cctggcaagg aggtggacga gacctacgtg cccaaggagt caacgccga ccttcacc | 1080 |
| ttccacgccg acgacatcca gatgacccag tctccatcct ccctgtctgc atctgtagga | 1140 |
| gaccgtgtca ccatcacttg ccgggcaagt cagtggattg gtcctgagtt aaagtggtac | 1200 |
| cagcagaaac cagggaaagc ccctaagctc ctgatctatc atggttccat tttgcaaagt | 1260 |
| ggggtcccat cacgtttcag tggcagtgga tctgggacag acttcactct caccatcagc | 1320 |
| agtctgcaac tgaagatttt tgctacgtac tactgtcaac agtatatgta ttatcctgag | 1380 |
| acgttcggcc aagggaccaa ggtggaaatc aaacgt | 1416 |

<210> SEQ ID NO 12
<211> LENGTH: 1392
<212> TYPE: DNA
<213> ORGANISM: Artificial Sequence
<220> FEATURE:
<223> OTHER INFORMATION: DT02-K-044-085-AS Linker-Fc-Albumin Domain 3
      Linker-DT02-K-044-085 Vk-Vk dAb-Fc-dAb nucleic acid
      sequence identified using molecular biology techniques.

<400> SEQUENCE: 12

```
gacatccaga tgacccagtc tccatcctcc ctgtctgcat ctgtaggaga ccgtgtcacc    60
atcacttgcc gggcaagtca gtggattggt cctgagttaa gtggtacca gcagaaacca   120 gggaaagccc ctaagctcct gatctatcat ggttccattt tgcaaagtgg ggtcccatca   180
cgtttcagtg gcagtggatc tgggacagac ttcactctca ccatcagcag tctgcaacct   240
gaagattttg ctacgtacta ctgtcaacag tatatgtatt atcctcatac gttcggccaa   300
gggaccaagg tggaaatcaa acgtgctagc acccacacct gccccccctg ccctgccccc   360
gagctgctgg gaggccccag cgtgttcctg ttccccccca agcctaagga caccctgatg   420
atcagcagaa cccccgaggt gacctgtgtg gtggtggatg tgagccacga ggaccctgag   480
gtgaagttca actggtacgt ggacggcgtg gaggtgcaca atgccaagac caagcccagg   540
gaggagcagt acaacagcac ctaccgggtg gtgtccgtgc tgaccgtgct gcaccaggat   600
tggctgaacg gcaaggagta caagtgtaag gtgtccaaca aggccctgcc tgcccctatc   660
gagaaaacca tcagcaaggc caagggccag cccagagagc cccaggtgta caccctgccc   720
cctagcagag atgagctgac caagaaccag gtgtccctga cctgcctggt gaagggcttc   780
taccccagcg acatcgccgt ggagtgggag agcaacggcc agcccgagaa caactacaag   840
accacccccc ctgtgctgga cagcgatggc agcttcttcc tgtacagcaa gctgaccgtg   900
gacaagagca gatggcagca gggcaacgtg ttcagctgct ccgtgatgca cgaggccctg   960
cacaatcact acacccagaa gagcctgagc ctgtcccctg gcaaggaggt ggacgagacc  1020
tacgtgccca ggagttcaa cgccgagacc ttcaccttcc acgccgacga catccagatg  1080
acccagtctc catcctccct gtctgcatct gtaggagacc gtgtcaccat cacttgccgg  1140
gcaagtcagt ggattggtcc tgagttaaag tggtaccagc agaaaccagg aaagcccct  1200 aagctcctga tctatcatgg ttccattttg caaagtgggg tcccatcacg tttcagtggc  1260
agtggatctg ggacagactt cactctcacc atcagcagtc tgcaacctga agattttgct  1320
acgtactact gtcaacagta tatgtattat cctcatacgt tcggccaagg gaccaaggtg  1380
gaaatcaaac gt                                                     1392
```

<210> SEQ ID NO 13
<211> LENGTH: 1398
<212> TYPE: DNA
<213> ORGANISM: Artificial Sequence
<220> FEATURE:
<223> OTHER INFORMATION: DT02-K-044-085-AAAS Linker-Fc-Albumin Domain 3
      Linker-DT02-K-044-085 Vk-Vk dAb-Fc-dAb nucleic acid
      sequence identified using molecular biology techniques.

<400> SEQUENCE: 13

```
gacatccaga tgacccagtc tccatcctcc ctgtctgcat ctgtaggaga ccgtgtcacc    60
atcacttgcc gggcaagtca gtggattggt cctgagttaa gtggtacca gcagaaacca   120 gggaaagccc ctaagctcct gatctatcat ggttccattt tgcaaagtgg ggtcccatca   180
cgtttcagtg gcagtggatc tgggacagac ttcactctca ccatcagcag tctgcaacct   240
gaagattttg ctacgtacta ctgtcaacag tatatgtatt atcctcatac gttcggccaa   300
gggaccaagg tggaaatcaa acgtgccgct gctagcaccc acacctgccc ccctgcccct   360
gcccccgagc tgctgggagg ccccagcgtg ttcctgttcc ccccaagcc taaggacacc   420 ctgatgatca gcagaacccc cgaggtgacc tgtgtggtgg tggatgtgag ccacgaggac   480
cctgaggtga agttcaactg gtacgtggac ggcgtggagg tgcacaatgc caagaccaag   540
```

```
cccagggagg agcagtacaa cagcacctac cgggtggtgt ccgtgctgac cgtgctgcac      600
caggattggc tgaacggcaa ggagtacaag tgtaaggtgt ccaacaaggc cctgcctgcc      660
cctatcgaga aaccatcag caaggccaag ggccagccca gagagcccca ggtgtacacc      720
ctgcccccta gcagagatga gctgaccaag aaccaggtgt ccctgacctg cctggtgaag      780
ggcttctacc ccagcgacat cgccgtggag tgggagagca cggccagcc cgagaacaac      840 tacaagacca cccccctgt gctggacagc gatggcagct tcttcctgta cagcaagctg      900
accgtggaca gagcagatg gcagcagggc aacgtgttca gctgctccgt gatgcacgag      960
gccctgcaca tcactacac ccagaagagc ctgagcctgt cccctggcaa ggaggtggac     1020
gagacctacg tgcccaagga gttcaacgcc gagaccttca ccttccacgc cgacgacatc     1080
cagatgaccc agtctccatc ctccctgtct gcatctgtag agaccgtgt caccatcact     1140 tgccgggcaa gtcagtggat tggtcctgag ttaaagtggt accagcagaa accagggaaa     1200
gcccctaagc tcctgatcta tcatggttcc attttgcaaa gtggggtccc atcacgtttc     1260
agtggcagtg gatctgggac agacttcact ctcaccatca gcagtctgca acctgaagat     1320
tttgctacgt actactgtca acagtatatg tattatcctc atacgttcgg ccaagggacc     1380
aaggtggaaa tcaaacgt                                                   1398

<210> SEQ ID NO 14
<211> LENGTH: 1392
<212> TYPE: DNA
<213> ORGANISM: Artificial Sequence
<220> FEATURE:
<223> OTHER INFORMATION: DT02-K-044-251-AS Linker-Fc-Albumin Domain 3
      Linker-DT02-K-044-251 Vk-Vk dAb-Fc-dAb nucleic acid
      sequence identified using molecular biology techniques.

<400> SEQUENCE: 14
gacatccaga tgacccagtc tccatcctcc ctgtctgcat ctgtaggaga ccgtgtcacc       60
atcacttgcc gggcaagtca gtggattggt cctgagttaa agtggtacca gcagaaacca      120
gggaaagccc ctaagctcct gatctatcat ggttccattt tgcaaagtgg ggtcccatca      180
cgtttcagtg gcagtggatc tgggacagac ttcactctca ccatcagcag tctgcaacct      240
gaagattttg ctacgtacta ctgtcaacag tatatgtatt atcctgagac gttcggccaa      300
gggaccaagg tggaaatcaa acgtgctagc acccacacct gccccccctg ccctgccccc      360
gagctgctgg gaggcccag cgtgttcctg ttcccccca gcctaagga caccctgatg      420 atcagcagaa cccccgaggt gacctgtgtg gtggtggatg tgagccacga ggaccctgag      480
gtgaagttca actggtacgt ggacggcgtg gaggtgcaca atgccaagac caagcccagg      540
gaggagcagt acaacagcac ctaccgggtg gtgtccgtgc tgaccgtgct gcaccaggat      600
tggctgaacg gcaaggagta caagtgtaag gtgtccaaca aggccctgcc tgcccctatc      660
gagaaaacca tcagcaaggc caagggccag cccagagagc ccaggtgta cccctgccc      720 cctagcagag atgagctgac caagaaccag gtgtccctga cctgcctggt gaagggcttc      780
taccccagcg acatcgccgt ggagtgggag agcaacggcc agcccgagaa caactacaag      840
accacccccc tgtgctgga cagcgatggc agcttcttcc tgtacagcaa gctgaccgtg      900
gacaagagca gatggcagca gggcaacgtg ttcagctgct ccgtgatgca cgaggccctg      960
cacaatcact acacccagaa gagcctgagc ctgtcccctg gcaaggaggt ggacgagacc     1020
tacgtgccca aggagttcaa cgccgagacc ttcaccttcc acgccgacga catccagatg     1080
acccagtctc catcctccct gtctgcatct gtaggagacc gtgtcaccat cacttgccgg     1140
```

```
gcaagtcagt ggattggtcc tgagttaaag tggtaccagc agaaaccagg gaaagcccct      1200
aagctcctga tctatcatgg ttccattttg caaagtgggg tcccatcacg tttcagtggc      1260
agtggatctg gacagactt cactctcacc atcagcagtc tgcaacctga agatttgct       1320 acgtactact gtcaacagta tatgtattat cctgagacgt tcggccaagg gaccaaggtg      1380
gaaatcaaac gt                                                          1392

<210> SEQ ID NO 15
<211> LENGTH: 1398
<212> TYPE: DNA
<213> ORGANISM: Artificial Sequence
<220> FEATURE:
<223> OTHER INFORMATION: DT02-K-044-251-AAAS Linker-Fc-Albumin Domain 3
      Linker-DT02-K-044-251 Vk-Vk d-Fc-dAb nucleic acid
      sequence identified using molecular biology techniques.

<400> SEQUENCE: 15
gacatccaga tgacccagtc tccatcctcc ctgtctgcat ctgtaggaga ccgtgtcacc       60
atcacttgcc gggcaagtca gtggattggt cctgagttaa agtggtacca gcagaaacca      120
gggaaagccc ctaagctcct gatctatcat ggttccattt tgcaaagtgg ggtcccatca      180
cgtttcagtg gcagtggatc tgggacagac ttcactctca ccatcagcag tctgcaacct      240
gaagattttg ctacgtacta ctgtcaacag tatatgtatt atcctgagac gttcggccaa      300
gggaccaagg tggaaatcaa acgtgccgct gctagcaccc acacctgccc ccctgccct      360 gcccccgagc tgctgggagg ccccagcgtg ttcctgttcc cccccaagcc taaggacacc      420
ctgatgatca gcagaacccc cgaggtgacc tgtgtggtgg tggatgtgag ccacgaggac      480
cctgaggtga agttcaactg gtacgtggac ggcgtggagg tgcacaatgc caagaccaag      540
cccagggagg agcagtacaa cagcacctac cgggtggtgt ccgtgctgac cgtgctgcac      600
caggattggc tgaacggcaa ggagtacaag tgtaaggtgt ccaacaaggc cctgcctgcc      660
cctatcgaga aaaccatcag caaggccaag ggccagccca gagagcccca ggtgtacacc      720 ctgccccta gcagagatga gctgaccaag aaccaggtgt ccctgacctg cctggtgaag      780
ggcttctacc ccagcgacat cgccgtggag tgggagagca cggccagcc cgagaacaac      840 tacaagacca cccccctgt gctggacagc gatggcagct tcttcctgta cagcaagctg      900
accgtggaca gagcagatg gcagcagggc aacgtgttca gctgctccgt gatgcacgag      960
gccctgcaca tcactacac ccagaagagc ctgagcctgt cccctggcaa ggaggtggac     1020
gagacctacg tgcccaagga gttcaacgcc gagaccttcc ccttccacgc cgacgacatc     1080
cagatgaccc agtctccatc ctccctgtct gcatctgtag agaccgtgt caccatcact     1140 tgccgggcaa gtcagtggat tggtcctgag ttaaagtggt accagcagaa accagggaaa     1200
gcccctaagc tcctgatcta tcatggttcc attttgcaaa gtggggtccc atcacgtttc     1260
agtggcagtg gatctgggac agacttcact ctcaccatca gcagtctgca acctgaagat     1320
tttgctacgt actactgtca acagtatatg tattatcctg agacgttcgg ccaagggacc     1380
aaggtggaaa tcaaacgt                                                   1398

<210> SEQ ID NO 16
<211> LENGTH: 1068
<212> TYPE: DNA
<213> ORGANISM: Artificial Sequence
<220> FEATURE:
<223> OTHER INFORMATION: C-terminal Fc fusion of K-044-085 DAB (Albumin
      Domain 3 Linker) Fc-dAb nucleic acid sequence
``` identified using molecular biology techniques.

<400> SEQUENCE: 16

| gctagcaccc acacctgccc ccctgccct gccccgagc tgctgggagg ccccagcgtg | 60 |
| ttcctgttcc cccccaagcc taaggacacc ctgatgatca gcagaacccc cgaggtgacc | 120 |
| tgtgtggtgg tggatgtgag ccacgaggac cctgaggtga agttcaactg gtacgtggac | 180 |
| ggcgtggagg tgcacaatgc caagaccaag cccaggggagg agcagtacaa cagcacctac | 240 |
| cgggtggtgt ccgtgctgac cgtgctgcac caggattggc tgaacggcaa ggagtacaag | 300 |
| tgtaaggtgt ccaacaaggc cctgcctgcc cctatcgaga aaccatcag caaggccaag | 360 |
| ggccagccca gagagcccca ggtgtacacc ctgcccccta gcagagatga gctgaccaag | 420 |
| aaccaggtgt ccctgacctg cctggtgaag ggcttctacc ccagcgacat cgccgtggag | 480 |
| tgggagagca cggccagcc cgagaacaac tacaagacca ccccccctgt gctggacagc | 540 |
| gatggcagct tcttcctgta cagcaagctg accgtggaca gagcagatg gcagcagggc | 600 |
| aacgtgttca gctgctccgt gatgcacgag gccctgcaca tcactacac ccagaagagc | 660 |
| ctgagcctgt ccctggcaa ggaggtggac gagacctacg tgcccaagga gttcaacgcc | 720 |
| gagaccttca ccttccacgc cgacgacatc cagatgaccc agtctccatc ctccctgtct | 780 |
| gcatctgtag gagaccgtgt caccatcact tgccgggcaa gtcagtggat tggtcctgag | 840 |
| ttaaagtggt accagcagaa accagggaaa gccctaagc tcctgatcta tcatggttcc | 900 |
| attttgcaaa gtggggtccc atcacgtttc agtggcagtg gatctgggac agacttcact | 960 |
| ctcaccatca gcagtctgca acctgaagat tttgctacgt actactgtca acagtatatg | 1020 |
| tattatcctc atacgttcgg ccaagggacc aaggtggaaa tcaaacgt | 1068 |

<210> SEQ ID NO 17
<211> LENGTH: 1062
<212> TYPE: DNA
<213> ORGANISM: Artificial Sequence
<220> FEATURE:
<223> OTHER INFORMATION: C-terminal Fc fusion of K-044-085 DAB (Albumin Domain 3 Linker) Fc-dAb nucleic acid sequence identified using molecular biology techniques.

<400> SEQUENCE: 17

| acccacacct gccccccctg ccctgccccc gagctgctgg gaggccccag cgtgttcctg | 60 |
| ttccccccca gcctaagga caccctgatg atcagcagaa ccccgaggt gacctgtgtg | 120 |
| gtggtggatg tgagccacga ggaccctgag gtgaagttca ctggtacgt ggacggcgtg | 180 |
| gaggtgcaca atgccaagac caagcccagg gaggagcagt acaacagcac ctaccgggtg | 240 |
| gtgtccgtgc tgaccgtgct gcaccaggat tggctgaacg gcaaggagta caagtgtaag | 300 |
| gtgtccaaca aggccctgcc tgcccctatc gagaaaacca tcagcaaggc caagggccag | 360 |
| cccagagagc ccaggtgta caccctgccc ctagcagag atgagctgac caagaaccag | 420 |
| gtgtccctga cctgcctggt gaagggcttc taccccagcg acatcgccgt ggagtgggag | 480 |
| agcaacggcc agcccgagaa caactacaag accacccccc ctgtgctgga cagcgatggc | 540 |
| agcttcttcc tgtacagcaa gctgaccgtg gacaagagca gatggcagca gggcaacgtg | 600 |
| ttcagctgct ccgtgatgca cgaggccctg cacaatcact acacccagaa gagcctgagc | 660 |
| ctgtcccctg gcaaggaggt ggacgagacc tacgtgccca aggagttcaa cgccgagacc | 720 |
| ttcaccttcc acgccgacga catccagatg acccagtctc catcctccct gtctgcatct | 780 |
| gtaggagacc gtgtcaccat cacttgccgg gcaagtcagt ggattggtcc tgagttaaag | 840 |

```
tggtaccagc agaaaccagg gaaagcccct aagctcctga tctatcatgg ttccattttg    900
caaagtgggg tccatcacg tttcagtggc agtggatctg ggacagactt cactctcacc    960
atcagcagtc tgcaacctga agattttgct acgtactact gtcaacagta tatgtattat   1020
cctcatacgt tcggccaagg gaccaaggtg gaaatcaaac gt                      1062

<210> SEQ ID NO 18
<211> LENGTH: 1068
<212> TYPE: DNA
<213> ORGANISM: Artificial Sequence
<220> FEATURE:
<223> OTHER INFORMATION: C-terminal Fc fusion of K-044-251 DAB (Albumin
      Domain 3 Linker) Fc-dAb nucleic acid sequence
      identified using molecular biology techniques.

<400> SEQUENCE: 18
gctagcaccc acacctgccc ccctgccct gccccgagc tgctgggagg ccccagcgtg      60
ttcctgttcc cccccaagcc taaggacacc ctgatgatca gcagaacccc cgaggtgacc   120
tgtgtggtgg tggatgtgag ccacgaggac cctgaggtga agttcaactg gtacgtggac   180
ggcgtggagg tgcacaatgc caagaccaag cccagggagg agcagtacaa cagcacctac   240
cgggtggtgt ccgtgctgac cgtgctgcac caggattggc tgaacggcaa ggagtacaag   300
tgtaaggtgt ccaacaaggc cctgcctgcc cctatcgaga aaaccatcag caaggccaag   360
ggccagccca gagagcccca ggtgtacacc ctgcccccta gcagagatga gctgaccaag   420
aaccaggtgt ccctgacctg cctggtgaag ggcttctacc ccagcgacat cgccgtggag   480
tgggagagca cggccagcc cgagaacaac tacaagacca cccccccgtg ctggacagc    540 gatggcagct tcttcctgta cagcaagctg accgtggaca gagcagatg gcagcagggc   600 aacgtgttca gctgctccgt gatgcacgag gccctgcaca tcactacac ccagaagagc    660 ctgagcctgt ccctggcaa ggaggtggac gagacctacg tgcccaagga gttcaacgcc   720
gagaccttca ccttccacgc cgacgacatc cagatgaccc agtctccatc ctccctgtct   780
gcatctgtag gagaccgtgt caccatcact tgccgggcaa gtcagtggat tggtcctgag   840
ttaaagtggt accagcagaa accagggaaa gcccctaagc tcctgatcta tcatggttcc    900
attttgcaaa gtggggtccc atcacgtttc agtggcagtg gatctgggac agacttcact   960
ctcaccatca gcagtctgca acctgaagat tttgctacgt actactgtca acagtatatg   1020
tattatcctg agacgttcgg ccaagggacc aaggtggaaa tcaaacgt                1068

<210> SEQ ID NO 19
<211> LENGTH: 1062
<212> TYPE: DNA
<213> ORGANISM: Artificial Sequence
<220> FEATURE:
<223> OTHER INFORMATION: C-terminal Fc fusion of K-044-251 DAB (Albumin
      Domain 3 Linker) Fc-dAb nucleic acid sequence
      identified using molecular biology techniques.

<400> SEQUENCE: 19
acccacacct gcccccctg ccctgcccc gagctgctgg gaggccccag cgtgttcctg      60
ttccccccca gcctaagga cacctgatg atcagcagaa ccccgaggt gacctgtgtg     120 gtggtggatg tgagccacga ggaccctgag gtgaagttca actggtacgt ggacggcgtg   180
gaggtgcaca atgccaagac caagcccagg gaggagcagt acaacagcac ctaccgggtg   240
gtgtccgtgc tgaccgtgct gcaccaggat tggctgaacg gcaaggagta caagtgtaag   300
```

| | |
|---|---|
| gtgtccaaca aggccctgcc tgcccctatc gagaaaacca tcagcaaggc caagggccag | 360 |
| cccagagagc cccaggtgta caccctgccc cctagcagag atgagctgac caagaaccag | 420 |
| gtgtccctga cctgcctggt gaagggcttc taccccagcg acatcgccgt ggagtgggag | 480 |
| agcaacggcc agcccgagaa caactacaag accacccccc ctgtgctgga cagcgatggc | 540 |
| agcttcttcc tgtacagcaa gctgaccgtg gacaagagca gatggcagca gggcaacgtg | 600 |
| ttcagctgct ccgtgatgca cgaggccctg cacaatcact acacccagaa gagcctgagc | 660 |
| ctgtcccctg caaggaggt ggacgagacc tacgtgccca aggagttcaa cgccgagacc | 720 |
| ttcaccttcc acgccgacga catccagatg acccagtctc catcctccct gtctgcatct | 780 |
| gtaggagacc gtgtcaccat cacttgccgg gcaagtcagt ggattggtcc tgagttaaag | 840 |
| tggtaccagc agaaaccagg gaaagcccct aagctcctga tctatcatgg ttccattttg | 900 |
| caaagtgggg tcccatcacg tttcagtggc agtggatctg gacagacttt cactctcacc | 960 |
| atcagcagtc tgcaacctga agattttgct acgtactact gtcaacagta tatgtattat | 1020 |
| cctgagacgt tcggccaagg gaccaaggtg gaaatcaaac gt | 1062 |

<210> SEQ ID NO 20
<211> LENGTH: 1017
<212> TYPE: DNA
<213> ORGANISM: Artificial Sequence
<220> FEATURE:
<223> OTHER INFORMATION: N-terminal Fc fusion of K-044-085 DAB (TVAAPS
   Linker) dAb-Fc nucleic acid sequence
   identified using molecular biology techniques.

<400> SEQUENCE: 20

| | |
|---|---|
| gacatccaga tgacccagtc tccatcctcc ctgtctgcat ctgtaggaga ccgtgtcacc | 60 |
| atcacttgcc gggcaagtca gtggattggt cctgagttaa agtggtacca gcagaaacca | 120 |
| gggaaagccc ctaagctcct gatctatcat ggttccattt tgcaaagtgg ggtcccatca | 180 |
| cgtttcagtg gcagtggatc tgggacagac ttcactctca ccatcagcag tctgcaacct | 240 |
| gaagattttg ctacgtacta ctgtcaacag tatatgtatt atcctcatac gttcggccaa | 300 |
| gggaccaagg tggaaatcaa acgtaccgtc gccgctccta gcacccacac ctgcccccc | 360 |
| tgccctgccc ccgagctgct gggcggacct agcgtgttcc tgttcccccc caagcctaag | 420 |
| gacaccctga tgatcagcag gacccccgaa gtgacctgcg tggtggtgga tgtgagccac | 480 |
| gaggaccctg aagtgaagtt caactggtac gtggacggcg tggaagtgca caacgccaag | 540 |
| accaagccca gagaggagca gtacaacagc acctaccgcg tggtgtctgt gctgaccgtg | 600 |
| ctgcaccagg attggctgaa cggcaaggag tacaagtgca agtgagcaa caaggccctg | 660 |
| cctgccccta tcgagaaaac catcagcaag gccaagggcc agcctagaga gccccaggtc | 720 |
| tacaccctgc ctccctccag agatgagctg accaagaacc aggtgtccct gacctgtctg | 780 |
| gtgaagggct ctaccccag cgacatcgcc gtggagtggg agagcaacgg ccagcccgag | 840 |
| aacaactaca gaccaccccc ccctgtgctg gacagcgatg gcagcttctt cctgtactcc | 900 |
| aagctgaccg tggacaagag cagatggcag cagggcaacg tgttcagctg cagcgtgatg | 960 |
| cacgaggccc tgcacaatca ctacacccag aagagtctga gcctgtcccc tggcaag | 1017 |

<210> SEQ ID NO 21
<211> LENGTH: 1017
<212> TYPE: DNA
<213> ORGANISM: Artificial Sequence
<220> FEATURE:
<223> OTHER INFORMATION: N-terminal Fc fusion of K-044-232 DAB (TVAAPS Linker) dAb-Fc nucleic acid sequence
identified using molecular biology techniques.

<400> SEQUENCE: 21

| | | | | | |
|---|---|---|---|---|---|
| gacatccaga | tgacccagtc | tccatcctcc | ctgtctgcat | ctgtaggaga | ccgtgtcacc | 60 |
| atcacttgcc | gggcaagtca | gtggattggt | cctgagttaa | gttggtacca | gcagaaacca | 120 |
| gggaaagccc | ctaagctcct | gatctatcat | ggttccattt | tgcaaagtgg | ggtcccatca | 180 |
| cgtttcagtg | gcagtggatc | tgggacagac | ttcactctca | ccatcagcag | tctgcaacct | 240 |
| gaagattttg | ctacgtacta | ctgtcaacag | tatatgtatt | atcctgagac | gttcggccaa | 300 |
| gggaccaagg | tggaaatcaa | acgtaccgtc | gccgctccta | gcacccacac | ctgcccccc | 360 |
| tgccctgccc | ccgagctgct | gggcggacct | agcgtgttcc | tgttcccccc | caagcctaag | 420 |
| gacaccctga | tgatcagcag | gacccccgaa | gtgacctgcg | tggtggtgga | tgtgagccac | 480 |
| gaggaccctg | aagtgaagtt | caactggtac | gtggacggcg | tggaagtgca | aacgccaag | 540 |
| accaagccca | gagaggagca | gtacaacagc | acctaccgcg | tggtgtctgt | gctgaccgtg | 600 |
| ctgcaccagg | attggctgaa | cggcaaggag | tacaagtgca | aagtgagcaa | caaggccctg | 660 |
| cctgccccta | tcgagaaaac | catcagcaag | gccaagggcc | agcctagaga | gccccaggtc | 720 |
| tacaccctgc | ctccctccag | agatgagctg | accaagaacc | aggtgtccct | gacctgtctg | 780 |
| gtgaagggct | tctaccccag | cgacatcgcc | gtggagtggg | agagcaacgg | ccagcccgag | 840 |
| aacaactaca | agaccacccc | ccctgtgctg | gacagcgatg | gcagcttctt | cctgtactcc | 900 |
| aagctgaccg | tggacaagag | cagatggcag | cagggcaacg | tgttcagctg | cagcgtgatg | 960 |
| cacgaggccc | tgcacaatca | ctacacccag | aagagtctga | gcctgtcccc | tggcaag | 1017 |

<210> SEQ ID NO 22
<211> LENGTH: 1017
<212> TYPE: DNA
<213> ORGANISM: Artificial Sequence
<220> FEATURE:
<223> OTHER INFORMATION: N-terminal Fc fusion of K-044-236 DAB(TVAAPS
Linker) dAb-Fc nucleic acid sequence
identified using molecular biology techniques.

<400> SEQUENCE: 22

| | | | | | |
|---|---|---|---|---|---|
| gacatccaga | tgacccagtc | tccatcctcc | ctgtctgcat | ctgtaggaga | ccgtgtcacc | 60 |
| atcacttgcc | gggcaagtca | gtggattggt | cctgagttaa | gttggtacca | gcagaaacca | 120 |
| gggaaagccc | ctaagctcct | gatctatcat | ggttccattt | tgcaaagtgg | ggtcccatca | 180 |
| cgtttcagtg | gcagtggatc | tgggacagac | ttcactctca | ccatcagcag | tctgcaacct | 240 |
| gaagattttg | ctacgtacta | ctgtcaacag | tatatgtatt | atcctaagac | gttcggccaa | 300 |
| gggaccaagg | tggaaatcaa | acgtaccgtc | gccgctccta | gcacccacac | ctgcccccc | 360 |
| tgccctgccc | ccgagctgct | gggcggacct | agcgtgttcc | tgttcccccc | caagcctaag | 420 |
| gacaccctga | tgatcagcag | gacccccgaa | gtgacctgcg | tggtggtgga | tgtgagccac | 480 |
| gaggaccctg | aagtgaagtt | caactggtac | gtggacggcg | tggaagtgca | aacgccaag | 540 |
| accaagccca | gagaggagca | gtacaacagc | acctaccgcg | tggtgtctgt | gctgaccgtg | 600 |
| ctgcaccagg | attggctgaa | cggcaaggag | tacaagtgca | aagtgagcaa | caaggccctg | 660 |
| cctgccccta | tcgagaaaac | catcagcaag | gccaagggcc | agcctagaga | gccccaggtc | 720 |
| tacaccctgc | ctccctccag | agatgagctg | accaagaacc | aggtgtccct | gacctgtctg | 780 |
| gtgaagggct | tctaccccag | cgacatcgcc | gtggagtggg | agagcaacgg | ccagcccgag | 840 |

| aacaactaca agaccacccc ccctgtgctg acagcgatg gcagcttctt cctgtactcc | 900 |
| aagctgaccg tggacaagag cagatggcag cagggcaacg tgttcagctg cagcgtgatg | 960 |
| cacgaggccc tgcacaatca ctacacccag aagagtctga gcctgtcccc tggcaag | 1017 |

<210> SEQ ID NO 23
<211> LENGTH: 1017
<212> TYPE: DNA
<213> ORGANISM: Artificial Sequence
<220> FEATURE:
<223> OTHER INFORMATION: N-terminal Fc fusion of K-044-251 DAB (TVAAPS Linker) dAb-Fc nucleic acid sequence identified using molecular biology techniques.

<400> SEQUENCE: 23

| gacatccaga tgacccagtc tccatcctcc ctgtctgcat ctgtaggaga ccgtgtcacc | 60 |
| atcacttgcc gggcaagtca gtggattggt cctgagttaa gtggtacca gcagaaacca | 120 |
| gggaaagccc ctaagctcct gatctatcat ggttccattt tgcaaagtgg ggtcccatca | 180 |
| cgtttcagtg gcagtggatc tgggacagac ttcactctca ccatcagcag tctgcaacct | 240 |
| gaagattttg ctacgtacta ctgtcaacag tatatgtatt atcctgagac gttcggccaa | 300 |
| gggaccaagg tggaaatcaa acgtaccgtc gccgctccta gcacccacac ctgccccccc | 360 |
| tgccctgccc ccgagctgct gggcggacct agcgtgttcc tgttcccccc caagcctaag | 420 |
| gacaccctga tgatcagcag accccccgaa gtgacctgcg tggtggtgga tgtgagccac | 480 |
| gaggaccctg aagtgaagtt caactggtac gtggacggcg tggaagtgca caacgccaag | 540 |
| accaagccca gagaggagca gtacaacagc acctaccgcg tggtgtctgt gctgaccgtg | 600 |
| ctgcaccagg attggctgaa cggcaaggag tacaagtgca agtgagcaa caaggccctg | 660 |
| cctgcccta tcgagaaaac catcagcaag gccaagggcc agcctagaga gccccaggtc | 720 |
| tacaccctgc ctccctccag agatgagctg accaagaacc aggtgtccct gacctgtctg | 780 |
| gtgaagggct tctaccccag cgacatcgcc gtggagtggg agagcaacgg ccagcccgag | 840 |
| aacaactaca agaccacccc ccctgtgctg gacagcgatg gcagcttctt cctgtactcc | 900 |
| aagctgaccg tggacaagag cagatggcag cagggcaacg tgttcagctg cagcgtgatg | 960 |
| cacgaggccc tgcacaatca ctacacccag aagagtctga gcctgtcccc tggcaag | 1017 |

<210> SEQ ID NO 24
<211> LENGTH: 1017
<212> TYPE: DNA
<213> ORGANISM: Artificial Sequence
<220> FEATURE:
<223> OTHER INFORMATION: N-terminal Fc fusion of K-044-255 DAB (TVAAPS Linker) dAb-Fc nucleic acid sequence identified using molecular biology techniques.

<400> SEQUENCE: 24

| gacatccaga tgacccagtc tccatcctcc ctgtctgcat ctgtaggaga ccgtgtcacc | 60 |
| atcacttgcc gggcaagtca gtggattggt cctgagttaa gtggtacca gcagaaacca | 120 |
| gggaaagccc ctaagctcct gatctatcat ggttccattt tgcaaagtgg ggtcccatca | 180 |
| cgtttcagtg gcagtggatc tgggacagac ttcactctca ccatcagcag tctgcaacct | 240 |
| gaagattttg ctacgtacta ctgtcaacag tatatgtatt atcctaagac gttcggccaa | 300 |
| gggaccaagg tggaaatcaa acgtaccgtc gccgctccta gcacccacac ctgccccccc | 360 |
| tgccctgccc ccgagctgct gggcggacct agcgtgttcc tgttcccccc caagcctaag | 420 |
| gacaccctga tgatcagcag accccccgaa gtgacctgcg tggtggtgga tgtgagccac | 480 |

```
gaggaccctg aagtgaagtt caactggtac gtggacggcg tggaagtgca caacgccaag      540
accaagccca gagaggagca gtacaacagc acctaccgcg tggtgtctgt gctgaccgtg      600
ctgcaccagg attggctgaa cggcaaggag tacaagtgca agtgagcaa caaggccctg       660 cctgcccta tcgagaaaac catcagcaag gccaagggcc agcctagaga gccccaggtc       720
tacaccctgc ctccctccag agatgagctg accaagaacc aggtgtccct gacctgtctg      780
gtgaagggct ctacccccag cgacatcgcc gtggagtggg agagcaacgg ccagcccgag      840
aacaactaca agaccacccc ccctgtgctg acagcgatg gcagcttctt cctgtactcc       900
aagctgaccg tggacaagag cagatggcag cagggcaacg tgttcagctg cagcgtgatg      960
cacgaggccc tgcacaatca ctacacccag aagagtctga gcctgtcccc tggcaag       1017
```

<210> SEQ ID NO 25
<211> LENGTH: 1431
<212> TYPE: DNA
<213> ORGANISM: Artificial Sequence
<220> FEATURE:
<223> OTHER INFORMATION: DOM15-26-597-AS Linker-Fc-GS(TVAAPSGS)x3
Linker-DT02-K-044-085 Vh-Vk dAb-Fc-dAb nucleic acid
sequence identified using molecular biology techniques.

<400> SEQUENCE: 25

```
gaggtgcagc tgctggtgtc tggcggcgga ctggtgcagc ctggcggcag cctgagactg       60
agctgcgccg ccagcggctt caccttcaag gcctacccca tgatgtgggt gcggcaggcc      120
cctggcaagg gcctggaatg ggtgtccgag atcagcccca gcggcagcaa cacctactac      180
gccgacagcg tgaagggccg gttcaccatc agccgggaca cagcaagaa caccctgtac       240 ctgcagatga acagcctgcg ggccgaggac accgccgtgt actactgcgc caaggacccc      300
cggaagctgg actactgggg ccagggcacc ctggtgaccg tgagcagcgc tagcacccac      360
acctgccccc cctgccctgc ccccgagctg ctgggaggcc cagcgtgtt cctgttcccc       420 cccaagccta aggacaccct gatgatcagc agaacccccg aggtgacctg tgtggtggtg      480
gatgtgagcc acgaggaccc tgaggtgaag ttcaactggt acgtggacgg cgtggaggtg      540
cacaatgcca agaccaagcc cagggaggag cagtacaaca gcacctaccg ggtggtgtcc      600
gtgctgaccg tgctgcacca ggattggctg aacggcaagg agtacaagtg taaggtgtcc      660
aacaaggccc tgcctgcccc tatcgagaaa accatcagca aggccaaggg ccagcccaga      720
gagccccagg tgtacaccct gcccccctagc agagatgagc tgaccaagaa ccaggtgtcc      780
ctgacctgcc tggtgaaggg cttctacccc agcgacatcg ccgtggagtg ggagagcaac      840
ggccagcccg agaacaacta caagaccacc cccctgtgc tggacagcga tggcagcttc       900
ttcctgtaca gcaagctgac cgtggacaag agcagatggc agcagggcaa cgtgttcagc      960
tgctccgtga tgcacgaggc cctgcacaat cactacaccc agaagagcct gagcctgtcc     1020
cctggcaagg gatctaccgt ggcagcacca tcaggatcta ccgtggcagc accatcaggt     1080
tcaacagtag ctgctccttc tggatccgac atccagatga cccagtctcc atcctccctg     1140
tctgcatctg taggagaccg tgtcaccatc acttgccggg caagtcagtg gattggtcct     1200
gagttaaagt ggtaccagca gaaaccaggg aaagccccta agctcctgat ctatcatggt     1260
tccattttgc aaagtggggt cccatcacgt ttcagtggca gtggatctgg gacagacttc     1320
actctcacca tcagcagtct gcaacctgaa gattttgcta cgtactactg tcaacagtat     1380
atgtattatc ctcatacgtt cggccaaggg accaaggtgg aaatcaaacg t             1431
```

<210> SEQ ID NO 26
<211> LENGTH: 1425
<212> TYPE: DNA
<213> ORGANISM: Artificial Sequence
<220> FEATURE:
<223> OTHER INFORMATION: DT02-K-044-085-HingeIgG1Linker-Fc-
GS(TVAAPSGS)x3 Linker-DT02-K-044-085 Vh-Vk dAb-Fc-dAb nucleic acid
sequence identified using molecular biology techniques.

<400> SEQUENCE: 26

```
gacatccaga tgacccagtc tccatcctcc ctgtctgcat ctgtaggaga ccgtgtcacc      60
atcacttgcc gggcaagtca gtggattggt cctgagttaa agtggtacca gcagaaacca    120
gggaaagccc ctaagctcct gatctatcat ggttccattt gcaaagtggg gtcccatca     180
cgtttcagtg gcagtggatc tgggacagac ttcactctca ccatcagcag tctgcaacct    240
gaagattttg ctacgtacta ctgtcaacag tatatgtatt atcctcatac gttcggccaa    300
gggaccaagg tggaaatcaa acgtgtggag cctaagtctt ctgacaagac ccacacctgc    360
ccccctgcc ctgccccga gctgctggga ggccccagcg tgttcctgtt cccccccaag     420
cctaaggaca ccctgatgat cagcagaacc cccgaggtga cctgtgtggt ggtggatgtg    480
agccacgagg accctgaggt gaagttcaac tggtacgtgg acggcgtgga ggtgcacaat    540
gccaagacca agcccaggga ggagcagtac aacagcacct accgggtggt gtccgtgctg    600
accgtgctgc accaggattg gctgaacggc aaggagtaca agtgtaaggt gtccaacaag    660
gccctgcctg ccctatcga gaaaaccatc agcaaggcca agggccagcc cagagagccc    720
caggtgtaca ccctgccccc tagcagagat gagctgacca gaaccaggt gtccctgacc    780
tgcctggtga agggcttcta ccccagcgac atcgccgtgg agtgggagag caacggccag    840
cccgagaaca actacaagac cacccccct gtgctggaca cgatggcag cttcttcctg     900
tacagcaagc tgaccgtgga caagagcaga tggcagcagg gcaacgtgtt cagctgctcc    960
gtgatgcacg aggccctgca caatcactac acccagaaga gcctgagcct gtcccctggc   1020
aagggatcta ccgtggcagc accatcagga tctaccgtgg cagcaccatc aggttcaaca   1080
gtagctgctc cttctggatc cgacatccag atgacccagt ctccatcctc cctgtctgca   1140
tctgtaggag accgtgtcac catcacttgc cgggcaagtc agtggattgg tcctgagtta   1200
aagtggtacc agcagaaacc agggaaagcc cctaagctcc tgatctatca tggttccatt   1260
tgcaaagtgg gtcccatc acgtttcagt ggcagtggat ctgggacaga cttcactctc    1320
accatcagca gtctgcaacc tgaagatttt gctacgtact actgtcaaca gtatatgtat   1380
tatcctcata cgttcggcca agggaccaag gtggaaatca aacgt                   1425
```

<210> SEQ ID NO 27
<211> LENGTH: 1407
<212> TYPE: DNA
<213> ORGANISM: Artificial Sequence
<220> FEATURE:
<223> OTHER INFORMATION: DT02-K-044-085-AS-Fc (H112A)-GS(TVAAPSGS)x3
Linker-DT02-K-044-085 Vh-Vk dAb-Fc-dAb nucleic acid
sequence identified using molecular biology techniques.

<400> SEQUENCE: 27

```
gacatccaga tgacccagtc tccatcctcc ctgtctgcat ctgtaggaga ccgtgtcacc      60
atcacttgcc gggcaagtca gtggattggt cctgagttaa agtggtacca gcagaaacca    120
gggaaagccc ctaagctcct gatctatcat ggttccattt gcaaagtggg gtcccatca     180
cgtttcagtg gcagtggatc tgggacagac ttcactctca ccatcagcag tctgcaacct    240
```

```
gaagattttg ctacgtacta ctgtcaacag tatatgtatt atcctcatac gttcggccaa      300
gggaccaagg tggaaatcaa acgtgctagc accgccacct gccccccctg ccctgccccc      360
gagctgctgg gaggcccag cgtgttcctg ttccccccca agcctaagga caccctgatg       420
atcagcagaa cccccgaggt gacctgtgtg gtggtggatg tgagccacga ggaccctgag      480
gtgaagttca actggtacgt ggacggcgtg gaggtgcaca atgccaagac caagcccagg      540
gaggagcagt acaacagcac ctaccgggtg gtgtccgtgc tgaccgtgct gcaccaggat      600
tggctgaacg gcaaggagta caagtgtaag gtgtccaaca aggccctgcc tgcccctatc      660
gagaaaacca tcagcaaggc caagggccag cccagagagc ccaggtgta cccctgccc       720 cctagcagag atgagctgac caagaaccag gtgtccctga cctgcctggt gaagggcttc      780 tacccagcg acatcgccgt ggagtgggag agcaacggcc agcccgagaa caactacaag       840
accacccccc ctgtgctgga cagcgatggc agcttcttcc tgtacagcaa gctgaccgtg      900
gacaagagca gatggcagca gggcaacgtg ttcagctgct ccgtgatgca cgaggccctg      960
cacaatcact acacccagaa gagcctgagc ctgtcccctg gcaagggatc taccgtggca     1020
gcaccatcag gatctaccgt ggcagcacca tcaggttcaa cagtagctgc tccttctgga     1080
tccgacatcc agatgaccca gtctccatcc tccctgtctg catctgtagg agaccgtgtc     1140
accatcactt gccgggcaag tcagtggatt ggtcctgagt taaagtggta ccagcagaaa     1200
ccagggaaag ccctaagct cctgatctat catggttcca ttttgcaaag tggggtccca      1260
tcacgtttca gtggcagtgg atctgggaca gacttcactc tcaccatcag cagtctgcaa     1320
cctgaagatt ttgctacgta ctactgtcaa cagtatatgt attatcctca tacgttcggc     1380
caagggacca aggtggaaat caaacgt                                         1407

<210> SEQ ID NO 28
<211> LENGTH: 1407
<212> TYPE: DNA
<213> ORGANISM: Artificial Sequence
<220> FEATURE:
<223> OTHER INFORMATION: DT02-K-044-085-AS-Fc (T113P)-GS(TVAAPSGS)x3
      Linker-DT02-K-044-085 Vh-Vk dAb-Fc-dAb nucleic acid
      sequence identified using molecular biology techniques.

<400> SEQUENCE: 28
gacatccaga tgacccagtc tccatcctcc ctgtctgcat ctgtaggaga ccgtgtcacc       60
atcacttgcc gggcaagtca gtggattggt cctgagttaa agtggtacca gcagaaacca     120
gggaaagccc ctaagctcct gatctatcat ggttccattt tgcaaagtgg ggtcccatca     180
cgtttcagtg gcagtggatc tgggacagac ttcactctca ccatcagcag tctgcaacct     240
gaagattttg ctacgtacta ctgtcaacag tatatgtatt atcctcatac gttcggccaa     300
gggaccaagg tggaaatcaa acgtgctagc acccacccct gccccccctg ccctgccccc     360
gagctgctgg gaggcccag cgtgttcctg ttccccccca agcctaagga caccctgatg      420
atcagcagaa cccccgaggt gacctgtgtg gtggtggatg tgagccacga ggaccctgag     480
gtgaagttca actggtacgt ggacggcgtg gaggtgcaca atgccaagac caagcccagg     540
gaggagcagt acaacagcac ctaccgggtg gtgtccgtgc tgaccgtgct gcaccaggat     600
tggctgaacg gcaaggagta caagtgtaag gtgtccaaca aggccctgcc tgcccctatc     660
gagaaaacca tcagcaaggc caagggccag cccagagagc ccaggtgta cccctgccc      720 cctagcagag atgagctgac caagaaccag gtgtccctga cctgcctggt gaagggcttc    780
```

-continued

```
tacccccagcg acatcgccgt ggagtgggag agcaacggcc agcccgagaa caactacaag    840
accacccccc ctgtgctgga cagcgatggc agcttcttcc tgtacagcaa gctgaccgtg    900
gacaagagca gatggcagca gggcaacgtg ttcagctgct ccgtgatgca cgaggccctg    960
cacaatcact acacccagaa gagcctgagc ctgtcccctg gcaagggatc taccgtggca   1020
gcaccatcag gatctaccgt ggcagcacca tcaggttcaa cagtagctgc tccttctgga   1080
tccgacatcc agatgaccca gtctccatcc tccctgtctg catctgtagg agaccgtgtc   1140
accatcactt gccgggcaag tcagtggatt ggtcctgagt taaagtggta ccagcagaaa   1200
ccagggaaag cccctaagct cctgatctat catggttcca ttttgcaaag tggggtccca   1260
tcacgtttca gtggcagtgg atctgggaca gacttcactc tcaccatcag cagtctgcaa   1320
cctgaagatt ttgctacgta ctactgtcaa cagtatatgt attatcctca tacgttcggc   1380
caagggacca aggtggaaat caaacgt                                       1407
```

<210> SEQ ID NO 29
<211> LENGTH: 343
<212> TYPE: PRT
<213> ORGANISM: Artificial Sequence
<220> FEATURE:
<223> OTHER INFORMATION: DOM15-26-593-Fc dAb-Fc amino acid sequence
      identified using molecular biology techniques.

<400> SEQUENCE: 29

```
Glu Val Gln Leu Leu Val Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Ala Ser Thr His Thr Cys Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
```

```
                        245                 250                 255
Asn Gln Val Ser Leu Thr Cys Leu Val Lys Gly Phe Tyr Pro Ser Asp
            260                 265                 270
Ile Ala Val Glu Trp Glu Ser Asn Gly Gln Pro Glu Asn Asn Tyr Lys
            275                 280                 285
Thr Thr Pro Pro Val Leu Asp Ser Asp Gly Ser Phe Phe Leu Tyr Ser
        290                 295                 300
Lys Leu Thr Val Asp Lys Ser Arg Trp Gln Gln Gly Asn Val Phe Ser
305                 310                 315                 320
Cys Ser Val Met His Glu Ala Leu His Asn His Tyr Thr Gln Lys Ser
                325                 330                 335
Leu Ser Leu Ser Pro Gly Lys
            340

<210> SEQ ID NO 30
<211> LENGTH: 343
<212> TYPE: PRT
<213> ORGANISM: Artificial Sequence
<220> FEATURE:
<223> OTHER INFORMATION: DOM15-26-597-Fc dAb-Fc amino acid sequence
      identified using molecular biology techniques.

<400> SEQUENCE: 30

Glu Val Gln Leu Leu Val Ser Gly Gly Gly Leu Val Gln Pro Gly Gly
1               5                   10                  15
Ser Leu Arg Leu Ser Cys Ala Ala Ser Gly Phe Thr Phe Lys Ala Tyr
            20                  25                  30
Pro Met Met Trp Val Arg Gln Ala Pro Gly Lys Gly Leu Glu Trp Val
        35                  40                  45
Ser Glu Ile Ser Pro Ser Gly Ser Asn Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Asp Pro Arg Lys Leu Asp Tyr Trp Gly Gln Gly Thr Leu Val
            100                 105                 110
Thr Val Ser Ser Ala Ser Thr His Thr Cys Pro Pro Cys Pro Ala Pro
        115                 120                 125
Glu Leu Leu Gly Gly Pro Ser Val Phe Leu Phe Pro Pro Lys Pro Lys
    130                 135                 140
Asp Thr Leu Met Ile Ser Arg Thr Pro Glu Val Thr Cys Val Val Val
145                 150                 155                 160
Asp Val Ser His Glu Asp Pro Glu Val Lys Phe Asn Trp Tyr Val Asp
                165                 170                 175
Gly Val Glu Val His Asn Ala Lys Thr Lys Pro Arg Glu Glu Gln Tyr
            180                 185                 190
Asn Ser Thr Tyr Arg Val Val Ser Val Leu Thr Val Leu His Gln Asp
        195                 200                 205
Trp Leu Asn Gly Lys Glu Tyr Lys Cys Lys Val Ser Asn Lys Ala Leu
    210                 215                 220
Pro Ala Pro Ile Glu Lys Thr Ile Ser Lys Ala Lys Gly Gln Pro Arg
225                 230                 235                 240
Glu Pro Gln Val Tyr Thr Leu Pro Pro Ser Arg Asp Glu Leu Thr Lys
                245                 250                 255
```

```
Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
            290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
            325                 330                 335

Leu Ser Leu Ser Pro Gly Lys
            340

<210> SEQ ID NO 31
<211> LENGTH: 365
<212> TYPE: PRT
<213> ORGANISM: Artificial Sequence
<220> FEATURE:
<223> OTHER INFORMATION: C-terminal Fc fusion of K-044-085 DAB
      (GS(TVAAPSGS)x3 Linker) Fc-dAb amino acid sequence
      identified using molecular biology techniques.

<400> SEQUENCE: 31

Gln Ala Ser Ser Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
            50                  55                  60

Gly Val Glu Val His Asn Ala Lys Thr Lys Pro Arg Glu Glu Gln Tyr
65              70                  75                  80

Asn Ser Thr Tyr Arg Val Val Ser Val Leu Thr Val Leu His Gln Asp
            85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
            130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
            165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
            210                 215                 220

Leu Ser Leu Ser Pro Gly Lys Gly Ser Thr Val Ala Ala Pro Ser Gly
225                 230                 235                 240

Ser Thr Val Ala Ala Pro Ser Gly Ser Thr Val Ala Ala Pro Ser Gly
            245                 250                 255

Ser Asp Ile Gln Met Thr Gln Ser Pro Ser Ser Leu Ser Ala Ser Val
```

```
                     260                 265                 270
Gly Asp Arg Val Thr Ile Thr Cys Arg Ala Ser Gln Trp Ile Gly Pro
                275                 280                 285

Glu Leu Lys Trp Tyr Gln Gln Lys Pro Gly Lys Ala Pro Lys Leu Leu
            290                 295                 300

Ile Tyr His Gly Ser Ile Leu Gln Ser Gly Val Pro Ser Arg Phe Ser
305                 310                 315                 320

Gly Ser Gly Ser Gly Thr Asp Phe Thr Leu Thr Ile Ser Ser Leu Gln
                325                 330                 335

Pro Glu Asp Phe Ala Thr Tyr Tyr Cys Gln Gln Tyr Met Tyr Tyr Pro
            340                 345                 350

His Thr Phe Gly Gln Gly Thr Lys Val Glu Ile Lys Arg
355                 360                 365

<210> SEQ ID NO 32
<211> LENGTH: 365
<212> TYPE: PRT
<213> ORGANISM: Artificial Sequence
<220> FEATURE:
<223> OTHER INFORMATION: C-terminal Fc fusion of K-044-232 DAB
      (GS(TVAAPSGS)x3 Linker) Fc-dAb amino acid sequence
      identified using molecular biology techniques.

<400> SEQUENCE: 32

Gln Ala Ser Ser Asp Lys Thr His Thr Cys Pro Pro Cys Pro Ala Pro
  1               5                  10                  15

Glu Leu Leu Gly Gly Pro Ser Val Phe Leu Phe Pro Pro Lys Pro Lys
             20                  25                  30

Asp Thr Leu Met Ile Ser Arg Thr Pro Glu Val Thr Cys Val Val Val
             35                  40                  45

Asp Val Ser His Glu Asp Pro Glu Val Lys Phe Asn Trp Tyr Val Asp
 50                  55                  60

Gly Val Glu Val His Asn Ala Lys Thr Lys Pro Arg Glu Glu Gln Tyr
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Gly Ser Thr Val Ala Ala Pro Ser Gly
225                 230                 235                 240

Ser Thr Val Ala Ala Pro Ser Gly Ser Thr Val Ala Ala Pro Ser Gly
                245                 250                 255
```

```
Ser Asp Ile Gln Met Thr Gln Ser Pro Ser Ser Leu Ser Ala Ser Val
        260                 265                 270

Gly Asp Arg Val Thr Ile Thr Cys Arg Ala Ser Gln Trp Ile Gly Pro
            275                 280                 285

Glu Leu Ser Trp Tyr Gln Gln Lys Pro Gly Lys Ala Pro Lys Leu Leu
        290                 295                 300

Ile Tyr His Gly Ser Ile Leu Gln Ser Gly Val Pro Ser Arg Phe Ser
305                 310                 315                 320

Gly Ser Gly Ser Gly Thr Asp Phe Thr Leu Thr Ile Ser Ser Leu Gln
            325                 330                 335

Pro Glu Asp Phe Ala Thr Tyr Tyr Cys Gln Gln Tyr Met Tyr Tyr Pro
        340                 345                 350

Glu Thr Phe Gly Gln Gly Thr Lys Val Glu Ile Lys Arg
        355                 360                 365

<210> SEQ ID NO 33
<211> LENGTH: 365
<212> TYPE: PRT
<213> ORGANISM: Artificial Sequence
<220> FEATURE:
<223> OTHER INFORMATION: C-terminal Fc fusion of K-044-236 DAB
      (GS(TVAAPSGS)x3 Linker) Fc-dAb amino acid sequence
      identified using molecular biology techniques.

<400> SEQUENCE: 33

Gln Ala Ser Ser Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Gly Ser Thr Val Ala Ala Pro Ser Gly
225                 230                 235                 240
```

```
Ser Thr Val Ala Ala Pro Ser Gly Ser Thr Val Ala Ala Pro Ser Gly
                245                 250                 255

Ser Asp Ile Gln Met Thr Gln Ser Pro Ser Ser Leu Ser Ala Ser Val
            260                 265                 270

Gly Asp Arg Val Thr Ile Thr Cys Arg Ala Ser Gln Trp Ile Gly Pro
        275                 280                 285

Glu Leu Ser Trp Tyr Gln Gln Lys Pro Gly Lys Ala Pro Lys Leu Leu
    290                 295                 300

Ile Tyr His Gly Ser Ile Leu Gln Ser Gly Val Pro Ser Arg Phe Ser
305                 310                 315                 320

Gly Ser Gly Ser Gly Thr Asp Phe Thr Leu Thr Ile Ser Ser Leu Gln
                325                 330                 335

Pro Glu Asp Phe Ala Thr Tyr Tyr Cys Gln Gln Tyr Met Tyr Tyr Pro
            340                 345                 350

Lys Thr Phe Gly Gln Gly Thr Lys Val Glu Ile Lys Arg
        355                 360                 365

<210> SEQ ID NO 34
<211> LENGTH: 365
<212> TYPE: PRT
<213> ORGANISM: Artificial Sequence
<220> FEATURE:
<223> OTHER INFORMATION: C-terminal Fc fusion of K-044-251 DAB
      (GS(TVAAPSGS)x3 Linker) Fc-dAb amino acid sequence
      identified using molecular biology techniques.

<400> SEQUENCE: 34

Gln Ala Ser Ser Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Gly Ser Thr Val Ala Ala Pro Ser Gly
```

```
225                 230                 235                 240
Ser Thr Val Ala Ala Pro Ser Gly Ser Thr Val Ala Ala Pro Ser Gly
                245                 250                 255

Ser Asp Ile Gln Met Thr Gln Ser Pro Ser Ser Leu Ser Ala Ser Val
                260                 265                 270

Gly Asp Arg Val Thr Ile Thr Cys Arg Ala Ser Gln Trp Ile Gly Pro
                275                 280                 285

Glu Leu Lys Trp Tyr Gln Gln Lys Pro Gly Lys Ala Pro Lys Leu Leu
                290                 295                 300

Ile Tyr His Gly Ser Ile Leu Gln Ser Gly Val Pro Ser Arg Phe Ser
305                 310                 315                 320

Gly Ser Gly Ser Gly Thr Asp Phe Thr Leu Thr Ile Ser Ser Leu Gln
                325                 330                 335

Pro Glu Asp Phe Ala Thr Tyr Tyr Cys Gln Gln Tyr Met Tyr Tyr Pro
                340                 345                 350

Glu Thr Phe Gly Gln Gly Thr Lys Val Glu Ile Lys Arg
                355                 360                 365

<210> SEQ ID NO 35
<211> LENGTH: 365
<212> TYPE: PRT
<213> ORGANISM: Artificial Sequence
<220> FEATURE:
<223> OTHER INFORMATION: C-terminal Fc fusion of K-044-255 DAB
      (GS(TVAAPSGS)x3 Linker) Fc-dAb amino acid sequence
      identified using molecular biology techniques.

<400> SEQUENCE: 35

Gln Ala Ser Ser Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
                20                  25                  30

Asp Thr Leu Met Ile Ser Arg Thr Pro Glu Val Thr Cys Val Val Val
                35                  40                  45

Asp Val Ser His Glu Asp Pro Glu Val Lys Phe Asn Trp Tyr Val Asp
            50                  55                  60

Gly Val Glu Val His Asn Ala Lys Thr Lys Pro Arg Glu Glu Gln Tyr
65              70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
                115                 120                 125

Glu Pro Gln Val Tyr Thr Leu Pro Pro Ser Arg Asp Glu Leu Thr Lys
                130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
                195                 200                 205

Cys Ser Val Met His Glu Ala Leu His Asn His Tyr Thr Gln Lys Ser
                210                 215                 220
```

Leu Ser Leu Ser Pro Gly Lys Gly Ser Thr Val Ala Ala Pro Ser Gly
225                 230                 235                 240

Ser Thr Val Ala Ala Pro Ser Gly Ser Thr Val Ala Ala Pro Ser Gly
                245                 250                 255

Ser Asp Ile Gln Met Thr Gln Ser Pro Ser Ser Leu Ser Ala Ser Val
            260                 265                 270

Gly Asp Arg Val Thr Ile Thr Cys Arg Ala Ser Gln Trp Ile Gly Pro
        275                 280                 285

Glu Leu Lys Trp Tyr Gln Gln Lys Pro Gly Lys Ala Pro Lys Leu Leu
    290                 295                 300

Ile Tyr His Gly Ser Ile Leu Gln Ser Gly Val Pro Ser Arg Phe Ser
305                 310                 315                 320

Gly Ser Gly Ser Gly Thr Asp Phe Thr Leu Thr Ile Ser Ser Leu Gln
                325                 330                 335

Pro Glu Asp Phe Ala Thr Tyr Tyr Cys Gln Gln Tyr Met Tyr Tyr Pro
            340                 345                 350

Lys Thr Phe Gly Gln Gly Thr Lys Val Glu Ile Lys Arg
        355                 360                 365

<210> SEQ ID NO 36
<211> LENGTH: 340
<212> TYPE: PRT
<213> ORGANISM: Artificial Sequence
<220> FEATURE:
<223> OTHER INFORMATION: N-terminal Fc fusion of K-044-251 DAB (AAAS
      Linker) dAb-Fc amino acid sequence identified
      using molecular biology techniques.

<400> SEQUENCE: 36

Glu Ser Thr Asp Ile Gln Met Thr Gln Ser Pro Ser Ser Leu Ser Ala
 1               5                  10                  15

Ser Val Gly Asp Arg Val Thr Ile Thr Cys Arg Ala Ser Gln Trp Ile
                20                  25                  30

Gly Pro Glu Leu Lys Trp Tyr Gln Gln Lys Pro Gly Lys Ala Pro Lys
            35                  40                  45

Leu Leu Ile Tyr His Gly Ser Ile Leu Gln Ser Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Met Tyr
                85                  90                  95

Tyr Pro Glu Thr Phe Gly Gln Gly Thr Lys Val Glu Ile Lys Arg Ala
            100                 105                 110

Ala Ala Ser Thr His Thr Cys Pro Pro Cys Pro Ala Pro Glu Leu Leu
        115                 120                 125

Gly Gly Pro Ser Val Phe Leu Phe Pro Pro Lys Pro Lys Asp Thr Leu
    130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
            180                 185                 190

Tyr Arg Val Val Ser Val Leu Thr Val Leu His Gln Asp Trp Leu Asn
        195                 200                 205

```
Gly Lys Glu Tyr Lys Cys Lys Val Ser Asn Lys Ala Leu Pro Ala Pro
    210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Asp Glu Leu Thr Lys Asn Gln Val
                245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
            275                 280                 285

Pro Val Leu Asp Ser Asp Gly Ser Phe Phe Leu Tyr Ser Lys Leu Thr
    290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro Gly Lys
            340
```

<210> SEQ ID NO 37
<211> LENGTH: 340
<212> TYPE: PRT
<213> ORGANISM: Artificial Sequence
<220> FEATURE:
<223> OTHER INFORMATION: N-terminal Fc fusion of K-044-255 DAB (AAAS Linker) dAb-Fc amino acid sequence identified using molecular biology techniques.

<400> SEQUENCE: 37

```
Glu Ser Thr Asp Ile Gln Met Thr Gln Ser Pro Ser Ser Leu Ser Ala
1               5                   10                  15

Ser Val Gly Asp Arg Val Thr Ile Thr Cys Arg Ala Ser Gln Trp Ile
                20                  25                  30

Gly Pro Glu Leu Lys Trp Tyr Gln Gln Lys Pro Gly Lys Ala Pro Lys
            35                  40                  45

Leu Leu Ile Tyr His Gly Ser Ile Leu Gln Ser Gly Val Pro Ser Arg
50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Met Tyr
                85                  90                  95

Tyr Pro Lys Thr Phe Gly Gln Gly Thr Lys Val Glu Ile Lys Arg Ala
            100                 105                 110

Ala Ala Ser Thr His Thr Cys Pro Pro Cys Pro Ala Pro Glu Leu Leu
        115                 120                 125

Gly Gly Pro Ser Val Phe Leu Phe Pro Pro Lys Pro Lys Asp Thr Leu
    130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
            180                 185                 190

Tyr Arg Val Val Ser Val Leu Thr Val Leu His Gln Asp Trp Leu Asn
        195                 200                 205

Gly Lys Glu Tyr Lys Cys Lys Val Ser Asn Lys Ala Leu Pro Ala Pro
```

Ile Glu Lys Thr Ile Ser Lys Ala Lys Gly Gln Pro Arg Glu Pro Gln
225                 230                 235                 240

Val Tyr Thr Leu Pro Pro Ser Arg Asp Glu Leu Thr Lys Asn Gln Val
            245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
            275                 280                 285

Pro Val Leu Asp Ser Asp Gly Ser Phe Phe Leu Tyr Ser Lys Leu Thr
        290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro Gly Lys
            340

<210> SEQ ID NO 38
<211> LENGTH: 472
<212> TYPE: PRT
<213> ORGANISM: Artificial Sequence
<220> FEATURE:
<223> OTHER INFORMATION: DOM15-26-597-AS Linker-Fc-Albumin Domain 3
      Linker-DT02-K-044-085 Vh-Vk dAb-Fc-dAb amino acid
      sequence identified using molecular biology techniques.

<400> SEQUENCE: 38

Glu Val Gln Leu Leu Val Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Ala Ser Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

```
Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys Glu Val Asp Glu Thr Tyr Val Pro Lys
            340                 345                 350

Glu Phe Asn Ala Glu Thr Phe Thr Phe His Ala Asp Ile Gln Met
        355                 360                 365

Thr Gln Ser Pro Ser Ser Leu Ser Ala Ser Val Gly Asp Arg Val Thr
    370                 375                 380

Ile Thr Cys Arg Ala Ser Gln Trp Ile Gly Pro Glu Leu Lys Trp Tyr
385                 390                 395                 400

Gln Gln Lys Pro Gly Lys Ala Pro Lys Leu Leu Ile Tyr His Gly Ser
                405                 410                 415

Ile Leu Gln Ser Gly Val Pro Ser Arg Phe Ser Gly Ser Gly Ser Gly
            420                 425                 430

Thr Asp Phe Thr Leu Thr Ile Ser Ser Leu Gln Pro Glu Asp Phe Ala
        435                 440                 445

Thr Tyr Tyr Cys Gln Gln Tyr Met Tyr Pro His Thr Phe Gly Gln
    450                 455                 460

Gly Thr Lys Val Glu Ile Lys Arg
465                 470
```

<210> SEQ ID NO 39
<211> LENGTH: 472
<212> TYPE: PRT
<213> ORGANISM: Artificial Sequence
<220> FEATURE:
<223> OTHER INFORMATION: DOM15-26-597-AS Linker-Fc-Albumin Domain 3
      Linker-DT02-K-044-251 Vh-Vk dAb-Fc-dAb amino acid
      sequence identified using molecular biology techniques.

<400> SEQUENCE: 39

```
Glu Val Gln Leu Leu Val Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Asp Pro Arg Lys Leu Asp Tyr Trp Gly Gln Gly Thr Leu Val
            100                 105                 110

Thr Val Ser Ser Ala Ser Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys Glu Val Asp Glu Thr Tyr Val Pro Lys
            340                 345                 350

Glu Phe Asn Ala Glu Thr Phe Thr Phe His Ala Asp Ile Gln Met
        355                 360                 365

Thr Gln Ser Pro Ser Ser Leu Ser Ala Ser Val Gly Asp Arg Val Thr
    370                 375                 380

Ile Thr Cys Arg Ala Ser Gln Trp Ile Gly Pro Glu Leu Lys Trp Tyr
385                 390                 395                 400

Gln Gln Lys Pro Gly Lys Ala Pro Lys Leu Leu Ile Tyr His Gly Ser
                405                 410                 415

Ile Leu Gln Ser Gly Val Pro Ser Arg Phe Ser Gly Ser Gly Ser Gly
            420                 425                 430

Thr Asp Phe Thr Leu Thr Ile Ser Ser Leu Gln Pro Glu Asp Phe Ala
        435                 440                 445

Thr Tyr Tyr Cys Gln Gln Tyr Met Tyr Tyr Pro Glu Thr Phe Gly Gln
    450                 455                 460

Gly Thr Lys Val Glu Ile Lys Arg
465                 470

<210> SEQ ID NO 40
<211> LENGTH: 464
<212> TYPE: PRT
<213> ORGANISM: Artificial Sequence
<220> FEATURE:
<223> OTHER INFORMATION: DT02-K-044-085-AS Linker-Fc-Albumin Domain 3
```

Linker-DT02-K-044-085 Vk-Vk dAb-Fc-dAb amino acid
sequence identified using molecular biology techniques.

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro His
                85                  90                  95

Thr Phe Gly Gln Gly Thr Lys Val Glu Ile Lys Arg Ala Ser Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys Glu
                325                 330                 335

Val Asp Glu Thr Tyr Val Pro Lys Glu Phe Asn Ala Glu Thr Phe Thr
            340                 345                 350

Phe His Ala Asp Asp Ile Gln Met Thr Gln Ser Pro Ser Ser Leu Ser
        355                 360                 365

Ala Ser Val Gly Asp Arg Val Thr Ile Thr Cys Arg Ala Ser Gln Trp
370                 375                 380

Ile Gly Pro Glu Leu Lys Trp Tyr Gln Gln Lys Pro Gly Lys Ala Pro
385                 390                 395                 400

Lys Leu Leu Ile Tyr His Gly Ser Ile Leu Gln Ser Gly Val Pro Ser
            405                 410                 415

Arg Phe Ser Gly Ser Gly Ser Gly Thr Asp Phe Thr Leu Thr Ile Ser
            420                 425                 430

Ser Leu Gln Pro Glu Asp Phe Ala Thr Tyr Tyr Cys Gln Gln Tyr Met
            435                 440                 445

Tyr Tyr Pro His Thr Phe Gly Gln Gly Thr Lys Val Glu Ile Lys Arg
        450                 455                 460

<210> SEQ ID NO 41
<211> LENGTH: 466
<212> TYPE: PRT
<213> ORGANISM: Artificial Sequence
<220> FEATURE:
<223> OTHER INFORMATION: DT02-K-044-085-AAAS Linker-Fc-Albumin Domain 3
    Linker-DT02-K-044-085 Vk-Vk dAb-Fc-dAb amino acid
    sequence identified using molecular biology techniques.

<400> SEQUENCE: 41

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro His
                85                  90                  95

Thr Phe Gly Gln Gly Thr Lys Val Glu Ile Lys Arg Ala Ala Ala Ser
            100                 105                 110

Thr His Thr Cys Pro Pro Cys Pro Ala Pro Glu Leu Leu Gly Gly Pro
        115                 120                 125

Ser Val Phe Leu Phe Pro Pro Lys Pro Lys Asp Thr Leu Met Ile Ser
    130                 135                 140

Arg Thr Pro Glu Val Thr Cys Val Val Val Asp Val Ser His Glu Asp
145                 150                 155                 160

Pro Glu Val Lys Phe Asn Trp Tyr Val Asp Gly Val Glu Val His Asn
                165                 170                 175

Ala Lys Thr Lys Pro Arg Glu Glu Gln Tyr Asn Ser Thr Tyr Arg Val
            180                 185                 190

Val Ser Val Leu Thr Val Leu His Gln Asp Trp Leu Asn Gly Lys Glu
        195                 200                 205

Tyr Lys Cys Lys Val Ser Asn Lys Ala Leu Pro Ala Pro Ile Glu Lys
    210                 215                 220

Thr Ile Ser Lys Ala Lys Gly Gln Pro Arg Glu Pro Gln Val Tyr Thr
225                 230                 235                 240

Leu Pro Pro Ser Arg Asp Glu Leu Thr Lys Asn Gln Val Ser Leu Thr
                245                 250                 255

Cys Leu Val Lys Gly Phe Tyr Pro Ser Asp Ile Ala Val Glu Trp Glu
            260                 265                 270

Ser Asn Gly Gln Pro Glu Asn Asn Tyr Lys Thr Thr Pro Pro Val Leu
        275                 280                 285

```
Asp Ser Asp Gly Ser Phe Phe Leu Tyr Ser Lys Leu Thr Val Asp Lys
            290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
                325                 330                 335

Lys Glu Val Asp Glu Thr Tyr Val Pro Lys Glu Phe Asn Ala Glu Thr
            340                 345                 350

Phe Thr Phe His Ala Asp Asp Ile Gln Met Thr Gln Ser Pro Ser Ser
        355                 360                 365

Leu Ser Ala Ser Val Gly Asp Arg Val Thr Ile Thr Cys Arg Ala Ser
370                 375                 380

Gln Trp Ile Gly Pro Glu Leu Lys Trp Tyr Gln Gln Lys Pro Gly Lys
385                 390                 395                 400

Ala Pro Lys Leu Leu Ile Tyr His Gly Ser Ile Leu Gln Ser Gly Val
                405                 410                 415

Pro Ser Arg Phe Ser Gly Ser Gly Ser Gly Thr Asp Phe Thr Leu Thr
            420                 425                 430

Ile Ser Ser Leu Gln Pro Glu Asp Phe Ala Thr Tyr Tyr Cys Gln Gln
        435                 440                 445

Tyr Met Tyr Tyr Pro His Thr Phe Gly Gln Gly Thr Lys Val Glu Ile
    450                 455                 460

Lys Arg
465

<210> SEQ ID NO 42
<211> LENGTH: 464
<212> TYPE: PRT
<213> ORGANISM: Artificial Sequence
<220> FEATURE:
<223> OTHER INFORMATION: DT02-K-044-251-AS Linker-Fc-Albumin Domain 3
      Linker-DT02-K-044-251 Vk-Vk dAb-Fc-dAb amino acid
      sequence identified using molecular biology techniques.

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro Glu
                85                  90                  95

Thr Phe Gly Gln Gly Thr Lys Val Glu Ile Lys Arg Ala Ser Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
```

```
            165                 170                 175
Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
            195                 200                 205

Cys Lys Val Ser Asn Lys Ala Leu Pro Ala Pro Ile Glu Lys Thr Ile
            210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
            245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
            275                 280                 285

Asp Gly Ser Phe Phe Leu Tyr Ser Lys Leu Thr Val Asp Lys Ser Arg
            290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys Glu
                        325                 330                 335

Val Asp Glu Thr Tyr Val Pro Lys Glu Phe Asn Ala Glu Thr Phe Thr
            340                 345                 350

Phe His Ala Asp Asp Ile Gln Met Thr Gln Ser Pro Ser Ser Leu Ser
            355                 360                 365

Ala Ser Val Gly Asp Arg Val Thr Ile Thr Cys Arg Ala Ser Gln Trp
370                 375                 380

Ile Gly Pro Glu Leu Lys Trp Tyr Gln Gln Lys Pro Gly Lys Ala Pro
385                 390                 395                 400

Lys Leu Leu Ile Tyr His Gly Ser Ile Leu Gln Ser Gly Val Pro Ser
                        405                 410                 415

Arg Phe Ser Gly Ser Gly Ser Gly Thr Asp Phe Thr Leu Thr Ile Ser
                        420                 425                 430

Ser Leu Gln Pro Glu Asp Phe Ala Thr Tyr Tyr Cys Gln Gln Tyr Met
            435                 440                 445

Tyr Tyr Pro Glu Thr Phe Gly Gln Gly Thr Lys Val Glu Ile Lys Arg
            450                 455                 460

<210> SEQ ID NO 43
<211> LENGTH: 466
<212> TYPE: PRT
<213> ORGANISM: Artificial Sequence
<220> FEATURE:
<223> OTHER INFORMATION: DT02-K-044-251-AAAS Linker-Fc-Albumin Domain 3
      Linker-DT02-K-044-251 Vk-Vk dAb-Fc-dAb amino acid
      sequence identified using molecular biology techniques.

<400> SEQUENCE: 43

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
            35                  40                  45

Tyr His Gly Ser Ile Leu Gln Ser Gly Val Pro Ser Arg Phe Ser Gly
        50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Met Tyr Tyr Pro Glu
                 85                  90                  95

Thr Phe Gly Gln Gly Thr Lys Val Glu Ile Lys Arg Ala Ala Ala Ser
            100                 105                 110

Thr His Thr Cys Pro Pro Cys Pro Ala Pro Glu Leu Leu Gly Gly Pro
            115                 120                 125

Ser Val Phe Leu Phe Pro Pro Lys Pro Lys Asp Thr Leu Met Ile Ser
        130                 135                 140

Arg Thr Pro Glu Val Thr Cys Val Val Val Asp Val Ser His Glu Asp
145                 150                 155                 160

Pro Glu Val Lys Phe Asn Trp Tyr Val Asp Gly Val Glu Val His Asn
                165                 170                 175

Ala Lys Thr Lys Pro Arg Glu Glu Gln Tyr Asn Ser Thr Tyr Arg Val
            180                 185                 190

Val Ser Val Leu Thr Val Leu His Gln Asp Trp Leu Asn Gly Lys Glu
        195                 200                 205

Tyr Lys Cys Lys Val Ser Asn Lys Ala Leu Pro Ala Pro Ile Glu Lys
            210                 215                 220

Thr Ile Ser Lys Ala Lys Gly Gln Pro Arg Glu Pro Gln Val Tyr Thr
225                 230                 235                 240

Leu Pro Pro Ser Arg Asp Glu Leu Thr Lys Asn Gln Val Ser Leu Thr
                245                 250                 255

Cys Leu Val Lys Gly Phe Tyr Pro Ser Asp Ile Ala Val Glu Trp Glu
            260                 265                 270

Ser Asn Gly Gln Pro Glu Asn Asn Tyr Lys Thr Thr Pro Pro Val Leu
        275                 280                 285

Asp Ser Asp Gly Ser Phe Phe Leu Tyr Ser Lys Leu Thr Val Asp Lys
    290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
                325                 330                 335

Lys Glu Val Asp Glu Thr Tyr Val Pro Lys Glu Phe Asn Ala Glu Thr
            340                 345                 350

Phe Thr Phe His Ala Asp Asp Ile Gln Met Thr Gln Ser Pro Ser Ser
        355                 360                 365

Leu Ser Ala Ser Val Gly Asp Arg Val Thr Ile Thr Cys Arg Ala Ser
    370                 375                 380

Gln Trp Ile Gly Pro Glu Leu Lys Trp Tyr Gln Gln Lys Pro Gly Lys
385                 390                 395                 400

Ala Pro Lys Leu Leu Ile Tyr His Gly Ser Ile Leu Gln Ser Gly Val
                405                 410                 415

Pro Ser Arg Phe Ser Gly Ser Gly Ser Gly Thr Asp Phe Thr Leu Thr
            420                 425                 430

Ile Ser Ser Leu Gln Pro Glu Asp Phe Ala Thr Tyr Tyr Cys Gln Gln
        435                 440                 445

Tyr Met Tyr Tyr Pro Glu Thr Phe Gly Gln Gly Thr Lys Val Glu Ile
    450                 455                 460

Lys Arg
465
```

-continued

<210> SEQ ID NO 44
<211> LENGTH: 356
<212> TYPE: PRT
<213> ORGANISM: Artificial Sequence
<220> FEATURE:
<223> OTHER INFORMATION: C-terminal Fc fusion of K-044-085 DAB(Albumin
      Domain 3 Linker) Fc-dAb amino acid sequence
      identified using molecular biology techniques.

<400> SEQUENCE: 44

Ala Ser Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Glu Val Asp Glu Thr Tyr Val Pro Lys Glu Phe Asn Ala
225                 230                 235                 240

Glu Thr Phe Thr Phe His Ala Asp Asp Ile Gln Met Thr Gln Ser Pro
                245                 250                 255

Ser Ser Leu Ser Ala Ser Val Gly Asp Arg Val Thr Ile Thr Cys Arg
            260                 265                 270

Ala Ser Gln Trp Ile Gly Pro Glu Leu Lys Trp Tyr Gln Gln Lys Pro
        275                 280                 285

Gly Lys Ala Pro Lys Leu Leu Ile Tyr His Gly Ser Ile Leu Gln Ser
    290                 295                 300

Gly Val Pro Ser Arg Phe Ser Gly Ser Gly Ser Gly Thr Asp Phe Thr
305                 310                 315                 320

Leu Thr Ile Ser Ser Leu Gln Pro Glu Asp Phe Ala Thr Tyr Tyr Cys
                325                 330                 335

Gln Gln Tyr Met Tyr Tyr Pro His Thr Phe Gly Gln Gly Thr Lys Val
            340                 345                 350

Glu Ile Lys Arg

<210> SEQ ID NO 45
<211> LENGTH: 354
<212> TYPE: PRT
<213> ORGANISM: Artificial Sequence
<220> FEATURE:
<223> OTHER INFORMATION: C-terminal Fc fusion of K-044-085 DAB(Albumin Domain 3 Linker) Fc-dAb amino acid sequence identified using molecular biology techniques.

<400> SEQUENCE: 45

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Glu Val Asp Glu Thr Tyr Val Pro Lys Glu Phe Asn Ala Glu Thr
225                 230                 235                 240

Phe Thr Phe His Ala Asp Asp Ile Gln Met Thr Gln Ser Pro Ser Ser
                245                 250                 255

Leu Ser Ala Ser Val Gly Asp Arg Val Thr Ile Thr Cys Arg Ala Ser
            260                 265                 270

Gln Trp Ile Gly Pro Glu Leu Lys Trp Tyr Gln Gln Lys Pro Gly Lys
        275                 280                 285

Ala Pro Lys Leu Leu Ile Tyr His Gly Ser Ile Leu Gln Ser Gly Val
    290                 295                 300

Pro Ser Arg Phe Ser Gly Ser Gly Ser Gly Thr Asp Phe Thr Leu Thr
305                 310                 315                 320

Ile Ser Ser Leu Gln Pro Glu Asp Phe Ala Thr Tyr Tyr Cys Gln Gln
                325                 330                 335

Tyr Met Tyr Tyr Pro His Thr Phe Gly Gln Gly Thr Lys Val Glu Ile
            340                 345                 350
```

Lys Arg

<210> SEQ ID NO 46
<211> LENGTH: 356
<212> TYPE: PRT
<213> ORGANISM: Artificial Sequence
<220> FEATURE:
<223> OTHER INFORMATION: C-terminal Fc fusion of K-044-251 DAB (Albumin Domain 3 Linker) Fc-dAb amino acid sequence identified using molecular biology techniques.

<400> SEQUENCE: 46

```
Ala Ser Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Glu Val Asp Glu Thr Tyr Val Pro Lys Glu Phe Asn Ala
225                 230                 235                 240

Glu Thr Phe Thr Phe His Ala Asp Asp Ile Gln Met Thr Gln Ser Pro
                245                 250                 255

Ser Ser Leu Ser Ala Ser Val Gly Asp Arg Val Thr Ile Thr Cys Arg
            260                 265                 270

Ala Ser Gln Trp Ile Gly Pro Glu Leu Lys Trp Tyr Gln Gln Lys Pro
        275                 280                 285

Gly Lys Ala Pro Lys Leu Leu Ile Tyr His Gly Ser Ile Leu Gln Ser
    290                 295                 300

Gly Val Pro Ser Arg Phe Ser Gly Ser Gly Ser Gly Thr Asp Phe Thr
305                 310                 315                 320

Leu Thr Ile Ser Ser Leu Gln Pro Glu Asp Phe Ala Thr Tyr Tyr Cys
                325                 330                 335

Gln Gln Tyr Met Tyr Tyr Pro Glu Thr Phe Gly Gln Gly Thr Lys Val
```

Glu Ile Lys Arg
        355

<210> SEQ ID NO 47
<211> LENGTH: 354
<212> TYPE: PRT
<213> ORGANISM: Artificial Sequence
<220> FEATURE:
<223> OTHER INFORMATION: C-terminal Fc fusion of K-044-251 DAB(Albumin
      Domain 3 Linker) Fc-dAb amino acid sequence
      identified using molecular biology techniques.

<400> SEQUENCE: 47

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Glu Val Asp Glu Thr Tyr Val Pro Lys Glu Phe Asn Ala Glu Thr
225                 230                 235                 240

Phe Thr Phe His Ala Asp Asp Ile Gln Met Thr Gln Ser Pro Ser Ser
                245                 250                 255

Leu Ser Ala Ser Val Gly Asp Arg Val Thr Ile Thr Cys Arg Ala Ser
            260                 265                 270

Gln Trp Ile Gly Pro Glu Leu Lys Trp Tyr Gln Gln Lys Pro Gly Lys
        275                 280                 285

Ala Pro Lys Leu Leu Ile Tyr His Gly Ser Ile Leu Gln Ser Gly Val
    290                 295                 300

Pro Ser Arg Phe Ser Gly Ser Gly Ser Gly Thr Asp Phe Thr Leu Thr
305                 310                 315                 320

Ile Ser Ser Leu Gln Pro Glu Asp Phe Ala Thr Tyr Tyr Cys Gln Gln
                325                 330                 335

Tyr Met Tyr Tyr Pro Glu Thr Phe Gly Gln Gly Thr Lys Val Glu Ile
                340                 345                 350

Lys Arg

<210> SEQ ID NO 48
<211> LENGTH: 339
<212> TYPE: PRT
<213> ORGANISM: Artificial Sequence
<220> FEATURE:
<223> OTHER INFORMATION: N-terminal Fc fusion of K-044-085 DAB (TVAAPS
      Linker) dAb-Fc amino acid sequence identified
      using molecular biology techniques.

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro His
                85                  90                  95

Thr Phe Gly Gln Gly Thr Lys Val Glu Ile Lys Arg Thr Val Ala Ala
            100                 105                 110

Pro Ser Thr His Thr Cys Pro Pro Cys Pro Ala Pro Glu Leu Leu Gly
        115                 120                 125

Gly Pro Ser Val Phe Leu Phe Pro Pro Lys Pro Lys Asp Thr Leu Met
130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
        195                 200                 205

Lys Glu Tyr Lys Cys Lys Val Ser Asn Lys Ala Leu Pro Ala Pro Ile
210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Asp Glu Leu Thr Lys Asn Gln Val Ser
                245                 250                 255

Leu Thr Cys Leu Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
        275                 280                 285

Val Leu Asp Ser Asp Gly Ser Phe Phe Leu Tyr Ser Lys Leu Thr Val
290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser

Pro Gly Lys

<210> SEQ ID NO 49
<211> LENGTH: 339
<212> TYPE: PRT
<213> ORGANISM: Artificial Sequence
<220> FEATURE:
<223> OTHER INFORMATION: N-terminal Fc fusion of K-044-232 DAB(TVAAPS
      Linker) dAb-Fc amino acid sequence identified
      using molecular biology techniques.

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Ser Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro Glu
                85                  90                  95

Thr Phe Gly Gln Gly Thr Lys Val Glu Ile Lys Arg Thr Val Ala Ala
            100                 105                 110

Pro Ser Thr His Thr Cys Pro Pro Cys Pro Ala Pro Glu Leu Leu Gly
        115                 120                 125

Gly Pro Ser Val Phe Leu Phe Pro Pro Lys Pro Lys Asp Thr Leu Met
    130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
        195                 200                 205

Lys Glu Tyr Lys Cys Lys Val Ser Asn Lys Ala Leu Pro Ala Pro Ile
    210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Asp Glu Leu Thr Lys Asn Gln Val Ser
                245                 250                 255

Leu Thr Cys Leu Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
        275                 280                 285

Val Leu Asp Ser Asp Gly Ser Phe Phe Leu Tyr Ser Lys Leu Thr Val
    290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys

<210> SEQ ID NO 50
<211> LENGTH: 339
<212> TYPE: PRT
<213> ORGANISM: Artificial Sequence
<220> FEATURE:
<223> OTHER INFORMATION: N-terminal Fc fusion of K-044-236 DAB(TVAAPS
      Linker) dAb-Fc amino acid sequence identified
      using molecular biology techniques.

<400> SEQUENCE: 50

```
Asp Ile Gln Met Thr Gln Ser Pro Ser Leu Ser Ala Ser Val Gly
 1               5                  10                  15

Asp Arg Val Thr Ile Thr Cys Arg Ala Ser Gln Trp Ile Gly Pro Glu
             20                  25                  30

Leu Ser Trp Tyr Gln Gln Lys Pro Gly Lys Ala Pro Lys Leu Leu Ile
         35                  40                  45

Tyr His Gly Ser Ile Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro Lys
                 85                  90                  95

Thr Phe Gly Gln Gly Thr Lys Val Glu Ile Lys Arg Thr Val Ala Ala
            100                 105                 110

Pro Ser Thr His Thr Cys Pro Pro Cys Pro Ala Pro Glu Leu Leu Gly
        115                 120                 125

Gly Pro Ser Val Phe Leu Phe Pro Pro Lys Pro Lys Asp Thr Leu Met
130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
        195                 200                 205

Lys Glu Tyr Lys Cys Lys Val Ser Asn Lys Ala Leu Pro Ala Pro Ile
    210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Asp Glu Leu Thr Lys Asn Gln Val Ser
                245                 250                 255

Leu Thr Cys Leu Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
        275                 280                 285

Val Leu Asp Ser Asp Gly Ser Phe Phe Leu Tyr Ser Lys Leu Thr Val
290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys
```

-continued

```
<210> SEQ ID NO 51
<211> LENGTH: 339
<212> TYPE: PRT
<213> ORGANISM: Artificial Sequence
<220> FEATURE:
<223> OTHER INFORMATION: N-terminal Fc fusion of K-044-251 DAB (TVAAPS
      Linker) dAb-Fc amino acid sequence identified
      using molecular biology techniques.

<400> SEQUENCE: 51

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Pro Glu
             20                  25                  30

Leu Lys Trp Tyr Gln Gln Lys Pro Gly Lys Ala Pro Lys Leu Leu Ile
         35                  40                  45

Tyr His Gly Ser Ile Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Met Tyr Tyr Pro Glu
                 85                  90                  95

Thr Phe Gly Gln Gly Thr Lys Val Glu Ile Lys Arg Thr Val Ala Ala
            100                 105                 110

Pro Ser Thr His Thr Cys Pro Pro Cys Pro Ala Pro Glu Leu Leu Gly
            115                 120                 125

Gly Pro Ser Val Phe Leu Phe Pro Pro Lys Pro Lys Asp Thr Leu Met
130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
            195                 200                 205

Lys Glu Tyr Lys Cys Lys Val Ser Asn Lys Ala Leu Pro Ala Pro Ile
        210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Asp Glu Leu Thr Lys Asn Gln Val Ser
                245                 250                 255

Leu Thr Cys Leu Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
        275                 280                 285

Val Leu Asp Ser Asp Gly Ser Phe Phe Leu Tyr Ser Lys Leu Thr Val
    290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys

<210> SEQ ID NO 52
```

<211> LENGTH: 339
<212> TYPE: PRT
<213> ORGANISM: Artificial Sequence
<220> FEATURE:
<223> OTHER INFORMATION: N-terminal Fc fusion of K-044-255 DAB (TVAAPS
      Linker) dAb-Fc amino acid sequence identified
      using molecular biology techniques.

<400> SEQUENCE: 52

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Pro Glu
             20                  25                  30

Leu Lys Trp Tyr Gln Gln Lys Pro Gly Lys Ala Pro Lys Leu Leu Ile
         35                  40                  45

Tyr His Gly Ser Ile Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Met Tyr Tyr Pro Lys
                 85                  90                  95

Thr Phe Gly Gln Gly Thr Lys Val Glu Ile Lys Arg Thr Val Ala Ala
            100                 105                 110

Pro Ser Thr His Thr Cys Pro Pro Cys Pro Ala Pro Glu Leu Leu Gly
        115                 120                 125

Gly Pro Ser Val Phe Leu Phe Pro Pro Lys Pro Lys Asp Thr Leu Met
130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
        195                 200                 205

Lys Glu Tyr Lys Cys Lys Val Ser Asn Lys Ala Leu Pro Ala Pro Ile
    210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Asp Glu Leu Thr Lys Asn Gln Val Ser
                245                 250                 255

Leu Thr Cys Leu Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
        275                 280                 285

Val Leu Asp Ser Asp Gly Ser Phe Phe Leu Tyr Ser Lys Leu Thr Val
    290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys
```

<210> SEQ ID NO 53
<211> LENGTH: 477
<212> TYPE: PRT

<213> ORGANISM: Artificial Sequence
<220> FEATURE:
<223> OTHER INFORMATION: DOM15-26-597-AS Linker-Fc-GS(TVAAPSGS)x3
Linker-DT02-K-044-085 Vh-Vk dAb-Fc-dAb amino acid
sequence identified using molecular biology techniques.

<400> SEQUENCE: 53

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Ala Ser Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys Gly Ser Thr Val Ala Ala Pro Ser Gly
            340                 345                 350

Ser Thr Val Ala Ala Pro Ser Gly Ser Thr Val Ala Ala Pro Ser Gly
        355                 360                 365

Ser Asp Ile Gln Met Thr Gln Ser Pro Ser Ser Leu Ser Ala Ser Val
    370                 375                 380

```
Gly Asp Arg Val Thr Ile Thr Cys Arg Ala Ser Gln Trp Ile Gly Pro
385                 390                 395                 400

Glu Leu Lys Trp Tyr Gln Gln Lys Pro Gly Lys Ala Pro Lys Leu Leu
            405                 410                 415

Ile Tyr His Gly Ser Ile Leu Gln Ser Gly Val Pro Ser Arg Phe Ser
        420                 425                 430

Gly Ser Gly Ser Gly Thr Asp Phe Thr Leu Thr Ile Ser Ser Leu Gln
    435                 440                 445

Pro Glu Asp Phe Ala Thr Tyr Tyr Cys Gln Gln Tyr Met Tyr Tyr Pro
450                 455                 460

His Thr Phe Gly Gln Gly Thr Lys Val Glu Ile Lys Arg
465                 470                 475

<210> SEQ ID NO 54
<211> LENGTH: 475
<212> TYPE: PRT
<213> ORGANISM: Artificial Sequence
<220> FEATURE:
<223> OTHER INFORMATION: DT02-K-044-085-HingeIgG1Linker-Fc-GS(TVAAPSGS)x3
      Linker-DT02-K-044-085 Vh-Vk dAb-Fc-dAb amino acid
      sequence identified using molecular biology techniques.

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro His
                85                  90                  95

Thr Phe Gly Gln Gly Thr Lys Val Glu Ile Lys Arg Val Glu Pro Lys
            100                 105                 110

Ser Ser Asp Lys Thr His Thr Cys Pro Pro Cys Pro Ala Pro Glu Leu
        115                 120                 125

Leu Gly Gly Pro Ser Val Phe Leu Phe Pro Pro Lys Pro Lys Asp Thr
    130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Ala Leu Pro Ala
    210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Asp Glu Leu Thr Lys Asn Gln
                245                 250                 255
```

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
        290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys Gly Ser Thr Val Ala Ala Pro Ser Gly Ser Thr
            340                 345                 350

Val Ala Ala Pro Ser Gly Ser Thr Val Ala Ala Pro Ser Gly Ser Asp
            355                 360                 365

Ile Gln Met Thr Gln Ser Pro Ser Ser Leu Ser Ala Ser Val Gly Asp
            370                 375                 380

Arg Val Thr Ile Thr Cys Arg Ala Ser Gln Trp Ile Gly Pro Glu Leu
385                 390                 395                 400

Lys Trp Tyr Gln Gln Lys Pro Gly Lys Ala Pro Lys Leu Leu Ile Tyr
                405                 410                 415

His Gly Ser Ile Leu Gln Ser Gly Val Pro Ser Arg Phe Ser Gly Ser
            420                 425                 430

Gly Ser Gly Thr Asp Phe Thr Leu Thr Ile Ser Ser Leu Gln Pro Glu
            435                 440                 445

Asp Phe Ala Thr Tyr Tyr Cys Gln Gln Tyr Met Tyr Tyr Pro His Thr
        450                 455                 460

Phe Gly Gln Gly Thr Lys Val Glu Ile Lys Arg
465                 470                 475

<210> SEQ ID NO 55
<211> LENGTH: 469
<212> TYPE: PRT
<213> ORGANISM: Artificial Sequence
<220> FEATURE:
<223> OTHER INFORMATION: DT02-K-044-085-AS-Fc (H112A)-GS(TVAAPSGS)x3
    Linker-DT02-K-044-085 Vh-Vk dAb-Fc-dAb amino acid
    sequence identified using molecular biology techniques.

<400> SEQUENCE: 55

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro His
                85                  90                  95

Thr Phe Gly Gln Gly Thr Lys Val Glu Ile Lys Arg Ala Ser Thr Ala
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr

```
            130             135             140
Pro Glu Val Thr Cys Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
                195                 200                 205

Cys Lys Val Ser Asn Lys Ala Leu Pro Ala Pro Ile Glu Lys Thr Ile
            210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
            275                 280                 285

Asp Gly Ser Phe Phe Leu Tyr Ser Lys Leu Thr Val Asp Lys Ser Arg
            290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys Gly
                325                 330                 335

Ser Thr Val Ala Ala Pro Ser Gly Ser Thr Val Ala Ala Pro Ser Gly
            340                 345                 350

Ser Thr Val Ala Ala Pro Ser Gly Ser Asp Ile Gln Met Thr Gln Ser
            355                 360                 365

Pro Ser Ser Leu Ser Ala Ser Val Gly Asp Arg Val Thr Ile Thr Cys
370                 375                 380

Arg Ala Ser Gln Trp Ile Gly Pro Glu Leu Lys Trp Tyr Gln Gln Lys
385                 390                 395                 400

Pro Gly Lys Ala Pro Lys Leu Leu Ile Tyr His Gly Ser Ile Leu Gln
                405                 410                 415

Ser Gly Val Pro Ser Arg Phe Ser Gly Ser Gly Ser Gly Thr Asp Phe
            420                 425                 430

Thr Leu Thr Ile Ser Ser Leu Gln Pro Glu Asp Phe Ala Thr Tyr Tyr
            435                 440                 445

Cys Gln Gln Tyr Met Tyr Tyr Pro His Thr Phe Gly Gln Gly Thr Lys
            450                 455                 460

Val Glu Ile Lys Arg
465

<210> SEQ ID NO 56
<211> LENGTH: 469
<212> TYPE: PRT
<213> ORGANISM: Artificial Sequence
<220> FEATURE:
<223> OTHER INFORMATION: DT02-K-044-085-AS-Fc (T113P)-GS(TVAAPSGS)x3
    Linker-DT02-K-044-085 Vh-Vk dAb-Fc-dAb amino acid
    sequence identified using molecular biology techniques.

<400> SEQUENCE: 56

Asp Ile Gln Met Thr Gln Ser Pro Ser Ser Leu Ser Ala Ser Val Gly
1               5                   10                  15
```

-continued

```
Asp Arg Val Thr Ile Thr Cys Arg Ala Ser Gln Trp Ile Gly Pro Glu
         20                  25                  30
Leu Lys Trp Tyr Gln Gln Lys Pro Gly Lys Ala Pro Lys Leu Leu Ile
             35                  40                  45
Tyr His Gly Ser Ile Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Met Tyr Tyr Pro His
                 85                  90                  95
Thr Phe Gly Gln Gly Thr Lys Val Glu Ile Lys Arg Ala Ser Thr His
                 100                 105                 110
Pro Cys Pro Pro Cys Pro Ala Pro Glu Leu Leu Gly Gly Pro Ser Val
         115                 120                 125
Phe Leu Phe Pro Pro Lys Pro Lys Asp Thr Leu Met Ile Ser Arg Thr
 130                 135                 140
Pro Glu Val Thr Cys Val Val Val Asp Val Ser His Glu Asp Pro Glu
 145                 150                 155                 160
Val Lys Phe Asn Trp Tyr Val Asp Gly Val Glu Val His Asn Ala Lys
                 165                 170                 175
Thr Lys Pro Arg Glu Glu Gln Tyr Asn Ser Thr Tyr Arg Val Val Ser
                 180                 185                 190
Val Leu Thr Val Leu His Gln Asp Trp Leu Asn Gly Lys Glu Tyr Lys
                 195                 200                 205
Cys Lys Val Ser Asn Lys Ala Leu Pro Ala Pro Ile Glu Lys Thr Ile
 210                 215                 220
Ser Lys Ala Lys Gly Gln Pro Arg Glu Pro Gln Val Tyr Thr Leu Pro
225                 230                 235                 240
Pro Ser Arg Asp Glu Leu Thr Lys Asn Gln Val Ser Leu Thr Cys Leu
                 245                 250                 255
Val Lys Gly Phe Tyr Pro Ser Asp Ile Ala Val Glu Trp Glu Ser Asn
                 260                 265                 270
Gly Gln Pro Glu Asn Asn Tyr Lys Thr Thr Pro Val Leu Asp Ser
                 275                 280                 285
Asp Gly Ser Phe Phe Leu Tyr Ser Lys Leu Thr Val Asp Lys Ser Arg
 290                 295                 300
Trp Gln Gln Gly Asn Val Phe Ser Cys Ser Val Met His Glu Ala Leu
305                 310                 315                 320
His Asn His Tyr Thr Gln Lys Ser Leu Ser Leu Ser Pro Gly Lys Gly
                 325                 330                 335
Ser Thr Val Ala Ala Pro Ser Gly Ser Thr Val Ala Ala Pro Ser Gly
                 340                 345                 350
Ser Thr Val Ala Ala Pro Ser Gly Ser Asp Ile Gln Met Thr Gln Ser
                 355                 360                 365
Pro Ser Ser Leu Ser Ala Ser Val Gly Asp Arg Val Thr Ile Thr Cys
         370                 375                 380
Arg Ala Ser Gln Trp Ile Gly Pro Glu Leu Lys Trp Tyr Gln Gln Lys
385                 390                 395                 400
Pro Gly Lys Ala Pro Lys Leu Leu Ile Tyr His Gly Ser Ile Leu Gln
                 405                 410                 415
Ser Gly Val Pro Ser Arg Phe Ser Gly Ser Gly Ser Gly Thr Asp Phe
                 420                 425                 430
```

-continued

```
Thr Leu Thr Ile Ser Ser Leu Gln Pro Glu Asp Phe Ala Thr Tyr Tyr
            435                 440                 445

Cys Gln Gln Tyr Met Tyr Tyr Pro His Thr Phe Gly Gln Gly Thr Lys
    450                 455                 460

Val Glu Ile Lys Arg
465

<210> SEQ ID NO 57
<211> LENGTH: 12
<212> TYPE: DNA
<213> ORGANISM: Artificial Sequence
<220> FEATURE:
<223> OTHER INFORMATION: AAAS Linker (N-terminal Linker) nucleic acid
      sequence identified using molecular biology techniques.

<400> SEQUENCE: 57
gcggccgcta gc                                                           12

<210> SEQ ID NO 58
<211> LENGTH: 6
<212> TYPE: DNA
<213> ORGANISM: Homo sapiens

<400> SEQUENCE: 58 gctagc                                                                   6

<210> SEQ ID NO 59
<211> LENGTH: 18
<212> TYPE: DNA
<213> ORGANISM: Homo sapiens

<400> SEQUENCE: 59
accgtcgccg ctcctagc                                                     18

<210> SEQ ID NO 60
<211> LENGTH: 24
<212> TYPE: DNA
<213> ORGANISM: Homo sapiens

<400> SEQUENCE: 60
gtggagccta agtcttctga caag                                              24

<210> SEQ ID NO 61
<211> LENGTH: 27
<212> TYPE: DNA
<213> ORGANISM: Homo sapiens

<400> SEQUENCE: 61
gagctcaaaa ccccacttgg tgacaca                                           27

<210> SEQ ID NO 62
<211> LENGTH: 54
<212> TYPE: DNA
<213> ORGANISM: Artificial Sequence
<220> FEATURE:
<223> OTHER INFORMATION: Fibronectin x3 Linker (N-terminal Linker)
      nucleic acid sequence identified using molecular biology
      techniques.

<400> SEQUENCE: 62
accggattag acagtcccac aggtctcgat tcacctactg gcttagactc tcca            54

<210> SEQ ID NO 63
<211> LENGTH: 72
```

<212> TYPE: DNA
<213> ORGANISM: Artificial Sequence
<220> FEATURE:
<223> OTHER INFORMATION: Fibronectin x4 Linker (N-terminal Linker) nucleic acid sequence identified using molecular biology techniques.

<400> SEQUENCE: 63

```
accggattag acagtcccac aggtctcgat tcacctactg cttagactc tccaaccggc    60
ctggacagcc cc                                                        72
```

<210> SEQ ID NO 64
<211> LENGTH: 675
<212> TYPE: DNA
<213> ORGANISM: Artificial Sequence
<220> FEATURE:
<223> OTHER INFORMATION: H2A IgG1 Fc nucleic acid sequence identified using molecular biology techniques.

<400> SEQUENCE: 64

```
accgccacct gccccccctg ccctgccccc gagctgctgg gaggcccag cgtgttcctg     60
ttcccccca agcctaagga caccctgatg atcagcagaa ccccgaggt gacctgtgtg    120
gtggtggatg tgagccacga ggaccctgag gtgaagttca ctggtacgt ggacggcgtg    180
gaggtgcaca atgccaagac caagcccagg gaggagcagt acaacagcac ctaccgggtg    240
gtgtccgtgc tgaccgtgct gcaccaggat tggctgaacg gcaaggagta caagtgtaag    300
gtgtccaaca aggccctgcc tgcccctatc gagaaaacca tcagcaaggc caagggccag    360
cccagagagc cccaggtgta caccctgccc ctagcagag atgagctgac caagaaccag    420
gtgtccctga cctgcctggt gaagggcttc taccccagcg acatcgccgt ggagtgggag    480
agcaacggcc agcccgagaa caactacaag accaccccc ctgtgctgga cagcgatggc    540
agcttcttcc tgtacagcaa gctgaccgtg gacaagagca gatggcagca gggcaacgtg    600
ttcagctgct ccgtgatgca cgaggccctg cacaatcact acacccagaa gagcctgagc    660
ctgtcccctg gcaag                                                     675
```

<210> SEQ ID NO 65
<211> LENGTH: 675
<212> TYPE: DNA
<213> ORGANISM: Artificial Sequence
<220> FEATURE:
<223> OTHER INFORMATION: T3P IgG1 Fc nucleic acid sequence identified using molecular biology techniques.

<400> SEQUENCE: 65

```
acccacccttt gccccccctg ccctgccccc gagctgctgg gaggcccag cgtgttcctg     60
ttcccccca agcctaagga caccctgatg atcagcagaa ccccgaggt gacctgtgtg    120
gtggtggatg tgagccacga ggaccctgag gtgaagttca ctggtacgt ggacggcgtg    180
gaggtgcaca atgccaagac caagcccagg gaggagcagt acaacagcac ctaccgggtg    240
gtgtccgtgc tgaccgtgct gcaccaggat tggctgaacg gcaaggagta caagtgtaag    300
gtgtccaaca aggccctgcc tgcccctatc gagaaaacca tcagcaaggc caagggccag    360
cccagagagc cccaggtgta caccctgccc ctagcagag atgagctgac caagaaccag    420
gtgtccctga cctgcctggt gaagggcttc taccccagcg acatcgccgt ggagtgggag    480
agcaacggcc agcccgagaa caactacaag accaccccc ctgtgctgga cagcgatggc    540
agcttcttcc tgtacagcaa gctgaccgtg gacaagagca gatggcagca gggcaacgtg    600
```

```
ttcagctgct ccgtgatgca cgaggccctg cacaatcact acacccagaa gagcctgagc    660
ctgtcccctg gcaag                                                     675
```

<210> SEQ ID NO 66
<211> LENGTH: 78
<212> TYPE: DNA
<213> ORGANISM: Artificial Sequence
<220> FEATURE:
<223> OTHER INFORMATION: ((GS(TVAAPSGS)x3)) Linker (C-terminal Linker)
      nucleic acid sequence identified
      using molecular biology techniques.

<400> SEQUENCE: 66

```
ggatctaccg tggcagcacc atcaggatct accgtggcag caccatcagg ttcaacagta    60
gctgctcctt ctggatcc                                                  78
```

<210> SEQ ID NO 67
<211> LENGTH: 54
<212> TYPE: DNA
<213> ORGANISM: Artificial Sequence
<220> FEATURE:
<223> OTHER INFORMATION: Fibronectin x3 Linker (C-terminal Linker)
      nucleic acid sequence identified
      using molecular biology techniques.

<400> SEQUENCE: 67

```
accggattag acagtcccac aggtctcgat tcacctactg gcttagactc tcca          54
```

<210> SEQ ID NO 68
<211> LENGTH: 72
<212> TYPE: DNA
<213> ORGANISM: Artificial Sequence
<220> FEATURE:
<223> OTHER INFORMATION: Fibronectin x4 Linker (C-terminal Linker)
      nucleic acid sequence identified
      using molecular biology techniques.

<400> SEQUENCE: 68

```
accggattag acagtcccac aggtctcgat tcacctactg gcttagactc tccaaccggc    60
ctggacagcc cc                                                        72
```

<210> SEQ ID NO 69
<211> LENGTH: 57
<212> TYPE: DNA
<213> ORGANISM: Homo sapiens

<400> SEQUENCE: 69

```
cacaaggacg acaaccccaa cctgcccagg ctggtgaggc ccgaggtgga cgtgatg       57
```

<210> SEQ ID NO 70
<211> LENGTH: 63
<212> TYPE: DNA
<213> ORGANISM: Homo sapiens

<400> SEQUENCE: 70

```
gagaacgacg agatgcccgc cgacctgccc agcctggccg ccgacttcgt ggagagcaag    60
gac                                                                  63
```

<210> SEQ ID NO 71
<211> LENGTH: 63
<212> TYPE: DNA
<213> ORGANISM: Homo sapiens

<400> SEQUENCE: 71

```
gaggtggacg agacctacgt gcccaaggag ttcaacgccg agaccttcac cttccacgcc    60
gac                                                                 63
```

<210> SEQ ID NO 72
<211> LENGTH: 48
<212> TYPE: DNA
<213> ORGANISM: Homo sapiens

<400> SEQUENCE: 72

```
gaggtggacg agacctacgt gcccaaggag ttcaacgccg agaccttc                 48
```

<210> SEQ ID NO 73
<211> LENGTH: 45
<212> TYPE: DNA
<213> ORGANISM: Artificial Sequence
<220> FEATURE:
<223> OTHER INFORMATION: Gly4Ser 3x Linker (C-terminal Linker)
      nucleic acid sequence identified
      using molecular biology techniques.

<400> SEQUENCE: 73

```
ggtggaggcg gttcaggcgg aggtggcagc ggcggtggcg ggtcg                    45
```

<210> SEQ ID NO 74
<211> LENGTH: 60
<212> TYPE: DNA
<213> ORGANISM: Artificial Sequence
<220> FEATURE:
<223> OTHER INFORMATION: Gly4Ser 4x Linker (C-terminal Linker) nucleic
      acid sequence identified using molecular biology techniques.

<400> SEQUENCE: 74

```
ggtggaggcg gttcaggcgg aggtggcagc ggcggtggcg ggtcgggtgg aggcggttca    60
```

<210> SEQ ID NO 75
<211> LENGTH: 120
<212> TYPE: DNA
<213> ORGANISM: Homo sapiens

<400> SEQUENCE: 75

```
aaagaagcgg cggcgaaaga agcggcggcg aaagaagcgg ccgccaagga gctggccgcc    60
aaggaggccg ccgccaagga ggccgccgcc aaggaggccg ccgccaaaga attggccgca   120
```

<210> SEQ ID NO 76
<211> LENGTH: 4
<212> TYPE: PRT
<213> ORGANISM: Artificial Sequence
<220> FEATURE:
<223> OTHER INFORMATION: AAAS Linker (N-terminal Linker) amino acid
      sequence identified using molecular biology techniques.

<400> SEQUENCE: 76

Ala Ala Ala Ser
 1

<210> SEQ ID NO 77
<211> LENGTH: 2
<212> TYPE: PRT
<213> ORGANISM: Homo sapiens

<400> SEQUENCE: 77

Ala Ser
 1

<210> SEQ ID NO 78
<211> LENGTH: 6
<212> TYPE: PRT
<213> ORGANISM: Homo sapiens

<400> SEQUENCE: 78

Thr Val Ala Ala Pro Ser
1               5

<210> SEQ ID NO 79
<211> LENGTH: 8
<212> TYPE: PRT
<213> ORGANISM: Homo sapiens

<400> SEQUENCE: 79

Val Glu Pro Lys Ser Ser Asp Lys
1               5

<210> SEQ ID NO 80
<211> LENGTH: 9
<212> TYPE: PRT
<213> ORGANISM: Homo sapiens

<400> SEQUENCE: 80

Glu Leu Lys Thr Pro Leu Gly Asp Thr
1               5

<210> SEQ ID NO 81
<211> LENGTH: 18
<212> TYPE: PRT
<213> ORGANISM: Artificial Sequence
<220> FEATURE:
<223> OTHER INFORMATION: Fibronectin x3 Linker (N-terminal Linker)
      amino acid sequence identified using molecular biology techniques.

<400> SEQUENCE: 81

Thr Gly Leu Asp Ser Pro Thr Gly Leu Asp Ser Pro Thr Gly Leu Asp
1               5                   10                  15

Ser Pro

<210> SEQ ID NO 82
<211> LENGTH: 24
<212> TYPE: PRT
<213> ORGANISM: Artificial Sequence
<220> FEATURE:
<223> OTHER INFORMATION: Fibronectin x4 Linker (N-terminal Linker) amino
      acid sequence identified using molecular biology techniques.

<400> SEQUENCE: 82

Thr Gly Leu Asp Ser Pro Thr Gly Leu Asp Ser Pro Thr Gly Leu Asp
1               5                   10                  15

Ser Pro Thr Gly Leu Asp Ser Pro
            20

<210> SEQ ID NO 83
<211> LENGTH: 225
<212> TYPE: PRT
<213> ORGANISM: Artificial Sequence
<220> FEATURE:
<223> OTHER INFORMATION: H2A IgG1 Fc amino acid sequence identified
      using molecular biology techniques.

<400> SEQUENCE: 83

Thr Ala Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
        20                  25                  30

Arg Thr Pro Glu Val Thr Cys Val Val Asp Val Ser His Glu Asp
            35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 84
<211> LENGTH: 225
<212> TYPE: PRT
<213> ORGANISM: Artificial Sequence
<220> FEATURE:
<223> OTHER INFORMATION: T3P IgG1 Fc amino acid sequence identified
      using molecular biology techniques.

<400> SEQUENCE: 84

Thr His Pro Cys Pro Pro Cys Pro Ala Pro Glu Leu Leu Gly Gly Pro
 1               5                  10                  15

Ser Val Phe Leu Phe Pro Pro Lys Pro Lys Asp Thr Leu Met Ile Ser
        20                  25                  30

Arg Thr Pro Glu Val Thr Cys Val Val Asp Val Ser His Glu Asp
            35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr

```
                130                 135                 140
Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 85
<211> LENGTH: 26
<212> TYPE: PRT
<213> ORGANISM: Artificial Sequence
<220> FEATURE:
<223> OTHER INFORMATION: ((GS(TVAAPSGS)x3)) Linker (C-terminal Linker)
      amino acid sequence identified using
      molecular biology techniques.

<400> SEQUENCE: 85

Gly Ser Thr Val Ala Ala Pro Ser Gly Ser Thr Val Ala Ala Pro Ser
1               5                   10                  15

Gly Ser Thr Val Ala Ala Pro Ser Gly Ser
            20                  25

<210> SEQ ID NO 86
<211> LENGTH: 18
<212> TYPE: PRT
<213> ORGANISM: Artificial Sequence
<220> FEATURE:
<223> OTHER INFORMATION: Fibronectin x3 Linker (C-terminal Linker)
      amino acid sequence identified using molecular biology techniques.

<400> SEQUENCE: 86

Thr Gly Leu Asp Ser Pro Thr Gly Leu Asp Ser Pro Thr Gly Leu Asp
1               5                   10                  15

Ser Pro

<210> SEQ ID NO 87
<211> LENGTH: 24
<212> TYPE: PRT
<213> ORGANISM: Artificial Sequence
<220> FEATURE:
<223> OTHER INFORMATION: Fibronectin x4 Linker (C-terminal Linker) amino
      acid sequence identified using molecular biology techniques.

<400> SEQUENCE: 87

Thr Gly Leu Asp Ser Pro Thr Gly Leu Asp Ser Pro Thr Gly Leu Asp
1               5                   10                  15

Ser Pro Thr Gly Leu Asp Ser Pro
            20

<210> SEQ ID NO 88
<211> LENGTH: 19
<212> TYPE: PRT
<213> ORGANISM: Homo sapiens

<400> SEQUENCE: 88
```

```
His Lys Asp Asp Asn Pro Asn Leu Pro Arg Leu Val Arg Pro Glu Val
1               5                   10                  15

Asp Val Met

<210> SEQ ID NO 89
<211> LENGTH: 21
<212> TYPE: PRT
<213> ORGANISM: Homo sapiens

<400> SEQUENCE: 89

Glu Asn Asp Glu Met Pro Ala Asp Leu Pro Ser Leu Ala Ala Asp Phe
1               5                   10                  15

Val Glu Ser Lys Asp
            20

<210> SEQ ID NO 90
<211> LENGTH: 21
<212> TYPE: PRT
<213> ORGANISM: Homo sapiens

<400> SEQUENCE: 90

Glu Val Asp Glu Thr Tyr Val Pro Lys Glu Phe Asn Ala Glu Thr Phe
1               5                   10                  15

Thr Phe His Ala Asp
            20

<210> SEQ ID NO 91
<211> LENGTH: 16
<212> TYPE: PRT
<213> ORGANISM: Homo sapiens

<400> SEQUENCE: 91

Glu Val Asp Glu Thr Tyr Val Pro Lys Glu Phe Asn Ala Glu Thr Phe
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Gly4Ser 3x Linker (C-terminal Linker) amino
      acid sequence identified using molecular biology techniques.

<400> SEQUENCE: 92

Gly Gly Gly Gly Ser Gly Gly Gly Gly Ser Gly Gly Gly Gly Ser
1               5                   10                  15

<210> SEQ ID NO 93
<211> LENGTH: 20
<212> TYPE: PRT
<213> ORGANISM: Artificial Sequence
<220> FEATURE:
<223> OTHER INFORMATION: Gly4Ser 4x Linker (C-terminal Linker) amino
      acid sequence identified using molecular biology techniques.

<400> SEQUENCE: 93

Gly Gly Gly Gly Ser Gly Gly Gly Gly Ser Gly Gly Gly Gly Ser Gly
1               5                   10                  15

Gly Gly Gly Ser
            20

<210> SEQ ID NO 94
<211> LENGTH: 40
<212> TYPE: PRT
```

<213> ORGANISM: Homo sapiens

<400> SEQUENCE: 94

```
Lys Glu Ala Ala Ala Lys Glu Ala Ala Lys Glu Ala Ala Ala Lys
 1               5                  10                  15
Glu Leu Ala Ala Lys Glu Ala Ala Lys Glu Ala Ala Ala Lys Glu
             20                  25                  30
Ala Ala Ala Lys Glu Leu Ala Ala
         35                  40
```

<210> SEQ ID NO 95
<211> LENGTH: 348
<212> TYPE: DNA
<213> ORGANISM: Artificial Sequence
<220> FEATURE:
<223> OTHER INFORMATION: DOM15-26-593 DAB nucleic acid sequence identified using molecular biology techniques.

<400> SEQUENCE: 95

| | | | | | |
|---|---|---|---|---|---|
| gaggtgcagc | tgttggtgtc | tgggggaggc | ttggtacagc | ctgggggtc | cctgcgtctc | 60 |
| tcctgtgcag | cctccggatt | cacctttaag | gcttatccga | tgatgtgggt | ccgccaggct | 120 |
| ccagggaagg | gtctagagtg | ggtttcagag | atttcgcctt | cgggttctta | tacatactac | 180 |
| gcagactccg | tgaagggccg | gttcaccatc | tcccgcgaca | attccaagaa | cacgctgtat | 240 |
| ctgcaaatga | acagcctgcg | tgccgaggac | accgcggtat | attactgtgc | gaaagatcct | 300 |
| cggaagttag | actactgggg | tcagggaacc | ctggtcaccg | tctcgagc | | 348 |

<210> SEQ ID NO 96
<211> LENGTH: 348
<212> TYPE: DNA
<213> ORGANISM: Artificial Sequence
<220> FEATURE:
<223> OTHER INFORMATION: DOM15-26-597 DAB nucleic acid sequence identified using molecular biology techniques.

<400> SEQUENCE: 96

| | | | | | |
|---|---|---|---|---|---|
| gaggtgcagc | tgctggtgtc | tggcggcgga | ctggtgcagc | ctggcggcag | cctgagactg | 60 |
| agctgcgccg | ccagcggctt | caccttcaag | gcctacccca | tgatgtgggt | gcggcaggcc | 120 |
| cctggcaagg | gcctggaatg | ggtgtccgag | atcagcccca | gcggcagcaa | cacctactac | 180 |
| gccgacagcg | tgaagggccg | gttcaccatc | agcgggaca | acagcaagaa | cacctgtac | 240 |
| ctgcagatga | acagcctgcg | ggccgaggac | accgccgtgt | actactgcgc | caaggacccc | 300 |
| cggaagctgg | actactgggg | ccagggcacc | ctggtgaccg | tgagcagc | | 348 |

<210> SEQ ID NO 97
<211> LENGTH: 324
<212> TYPE: DNA
<213> ORGANISM: Artificial Sequence
<220> FEATURE:
<223> OTHER INFORMATION: DT02-K-044-085 DAB nucleic acid sequence identified using molecular biology techniques.

<400> SEQUENCE: 97

| | | | | | |
|---|---|---|---|---|---|
| gacatccaga | tgacccagtc | tccatcctcc | ctgtctgcat | ctgtaggaga | ccgtgtcacc | 60 |
| atcacttgcc | gggcaagtca | gtggattggt | cctgagttaa | agtggtacca | gcagaaacca | 120 |
| gggaaagccc | ctaagctcct | gatctatcat | ggttccattt | tgcaaagtgg | ggtcccatca | 180 |
| cgtttcagtg | gcagtggatc | tgggacagac | ttcactctca | ccatcagcag | tctgcaacct | 240 |
| gaagattttg | ctacgtacta | ctgtcaacag | tatatgtatt | atcctcatac | gttcggccaa | 300 |

```
gggaccaagg tggaaatcaa acgt                                           324

<210> SEQ ID NO 98
<211> LENGTH: 324
<212> TYPE: DNA
<213> ORGANISM: Artificial Sequence
<220> FEATURE:
<223> OTHER INFORMATION: DT02-K-044-232 DAB nucleic acid sequence
      identified using molecular biology techniques.

<400> SEQUENCE: 98
gacatccaga tgacccagtc tccatcctcc ctgtctgcat ctgtaggaga ccgtgtcacc     60
atcacttgcc gggcaagtca gtggattggt cctgagttaa gttggtacca gcagaaacca   120
gggaaagccc ctaagctcct gatctatcat ggttccattt tgcaaagtgg ggtcccatca   180
cgtttcagtg gcagtggatc tgggacagac ttcactctca ccatcagcag tctgcaacct   240
gaagattttg ctacgtacta ctgtcaacag tatatgtatt atcctgagac gttcggccaa   300
gggaccaagg tggaaatcaa acgt                                           324

<210> SEQ ID NO 99
<211> LENGTH: 324
<212> TYPE: DNA
<213> ORGANISM: Artificial Sequence
<220> FEATURE:
<223> OTHER INFORMATION: DT02-K-044-236 DAB nucleic acid sequence
      identified using molecular biology techniques.

<400> SEQUENCE: 99
gacatccaga tgacccagtc tccatcctcc ctgtctgcat ctgtaggaga ccgtgtcacc     60
atcacttgcc gggcaagtca gtggattggt cctgagttaa gttggtacca gcagaaacca   120
gggaaagccc ctaagctcct gatctatcat ggttccattt tgcaaagtgg ggtcccatca   180
cgtttcagtg gcagtggatc tgggacagac ttcactctca ccatcagcag tctgcaacct   240
gaagattttg ctacgtacta ctgtcaacag tatatgtatt atcctaagac gttcggccaa   300
gggaccaagg tggaaatcaa acgt                                           324

<210> SEQ ID NO 100
<211> LENGTH: 324
<212> TYPE: DNA
<213> ORGANISM: Artificial Sequence
<220> FEATURE:
<223> OTHER INFORMATION: DT02-K-044-251 DAB nucleic acid sequence
      identified using molecular biology techniques.

<400> SEQUENCE: 100
gacatccaga tgacccagtc tccatcctcc ctgtctgcat ctgtaggaga ccgtgtcacc     60
atcacttgcc gggcaagtca gtggattggt cctgagttaa agtggtacca gcagaaacca   120
gggaaagccc ctaagctcct gatctatcat ggttccatttt tgcaaagtgg ggtcccatca  180
cgtttcagtg gcagtggatc tgggacagac ttcactctca ccatcagcag tctgcaacct   240
gaagattttg ctacgtacta ctgtcaacag tatatgtatt atcctgagac gttcggccaa   300
gggaccaagg tggaaatcaa acgt                                           324

<210> SEQ ID NO 101
<211> LENGTH: 324
<212> TYPE: DNA
<213> ORGANISM: Artificial Sequence
<220> FEATURE:
<223> OTHER INFORMATION: DT02-K-044-255 DAB nucleic acid sequence
``` identified using molecular biology techniques.

<400> SEQUENCE: 101

```
gacatccaga tgacccagtc tccatcctcc ctgtctgcat ctgtaggaga ccgtgtcacc    60
atcacttgcc gggcaagtca gtggattggt cctgagttaa agtggtacca gcagaaacca   120
gggaaagccc ctaagctcct gatctatcat ggttccattt gcaaagtggg gtcccatca   180
cgtttcagtg gcagtggatc tgggacagac ttcactctca ccatcagcag tctgcaacct   240
gaagattttg ctacgtacta ctgtcaacag tatatgtatt atcctaagac gttcggccaa   300
gggaccaagg tggaaatcaa acgt                                          324
```

<210> SEQ ID NO 102
<211> LENGTH: 675
<212> TYPE: DNA
<213> ORGANISM: Artificial Sequence
<220> FEATURE:
<223> OTHER INFORMATION: Fc IgG1 nucleic acid sequence identified using molecular biology techniques.

<400> SEQUENCE: 102

```
acccacacct gccccccctg ccctgccccc gagctgctgg gaggccccag cgtgttcctg    60
ttccccccca agcctaagga caccctgatg atcagcagaa ccccgaggt gacctgtgtg   120
gtggtggatg tgagccacga ggaccctgag gtgaagttca actggtacgt ggacggcgtg   180
gaggtgcaca atgccaagac caagcccagg gaggagcagt acaacagcac ctaccgggtg   240
gtgtccgtgc tgaccgtgct gcaccaggat tggctgaacg gcaaggagta caagtgtaag   300
gtgtccaaca aggccctgcc tgcccctatc gagaaaacca tcagcaaggc caagggccag   360
cccagagagc cccaggtgta caccctgccc ctagcagag atgagctgac caagaaccag   420
gtgtccctga cctgcctggt gaagggcttc taccccagcg acatcgccgt ggagtgggag   480
agcaacggcc agcccgagaa caactacaag accaccccc ctgtgctgga cagcgatggc   540
agcttcttcc tgtacagcaa gctgaccgtg gacaagagca gatggcagca gggcaacgtg   600
ttcagctgct ccgtgatgca cgaggccctg cacaatcact acacccagaa gagcctgagc   660
ctgtcccctg gcaag                                                    675
```

<210> SEQ ID NO 103
<211> LENGTH: 116
<212> TYPE: PRT
<213> ORGANISM: Artificial Sequence
<220> FEATURE:
<223> OTHER INFORMATION: DOM15-26-593 DAB amino acid sequence identified using molecular biology techniques.

<400> SEQUENCE: 103

```
Glu Val Gln Leu Leu Val Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
             20                  25                  30

Pro Met Met Trp Val Arg Gln Ala Pro Gly Lys Gly Leu Glu Trp Val
         35                  40                  45

Ser Glu Ile Ser Pro Ser Gly Ser Tyr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95
```

```
Ala Lys Asp Pro Arg Lys Leu Asp Tyr Trp Gly Gln Gly Thr Leu Val
            100                 105                 110

Thr Val Ser Ser
        115

<210> SEQ ID NO 104
<211> LENGTH: 116
<212> TYPE: PRT
<213> ORGANISM: Artificial Sequence
<220> FEATURE:
<223> OTHER INFORMATION: DOM15-26-597 DAB amino acid sequence
      identified using molecular biology techniques.

<400> SEQUENCE: 104

Glu Val Gln Leu Leu Val Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser
        115

<210> SEQ ID NO 105
<211> LENGTH: 108
<212> TYPE: PRT
<213> ORGANISM: Artificial Sequence
<220> FEATURE:
<223> OTHER INFORMATION: DT02-K-044-085 DAB amino acid sequence
      identified using molecular biology techniques.

<400> SEQUENCE: 105

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Met Tyr Tyr Pro His
                85                  90                  95

Thr Phe Gly Gln Gly Thr Lys Val Glu Ile Lys Arg
            100                 105

<210> SEQ ID NO 106
<211> LENGTH: 108
<212> TYPE: PRT
<213> ORGANISM: Artificial Sequence
```

<220> FEATURE:
<223> OTHER INFORMATION: DT02-K-044-232 DAB amino acid sequence
      identified using molecular biology techniques.

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Ser Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro Glu
                85                  90                  95

Thr Phe Gly Gln Gly Thr Lys Val Glu Ile Lys Arg
            100                 105

<210> SEQ ID NO 107
<211> LENGTH: 108
<212> TYPE: PRT
<213> ORGANISM: Artificial Sequence
<220> FEATURE:
<223> OTHER INFORMATION: DT02-K-044-236 DAB amino acid sequence
      identified using molecular biology techniques.

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Ser Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro Lys
                85                  90                  95

Thr Phe Gly Gln Gly Thr Lys Val Glu Ile Lys Arg
            100                 105

<210> SEQ ID NO 108
<211> LENGTH: 108
<212> TYPE: PRT
<213> ORGANISM: Artificial Sequence
<220> FEATURE:
<223> OTHER INFORMATION: DT02-K-044-251 DAB amino acid sequence
      identified using molecular biology techniques.

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

```
Tyr His Gly Ser Ile Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Met Tyr Tyr Pro Glu
                    85                  90                  95

Thr Phe Gly Gln Gly Thr Lys Val Glu Ile Lys Arg
                100                 105
```

<210> SEQ ID NO 109
<211> LENGTH: 108
<212> TYPE: PRT
<213> ORGANISM: Artificial Sequence
<220> FEATURE:
<223> OTHER INFORMATION: DT02-K-044-255 DAB amino acid sequence
      identified using molecular biology techniques.

<400> SEQUENCE: 109

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Pro Glu
                20                  25                  30

Leu Lys Trp Tyr Gln Gln Lys Pro Gly Lys Ala Pro Lys Leu Leu Ile
                35                  40                  45

Tyr His Gly Ser Ile Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Met Tyr Tyr Pro Lys
                    85                  90                  95

Thr Phe Gly Gln Gly Thr Lys Val Glu Ile Lys Arg
                100                 105
```

<210> SEQ ID NO 110
<211> LENGTH: 225
<212> TYPE: PRT
<213> ORGANISM: Artificial Sequence
<220> FEATURE:
<223> OTHER INFORMATION: Fc IgG1 DAB amino acid sequence
      identified using molecular biology techniques.

<400> SEQUENCE: 110

```
Thr His Thr Cys Pro Pro Cys Pro Ala Pro Glu Leu Leu Gly Gly Pro
  1               5                  10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
                35                  40                  45

Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                    85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
                115                 120                 125
```

```
Leu Pro Pro Ser Arg Asp Glu Leu Thr Lys Asn Gln Val Ser Leu Thr
        130                 135                 140
Cys Leu Val Lys Gly Phe Tyr Pro Ser Asp Ile Ala Val Glu Trp Glu
145                 150                 155                 160
Ser Asn Gly Gln Pro Glu Asn Asn Tyr Lys Thr Thr Pro Pro Val Leu
                165                 170                 175
Asp Ser Asp Gly Ser Phe Phe Leu Tyr Ser Lys Leu Thr Val Asp Lys
            180                 185                 190
Ser Arg Trp Gln Gln Gly Asn Val Phe Ser Cys Ser Val Met His Glu
        195                 200                 205
Ala Leu His Asn His Tyr Thr Gln Lys Ser Leu Ser Leu Ser Pro Gly
    210                 215                 220
Lys
225

<210> SEQ ID NO 111
<211> LENGTH: 5
<212> TYPE: PRT
<213> ORGANISM: Artificial Sequence
<220> FEATURE:
<223> OTHER INFORMATION: DOM15-26-593 CDR1 amino acid sequence
      identified using molecular biology techniques.

<400> SEQUENCE: 111

Ala Tyr Pro Met Met
1               5

<210> SEQ ID NO 112
<211> LENGTH: 17
<212> TYPE: PRT
<213> ORGANISM: Artificial Sequence
<220> FEATURE:
<223> OTHER INFORMATION: DOM15-26-593 CDR2 amino acid sequence
      identified using molecular biology techniques.

<400> SEQUENCE: 112

Glu Ile Ser Pro Ser Gly Ser Tyr Thr Tyr Tyr Ala Asp Ser Val Lys
1               5                   10                  15
Gly

<210> SEQ ID NO 113
<211> LENGTH: 7
<212> TYPE: PRT
<213> ORGANISM: Artificial Sequence
<220> FEATURE:
<223> OTHER INFORMATION: DOM15-26-593 CDR3 amino acid sequence
      identified using molecular biology techniques.

<400> SEQUENCE: 113

Asp Pro Arg Lys Leu Asp Tyr
1               5

<210> SEQ ID NO 114
<211> LENGTH: 5
<212> TYPE: PRT
<213> ORGANISM: Artificial Sequence
<220> FEATURE:
<223> OTHER INFORMATION: DOM15-26-597 CDR1 amino acid sequence
      identified using molecular biology techniques.

<400> SEQUENCE: 114

Ala Tyr Pro Met Met
1               5
```

<210> SEQ ID NO 115
<211> LENGTH: 17
<212> TYPE: PRT
<213> ORGANISM: Artificial Sequence
<220> FEATURE:
<223> OTHER INFORMATION: DOM15-26-597 CDR2 amino acid sequence
      identified using molecular biology techniques.

<400> SEQUENCE: 115

Glu Ile Ser Pro Ser Gly Ser Asn Thr Tyr Tyr Ala Asp Ser Val Lys
1               5                   10                  15

Gly

<210> SEQ ID NO 116
<211> LENGTH: 7
<212> TYPE: PRT
<213> ORGANISM: Artificial Sequence
<220> FEATURE:
<223> OTHER INFORMATION: DOM15-26-597 CDR3 amino acid sequence
      identified using molecular biology techniques.

<400> SEQUENCE: 116

Asp Pro Arg Lys Leu Asp Tyr
1               5

<210> SEQ ID NO 117
<211> LENGTH: 11
<212> TYPE: PRT
<213> ORGANISM: Artificial Sequence
<220> FEATURE:
<223> OTHER INFORMATION: DT02-K-044-085 CDR1 amino acid sequence
      identified using molecular biology techniques.

<400> SEQUENCE: 117

Arg Ala Ser Gln Trp Ile Gly Pro Glu Leu Lys
1               5                   10

<210> SEQ ID NO 118
<211> LENGTH: 7
<212> TYPE: PRT
<213> ORGANISM: Artificial Sequence
<220> FEATURE:
<223> OTHER INFORMATION: DT02-K-044-085 CDR2 amino acid sequence
      identified using molecular biology techniques.

<400> SEQUENCE: 118

His Gly Ser Ile Leu Gln Ser
1               5

<210> SEQ ID NO 119
<211> LENGTH: 9
<212> TYPE: PRT
<213> ORGANISM: Artificial Sequence
<220> FEATURE:
<223> OTHER INFORMATION: DT02-K-044-085 CDR3 amino acid sequence
      identified using molecular biology techniques.

<400> SEQUENCE: 119

Gln Gln Tyr Met Tyr Tyr Pro His Thr
1               5

<210> SEQ ID NO 120
<211> LENGTH: 11
<212> TYPE: PRT
<213> ORGANISM: Artificial Sequence
<220> FEATURE:
<223> OTHER INFORMATION: DT02-K-044-232 CDR1 amino acid sequence -continued identified using molecular biology techniques.

<400> SEQUENCE: 120

Arg Ala Ser Gln Trp Ile Gly Pro Glu Leu Ser
1               5                   10

<210> SEQ ID NO 121
<211> LENGTH: 7
<212> TYPE: PRT
<213> ORGANISM: Artificial Sequence
<220> FEATURE:
<223> OTHER INFORMATION: DT02-K-044-232 CDR2 amino acid sequence
      identified using molecular biology techniques.

<400> SEQUENCE: 121

His Gly Ser Ile Leu Gln Ser
1               5

<210> SEQ ID NO 122
<211> LENGTH: 9
<212> TYPE: PRT
<213> ORGANISM: Artificial Sequence
<220> FEATURE:
<223> OTHER INFORMATION: DT02-K-044-232 CDR3 amino acid sequence
      identified using molecular biology techniques.

<400> SEQUENCE: 122

Gln Gln Tyr Met Tyr Tyr Pro Glu Thr
1               5

<210> SEQ ID NO 123
<211> LENGTH: 11
<212> TYPE: PRT
<213> ORGANISM: Artificial Sequence
<220> FEATURE:
<223> OTHER INFORMATION: DT02-K-044-236 CDR1 amino acid sequence
      identified using molecular biology techniques.

<400> SEQUENCE: 123

Arg Ala Ser Gln Trp Ile Gly Pro Glu Leu Ser
1               5                   10

<210> SEQ ID NO 124
<211> LENGTH: 7
<212> TYPE: PRT
<213> ORGANISM: Artificial Sequence
<220> FEATURE:
<223> OTHER INFORMATION: DT02-K-044-236 CDR2 amino acid sequence
      identified using molecular biology techniques.

<400> SEQUENCE: 124

His Gly Ser Ile Leu Gln Ser
1               5

<210> SEQ ID NO 125
<211> LENGTH: 9
<212> TYPE: PRT
<213> ORGANISM: Artificial Sequence
<220> FEATURE:
<223> OTHER INFORMATION: DT02-K-044-236 CDR3 amino acid sequence
      identified using molecular biology techniques.

<400> SEQUENCE: 125

Gln Gln Tyr Met Tyr Tyr Pro Lys Thr
1               5

<210> SEQ ID NO 126

```
<211> LENGTH: 11
<212> TYPE: PRT
<213> ORGANISM: Artificial Sequence
<220> FEATURE:
<223> OTHER INFORMATION: DT02-K-044-251 CDR1 amino acid sequence
      identified using molecular biology techniques.

<400> SEQUENCE: 126

Arg Ala Ser Gln Trp Ile Gly Pro Glu Leu Lys
 1               5                  10

<210> SEQ ID NO 127
<211> LENGTH: 7
<212> TYPE: PRT
<213> ORGANISM: Artificial Sequence
<220> FEATURE:
<223> OTHER INFORMATION: DT02-K-044-251 CDR2 amino acid sequence
      identified using molecular biology techniques.

<400> SEQUENCE: 127

His Gly Ser Ile Leu Gln Ser
 1               5

<210> SEQ ID NO 128
<211> LENGTH: 9
<212> TYPE: PRT
<213> ORGANISM: Artificial Sequence
<220> FEATURE:
<223> OTHER INFORMATION: DT02-K-044-251 CDR3 amino acid sequence
      identified using molecular biology techniques.

<400> SEQUENCE: 128

Gln Gln Tyr Met Tyr Tyr Pro Glu Thr
 1               5

<210> SEQ ID NO 129
<211> LENGTH: 11
<212> TYPE: PRT
<213> ORGANISM: Artificial Sequence
<220> FEATURE:
<223> OTHER INFORMATION: DT02-K-044-255 CDR1 amino acid sequence
      identified using molecular biology techniques.

<400> SEQUENCE: 129

Arg Ala Ser Gln Trp Ile Gly Pro Glu Leu Lys
 1               5                  10

<210> SEQ ID NO 130
<211> LENGTH: 7
<212> TYPE: PRT
<213> ORGANISM: Artificial Sequence
<220> FEATURE:
<223> OTHER INFORMATION: DT02-K-044-255 CDR2 amino acid sequence
      identified using molecular biology techniques.

<400> SEQUENCE: 130

His Gly Ser Ile Leu Gln Ser
 1               5

<210> SEQ ID NO 131
<211> LENGTH: 9
<212> TYPE: PRT
<213> ORGANISM: Artificial Sequence
<220> FEATURE:
<223> OTHER INFORMATION: DT02-K-044-255 CDR3 amino acid sequence
      identified using molecular biology techniques.

<400> SEQUENCE: 131
```

Gln Gln Tyr Met Tyr Tyr Pro Lys Thr
 1               5

<210> SEQ ID NO 132
<211> LENGTH: 1077
<212> TYPE: DNA
<213> ORGANISM: Artificial Sequence
<220> FEATURE:
<223> OTHER INFORMATION: N-terminal Fc fusion of DOM15-26-597 DAB
      ((TGLDSP)x3) nucleic acid sequence identified
      using molecular biology techniques.

<400> SEQUENCE: 132

| | |
|---|---|
| gaggtgcagc tgctggtgtc tggcggcgga ctggtgcagc ctggcggcag cctgagactg | 60 |
| agctgcgccg ccagcggctt caccttcaag gcctacccta tgatgtgggt gcggcaggcc | 120 |
| cctggtaagg gcctggaatg ggtgtccgag atcagcccaa gcggcagcaa cacctactac | 180 |
| gcagacagcg tgaagggccg gttcaccatc agccgggaca cagcaagaa cacactgtac | 240 |
| ctgcagatga acagcctgcg ggccgaggac accgcagtgt actactgcgc caaggaccca | 300 |
| cggaagctgg actactgggg tcagggcacc ctggtgaccg tgagcagcac cggattagac | 360 |
| agtcccacag gtctcgattc acctactggc ttagactctc caacccacac ctgcccccc | 420 |
| tgccctgccc cagagctgct gggcggacct agcgtgttcc tgttcccacc aaagcctaag | 480 |
| gacaccctga tgatcagcag aaccccgag gtgacctgtg tggtggtgga tgtgagccac | 540 |
| gaggaccctg aggtgaagtt caactggtac gtggacggcg tggaggtgca aatgccaag | 600 |
| accaagccca gggaggagca gtacaacagc acctaccggg tggtgtccgt gctgaccgtg | 660 |
| ctgcaccagg attggctgaa cggcaaggag tacaagtgta aggtgtccaa caaggccctg | 720 |
| cctgccccta tcgagaaaac catcagcaag gccaagggcc agcccagaga gccccaggtg | 780 |
| tacaccctgc ccctagcag aaatgagctg accaagaacc aggtgtccct gacctgcctg | 840 |
| gtgaagggct tctaccccag cgacatcgcc gtggagtggg agagcaatgg ccagcccgag | 900 |
| aacaactaca agaccacccc ccctgtgctg gacagcgatg gcagcttctt cctgtacagc | 960 |
| aagctgaccg tggacaagag cagatggcag cagggcaacg tgttcagctg ctccgtgatg | 1020 |
| cacgaggccc tgcacaatca ctacacccag aagagcctga cctgtcccc tggcaag | 1077 |

<210> SEQ ID NO 133
<211> LENGTH: 1077
<212> TYPE: DNA
<213> ORGANISM: Artificial Sequence
<220> FEATURE:
<223> OTHER INFORMATION: N-terminal Fc fusion of DOM15-26-597 DAB
      (TGLDSP)x3 T113P mutation Fc) nucleic acid sequence
      identified using molecular biology techniques.

<400> SEQUENCE: 133

| | |
|---|---|
| gaggtgcagc tgctggtgtc tggcggcgga ctggtgcagc ctggcggcag cctgagactg | 60 |
| agctgcgccg ccagcggctt caccttcaag gcctaccca tgatgtgggt gcggcaggcc | 120 |
| cctggcaagg gcctggaatg ggtgtccgag atcagcccca gcggcagcaa cacctactac | 180 |
| gccgacagcg tgaagggccg gttcaccatc agccgggaca cagcaagaa caccctgtac | 240 |
| ctgcagatga acagcctgcg ggccgaggac accgccgtgt actactgcgc caaggacccc | 300 |
| cggaagctgg actactgggg ccagggcacc ctggtgaccg tgagcagcac gggtctggac | 360 |
| agtccgactg gtttagattc acctacgggc ttgactcccc aacccacccc ttgcccccc | 420 |
| tgccctgccc ccgagctgct gggaggcccc agcgtgttcc tgttcccccc caagcctaag | 480 |

```
gacaccctga tgatcagcag gacccccgaa gtgacctgcg tggtggtgga tgtgagccac    540
gaggaccctg aagtgaagtt caactggtac gtggacggcg tggaagtgca caacgccaag    600
accaagccca gagaggagca gtacaacagc acctaccgcg tggtgtctgt gctgaccgtg    660
ctgcaccagg attggctgaa cggcaaggag tacaagtgca agtgagcaa caaggccctg    720 cctgcccta tcgagaaaac catcagcaag gccaagggcc agcctagaga gccccaggtc    780
tacaccctgc ctccctccag agatgagctg accaagaacc aggtgtccct gacctgtctg    840
gtgaagggct tctaccccag cgacatcgcc gtggagtggg agagcaacgg ccagcccgag    900
aacaactaca agaccacccc ccctgtgctg gacagcgatg gcagcttctt cctgtactcc    960
aagctgaccg tggacaagag cagatggcag cagggcaacg tgttcagctg cagcgtgatg   1020
cacgaggccc tgcacaatca ctacacccag aagagcctga gcctgtcccc cggcaag     1077
```

```
<210> SEQ ID NO 134
<211> LENGTH: 1095
<212> TYPE: DNA
<213> ORGANISM: Artificial Sequence
<220> FEATURE:
<223> OTHER INFORMATION: N-terminal Fc fusion of DOM15-26-597 DAB
      (TGLDSP)x4 T113P mutation Fc) nucleic acid sequence
      identified using molecular biology techniques.

<400> SEQUENCE: 134
```

```
gaggtgcagc tgctggtgtc tggcggcgga ctggtgcagc ctggcggcag cctgagactg     60
agctgcgccg ccagcggctt caccttcaag gcctacccca tgatgtgggt gcggcaggcc    120
cctggcaagg gcctggaatg ggtgtccgag atcagcccca gcggcagcaa cacctactac    180
gccgacagcg tgaagggccg gttcaccatc agccgggaca acagcaagaa caccctgtac    240
ctgcagatga acagcctgcg ggccgaggac accgccgtgt actactgcgc caaggacccc    300
cggaagctgg actactgggg ccagggcacc ctggtgaccg tgagcagcac gggtctggac    360
agtccgactg gtttagattc acctacgggc ttggactccc caaccggctt agatagcccg    420 acccacccctt gccccccctg ccctgccccc gagctgctgg gaggcccag cgtgttcctg    480 ttccccccca gcctaagga cacctgatg atcagcagga cccccgaagt gacctgcgtg    540
gtggtggatg tgagccacga ggaccctgaa gtgaagttca actggtacgt ggacggcgtg    600
gaagtgcaca cgccaagac caagcccaga gaggagcagt acaacagcac ctaccgcgtg    660
gtgtctgtgc tgaccgtgct gcaccaggat tggctgaacg gcaaggagta caagtgcaaa    720
gtgagcaaca aggccctgcc tgcccctatc gagaaaacca tcagcaaggc caagggccag    780
cctagagagc cccaggtcta caccctgcct ccctccagag atgagctgac caagaaccag    840
gtgtccctga cctgtctggt gaagggcttc taccccagcg acatcgccgt ggagtgggag    900
agcaacggcc agcccgagaa caactacaag accacccccc ctgtgctgga cagcgatggc    960
agcttcttcc tgtactccaa gctgaccgtg gacaagagca gatggcagca gggcaacgtg   1020
ttcagctgca gcgtgatgca cgaggccctg cacaatcact acacccagaa gagcctgagc   1080
ctgtcccccg gcaag                                                    1095
```

```
<210> SEQ ID NO 135
<211> LENGTH: 1419
<212> TYPE: DNA
<213> ORGANISM: Artificial Sequence
<220> FEATURE:
<223> OTHER INFORMATION: K-044-085 DAB N-(VEPKSSDK linker) & C-terminal
      ((TGLDSP)x4) nucleic acid sequence identified
      using molecular biology techniques.
```

<400> SEQUENCE: 135

```
gacatccaga tgacccagag ccccagcagc ctgagcgcct ctgtgggaga cagggtgact        60
atcacctgca gggccagcca gtggattggc cccgagctga gtggtatca gcagaagccc       120
ggcaaggccc ccaagctgct gatctaccac ggcagcatcc tgcagtccgg cgtgcctagc       180
aggttctcag gcagcggcag cggcaccgac ttcaccctca ccatcagcag cctgcagccc       240
gaggacttcg ccacctacta ctgccagcag tatatgtact accccacac cttcggccag        300
ggcaccaagg tggagatcaa gagggtggag cctaagtctt ctgacaagac ccacacctgc       360
ccccctgcc ctgccccaga gctgctggga ggacccagcg tgttcctgtt cccacccaag        420
cctaaggaca ccctgatgat cagcagaacc cccgaggtga cctgtgtggt ggtggatgtg       480
agccacgagg accctgaggt gaagttcaac tggtacgtgg acggcgtgga ggtgcacaat       540
gccaagacca gcccaggga ggagcagtac aacagcacct accgggtggt gtccgtgctg        600
accgtgctgc accaggattg gctgaacggc aaggagtaca agtgtaaggt gtccaacaag       660
gccctgcctg cccctatcga aaaaccatc agcaaggcca agggccagcc cagagagccc        720
caggtgtaca ccctgccccc tagcagagat gagctgacca gaaccaggt gtccctgacc        780
tgcctggtga agggcttcta ccccagcgac atcgccgtgg agtgggagag caatggccag       840
cccgagaaca actacaagac cacccccct gtgctggaca cgatggcag cttcttcctg         900
tacagcaagc tgaccgtgga caagagcaga tggcagcagg caacgtgtt cagctgctcc        960
gtgatgcacg aggccctgca caatcactac acccagaaga gcctgagcct gtcccctggc      1020
aagaccggat tagacagtcc cacaggtctc gattcaccta ctggcttaga ctctccaacc      1080
ggcctggaca gccccgacat ccagatgacc cagtctccat cctccctgtc tgcatctgta      1140
ggagaccgtg tcaccatcac ttgccgggca agtcagtgga ttggtcctga gttaaagtgg      1200
taccagcaga aaccagggaa agcccctaag ctcctgatct atcatggttc cattttgcaa      1260
agtggggtcc catcacgttt cagtggcagt ggatctggga cagacttcac tctcaccatc      1320
agcagtctgc aacctgaaga ttttgctacg tactactgtc aacagtatat gtattatcct      1380
catacgttcg gccaagggac caaggtggaa atcaaacgt                             1419
```

<210> SEQ ID NO 136
<211> LENGTH: 1401
<212> TYPE: DNA
<213> ORGANISM: Artificial Sequence
<220> FEATURE:
<223> OTHER INFORMATION: K-044-085 DAB N-(ASTHP linker) & C-terminal
    ((TGLDSP)x4) nucleic acid sequence identified
    using molecular biology techniques.

<400> SEQUENCE: 136

```
gacatccaga tgacccagag ccccagcagc ctgagcgcct ctgtgggaga cagggtgact        60
atcacctgca gggccagcca gtggattggc cccgagctga gtggtatca gcagaagccc       120
ggcaaggccc ccaagctgct gatctaccac ggcagcatcc tgcagtccgg cgtgcctagc       180
aggttctcag gcagcggcag cggcaccgac ttcaccctca ccatcagcag cctgcagccc       240
gaggacttcg ccacctacta ctgccagcag tatatgtact accccacac cttcggccag        300
ggcaccaagg tggagatcaa gagggctagc acccacccctt gccccccctg ccctgccccc      360
gagctgctgg gaggccccag cgtgttcctg ttcccccca gcctaaggga caccctgatg       420
atcagcagga ccccgaagt gacctgcgtg gtggtggatg tgagccacga ggaccctgaa       480
```

```
gtgaagttca actggtacgt ggacggcgtg gaagtgcaca acgccaagac caagcccaga        540
gaggagcagt acaacagcac ctaccgcgtg gtgtctgtgc tgaccgtgct gcaccaggat        600
tggctgaacg gcaaggagta caagtgcaaa gtgagcaaca aggccctgcc tgcccctatc        660
gagaaaacca tcagcaaggc caagggccag cctagagagc cccaggtcta caccctgcct        720 cccctccagag atgagctgac caagaaccag gtgtccctga cctgtctggt gaagggcttc        780 tacccccagcg acatcgccgt ggagtgggag agcaacggcc agcccgagaa caactacaag        840
accacccccc ctgtgctgga cagcgatggc agcttcttcc tgtactccaa gctgaccgtg        900
gacaagagca atggcagca gggcaacgtg ttcagctgca gcgtgatgca cgaggccctg         960
cacaatcact acacccagaa gagtctgagc ctgtcccctg gcaagaccgg attagacagt       1020
cccacaggtc tcgattcacc tactggctta gactctccaa ccggcctgga cagccccgac       1080
atccagatga cccagtctcc atcctccctg tctgcatctg taggagaccg tgtcaccatc       1140
acttgccggg caagtcagtg gattggtcct gagttaaagt ggtaccagca gaaaccaggg       1200 aaagcccta agctcctgat ctatcatggt tccattttgc aaagtggggt cccatcacgt       1260
ttcagtggca gtggatctgg gacagacttc actctcacca tcagcagtct gcaacctgaa       1320
gattttgcta cgtactactg tcaacagtat atgtattatc ctcatacgtt cggccaaggg       1380
accaaggtgg aaatcaaacg t                                                 1401
```

<210> SEQ ID NO 137
<211> LENGTH: 1473
<212> TYPE: DNA
<213> ORGANISM: Artificial Sequence
<220> FEATURE:
<223> OTHER INFORMATION: DOM15-26-597 DAB N-((TGLDSP)x3) & C-terminal
      K-044-085 DAB ((TGLDSP)x4) nucleic acid sequence
      identified using molecular biology techniques.

<400> SEQUENCE: 137

```
gaggtgcagc tgctggtgtc tggcggcgga ctggtgcagc ctggcggcag cctgagactg         60
agctgcgccg ccagcggctt caccttcaag gcctacccca tgatgtgggt gcggcaggcc       120
cctggcaagg gcctggaatg ggtgtccgag atcagcccca gcggcagcaa cacctactac       180
gccgacagcg tgaagggccg gttcaccatc agccgggaca acagcaagaa caccctgtac       240
ctgcagatga acagcctgcg ggccgaggac accgccgtgt actactgcgc caaggacccc       300
cggaagctgg actactgggg ccagggcacc ctggtgaccg tgagcagcac gggtctggac       360
agtccgactg gtttagattc acctacgggc ttggactccc caacccacac ctgccccccc       420
tgccctgccc ctgagctgct gggcggaccc agcgtgttcc tgttcccccc caagcccaag       480 gacacccctga tgatcagccg gacccccgag gtgacctgcg tggtggtgga cgtgagccac       540
gaggaccctg aggtgaagtt caattggtac gtggacggcg tggaggtgca acgccaag        600 accaagcccc gggaggaaca gtacaacagc acctaccggg tggtgtccgt gctgaccgtg       660
ctgcaccagg actggctgaa cggcaaagaa tacaagtgca aggtgtccaa caaggccctg       720
cctgccccca tcgagaaaac catcagcaag gccaagggcc agccccaggga accccaggtg       780 tacaccctgc cccccagccg ggacgagctg accaagaacc aggtgtccct gacctgcctg       840
gtgaagggct tctacccccag cgacatcgcc gtggagtggg agagcaacgg ccagcccgag       900
aacaactaca agaccacccc ccctgtgctg gacagcgacg gcagcttctt cctgtacagc       960
aagctgaccg tggacaagag ccggtggcag cagggcaacg tgttcagctg cagcgtgatg      1020
cacgaggccc tgcacaacca ctacacccag aagagcctga gcctgtcccc cggcaagacc      1080
```

```
ggattagaca gtcccacagg tctcgattca cctactggct tagactctcc aaccggcctg    1140 gacagcccg acatccagat gacccagtct ccatcctccc tgtctgcatc tgtaggagac    1200
cgtgtcacca tcacttgccg ggcaagtcag tggattggtc ctgagttaaa gtggtaccag    1260
cagaaaccag ggaaagcccc taagctcctg atctatcatg gttccatttt gcaaagtggg    1320
gtcccatcac gtttcagtgg cagtggatct gggacagact tcactctcac catcagcagt    1380
ctgcaacctg aagattttgc tacgtactac tgtcaacagt atatgtatta tcctcatacg    1440
ttcggccaag ggaccaaggt ggaaatcaaa cgt                                 1473
```

<210> SEQ ID NO 138
<211> LENGTH: 1443
<212> TYPE: DNA
<213> ORGANISM: Artificial Sequence
<220> FEATURE:
<223> OTHER INFORMATION: DOM15-26-597 DAB N-(VEPKSSDK linker) &
      C-terminal K-044-085 DAB ((TGLDSP)x4) nucleic acid sequence
      identified using molecular biology techniques.

<400> SEQUENCE: 138

```
gaggtgcagc tgctggtgtc tggcggcgga ctggtgcagc ctggcggcag cctgagactg     60
agctgcgccg ccagcggctt caccttcaag gcctacccta tgatgtgggt gcggcaggcc    120
cctggtaagg gcctggaatg ggtgtccgag atcagcccaa gcggcagcaa cacctactac    180
gcagacagcg tgaagggccg gttcaccatc agccgggaca cagcaagaa cacactgtac    240 ctgcagatga acagcctgcg ggccgaggac accgcagtgt actactgcgc caaggaccca    300
cggaagctgg actactgggg tcagggcacc ctggtgaccg tgagcagcgt ggagcctaag    360
tcttctgaca gacccacac ctgcccaccc tgccctgccc cagagctgct gggaggaccc    420
agcgtgttcc tgttcccacc caagcctaag gacaccctga tgatcagcag aacccccgag    480
gtgacctgtg tggtggtgga tgtgagccac gaggaccctg aggtgaagtt caactggtac    540
gtggacggcg tggaggtgca caatgccaag accaagccca gggaggagca gtacaacagc    600
acctaccggg tggtgtccgt gctgaccgtg ctgcaccagg attggctgaa cggcaaggag    660
tacaagtgta aggtgtccaa caaggccctg cctgcccta tcgagaaaac catcagcaag    720
gccaagggcc agcccagaga gccccaggtg tacaccctgc cccctagcag agatgagctg    780
accaagaacc aggtgtccct gacctgcctg gtgaagggct tctacccag cgacatcgcc    840 gtggagtggg agagcaatgg ccagcccgag aacaactaca agaccacccc ccctgtgctg    900
gacagcgatg gcagcttctt cctgtacagc aagctgaccg tggacaagag cagatggcag    960
cagggcaacg tgttcagctg ctccgtgatg cacgaggccc tgcacaatca ctacacccag   1020
aagagcctga gcctgtcccc tggcaagacc ggattagaca gtcccacagg tctcgattca   1080
cctactggct tagactctcc aaccggcctg gacagcccg acatccagat gacccagtct   1140
ccatcctccc tgtctgcatc tgtaggagac cgtgtcacca tcacttgccg ggcaagtcag   1200
tggattggtc ctgagttaaa gtggtaccag cagaaaccag ggaaagcccc taagctcctg   1260
atctatcatg gttccatttt gcaaagtggg gtcccatcac gtttcagtgg cagtggatct   1320
gggacagact tcactctcac catcagcagt ctgcaacctg aagattttgc tacgtactac   1380
tgtcaacagt atatgtatta tcctcatacg ttcggccaag ggaccaaggt ggaaatcaaa   1440
cgt                                                                1443
```

<210> SEQ ID NO 139

```
<211> LENGTH: 1425
<212> TYPE: DNA
<213> ORGANISM: Artificial Sequence
<220> FEATURE:
<223> OTHER INFORMATION: DMS1576 with C-terminal K-044-085 DAB
      ((TGLDSP)x4) nucleic acid sequence identified using
      molecular biology techniques.

<400> SEQUENCE: 139
gaggtgcagc tgctggtgtc tggcggcgga ctggtgcagc ctggcggcag cctgagactg      60
agctgcgccg ccagcggctt caccttcaag gcctacccca tgatgtgggt gcggcaggcc     120
cctggcaagg gcctggaatg ggtgtccgag atcagcccca gcggcagcaa cacctactac     180
gccgacagcg tgaagggccg gttcaccatc agccgggaca acagcaagaa caccctgtac     240
ctgcagatga acagcctgcg ggccgaggac accgccgtgt actactgcgc caaggacccc     300
cggaagctgg actactgggg ccagggcacc ctggtgaccg tgagcagcgc tagcacccac     360
acctgccccc cctgccctgc ccctgagctg ctgggcggac ccagcgtgtt cctgttcccc     420
cccaagccca aggacaccct gatgatcagc cggacccccg aggtgacctg cgtggtggtg     480
gacgtgagcc acgaggaccc tgaggtgaag ttcaattggt acgtggacgg cgtggaggtg     540
cacaacgcca agaccaagcc ccgggaggaa cagtacaaca gcacctaccg ggtggtgtcc     600
gtgctgaccg tgctgcacca ggactggctg aacggcaaag aatacaagtg caaggtgtcc     660
aacaaggccc tgcctgcccc catcgagaaa accatcagca aggccaaggg ccagcccagg     720 gaacccccagg tgtacaccct gccccccagc cgggacgagc tgaccaagaa ccaggtgtcc     780
ctgacctgcc tggtgaaggg cttctacccc agcgacatcg ccgtggagtg ggagagcaac     840
ggccagcccg agaacaacta caagaccacc cccctgtgc tggacagcga cggcagcttc      900
ttcctgtaca gcaagctgac cgtggacaag agccggtggc agcagggcaa cgtgttcagc     960
tgcagcgtga tgcacgaggc cctgcacaac cactacaccc agaagagcct gagcctgtcc    1020
cctggcaaga ccggattaga cagtcccaca ggtctcgatt cacctactgg cttagactct    1080
ccaaccggcc tggacagccc cgacatccag atgacccagt ctccatcctc cctgtctgca    1140
tctgtaggag accgtgtcac catcacttgc cgggcaagtc agtggattgg tcctgagtta    1200
aagtggtacc agcagaaacc agggaaagcc cctaagctcc tgatctatca tggttccatt    1260
ttgcaaagtg ggtcccatc acgtttcagt ggcagtggat ctgggacaga cttcactctc    1320
accatcagca gtctgcaacc tgaagatttt gctacgtact actgtcaaca gtatatgtat    1380
tatcctcata cgttcggcca agggaccaag gtggaaatca aacgt                   1425

<210> SEQ ID NO 140
<211> LENGTH: 1491
<212> TYPE: DNA
<213> ORGANISM: Artificial Sequence
<220> FEATURE:
<223> OTHER INFORMATION: DOM15-26-597 DAB N-((TGLDSP)x4) & C-terminal
      K-044-085 DAB ((TGLDSP)x4) nucleic acid sequence
      identified using molecular biology techniques.

<400> SEQUENCE: 140
gaggtgcagc tgctggtgtc tggcggcgga ctggtgcagc ctggcggcag cctgagactg      60
agctgcgccg ccagcggctt caccttcaag gcctacccca tgatgtgggt gcggcaggcc     120
cctggcaagg gcctggaatg ggtgtccgag atcagcccca gcggcagcaa cacctactac     180
gccgacagcg tgaagggccg gttcaccatc agccgggaca acagcaagaa caccctgtac     240
ctgcagatga acagcctgcg ggccgaggac accgccgtgt actactgcgc caaggacccc     300
```

```
cggaagctgg actactgggg ccagggcacc ctggtgaccg tgagcagcac gggtctggac      360
agtccgactg gtttagattc acctacgggc ttggactccc caaccggctt agatagcccg      420
acccacacct gccccccctg ccctgcccct gagctgctgg gcggacccag cgtgttcctg      480
ttccccccca agcccaagga caccctgatg atcagccgga cccccgaggt gacctgcgtg      540
gtggtggacg tgagccacga ggaccctgag gtgaagttca attggtacgt ggacggcgtg      600
gaggtgcaca cgccaagac caagccccgg gaggaacagt acaacagcac ctaccgggtg       660
gtgtccgtgc tgaccgtgct gcaccaggac tggctgaacg gcaaagaata caagtgcaag      720
gtgtccaaca aggccctgcc tgcccccatc gagaaaacca tcagcaaggc caagggccag      780
cccagggaac ccagggtgta caccctgccc ccагссggga cgagctgac caagaaccag       840 gtgtccctga cctgcctggt gaagggcttc taccccagcg acatcgccgt ggagtgggag      900
agcaacggcc agcccgagaa caactacaag accacccccc ctgtgctgga cagcgacggc      960
agcttcttcc tgtacagcaa gctgaccgtg gacaagagcc ggtggcagca gggcaacgtg     1020
ttcagctgca gcgtgatgca cgaggccctg cacaaccact acacccagaa gagcctgagc     1080
ctgtcccctg gcaagaccgg attagacagt cccacaggtc tcgattcacc tactggctta     1140
gactctccaa ccggcctgga cagccccgac atccagatga cccagtctcc atcctccctg     1200
tctgcatctg taggagaccg tgtcaccatc acttgccggg caagtcagtg gattggtcct     1260
gagttaaagt ggtaccagca gaaaccaggg aaagccccta agctcctgat ctatcatggt     1320
tccattttgc aaagtggggt cccatcacgt ttcagtggca gtggatctgg gacagacttc     1380
actctcacca tcagcagtct gcaacctgaa gattttgcta cgtactactg tcaacagtat     1440
atgtattatc ctcatacgtt cggccaaggg accaaggtgg aaatcaaacg t             1491

<210> SEQ ID NO 141
<211> LENGTH: 1473
<212> TYPE: DNA
<213> ORGANISM: Artificial Sequence
<220> FEATURE:
<223> OTHER INFORMATION: DOM15-26-597 DAB N-((TGLDSP)x3 T113P mutation
      Fc) & C-terminal K-044-085 DAB ((TGLDSP)x4) nucleic acid
      sequence identified using molecular biology techniques.

<400> SEQUENCE: 141
gaggtgcagc tgctggtgtc tggcggcgga ctggtgcagc ctggcggcag cctgagactg       60
agctgcgccg ccagcggctt caccttcaag gcctacccca tgatgtgggt gcggcaggcc      120
cctggcaagg gcctggaatg ggtgtccgag atcagcccca cggcagcaa cacctactac       180 gccgacagcg tgaagggccg gttcaccatc agccgggaca acagcaagaa caccctgtac      240
ctgcagatga acagcctgcg ggccgaggac accgccgtgt actactgcgc caaggacccc      300
cggaagctgg actactgggg ccagggcacc ctggtgaccg tgagcagcac gggtctggac      360
agtccgactg gtttagattc acctacgggc ttggactccc caacccaccc ttgccccccc      420
tgccctgccc ccgagctgct gggaggcccc agcgtgttcc tgttcccccc caagcctaag      480
gacaccctga tgatcagcag gacccccgaa gtgacctgcg tggtggtgga tgtgagccac      540
gaggacccta agtgaagtt caactggtac gtggacggcg tggaagtgca acgccaag        600 accaagccca gagaggagca gtacaacagc acctaccgcg tggtgtctgt gctgaccgtg      660
ctgcaccagg attggctgaa cggcaaggag tacaagtgca agtgagcaa caaggccctg      720 cctgccccta tcgagaaaac catcagcaag gccaagggcc agcctagaga gccccaggtc     780
```

```
tacaccctgc tcccctccag agatgagctg accaagaacc aggtgtccct gacctgtctg    840
gtgaagggct tctaccccag cgacatcgcc gtggagtggg agagcaacgg ccagcccgag    900
aacaactaca agaccacccc ccctgtgctg gacagcgatg gcagcttctt cctgtactcc    960
aagctgaccg tggacaagag cagatggcag cagggcaacg tgttcagctg cagcgtgatg   1020
cacgaggccc tgcacaatca ctacacccag aagagtctga gcctgtcccc tggcaagacc   1080
ggattagaca gtcccacagg tctcgattca cctactggct tagactctcc aaccggcctg   1140
gacagccccg acatccagat gacccagtct ccatcctccc tgtctgcatc tgtaggagac   1200
cgtgtcacca tcacttgccg ggcaagtcag tggattggtc tgagttaaa gtggtaccag    1260 cagaaaccag ggaaagcccc taagctcctg atctatcatg gttccatttt gcaaagtggg   1320
gtcccatcac gtttcagtgg cagtggatct gggacagact tcactctcac catcagcagt   1380
ctgcaacctg aagattttgc tacgtactac tgtcaacagt atatgtatta cctcatacg   1440 ttcggccaag ggaccaaggt ggaaatcaaa cgt                                1473
```

<210> SEQ ID NO 142
<211> LENGTH: 1491
<212> TYPE: DNA
<213> ORGANISM: Artificial Sequence
<220> FEATURE:
<223> OTHER INFORMATION: DOM15-26-597 DAB N-((TGLDSP)x4 T113P mutation Fc) & C-terminal K-044-085 DAB ((TGLDSP)x4) nucleic acid sequence identified using molecular biology techniques.

<400> SEQUENCE: 142

```
gaggtgcagc tgctggtgtc tggcggcgga ctggtgcagc ctggcggcag cctgagactg     60
agctgcgccg ccagcggctt caccttcaag gcctacccca tgatgtgggt gcggcaggcc    120
cctggcaagg gcctggaatg ggtgtccgag atcagcccca cgcagcagca cacctactac    180
gccgacagcg tgaagggccg gttcaccatc agccgggaca acagcaagaa caccctgtac    240
ctgcagatga acagcctgcg ggccgaggac accgccgtgt actactgcgc caaggacccc    300
cggaagctgg actactgggg ccagggcacc ctggtgaccg tgagcagcac gggtctggac    360
agtccgactg gttagattc acctacgggc ttggactccc caaccggctt agatagcccg    420 acccacccctt gccccccctg ccctgcccccc gagctgctgg gaggcccag cgtgttcctg    480 ttccccccca gcctaagga caccctgatg atcagcagga ccccgaagt gacctgcgtg      540 gtggtggatg tgagccacga ggaccctgaa gtgaagttca ctggtacgt ggacggcgtg     600 gaagtgcaca acgccaagac caagcccaga ggagcagt acaacagcac ctaccgcgtg      660
gtgtctgtgc tgaccgtgct gcaccaggat tggctgaacg gcaaggagta caagtgcaaa    720
gtgagcaaca aggccctgcc tgcccctatc gagaaaacca tcagcaaggc caagggccag    780
cctagagagc cccaggtcta caccctgcct ccctccagag atgagctgac caagaaccag    840
gtgtccctga cctgtctggt gaagggcttc taccccagcg acatcgccgt ggagtggag     900 agcaacggcc agcccgagaa caactacaag accaccccc ctgtgctgga cagcgatggc    960
agcttcttcc tgtactccaa gctgaccgtg gacaagagca gatggcagca gggcaacgtg   1020
ttcagctgca gcgtgatgca cgaggccctg cacaatcact acacccagaa gagtctgagc   1080
ctgtcccctg gcaagaccgg attagacagt cccacaggtc tcgattcacc tactggctta   1140
gactctccaa ccggcctgga cagccccgac atccagatga cccagtctcc atcctccctg   1200
tctgcatctg taggagaccg tgtcaccatc acttgccggg caagtcagtg gattggtcct   1260
gagttaaagt ggtaccagca gaaaccaggg aaagccccta agctcctgat ctatcatggt   1320
```

```
tccattttgc aaagtggggt cccatcacgt ttcagtggca gtggatctgg gacagacttc    1380
actctcacca tcagcagtct gcaacctgaa gattttgcta cgtactactg tcaacagtat    1440
atgtattatc ctcatacgtt cggccaaggg accaaggtgg aaatcaaacg t             1491
```

<210> SEQ ID NO 143
<211> LENGTH: 1419
<212> TYPE: DNA
<213> ORGANISM: Artificial Sequence
<220> FEATURE:
<223> OTHER INFORMATION: K-044-085 DAB N-(VEPKSSDK linker) & C-terminal
      ((TGLDSP)x4) Codon optimised nucleic acid sequence
      identified using molecular biology techniques.

<400> SEQUENCE: 143

```
gacatccaga tgacccagag ccccagcagc ctgagcgcct ctgtgggaga cagggtgact     60
atcacctgca gggccagcca gtggattggc cccgagctga gtggtatca gcagaagccc    120 ggcaaggccc ccaagctgct gatctaccac ggcagcatcc tgcagtccgg cgtgcctagc    180
aggttctcag gcagcggcag cggcaccgac ttcaccctca ccatcagcag cctgcagccc    240
gaggacttcg ccacctacta ctgccagcag tatatgtact accccacac cttcggccag    300 ggcaccaagg tggagatcaa gagggtggag cctaagtctt ctgacaagac ccacacctgc    360 ccccctgcc ctgccccaga gctgctggga ggacccagcg tgttcctgtt cccacccaag    420
cctaaggaca ccctgatgat cagcagaacc cccgaggtga cctgtgtggt ggtggatgtg    480
agccacgagg accctgaggt gaagttcaac tggtacgtgg acggcgtgga ggtgcacaat    540
gccaagacca gcccaggga ggagcagtac aacagcacct accgggtggt gtccgtgctg    600
accgtgctgc accaggattg gctgaacggc aaggagtaca agtgtaaggt gtccaacaag    660
gccctgcctg cccctatcga gaaaaccatc agcaaggcca agggccagcc cagagagccc    720
caggtgtaca ccctgccccc tagcagagat gagctgacca gaaccaggt gtccctgacc    780 tgcctggtga agggcttcta ccccagcgac atcgccgtgg agtgggagag caatggccag    840
cccgagaaca actacaagac cacccccct gtgctggaca gcgatggcag cttcttcctg    900
tacagcaagc tgaccgtgga caagagcaga tggcagcagg gcaacgtgtt cagctgctcc    960
gtgatgcacg aggccctgca caatcactac acccagaaga gcctgagcct gtcccctggc   1020
aagaccggcc tcgacagccc cactggcctg acagcccaa ccggactgga ttctcccacc   1080
ggcctggaca gccccgacat ccagatgacc cagagcccca gcagcctgag cgccagcgtg   1140
ggggacaggg tgactatcac ctgcagggcc tcccagtgga ttggccccga gctgaagtgg   1200
tatcagcaga agcccggcaa ggccccaag ctgctgatct accacggcag catcctgcag   1260
agcggcgtgc cctcaaggtt ctcaggcagc ggcagcggca ccgacttcac cctgaccatc   1320
agcagcctgc agcccgagga cttcgccacc tactactgcc agcagtacat gtactacccc   1380
cacaccttcg gccagggcac caaggtggag atcaaaagg                           1419
```

<210> SEQ ID NO 144
<211> LENGTH: 1473
<212> TYPE: DNA
<213> ORGANISM: Artificial Sequence
<220> FEATURE:
<223> OTHER INFORMATION: DOM15-26-597 DAB N-((TGLDSP)x3) & C-terminal
      K-044-085 DAB ((TGLDSP)x4) Codon optimised nucleic acid
      sequence identified using molecular biology techniques.

<400> SEQUENCE: 144

```
gaggtgcagc tgctggtgtc tggcggcgga ctggtgcagc tggcggcag cctgagactg    60 agctgcgccg ccagcggctt caccttcaag gcctacccca tgatgtgggt gcggcaggcc   120
cctggcaagg gcctggaatg ggtgtccgag atcagcccca gcggcagcaa cacctactac   180
gccgacagcg tgaagggccg gttcaccatc agccgggaca cagcaagaa caccctgtac   240 ctgcagatga acagcctgcg ggccgaggac accgccgtgt actactgcgc caaggacccc   300
cggaagctgg actactgggg ccagggcacc ctggtgaccg tgagcagcac gggtctggac   360
agtccgactg gtttagattc acctacgggc ttggactccc aacccacac ctgcccccc    420 tgccctgccc ctgagctgct gggcggaccc agcgtgttcc tgttcccccc caagcccaag   480
gacaccctga tgatcagccg gacccccgag gtgacctgcg tggtggtgga cgtgagccac   540
gaggaccctg aggtgaagtt caattggtac gtggacggcg tggaggtgca aacgccaag   600 accaagcccc gggaggaaca gtacaacagc acctaccggg tggtgtccgt gctgaccgtg   660
ctgcaccagg actggctgaa cggcaaagaa tacaagtgca aggtgtccaa caaggccctg   720 cctgcccccca tcgagaaaac catcagcaag gccaagggcc agcccaggga cccccaggtg   780
tacaccctgc cccccagccg ggacgagctg accaagaacc aggtgtccct gacctgcctg   840
gtgaagggct tctaccccag cgacatcgcc gtggagtggg agagcaacgg ccagcccgag   900
aacaactaca agaccacccc ccctgtgctg gacagcgacg gcagcttctt cctgtacagc   960
aagctgaccg tggacaagag ccggtggcag cagggcaacg tgttcagctg cagcgtgatg  1020
cacgaggccc tgcacaacca ctacacccag aagagcctga gcctgtcccc tggcaagacc  1080
ggcctcgaca gccccactgg cctggacagc ccaaccggac tggattctcc accggcctg   1140 gacagccccg acatccagat gacccagagc cccagcagcc tgagcgccag cgtgggggac  1200
agggtgacta tcacctgcag ggcctccag tggattggcc ccgagctgaa gtggtatcag  1260
cagaagcccg gcaaggcccc caagctgctg atctaccacg gcagcatcct gcagagcggc  1320
gtgccctcaa ggttctcagg cagcggcagc ggcaccgact tcaccctgac catcagcagc  1380
ctgcagcccg aggacttcgc cacctactac tgccagcagt acatgtacta ccccccacacc  1440 ttcggccagg gcaccaaggt ggagatcaaa agg                                1473
```

<210> SEQ ID NO 145
<211> LENGTH: 1443
<212> TYPE: DNA
<213> ORGANISM: Artificial Sequence
<220> FEATURE:
<223> OTHER INFORMATION: DOM15-26-597 DAB N-(VEPKSSDK linker) &
    C-terminal K-044-085 DAB ((TGLDSP)x4) Codon optimised nucleic acid
    sequence identified using molecular biology techniques.

<400> SEQUENCE: 145

```
gaggtgcagc tgctggtgtc tggcggcgga ctggtgcagc tggcggcag cctgagactg    60 agctgcgccg ccagcggctt caccttcaag gcctacccta tgatgtgggt gcggcaggcc   120
cctggtaagg gcctggaatg ggtgtccgag atcagcccaa gcggcagcaa cacctactac   180
gcagacagcg tgaagggccg gttcaccatc agccgggaca cagcaagaa cacactgtac   240 ctgcagatga acagcctgcg ggccgaggac accgcagtgt actactgcgc caaggaccca   300
cggaagctgg actactgggg tcagggcacc ctggtgaccg tgagcagcgt ggagcctaag   360
tcttctgaca agacccacac ctgcccaccc tgcctgccc cagagctgct gggaggaccc   420
agcgtgttcc tgttcccacc caagcctaag gacaccctga tgatcagcag aacccccgag   480
gtgacctgtg tggtggtgga tgtgagccac gaggaccctg aggtgaagtt caactggtac   540
```

-continued

```
gtggacggcg tggaggtgca caatgccaag accaagccca gggaggagca gtacaacagc    600
acctaccggg tggtgtccgt gctgaccgtg ctgcaccagg attggctgaa cggcaaggag    660
tacaagtgta aggtgtccaa caaggccctg cctgccccta tcgagaaaac catcagcaag    720
gccaagggcc agcccagaga gccccaggtg tacacccctg cccctagcag agatgagctg    780
accaagaacc aggtgtccct gacctgcctg gtgaagggct tctaccccag cgacatcgcc    840
gtggagtggg agagcaatgg ccagcccgag aacaactaca agaccacccc ccctgtgctg    900
gacagcgatg gcagcttctt cctgtacagc aagctgaccg tggacaagag cagatggcag    960
cagggcaacg tgttcagctg ctccgtgatg cacgaggccc tgcacaatca ctacacccag   1020
aagagcctga gcctgtcccc tggcaagacc ggcctcgaca gccccactgg cctggacagc   1080
ccaaccggac tggattctcc caccggcctg acagccccg acatccagat gacccagagc   1140
cccagcagcc tgagcgccag cgtggggac agggtgacta tcacctgcag ggcctcccag   1200
tggattggcc ccgagctgaa gtggtatcag cagaagcccg gcaaggcccc caagctgctg   1260
atctaccacg gcagcatcct gcagagcggc gtgccctcaa ggttctcagg cagcggcagc   1320
ggcaccgact tcaccctgac catcagcagc ctgcagcccg aggacttcgc cacctactac   1380
tgccagcagt acatgtacta ccccccacacc ttcggccagg gcaccaaggt ggagatcaaa   1440
agg                                                                  1443
```

<210> SEQ ID NO 146
<211> LENGTH: 1425
<212> TYPE: DNA
<213> ORGANISM: Artificial Sequence
<220> FEATURE:
<223> OTHER INFORMATION: DMS1576 with C-terminal K-044-085 DAB
      ((TGLDSP)x4) Codon optimised nucleic acid sequence identified
      using molecular biology techniques.

<400> SEQUENCE: 146

```
gaggtgcagc tgctggtgtc tggcggcgga ctggtgcagc ctggcggcag cctgagactg     60
agctgcgccg ccagcggctt caccttcaag gcctacccca tgatgtgggt gcggcaggcc    120
cctggcaagg gcctggaatg ggtgtccgag atcagcccca gcggcagcaa cacctactac    180
gccgacagcg tgaagggccg gttcaccatc agccgggaca acagcaagaa caccctgtac    240
ctgcagatga acagcctgcg ggccgaggac accgccgtgt actactgcgc caaggacccc    300
cggaagctgg actactgggg ccagggcacc ctggtgaccg tgagcagcgc tagcacccac    360
acctgccccc cctgccctgc ccctgagctg ctgggcggac ccagcgtgtt cctgttcccc    420
cccaagccca aggacaccct gatgatcagc cggacccccg aggtgacctg cgtggtggtg    480
gacgtgagcc acgaggaccc tgaggtgaag ttcaattggt acgtggacgg cgtggaggtg    540
cacaacgcca agaccaagcc ccgggaggaa cagtacaaca gcacctaccg ggtggtgtcc    600
gtgctgaccg tgctgcacca ggactggctg aacggcaaag aatacaagtg caaggtgtcc    660
aacaaggccc tgcctgcccc catcgagaaa accatcagca aggccaaggg ccagcccagg    720
gaacccaggg tgtacacccc tgcccccagc cgggacgagc tgaccaagaa ccaggtgtcc    780
ctgacctgcc tggtgaaggg cttctacccc agcgacatcg ccgtggagtg ggagagcaac    840
ggccagcccg agaacaacta caagaccacc ccccctgtgc tggacagcga cggcagcttc    900
ttcctgtaca gcaagctgac cgtggacaag agccggtggc agcagggcaa cgtgttcagc    960
tgcagcgtga tgcacgaggc cctgcacaac cactacaccc agaagagcct gagcctgtcc   1020
```

| | |
|---|---|
| cctggcaaga ccggcctcga cagccccact ggcctggaca gcccaaccgg actggattct | 1080 |
| cccaccggcc tggacagccc cgacatccag atgacccaga gccccagcag cctgagcgcc | 1140 |
| agcgtggggg acagggtgac tatcacctgc agggcctccc agtggattgg ccccgagctg | 1200 |
| aagtggtatc agcagaagcc cggcaaggcc cccaagctgc tgatctacca cggcagcatc | 1260 |
| ctgcagagcg gcgtgccctc aaggttctca ggcagcggca gcggcaccga cttcaccctg | 1320 |
| accatcagca gcctgcagcc cgaggacttc gccacctact actgccagca gtacatgtac | 1380 |
| taccccacac ccttcggcca gggcaccaag gtggagatca aaagg | 1425 |

<210> SEQ ID NO 147
<211> LENGTH: 1440
<212> TYPE: DNA
<213> ORGANISM: Artificial Sequence
<220> FEATURE:
<223> OTHER INFORMATION: DOM15-26-597 DAB N-(VEPKSSDK linker) &
    C-terminal K-044-085 DAB minus C-term R ((TGLDSP)x4) Codon
    optimised nucleic acid sequence identified using
    molecular biology techniques.

<400> SEQUENCE: 147

| | |
|---|---|
| gaggtgcagc tgctggtgtc tggcggcgga ctggtgcagc ctggcggcag cctgagactg | 60 |
| agctgcgccg ccagcggctt caccttcaag gcctacccta tgatgtgggt gcggcaggcc | 120 |
| cctggtaagg gcctggaatg ggtgtccgag atcagcccaa gcggcagcaa cacctactac | 180 |
| gcagacagcg tgaagggccg gttcaccatc agccgggaca cagcaagaa cacactgtac | 240 |
| ctgcagatga acagcctgcg ggccgaggac accgcagtgt actactgcgc caaggaccca | 300 |
| cggaagctgg actactgggg tcagggcacc ctggtgaccg tgagcagcgt ggagcctaag | 360 |
| tcttctgaca gacccacac ctgcccaccc tgccctgccc cagagctgct gggaggaccc | 420 |
| agcgtgttcc tgttcccacc caagcctaag gacaccctga tgatcagcag aacccccgag | 480 |
| gtgacctgtg tggtggtgga tgtgagccac gaggaccctg aggtgaagtt caactggtac | 540 |
| gtggacggcg tggaggtgca caatgccaag accaagccca gggaggagca gtacaacagc | 600 |
| acctaccggg tggtgtccgt gctgaccgtg ctgcaccagg attggctgaa cggcaaggag | 660 |
| tacaagtgta aggtgtccaa caaggccctg cctcccccta tcgagaaaac catcagcaag | 720 |
| gccaagggcc agcccagaga gccccaggtg tacaccctgc ccctagcag agatgagctg | 780 |
| accaagaacc aggtgtccct gacctgcctg gtgaagggct tctacccag cgacatcgcc | 840 |
| gtggagtggg agagcaatgg ccagcccgag aacaactaca agaccacccc ccctgtgctg | 900 |
| gacagcgatg gcagcttctt cctgtacagc aagctgaccg tggacaagag cagatggcag | 960 |
| cagggcaacg tgttcagctg ctccgtgatg cacgaggccc tgcacaatca ctacacccag | 1020 |
| aagagcctga gcctgtcccc tggcaagacc ggcctcgaca gccccactgg cctggacagc | 1080 |
| ccaaccggac tggattctcc caccggcctg gacagcccg acatccagat gacccagagc | 1140 |
| cccagcagcc tgagcgccag cgtggggac agggtgacta tcacctgcag ggcctcccag | 1200 |
| tggattggcc ccgagctgaa gtggtatcag cagaagcccg gcaaggcccc caagctgctg | 1260 |
| atctaccacg gcagcatcct gcagagcggc gtgccctcaa ggttctcagg cagcggcagc | 1320 |
| ggcaccgact tcaccctgac catcagcagc ctgcagcccg aggacttcgc cacctactac | 1380 |
| tgccagcagt acatgtacta ccccccacacc ttcggcagg gcaccaaggt ggagatcaaa | 1440 |

<210> SEQ ID NO 148
<211> LENGTH: 1446
<212> TYPE: DNA

<213> ORGANISM: Artificial Sequence
<220> FEATURE:
<223> OTHER INFORMATION: DOM15-26-597 DAB N-(VEPKSSDK linker) &
C-terminal K-044-085 DAB + A ((TGLDSP)x4) Codon
optimised nucleic acid sequence identified
using molecular biology techniques.

<400> SEQUENCE: 148

```
gaggtgcagc tgctggtgtc tggcggcgga ctggtgcagc ctggcggcag cctgagactg      60
agctgcgccg ccagcggctt caccttcaag gcctacccta tgatgtgggt gcggcaggcc     120
cctggtaagg gcctggaatg ggtgtccgag atcagcccaa gcggcagcaa cacctactac     180
gcagacagcg tgaagggccg gttcaccatc agccgggaca cagcaagaa cacactgtac      240
ctgcagatga acagcctgcg ggccgaggac accgcagtgt actactgcgc caaggaccca     300
cggaagctgg actactgggg tcagggcacc ctggtgaccg tgagcagcgt ggagcctaag     360
tcttctgaca gacccacac ctgcccaccc tgccctgccc cagagctgct gggaggaccc      420
agcgtgttcc tgttcccacc caagcctaag gacaccctga tgatcagcag aaccccgag      480
gtgacctgtg tggtggtgga tgtgagccac gaggaccctg aggtgaagtt caactggtac     540
gtggacggcg tggaggtgca caatgccaag accaagccca gggaggagca gtacaacagc     600
acctaccggg tggtgtccgt gctgaccgtg ctgcaccagg attggctgaa cggcaaggag     660
tacaagtgta aggtgtccaa caaggccctg cctgccccta tcgagaaaac catcagcaag     720
gccaagggcc agcccagaga gccccaggtg tacaccctgc ccctagcag agatgagctg      780
accaagaacc aggtgtccct gacctgcctg gtgaagggct ctacccag cgacatcgcc       840
gtggagtggg agagcaatgg ccagcccgag aacaactaca agaccacccc cctgtgctg      900
gacagcgatg gcagcttctt cctgtacagc aagctgaccg tggacaagag cagatggcag     960
cagggcaacg tgttcagctg ctccgtgatg cacgaggccc tgcacaatca ctacacccag    1020
aagagcctga cctgtcccc tggcaagacc ggcctcgaca gccccactgg cctggacagc     1080
ccaaccggac tggattctcc caccggcctg acagccccg acatccagat gacccagagc     1140
cccagcagcc tgagcgccag cgtgggggac agggtgacta tcacctgcag ggcctcccag    1200
tggattggcc ccgagctgaa gtggtatcag cagaagcccg gcaaggcccc caagctgctg    1260
atctaccacg gcagcatcct gcagagcggc gtgccctcaa ggttctcagg cagcggcagc    1320
ggcaccgact tcaccctgac catcagcagc ctgcagcccg aggacttcgc cacctactac    1380
tgccagcagt acatgtacta ccccacacc ttcggccagg gcaccaaggt ggagatcaaa    1440
agggcc                                                                1446
```

<210> SEQ ID NO 149
<211> LENGTH: 1452
<212> TYPE: DNA
<213> ORGANISM: Artificial Sequence
<220> FEATURE:
<223> OTHER INFORMATION: DOM15-26-597 DAB N-(VEPKSSDK linker) &
C-terminal K-044-085 DAB +AAA ((TGLDSP)x4) Codon optimised
nucleic acid sequence identified using
molecular biology techniques.

<400> SEQUENCE: 149

```
gaggtgcagc tgctggtgtc tggcggcgga ctggtgcagc ctggcggcag cctgagactg      60
agctgcgccg ccagcggctt caccttcaag gcctacccta tgatgtgggt gcggcaggcc     120
cctggtaagg gcctggaatg ggtgtccgag atcagcccaa gcggcagcaa cacctactac     180
gcagacagcg tgaagggccg gttcaccatc agccgggaca cagcaagaa cacactgtac      240
```

```
ctgcagatga acagcctgcg ggccgaggac accgcagtgt actactgcgc caaggaccca      300
cggaagctgg actactgggg tcagggcacc ctggtgaccg tgagcagcgt ggagcctaag      360
tcttctgaca agacccacac ctgcccaccc tgccctgccc cagagctgct gggaggaccc      420
agcgtgttcc tgttcccacc caagcctaag gacaccctga tgatcagcag aaccccgag      480 gtgacctgtg tggtggtgga tgtgagccac gaggaccctg aggtgaagtt caactggtac      540
gtggacggcg tggaggtgca caatgccaag accaagccca gggaggagca gtacaacagc      600
acctaccggg tggtgtccgt gctgaccgtg ctgcaccagg attggctgaa cggcaaggag      660
tacaagtgta aggtgtccaa caaggccctg cctgccccta tcgagaaaac catcagcaag      720
gccaagggcc agcccagaga gccccaggtg tacaccctgc ccctagcag agatgagctg      780 accaagaacc aggtgtccct gacctgcctg gtgaagggct tctacccag cgacatcgcc      840 gtggagtggg agagcaatgg ccagcccgag aacaactaca agaccacccc ccctgtgctg      900
gacagcgatg gcagcttctt cctgtacagc aagctgaccg tggacaagag cagatggcag      960
cagggcaacg tgttcagctg ctccgtgatg cacgaggccc tgcacaatca ctacacccag     1020
aagagcctga gcctgtcccc tggcaagacc ggcctcgaca gccccactgg cctggacagc     1080
ccaaccggac tggattctcc caccggcctg acagccccg acatccagat gacccagagc     1140
cccagcagcc tgagcgccag cgtgggggac agggtgacta tcacctgcag ggcctcccag     1200
tggattggcc ccgagctgaa gtggtatcag cagaagcccg gcaaggcccc caagctgctg     1260
atctaccacg gcagcatcct gcagagcggc gtgccctcaa ggttctcagg cagcggcagc     1320
ggcaccgact tcaccctgac catcagcagc ctgcagcccg aggacttcgc cacctactac     1380
tgccagcagt acatgtacta ccccccacac ctcggccagg gcaccaaggt ggagatcaaa     1440
agggccgccg cc                                                         1452

<210> SEQ ID NO 150
<211> LENGTH: 1446
<212> TYPE: DNA
<213> ORGANISM: Artificial Sequence
<220> FEATURE:
<223> OTHER INFORMATION: DOM15-26-597 DAB N-(VEPKSSDK linker) &
      C-terminal K-044-085 DAB +T ((TGLDSP)x4) Codon optimised
      nucleic acid sequence identified
      using molecular biology techniques.

<400> SEQUENCE: 150
gaggtgcagc tgctggtgtc tggcggcgga ctggtgcagc ctggcggcag cctgagactg       60
agctgcgccg ccagcggctt caccttcaag gcctacccta tgatgtgggt gcggcaggcc      120
cctggtaagg gcctggaatg ggtgtccgag atcagcccaa gcggcagcaa cacctactac      180
gcagacagcg tgaagggccg gttcaccatc agccgggaca acagcaagaa cacactgtac      240
ctgcagatga acagcctgcg ggccgaggac accgcagtgt actactgcgc caaggaccca      300
cggaagctgg actactgggg tcagggcacc ctggtgaccg tgagcagcgt ggagcctaag      360
tcttctgaca agacccacac ctgcccaccc tgccctgccc cagagctgct gggaggaccc      420
agcgtgttcc tgttcccacc caagcctaag gacaccctga tgatcagcag aaccccgag      480 gtgacctgtg tggtggtgga tgtgagccac gaggaccctg aggtgaagtt caactggtac      540
gtggacggcg tggaggtgca caatgccaag accaagccca gggaggagca gtacaacagc      600
acctaccggg tggtgtccgt gctgaccgtg ctgcaccagg attggctgaa cggcaaggag      660
tacaagtgta aggtgtccaa caaggccctg cctgccccta tcgagaaaac catcagcaag      720
```

| | |
|---|---|
| gccaagggcc agcccagaga gccccaggtg tacaccctgc cccctagcag agatgagctg | 780 |
| accaagaacc aggtgtccct gacctgcctg gtgaagggct tctacccag cgacatcgcc | 840 |
| gtggagtggg agagcaatgg ccagcccgag aacaactaca agaccacccc ccctgtgctg | 900 |
| gacagcgatg gcagcttctt cctgtacagc aagctgaccg tggacaagag cagatggcag | 960 |
| cagggcaacg tgttcagctg ctccgtgatg cacgaggccc tgcacaatca ctacacccag | 1020 |
| aagagcctga gcctgtcccc tggcaagacc ggcctcgaca gccccactgg cctggacagc | 1080 |
| ccaaccggac tggattctcc caccggcctg acagccccg acatccagat gacccagagc | 1140 |
| cccagcagcc tgagcgccag cgtggggggac agggtgacta tcacctgcag ggcctcccag | 1200 |
| tggattggcc ccgagctgaa gtggtatcag cagaagcccg gcaaggcccc caagctgctg | 1260 |
| atctaccacg gcagcatcct gcagagcggc gtgccctcaa ggttctcagg cagcggcagc | 1320 |
| ggcaccgact tcaccctgac catcagcagc ctgcagcccg aggacttcgc cacctactac | 1380 |
| tgccagcagt acatgtacta ccccacacc ttcggccagg gcaccaaggt ggagatcaaa | 1440 |
| aggacc | 1446 |

<210> SEQ ID NO 151
<211> LENGTH: 1422
<212> TYPE: DNA
<213> ORGANISM: Artificial Sequence
<220> FEATURE:
<223> OTHER INFORMATION: DMS1576 with C-terminal K-044-085 DAB minus
     C-term R ((TGLDSP)x4) Codon optimised nucleic acid sequence
     identified using molecular biology techniques.

<400> SEQUENCE: 151

| | |
|---|---|
| gaggtgcagc tgctggtgtc tggcggcgga ctggtgcagc ctggcggcag cctgagactg | 60 |
| agctgcgccg ccagcggctt caccttcaag gcctaccccca tgatgtgggt gcggcaggcc | 120 |
| cctggcaagg gcctggaatg ggtgtccgag atcagcccca gcggcagcaa cacctactac | 180 |
| gccgacagcg tgaagggccg gttcaccatc agccgggaca cagcaagaa cacccctgtac | 240 |
| ctgcagatga acagcctgcg ggccgaggac accgccgtgt actactgcgc caaggacccc | 300 |
| cggaagctgg actactgggg ccagggcacc ctggtgaccg tgagcagcgc tagcacccac | 360 |
| acctgccccc cctgccctgc ccctgagctc ctgggcggac ccagcgtgtt cctgttcccc | 420 |
| cccaagccca aggacaccct gatgatcagc cggacccccg aggtgacctg cgtggtggtg | 480 |
| gacgtgagcc acgaggaccc tgaggtgaag ttcaattggt acgtggacgg cgtggaggtg | 540 |
| cacaacgcca agaccaagcc ccgggaggaa cagtacaaca gcacctaccg ggtggtgtcc | 600 |
| gtgctgaccg tgctgcacca ggactggctg aacggcaaag aatacaagtg caaggtgtcc | 660 |
| aacaaggccc tgcctgcccc catcgagaaa accatcagca aggccaaggg ccagcccagg | 720 |
| gaaccccagg tgtacaccct gccccccagc cgggacgagc tgaccaagaa ccaggtgtcc | 780 |
| ctgacctgcc tggtgaaggg cttctacccc agcgacatcg ccgtgagtg ggagagcaac | 840 |
| ggccagcccg agaacaacta caagaccacc cccctgtgc tggacagcga cggcagcttc | 900 |
| ttcctgtaca gcaagctgac cgtggacaag agccggtggc agcagggcaa cgtgttcagc | 960 |
| tgcagcgtga tgcacgaggc cctgcacaac cactacaccc agaagagcct gagcctgtcc | 1020 |
| cctggcaaga ccggcctcga cagccccact ggcctggaca gcccaaccgg actggattct | 1080 |
| cccaccggcc tggacagccc cgacatccag atgacccaga gccccagcag cctgagcgcc | 1140 |
| agcgtggggg acagggtgac tatcacctgc agggcctcca gtggattgg ccccgagctg | 1200 |

| | |
|---|---|
| aagtggtatc agcagaagcc cggcaaggcc cccaagctgc tgatctacca cggcagcatc | 1260 |
| ctgcagagcg gcgtgccctc aaggttctca ggcagcggca gcggcaccga cttcaccctg | 1320 |
| accatcagca gcctgcagcc cgaggacttc gccacctact actgccagca gtacatgtac | 1380 |
| tacccccaca ccttcggcca gggcaccaag gtggagatca aa | 1422 |

<210> SEQ ID NO 152
<211> LENGTH: 1428
<212> TYPE: DNA
<213> ORGANISM: Artificial Sequence
<220> FEATURE:
<223> OTHER INFORMATION: DMS1576 with C-terminal K-044-085 DAB +A
((TGLDSP)x4) Codon optimised nucleic acid sequence
identified using molecular biology techniques.

<400> SEQUENCE: 152

| | |
|---|---|
| gaggtgcagc tgctggtgtc tggcggcgga ctggtgcagc ctggcggcag cctgagactg | 60 |
| agctgcgccg ccagcggctt caccttcaag gcctacccca tgatgtgggt gcggcaggcc | 120 |
| cctggcaagg gcctggaatg ggtgtccgag atcagcccca gcggcagcaa cacctactac | 180 |
| gccgacagcg tgaagggccg gttcaccatc agccgggaca acagcaagaa caccctgtac | 240 |
| ctgcagatga acagcctgcg ggccgaggac accgccgtgt actactgcgc caaggacccc | 300 |
| cggaagctgg actactgggg ccagggcacc ctggtgaccg tgagcagcgc tagcacccac | 360 |
| acctgccccc cctgccctgc ccctgagctg ctggcggac ccagcgtgtt cctgttcccc | 420 |
| cccaagccca aggacaccct gatgatcagc cggaccccg aggtgacctg cgtggtggtg | 480 |
| gacgtgagcc acgaggaccc tgaggtgaag ttcaattggt acgtggacgg cgtggaggtg | 540 |
| cacaacgcca agaccaagcc ccgggaggaa cagtacaaca gcacctaccg ggtggtgtcc | 600 |
| gtgctgaccg tgctgcacca ggactggctg aacggcaaag aatacaagtg caaggtgtcc | 660 |
| aacaaggccc tgcctgcccc catcgagaaa accatcagca aggccaaggg ccagcccagg | 720 |
| gaacccagg tgtacaccct gccccccagc cgggacgagc tgaccaagaa ccaggtgtcc | 780 |
| ctgacctgcc tggtgaaggg cttctacccc agcgacatcg ccgtggagtg ggagagcaac | 840 |
| ggccagcccg agaacaacta caagaccacc ccccctgtgc tggacagcga cggcagcttc | 900 |
| ttcctgtaca gcaagctgac cgtggacaag agccggtggc agcagggcaa cgtgttcagc | 960 |
| tgcagcgtga tgcacgaggc cctgcacaac cactacaccc agaagagcct gagcctgtcc | 1020 |
| cctggcaaga ccggcctcga cagccccact ggcctggaca gcccaaccgg actggattct | 1080 |
| cccaccggcc tggacagccc cgacatccag atgacccaga gccccagcag cctgagcgcc | 1140 |
| agcgtggggg acagggtgac tatcacctgc agggcctccc agtggattgg ccccgagctg | 1200 |
| aagtggtatc agcagaagcc cggcaaggcc cccaagctgc tgatctacca cggcagcatc | 1260 |
| ctgcagagcg gcgtgccctc aaggttctca ggcagcggca gcggcaccga cttcaccctg | 1320 |
| accatcagca gcctgcagcc cgaggacttc gccacctact actgccagca gtacatgtac | 1380 |
| tacccccaca ccttcggcca gggcaccaag gtggagatca aagggcc | 1428 |

<210> SEQ ID NO 153
<211> LENGTH: 1434
<212> TYPE: DNA
<213> ORGANISM: Artificial Sequence
<220> FEATURE:
<223> OTHER INFORMATION: DMS1576 with C-terminal K-044-085 DAB +AAA
((TGLDSP)x4) Codon optimised nucleic acid sequence
identified using molecular biology techniques.

<400> SEQUENCE: 153

```
gaggtgcagc tgctggtgtc tggcggcgga ctggtgcagc ctggcggcag cctgagactg      60
agctgcgccg ccagcggctt caccttcaag gcctacccca tgatgtgggt gcggcaggcc     120
cctggcaagg gcctggaatg ggtgtccgag atcagcccca gcggcagcaa cacctactac     180
gccgacagcg tgaagggccg gttcaccatc agccgggaca cagcaagaa caccctgtac     240 ctgcagatga acagcctgcg ggccgaggac accgccgtgt actactgcgc caaggacccc     300
cggaagctgg actactgggg ccagggcacc ctggtgaccg tgagcagcgc tagcacccac     360
acctgccccc cctgccctgc cctgagctg ctgggcggac ccagcgtgtt cctgttcccc      420
cccaagccca aggacaccct gatgatcagc cggaccccg aggtgacctg cgtggtggtg      480
gacgtgagcc acgaggaccc tgaggtgaag ttcaattggt acgtggacgg cgtggaggtg     540
cacaacgcca agaccaagcc ccgggaggaa cagtacaaca gcacctaccg ggtggtgtcc     600
gtgctgaccg tgctgcacca ggactggctg aacggcaaag aatacaagtg caaggtgtcc     660
aacaaggccc tgcctgcccc catcgagaaa accatcagca aggccaaggg ccagccccagg    720 gaacccccagg tgtacaccct gcccccccagc cgggacgagc tgaccaagaa ccaggtgtcc   780
ctgacctgcc tggtgaaggg cttctacccc agcgacatcg ccgtggagtg ggagagcaac     840
ggccagcccg agaacaacta caagaccacc cccctgtgc tggacagcga cggcagcttc      900
ttcctgtaca gcaagctgac cgtggacaag agccggtggc agcagggcaa cgtgttcagc     960
tgcagcgtga tgcacgaggc cctgcacaac cactacaccc agaagagcct gagcctgtcc    1020
cctggcaaga ccggcctcga cagccccact ggcctggaca gcccaaccgg actggattct    1080
cccaccggcc tggacagccc cgacatccag atgacccaga gccccagcag cctgagcgcc    1140
agcgtggggg acagggtgac tatcacctgc agggcctccc agtggattgg ccccgagctg    1200
aagtggtatc agcagaagcc cggcaaggcc cccaagctgc tgatctacca cggcagcatc    1260
ctgcagagcg gcgtgccctc aaggttctca ggcagcggca gcggcaccga cttcacccct   1320
accatcagca gcctgcagcc cgaggacttc gccacctact actgccagca gtacatgtac    1380
tacccccaca ccttcggcca gggcaccaag gtggagatca aaagggccgc cgcc          1434
```

<210> SEQ ID NO 154
<211> LENGTH: 1428
<212> TYPE: DNA
<213> ORGANISM: Artificial Sequence
<220> FEATURE:
<223> OTHER INFORMATION: DMS1576 with C-terminal K-044-085 DAB +T ((TGLDSP)x4) Codon optimised nucleic acid sequence identified using molecular biology techniques.

<400> SEQUENCE: 154

```
gaggtgcagc tgctggtgtc tggcggcgga ctggtgcagc ctggcggcag cctgagactg      60
agctgcgccg ccagcggctt caccttcaag gcctacccca tgatgtgggt gcggcaggcc     120
cctggcaagg gcctggaatg ggtgtccgag atcagcccca gcggcagcaa cacctactac     180
gccgacagcg tgaagggccg gttcaccatc agccgggaca cagcaagaa caccctgtac     240 ctgcagatga acagcctgcg ggccgaggac accgccgtgt actactgcgc caaggacccc     300
cggaagctgg actactgggg ccagggcacc ctggtgaccg tgagcagcgc tagcacccac     360
acctgccccc cctgccctgc cctgagctg ctgggcggac ccagcgtgtt cctgttcccc      420
cccaagccca aggacaccct gatgatcagc cggaccccg aggtgacctg cgtggtggtg      480
gacgtgagcc acgaggaccc tgaggtgaag ttcaattggt acgtggacgg cgtggaggtg     540
```

-continued

```
cacaacgcca agaccaagcc ccgggaggaa cagtacaaca gcacctaccg ggtggtgtcc    600
gtgctgaccg tgctgcacca ggactggctg aacggcaaag aatacaagtg caaggtgtcc    660
aacaaggccc tgcctgcccc catcgagaaa accatcagca aggccaaggg ccagcccagg    720 gaacccagg tgtacaccct gccccccagc cgggacgagc tgaccaagaa ccaggtgtcc     780
ctgacctgcc tggtgaaggg cttctacccc agcgacatcg ccgtggagtg ggagagcaac    840
ggccagcccg agaacaacta caagaccacc ccccctgtgc tggacagcga cggcagcttc    900
ttcctgtaca gcaagctgac cgtggacaag agccggtggc agcagggcaa cgtgttcagc    960
tgcagcgtga tgcacgaggc cctgcacaac cactacaccc agaagagcct gagcctgtcc   1020
cctggcaaga ccggcctcga cagccccact ggcctggaca gcccaaccgg actggattct   1080
cccaccggcc tggacagccc cgacatccag atgacccaga gccccagcag cctgagcgcc   1140
agcgtggggg acagggtgac tatcacctgc agggcctccc agtggattgg ccccgagctg   1200
aagtggtatc agcagaagcc cggcaaggcc cccaagctgc tgatctacca cggcagcatc   1260
ctgcagagcg gcgtgccctc aaggttctca ggcagcggca gcggcaccga cttcaccctg   1320
accatcagca gcctgcagcc cgaggacttc gccacctact actgccagca gtacatgtac   1380
tacccccaca ccttcggcca gggcaccaag gtggagatca aaaggacc                1428
```

<210> SEQ ID NO 155
<211> LENGTH: 359
<212> TYPE: PRT
<213> ORGANISM: Artificial Sequence
<220> FEATURE:
<223> OTHER INFORMATION: N-terminal Fc fusion of DOM15-26-597 DAB
((TGLDSP)x3) amino acid sequence identified
using molecular biology techniques.

<400> SEQUENCE: 155

```
Glu Val Gln Leu Leu Val Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Thr Gly Leu Asp Ser Pro Thr Gly Leu Asp Ser Pro
        115                 120                 125

Thr Gly Leu Asp Ser Pro Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
```

```
                195                 200                 205
Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asn Glu Leu Thr Lys
            260                 265                 270

Asn Gln Val Ser Leu Thr Cys Leu Val Lys Gly Phe Tyr Pro Ser Asp
            275                 280                 285

Ile Ala Val Glu Trp Glu Ser Asn Gly Gln Pro Glu Asn Asn Tyr Lys
        290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
            355

<210> SEQ ID NO 156
<211> LENGTH: 365
<212> TYPE: PRT
<213> ORGANISM: Artificial Sequence
<220> FEATURE:
<223> OTHER INFORMATION: N-terminal Fc fusion of DOM15-26-597 DAB
      ((TGLDSP)x4) amino acid sequence identified
      using molecular biology techniques.

<400> SEQUENCE: 156

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Thr Gly Leu Asp Ser Pro Thr Gly Leu Asp Ser Pro
        115                 120                 125

Thr Gly Leu Asp Ser Pro Thr Gly Leu Asp Ser Pro Thr His Thr Cys
    130                 135                 140

Pro Pro Cys Pro Ala Pro Glu Leu Leu Gly Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190
```

```
Phe Asn Trp Tyr Val Asp Gly Val Glu Val His Asn Ala Lys Thr Lys
            195                 200                 205

Pro Arg Glu Glu Gln Tyr Asn Ser Thr Tyr Arg Val Val Ser Val Leu
210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
            245                 250                 255

Ala Lys Gly Gln Pro Arg Glu Pro Gln Val Tyr Thr Leu Pro Pro Ser
            260                 265                 270

Arg Asp Glu Leu Thr Lys Asn Gln Val Ser Leu Thr Cys Leu Val Lys
            275                 280                 285

Gly Phe Tyr Pro Ser Asp Ile Ala Val Glu Trp Glu Ser Asn Gly Gln
290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Lys
            355                 360                 365

<210> SEQ ID NO 157
<211> LENGTH: 359
<212> TYPE: PRT
<213> ORGANISM: Artificial Sequence
<220> FEATURE:
<223> OTHER INFORMATION: N-terminal Fc fusion of DOM15-26-597 DAB
      ((TGLDSP)x3 T113P mutation Fc) amino acid sequence
      identified using molecular biology techniques.

<400> SEQUENCE: 157

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
            35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Thr Gly Leu Asp Ser Pro Thr Gly Leu Asp Ser Pro
            115                 120                 125

Thr Gly Leu Asp Ser Pro Thr His Pro Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175
```

-continued

```
Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355
```

<210> SEQ ID NO 158
<211> LENGTH: 365
<212> TYPE: PRT
<213> ORGANISM: Artificial Sequence
<220> FEATURE:
<223> OTHER INFORMATION: N-terminal Fc fusion of DOM15-26-597 DAB
    ((TGLDSP)x4 T113P mutation Fc) amino acid sequence
    identified using molecular biology techniques.

<400> SEQUENCE: 158

```
Glu Val Gln Leu Leu Val Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Thr Gly Leu Asp Ser Pro Thr Gly Leu Asp Ser Pro
        115                 120                 125

Thr Gly Leu Asp Ser Pro Thr Gly Leu Asp Ser Pro Thr His Pro Cys
    130                 135                 140

Pro Pro Cys Pro Ala Pro Glu Leu Leu Gly Gly Pro Ser Val Phe Leu
145                 150                 155                 160

Phe Pro Pro Lys Pro Lys Asp Thr Leu Met Ile Ser Arg Thr Pro Glu
```

```
                      165                 170                 175
Val Thr Cys Val Val Asp Val Ser His Glu Asp Pro Glu Val Lys
                180                 185                 190

Phe Asn Trp Tyr Val Asp Gly Val Glu Val His Asn Ala Lys Thr Lys
            195                 200                 205

Pro Arg Glu Glu Gln Tyr Asn Ser Thr Tyr Arg Val Val Ser Val Leu
        210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Leu Pro Pro Ser
            260                 265                 270

Arg Asp Glu Leu Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Lys
        355                 360                 365

<210> SEQ ID NO 159
<211> LENGTH: 349
<212> TYPE: PRT
<213> ORGANISM: Artificial Sequence
<220> FEATURE:
<223> OTHER INFORMATION: N-terminal Fc fusion of DOM15-26-597 DAB
      (IgG1 Hinge) amino acid sequence identified
      using molecular biology techniques.

<400> SEQUENCE: 159

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Val Glu Pro Lys Ser Ser Asp Lys Thr His Thr Cys
        115                 120                 125

Pro Pro Cys Pro Ala Pro Glu Leu Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160
```

```
Val Thr Cys Val Val Val Asp Val Ser His Glu Asp Pro Glu Val Lys
            165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
            195                 200                 205

Thr Val Leu His Gln Asp Trp Leu Asn Gly Lys Glu Tyr Lys Cys Lys
            210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
            245                 250                 255

Arg Asp Glu Leu Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
            275                 280                 285

Pro Glu Asn Asn Tyr Lys Thr Thr Pro Pro Val Leu Asp Ser Asp Gly
            290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
            325                 330                 335

His Tyr Thr Gln Lys Ser Leu Ser Leu Ser Pro Gly Lys
            340                 345

<210> SEQ ID NO 160
<211> LENGTH: 350
<212> TYPE: PRT
<213> ORGANISM: Artificial Sequence
<220> FEATURE:
<223> OTHER INFORMATION: N-terminal Fc fusion of 15-26-597 DAB (IgG3
      Hinge) amino acid sequence identified using
      molecular biology techniques.

<400> SEQUENCE: 160

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
            35                  40                  45

Ser Glu Ile Ser Pro Ser Gly Ser Asn Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Pro Arg Lys Leu Asp Tyr Trp Gly Gln Gly Thr Leu Val
            100                 105                 110

Thr Val Ser Ser Glu Leu Lys Thr Pro Leu Gly Asp Thr Thr His Thr
            115                 120                 125

Cys Pro Pro Cys Pro Ala Pro Glu Leu Leu Gly Gly Pro Ser Val Phe
            130                 135                 140

Leu Phe Pro Pro Lys Pro Lys Asp Thr Leu Met Ile Ser Arg Thr Pro
145                 150                 155                 160
```

```
Glu Val Thr Cys Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
                260                 265                 270

Lys Gly Phe Tyr Pro Ser Asp Ile Ala Val Glu Trp Glu Ser Asn Gly
            275                 280                 285

Gln Pro Glu Asn Asn Tyr Lys Thr Thr Pro Pro Val Leu Asp Ser Asp
        290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
                340                 345                 350

<210> SEQ ID NO 161
<211> LENGTH: 347
<212> TYPE: PRT
<213> ORGANISM: Artificial Sequence
<220> FEATURE:
<223> OTHER INFORMATION: N-terminal Fc fusion of 15-26-597 DAB (TVAAPS)
      amino acid sequence identified using
      molecular biology techniques.

<400> SEQUENCE: 161

Glu Val Gln Leu Leu Val Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
             20                  25                  30

Pro Met Met Trp Val Arg Gln Ala Pro Gly Lys Gly Leu Glu Trp Val
         35                  40                  45

Ser Glu Ile Ser Pro Ser Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Lys Asp Pro Arg Lys Leu Asp Tyr Trp Gly Gln Gly Thr Leu Val
            100                 105                 110

Thr Val Ser Ser Thr Val Ala Ala Pro Ser Thr His Thr Cys Pro Pro
        115                 120                 125

Cys Pro Ala Pro Glu Leu Leu Gly Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Lys Phe Asn
```

```
                165                 170                 175
Trp Tyr Val Asp Gly Val Glu Val His Asn Ala Lys Thr Lys Pro Arg
            180                 185                 190
Glu Glu Gln Tyr Asn Ser Thr Tyr Arg Val Val Ser Val Leu Thr Val
            195                 200                 205
Leu His Gln Asp Trp Leu Asn Gly Lys Glu Tyr Lys Cys Lys Val Ser
            210                 215                 220
Asn Lys Ala Leu Pro Ala Pro Ile Glu Lys Thr Ile Ser Lys Ala Lys
225                 230                 235                 240
Gly Gln Pro Arg Glu Pro Gln Val Tyr Thr Leu Pro Pro Ser Arg Asp
            245                 250                 255
Glu Leu Thr Lys Asn Gln Val Ser Leu Thr Cys Leu Val Lys Gly Phe
            260                 265                 270
Tyr Pro Ser Asp Ile Ala Val Glu Trp Glu Ser Asn Gly Gln Pro Glu
            275                 280                 285
Asn Asn Tyr Lys Thr Thr Pro Pro Val Leu Asp Ser Asp Gly Ser Phe
            290                 295                 300
Phe Leu Tyr Ser Lys Leu Thr Val Asp Lys Ser Arg Trp Gln Gln Gly
305                 310                 315                 320
Asn Val Phe Ser Cys Ser Val Met His Glu Ala Leu His Asn His Tyr
                325                 330                 335
Thr Gln Lys Ser Leu Ser Leu Ser Pro Gly Lys
            340                 345

<210> SEQ ID NO 162
<211> LENGTH: 357
<212> TYPE: PRT
<213> ORGANISM: Artificial Sequence
<220> FEATURE:
<223> OTHER INFORMATION: C-terminal Fc fusion of K-044-085 DAB
      ((TGLDSP)x4) amino acid sequence identified
      using molecular biology tech

```
Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Thr Gly Leu Asp Ser Pro Thr Gly Leu Asp Ser Pro Thr Gly Leu
225                 230                 235                 240

Asp Ser Pro Thr Gly Leu Asp Ser Pro Asp Ile Gln Met Thr Gln Ser
                245                 250                 255

Pro Ser Ser Leu Ser Ala Ser Val Gly Asp Arg Val Thr Ile Thr Cys
            260                 265                 270

Arg Ala Ser Gln Trp Ile Gly Pro Glu Leu Lys Trp Tyr Gln Gln Lys
        275                 280                 285

Pro Gly Lys Ala Pro Lys Leu Leu Ile Tyr His Gly Ser Ile Leu Gln
    290                 295                 300

Ser Gly Val Pro Ser Arg Phe Ser Gly Ser Gly Ser Gly Thr Asp Phe
305                 310                 315                 320

Thr Leu Thr Ile Ser Ser Leu Gln Pro Glu Asp Phe Ala Thr Tyr Tyr
                325                 330                 335

Cys Gln Gln Tyr Met Tyr Tyr Pro His Thr Phe Gly Gln Gly Thr Lys
            340                 345                 350

Val Glu Ile Lys Arg
        355

<210> SEQ ID NO 163
<211> LENGTH: 373
<212> TYPE: PRT
<213> ORGANISM: Artificial Sequence
<220> FEATURE:
<223> OTHER INFORMATION: C-terminal Fc fusion of K-044-085 DAB (Helical
      Linker) amino acid sequence identified
      using molecular biology techniques.

<400> SEQUENCE: 163

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160
```

Ser Asn Gly Gln Pro Glu Asn Asn Tyr Lys Thr Thr Pro Val Leu
          165                 170                 175

Asp Ser Asp Gly Ser Phe Phe Leu Tyr Ser Lys Leu Thr Val Asp Lys
    180                 185                 190

Ser Arg Trp Gln Gln Gly Asn Val Phe Ser Cys Ser Val Met His Glu
    195                 200                 205

Ala Leu His Asn His Tyr Thr Gln Lys Ser Leu Ser Leu Ser Pro Gly
    210                 215                 220

Lys Lys Glu Ala Ala Lys Glu Ala Ala Lys Glu Ala Ala
225                 230                 235                 240

Lys Glu Leu Ala Ala Lys Glu Ala Ala Lys Glu Ala Ala Lys
                245                 250                 255

Glu Ala Ala Lys Glu Leu Ala Ala Asp Ile Gln Met Thr Gln Ser
        260                 265                 270

Pro Ser Ser Leu Ser Ala Ser Val Gly Asp Arg Val Thr Ile Thr Cys
            275                 280                 285

Arg Ala Ser Gln Trp Ile Gly Pro Glu Leu Lys Trp Tyr Gln Gln Lys
    290                 295                 300

Pro Gly Lys Ala Pro Lys Leu Leu Ile Tyr His Gly Ser Ile Leu Gln
305                 310                 315                 320

Ser Gly Val Pro Ser Arg Phe Ser Gly Ser Gly Ser Gly Thr Asp Phe
            325                 330                 335

Thr Leu Thr Ile Ser Ser Leu Gln Pro Glu Asp Phe Ala Thr Tyr Tyr
                340                 345                 350

Cys Gln Gln Tyr Met Tyr Tyr Pro His Thr Phe Gly Gln Gly Thr Lys
            355                 360                 365

Val Glu Ile Lys Arg
    370

<210> SEQ ID NO 164
<211> LENGTH: 341
<212> TYPE: PRT
<213> ORGANISM: Artificial Sequence
<220> FEATURE:
<223> OTHER INFORMATION: N-terminal Fc fusion of K-044-085 DAB (IgG1
      Hinge) amino acid sequence identified
      using molecular biology techniques.

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro His
                85                  90                  95

Thr Phe Gly Gln Gly Thr Lys Val Glu Ile Lys Arg Val Glu Pro Lys
            100                 105                 110

Ser Ser Asp Lys Thr His Thr Cys Pro Pro Cys Pro Ala Pro Glu Leu
        115                 120                 125

Leu Gly Gly Pro Ser Val Phe Leu Phe Pro Pro Lys Pro Lys Asp Thr

```
                130                 135                 140
Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Ala Leu Pro Ala
    210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Asp Glu Leu Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
    290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys
            340

<210> SEQ ID NO 165
<211> LENGTH: 335
<212> TYPE: PRT
<213> ORGANISM: Artificial Sequence
<220> FEATURE:
<223> OTHER INFORMATION: N-terminal Fc fusion of K-044-085 DAB (ASTHP
      linker) amino acid sequence
      identified using molecular biology techniques.

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro His
                85                  90                  95

Thr Phe Gly Gln Gly Thr Lys Val Glu Ile Lys Arg Ala Ser Thr His
            100                 105                 110

Pro Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140
```

```
Pro Glu Val Thr Cys Val Val Asp Val Ser His Glu Asp Pro Glu
145                 150                 155                 160

Val Lys Phe Asn Trp Tyr Val Asp Gly Val Glu Val His Asn Ala Lys
            165                 170                 175

Thr Lys Pro Arg Glu Glu Gln Tyr Asn Ser Thr Tyr Arg Val Val Ser
        180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
        290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 166
<211> LENGTH: 357
<212> TYPE: PRT
<213> ORGANISM: Artificial Sequence
<220> FEATURE:
<223> OTHER INFORMATION: N-terminal Fc fusion of K-044-085 DAB
      ((TGLDSP)x4) amino acid sequence identified
      using molecular biology techniques.

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro His
                85                  90                  95

Thr Phe Gly Gln Gly Thr Lys Val Glu Ile Lys Arg Thr Gly Leu Asp
            100                 105                 110

Ser Pro Thr Gly Leu Asp Ser Pro Thr Gly Leu Asp Ser Pro Thr Gly
        115                 120                 125

Leu Asp Ser Pro Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160
```

Leu Met Ile Ser Arg Thr Pro Glu Val Thr Cys Val Val Val Asp Val
            165                 170                 175

Ser His Glu Asp Pro Glu Val Lys Phe Asn Trp Tyr Val Asp Gly Val
        180                 185                 190

Glu Val His Asn Ala Lys Thr Lys Pro Arg Glu Glu Gln Tyr Asn Ser
    195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 167
<211> LENGTH: 339
<212> TYPE: PRT
<213> ORGANISM: Artificial Sequence
<220> FEATURE:
<223> OTHER INFORMATION: N-terminal Fc fusion of K-044-085 DAB (TVAAPS)
      amino acid sequence identified
      using molecular biology techniques.

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro His
            85                  90                  95

Thr Phe Gly Gln Gly Thr Lys Val Glu Ile Lys Arg Thr Val Ala Ala
            100                 105                 110

Pro Ser Thr His Thr Cys Pro Pro Cys Pro Ala Pro Glu Leu Leu Gly
            115                 120                 125

Gly Pro Ser Val Phe Leu Phe Pro Pro Lys Pro Lys Asp Thr Leu Met
130                 135                 140

Ile Ser Arg Thr Pro Glu Val Thr Cys Val Val Val Asp Val Ser His

```
145                 150                 155                 160
Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
                180                 185                 190

Arg Val Val Ser Val Leu Thr Val Leu His Gln Asp Trp Leu Asn Gly
                195                 200                 205

Lys Glu Tyr Lys Cys Lys Val Ser Asn Lys Ala Leu Pro Ala Pro Ile
                210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Asp Glu Leu Thr Lys Asn Gln Val Ser
                245                 250                 255

Leu Thr Cys Leu Val Lys Gly Phe Tyr Pro Ser Asp Ile Ala Val Glu
                260                 265                 270

Trp Glu Ser Asn Gly Gln Pro Glu Asn Asn Tyr Lys Thr Thr Pro Pro
                275                 280                 285

Val Leu Asp Ser Asp Gly Ser Phe Phe Leu Tyr Ser Lys Leu Thr Val
                290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys
```

<210> SEQ ID NO 168
<211> LENGTH: 351
<212> TYPE: PRT
<213> ORGANISM: Artificial Sequence
<220> FEATURE:
<223> OTHER INFORMATION: N-terminal Fc fusion of K-044-085 DAB
      ((TGLDSP)x3) amino acid sequence identified
      using molecular biology techniques.

<400> SEQUENCE: 168

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
                20                  25                  30

Leu Lys Trp Tyr Gln Gln Lys Pro Gly Lys Ala Pro Lys Leu Leu Ile
            35                  40                  45

Tyr His Gly Ser Ile Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro His
                85                  90                  95

Thr Phe Gly Gln Gly Thr Lys Val Glu Ile Lys Arg Thr Gly Leu Asp
                100                 105                 110

Ser Pro Thr Gly Leu Asp Ser Pro Thr Gly Leu Asp Ser Pro Thr His
            115                 120                 125

Thr Cys Pro Pro Cys Pro Ala Pro Glu Leu Leu Gly Gly Pro Ser Val
        130                 135                 140

Phe Leu Phe Pro Pro Lys Pro Lys Asp Thr Leu Met Ile Ser Arg Thr
145                 150                 155                 160
```

```
Pro Glu Val Thr Cys Val Val Asp Val Ser His Glu Asp Pro Glu
            165                 170                 175

Val Lys Phe Asn Trp Tyr Val Asp Gly Val Glu Val His Asn Ala Lys
        180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
        210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Arg Asp Glu Leu Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Val Leu Asp Ser
        290                 295                 300

Asp Gly Ser Phe Phe Leu Tyr Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly Lys
            340                 345                 350

<210> SEQ ID NO 169
<211> LENGTH: 342
<212> TYPE: PRT
<213> ORGANISM: Artificial Sequence
<220> FEATURE:
<223> OTHER INFORMATION: N-terminal Fc fusion of K-044-085 DAB
      (IgG3 Hinge) amino acid sequence identified
      using molecular biology techniques.

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro His
                85                  90                  95

Thr Phe Gly Gln Gly Thr Lys Val Glu Ile Lys Arg Glu Leu Lys Thr
            100                 105                 110

Pro Leu Gly Asp Thr Thr His Thr Cys Pro Pro Cys Pro Ala Pro Glu
        115                 120                 125

Leu Leu Gly Gly Pro Ser Val Phe Leu Phe Pro Lys Pro Lys Asp
        130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
```

```
                      165                 170                 175
Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Asp Glu Leu Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 170
<211> LENGTH: 335
<212> TYPE: PRT
<213> ORGANISM: Artificial Sequence
<220> FEATURE:
<223> OTHER INFORMATION: N-terminal Fc fusion of K-044-085-AS-Fc
      (H112A) amino acid sequence identified
      using molecular biology techniques.

<400> SEQUENCE: 170

Asp Ile Gln Met Thr Gln Ser Pro Ser Ser Leu Ser Ala Ser Val Gly
 1                5                  10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro His
                85                  90                  95

Thr Phe Gly Gln Gly Thr Lys Val Glu Ile Lys Arg Ala Ser Thr Ala
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175
```

```
Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 171
<211> LENGTH: 351
<212> TYPE: PRT
<213> ORGANISM: Artificial Sequence
<220> FEATURE:
<223> OTHER INFORMATION: C-terminal Fc fusion of K-044-085 DAB
      ((TGLDSP)x3) amino acid sequence identified
      using molecular biology techniques.

<400> SEQUENCE: 171

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190
```

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Thr Gly Leu Asp Ser Pro Thr Gly Leu Asp Ser Pro Thr Gly Leu
225                 230                 235                 240

Asp Ser Pro Asp Ile Gln Met Thr Gln Ser Pro Ser Ser Leu Ser Ala
                245                 250                 255

Ser Val Gly Asp Arg Val Thr Ile Thr Cys Arg Ala Ser Gln Trp Ile
                260                 265                 270

Gly Pro Glu Leu Lys Trp Tyr Gln Gln Lys Pro Gly Lys Ala Pro Lys
            275                 280                 285

Leu Leu Ile Tyr His Gly Ser Ile Leu Gln Ser Gly Val Pro Ser Arg
        290                 295                 300

Phe Ser Gly Ser Gly Ser Gly Thr Asp Phe Thr Leu Thr Ile Ser Ser
305                 310                 315                 320

Leu Gln Pro Glu Asp Phe Ala Thr Tyr Tyr Cys Gln Gln Tyr Met Tyr
                325                 330                 335

Tyr Pro His Thr Phe Gly Gln Gly Thr Lys Val Glu Ile Lys Arg
            340                 345                 350

<210> SEQ ID NO 172
<211> LENGTH: 352
<212> TYPE: PRT
<213> ORGANISM: Artificial Sequence
<220> FEATURE:
<223> OTHER INFORMATION: C-terminal Fc fusion of K-044-085 DAB
      (Albumin Domain 1) amino acid sequence identified
      using molecular biology techniques.

<400> SEQUENCE: 172

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

```
                195                 200                 205
Ala Leu His Asn His Tyr Thr Gln Lys Ser Leu Ser Leu Ser Pro Gly
    210                 215                 220

Lys His Lys Asp Asp Asn Pro Asn Leu Pro Arg Leu Val Arg Pro Glu
225                 230                 235                 240

Val Asp Val Met Asp Ile Gln Met Thr Gln Ser Pro Ser Ser Leu Ser
                245                 250                 255

Ala Ser Val Gly Asp Arg Val Thr Ile Thr Cys Arg Ala Ser Gln Trp
            260                 265                 270

Ile Gly Pro Glu Leu Lys Trp Tyr Gln Gln Lys Pro Gly Lys Ala Pro
        275                 280                 285

Lys Leu Leu Ile Tyr His Gly Ser Ile Leu Gln Ser Gly Val Pro Ser
290                 295                 300

Arg Phe Ser Gly Ser Gly Ser Gly Thr Asp Phe Thr Leu Thr Ile Ser
305                 310                 315                 320

Ser Leu Gln Pro Glu Asp Phe Ala Thr Tyr Tyr Cys Gln Gln Tyr Met
                325                 330                 335

Tyr Tyr Pro His Thr Phe Gly Gln Gly Thr Lys Val Glu Ile Lys Arg
            340                 345                 350

<210> SEQ ID NO 173
<211> LENGTH: 354
<212> TYPE: PRT
<213> ORGANISM: Artificial Sequence
<220> FEATURE:
<223> OTHER INFORMATION: C-terminal Fc fusion of K-044-085 DAB
      (Albumin Domain 2) amino acid sequence identified
      using molecular biology techniques.

<400> SEQUENCE: 173

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205
```

Ala Leu His Asn His Tyr Thr Gln Lys Ser Leu Ser Leu Ser Pro Gly
    210                 215                 220

Lys Glu Asn Asp Glu Met Pro Ala Asp Leu Pro Ser Leu Ala Ala Asp
225                 230                 235                 240

Phe Val Glu Ser Lys Asp Asp Ile Gln Met Thr Gln Ser Pro Ser Ser
            245                 250                 255

Leu Ser Ala Ser Val Gly Asp Arg Val Thr Ile Thr Cys Arg Ala Ser
            260                 265                 270

Gln Trp Ile Gly Pro Glu Leu Lys Trp Tyr Gln Gln Lys Pro Gly Lys
        275                 280                 285

Ala Pro Lys Leu Leu Ile Tyr His Gly Ser Ile Leu Gln Ser Gly Val
    290                 295                 300

Pro Ser Arg Phe Ser Gly Ser Gly Ser Gly Thr Asp Phe Thr Leu Thr
305                 310                 315                 320

Ile Ser Ser Leu Gln Pro Glu Asp Phe Ala Thr Tyr Tyr Cys Gln Gln
            325                 330                 335

Tyr Met Tyr Tyr Pro His Thr Phe Gly Gln Gly Thr Lys Val Glu Ile
            340                 345                 350

Lys Arg

<210> SEQ ID NO 174
<211> LENGTH: 349
<212> TYPE: PRT
<213> ORGANISM: Artificial Sequence
<220> FEATURE:
<223> OTHER INFORMATION: C-terminal Fc fusion of K-044-085 DAB
      (Albumin Domain 3-TFHAD) amino acid sequence identified
      using molecular biology techniques.

<400> SEQUENCE: 174

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
        100                 105                 110

Thr Ile Ser Lys Ala Lys Gly Gln Pro Arg Glu Pro Gln Val Tyr Thr
    115                 120                 125

Leu Pro Pro Ser Arg Asp Glu Leu Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Ser Phe Phe Leu Tyr Ser Lys Leu Thr Val Asp Lys
        180                 185                 190

Ser Arg Trp Gln Gln Gly Asn Val Phe Ser Cys Ser Val Met His Glu

```
            195                 200                 205
Ala Leu His Asn His Tyr Thr Gln Lys Ser Leu Ser Leu Ser Pro Gly
    210                 215                 220

Lys Glu Val Asp Glu Thr Tyr Val Pro Lys Glu Phe Asn Ala Glu Thr
225                 230                 235                 240

Phe Asp Ile Gln Met Thr Gln Ser Pro Ser Ser Leu Ser Ala Ser Val
                245                 250                 255

Gly Asp Arg Val Thr Ile Thr Cys Arg Ala Ser Gln Trp Ile Gly Pro
            260                 265                 270

Glu Leu Lys Trp Tyr Gln Gln Lys Pro Gly Lys Ala Pro Lys Leu Leu
        275                 280                 285

Ile Tyr His Gly Ser Ile Leu Gln Ser Gly Val Pro Ser Arg Phe Ser
    290                 295                 300

Gly Ser Gly Ser Gly Thr Asp Phe Thr Leu Thr Ile Ser Ser Leu Gln
305                 310                 315                 320

Pro Glu Asp Phe Ala Thr Tyr Tyr Cys Gln Gln Tyr Met Tyr Tyr Pro
                325                 330                 335

His Thr Phe Gly Gln Gly Thr Lys Val Glu Ile Lys Arg
            340                 345
```

<210> SEQ ID NO 175
<211> LENGTH: 348
<212> TYPE: PRT
<213> ORGANISM: Artificial Sequence
<220> FEATURE:
<223> OTHER INFORMATION: C-terminal Fc fusion of K-044-085 DAB
      ((Gly4Ser)x3) amino acid sequence identified
      using molecular biology techniques.

<400> SEQUENCE: 175

```
Thr His Thr Cys Pro Pro Cys Pro Ala Pro Glu Leu Leu Gly Gly Pro
  1               5                  10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205
```

Ala Leu His Asn His Tyr Thr Gln Lys Ser Leu Ser Leu Ser Pro Gly
    210                 215                 220

Lys Gly Gly Gly Gly Ser Gly Gly Gly Gly Ser Gly Gly Gly Gly Ser
225                 230                 235                 240

Asp Ile Gln Met Thr Gln Ser Pro Ser Ser Leu Ser Ala Ser Val Gly
                245                 250                 255

Asp Arg Val Thr Ile Thr Cys Arg Ala Ser Gln Trp Ile Gly Pro Glu
            260                 265                 270

Leu Lys Trp Tyr Gln Gln Lys Pro Gly Lys Ala Pro Lys Leu Leu Ile
        275                 280                 285

Tyr His Gly Ser Ile Leu Gln Ser Gly Val Pro Ser Arg Phe Ser Gly
    290                 295                 300

Ser Gly Ser Gly Thr Asp Phe Thr Leu Thr Ile Ser Ser Leu Gln Pro
305                 310                 315                 320

Glu Asp Phe Ala Thr Tyr Tyr Cys Gln Gln Tyr Met Tyr Tyr Pro His
                325                 330                 335

Thr Phe Gly Gln Gly Thr Lys Val Glu Ile Lys Arg
            340                 345

<210> SEQ ID NO 176
<211> LENGTH: 353
<212> TYPE: PRT
<213> ORGANISM: Artificial Sequence
<220> FEATURE:
<223> OTHER INFORMATION: C-terminal Fc fusion of K-044-085 DAB
      ((Gly4Ser)x4) amino acid sequence identified
      using molecular biology techniques.

<400> SEQUENCE: 176

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

```
Ala Leu His Asn His Tyr Thr Gln Lys Ser Leu Ser Leu Ser Pro Gly
    210                 215                 220

Lys Gly Gly Gly Ser Gly Gly Gly Ser Gly Gly Gly Gly Ser
225                 230                 235                 240

Gly Gly Gly Gly Ser Asp Ile Gln Met Thr Gln Ser Pro Ser Ser Leu
                245                 250                 255

Ser Ala Ser Val Gly Asp Arg Val Thr Ile Thr Cys Arg Ala Ser Gln
            260                 265                 270

Trp Ile Gly Pro Glu Leu Lys Trp Tyr Gln Gln Lys Pro Gly Lys Ala
        275                 280                 285

Pro Lys Leu Leu Ile Tyr His Gly Ser Ile Leu Gln Ser Gly Val Pro
    290                 295                 300

Ser Arg Phe Ser Gly Ser Gly Ser Gly Thr Asp Phe Thr Leu Thr Ile
305                 310                 315                 320

Ser Ser Leu Gln Pro Glu Asp Phe Ala Thr Tyr Tyr Cys Gln Gln Tyr
                325                 330                 335

Met Tyr Tyr Pro His Thr Phe Gly Gln Gly Thr Lys Val Glu Ile Lys
            340                 345                 350

Arg

<210> SEQ ID NO 177
<211> LENGTH: 473
<212> TYPE: PRT
<213> ORGANISM: Artificial Sequence
<220> FEATURE:
<223> OTHER INFORMATION: K-044-085 DAB N-(VEPKSSDK linker) & C-terminal
      ((TGLDSP)x4) amino acid sequence identified
      using molecular biology techniques.

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Tyr Pro His
                85                  90                  95

Thr Phe Gly Gln Gly Thr Lys Val Glu Ile Lys Arg Val Glu Pro Lys
            100                 105                 110

Ser Ser Asp Lys Thr His Thr Cys Pro Pro Cys Pro Ala Pro Glu Leu
        115                 120                 125

Leu Gly Gly Pro Ser Val Phe Leu Phe Pro Pro Lys Pro Lys Asp Thr
    130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
        195                 200                 205
```

-continued

```
Asn Gly Lys Glu Tyr Lys Cys Lys Val Ser Asn Lys Ala Leu Pro Ala
            210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Asp Glu Leu Thr Lys Asn Gln
                245                 250                 255

Val Ser Leu Thr Cys Leu Val Lys Gly Phe Tyr Pro Ser Asp Ile Ala
                260                 265                 270

Val Glu Trp Glu Ser Asn Gly Gln Pro Glu Asn Asn Tyr Lys Thr Thr
            275                 280                 285

Pro Pro Val Leu Asp Ser Asp Gly Ser Phe Phe Leu Tyr Ser Lys Leu
290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys Thr Gly Leu Asp Ser Pro Thr Gly Leu Asp Ser
                340                 345                 350

Pro Thr Gly Leu Asp Ser Pro Thr Gly Leu Asp Ser Pro Asp Ile Gln
            355                 360                 365

Met Thr Gln Ser Pro Ser Ser Leu Ser Ala Ser Val Gly Asp Arg Val
370                 375                 380

Thr Ile Thr Cys Arg Ala Ser Gln Trp Ile Gly Pro Glu Leu Lys Trp
385                 390                 395                 400

Tyr Gln Gln Lys Pro Gly Lys Ala Pro Lys Leu Leu Ile Tyr His Gly
                405                 410                 415

Ser Ile Leu Gln Ser Gly Val Pro Ser Arg Phe Ser Gly Ser Gly Ser
                420                 425                 430

Gly Thr Asp Phe Thr Leu Thr Ile Ser Ser Leu Gln Pro Glu Asp Phe
            435                 440                 445

Ala Thr Tyr Tyr Cys Gln Gln Tyr Met Tyr Tyr Pro His Thr Phe Gly
        450                 455                 460

Gln Gly Thr Lys Val Glu Ile Lys Arg
465                 470

<210> SEQ ID NO 178
<211> LENGTH: 467
<212> TYPE: PRT
<213> ORGANISM: Artificial Sequence
<220> FEATURE:
<223> OTHER INFORMATION: K-044-085 DAB N-(ASTHP linker) & C-terminal
      ((TGLDSP)x4) amino acid sequence identified
      using molecular biology techniques.

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Lys Trp Tyr Gln Gln Lys Pro Gly Lys Ala Pro Lys Leu Leu Ile
        35                  40                  45

Tyr His Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Met Tyr Tyr Pro His
                 85                  90                  95

Thr Phe Gly Gln Gly Thr Lys Val Glu Ile Lys Arg Ala Ser Thr His
            100                 105                 110

Pro Cys Pro Pro Cys Pro Ala Pro Glu Leu Leu Gly Gly Pro Ser Val
            115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
            195                 200                 205

Cys Lys Val Ser Asn Lys Ala Leu Pro Ala Pro Ile Glu Lys Thr Ile
            210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
            275                 280                 285

Asp Gly Ser Phe Phe Leu Tyr Ser Lys Leu Thr Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys Thr
                325                 330                 335

Gly Leu Asp Ser Pro Thr Gly Leu Asp Ser Pro Thr Gly Leu Asp Ser
            340                 345                 350

Pro Thr Gly Leu Asp Ser Pro Asp Ile Gln Met Thr Gln Ser Pro Ser
            355                 360                 365

Ser Leu Ser Ala Ser Val Gly Asp Arg Val Thr Ile Thr Cys Arg Ala
            370                 375                 380

Ser Gln Trp Ile Gly Pro Glu Leu Lys Trp Tyr Gln Gln Lys Pro Gly
385                 390                 395                 400

Lys Ala Pro Lys Leu Leu Ile Tyr His Gly Ser Ile Leu Gln Ser Gly
                405                 410                 415

Val Pro Ser Arg Phe Ser Gly Ser Gly Ser Gly Thr Asp Phe Thr Leu
            420                 425                 430

Thr Ile Ser Ser Leu Gln Pro Glu Asp Phe Ala Thr Tyr Tyr Cys Gln
            435                 440                 445

Gln Tyr Met Tyr Tyr Pro His Thr Phe Gly Gln Gly Thr Lys Val Glu
    450                 455                 460

Ile Lys Arg
465

<210> SEQ ID NO 179
<211> LENGTH: 491
<212> TYPE: PRT
```

<213> ORGANISM: Artificial Sequence
<220> FEATURE:
<223> OTHER INFORMATION: DOM15-26-597 DAB N-((TGLDSP)x3) & C-terminal
K-044-085 DAB ((TGLDSP)x4) amino acid sequence
identified using molecular biology techniques.

<400> SEQUENCE: 179

```
Glu Val Gln Leu Leu Val Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
             20                  25                  30

Pro Met Met Trp Val Arg Gln Ala Pro Gly Lys Gly Leu Glu Trp Val
         35                  40                  45

Ser Glu Ile Ser Pro Ser Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Lys Leu Asp Tyr Trp Gly Gln Gly Thr Leu Val
            100                 105                 110

Thr Val Ser Ser Thr Gly Leu Asp Ser Pro Thr Gly Leu Asp Ser Pro
        115                 120                 125

Thr Gly Leu Asp Ser Pro Thr His Thr Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Thr Gly Leu Asp Ser Pro Thr Gly Leu
        355                 360                 365

Asp Ser Pro Thr Gly Leu Asp Ser Pro Thr Gly Leu Asp Ser Pro Asp
370                 375                 380
```

```
Ile Gln Met Thr Gln Ser Pro Ser Leu Ser Ala Ser Val Gly Asp
385                 390                 395                 400

Arg Val Thr Ile Thr Cys Arg Ala Ser Gln Trp Ile Gly Pro Glu Leu
                405                 410                 415

Lys Trp Tyr Gln Gln Lys Pro Gly Lys Ala Pro Lys Leu Leu Ile Tyr
            420                 425                 430

His Gly Ser Ile Leu Gln Ser Gly Val Pro Ser Arg Phe Ser Gly Ser
            435                 440                 445

Gly Ser Gly Thr Asp Phe Thr Leu Thr Ile Ser Ser Leu Gln Pro Glu
        450                 455                 460

Asp Phe Ala Thr Tyr Tyr Cys Gln Gln Tyr Met Tyr Tyr Pro His Thr
465                 470                 475                 480

Phe Gly Gln Gly Thr Lys Val Glu Ile Lys Arg
                485                 490

<210> SEQ ID NO 180
<211> LENGTH: 481
<212> TYPE: PRT
<213> ORGANISM: Artificial Sequence
<220> FEATURE:
<223> OTHER INFORMATION: DOM15-26-597 DAB N-(VEPKSSDK linker) &
      C-terminal K-044-085 DAB ((TGLDSP)x4) amino acid sequence
      identified using molecular biology techniques.

<400> SEQUENCE: 180

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
            35                  40                  45

Ser Glu Ile Ser Pro Ser Gly Ser Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Val Glu Pro Lys Ser Ser Asp Lys Thr His Thr Cys
            115                 120                 125

Pro Pro Cys Pro Ala Pro Glu Leu Leu Gly Gly Pro Ser Val Phe Leu
130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
            195                 200                 205

Thr Val Leu His Gln Asp Trp Leu Asn Gly Lys Glu Tyr Lys Cys Lys
        210                 215                 220

Val Ser Asn Lys Ala Leu Pro Ala Pro Ile Glu Lys Thr Ile Ser Lys
225                 230                 235                 240
```

```
Ala Lys Gly Gln Pro Arg Glu Pro Gln Val Tyr Thr Leu Pro Pro Ser
                245                 250                 255

Arg Asp Glu Leu Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys Thr Gly Leu
            340                 345                 350

Asp Ser Pro Thr Gly Leu Asp Ser Pro Thr Gly Leu Asp Ser Pro Thr
        355                 360                 365

Gly Leu Asp Ser Pro Asp Ile Gln Met Thr Gln Ser Pro Ser Ser Leu
    370                 375                 380

Ser Ala Ser Val Gly Asp Arg Val Thr Ile Thr Cys Arg Ala Ser Gln
385                 390                 395                 400

Trp Ile Gly Pro Glu Leu Lys Trp Tyr Gln Gln Lys Pro Gly Lys Ala
                405                 410                 415

Pro Lys Leu Leu Ile Tyr His Gly Ser Ile Leu Gln Ser Gly Val Pro
            420                 425                 430

Ser Arg Phe Ser Gly Ser Gly Ser Gly Thr Asp Phe Thr Leu Thr Ile
        435                 440                 445

Ser Ser Leu Gln Pro Glu Asp Phe Ala Thr Tyr Tyr Cys Gln Gln Tyr
    450                 455                 460

Met Tyr Tyr Pro His Thr Phe Gly Gln Gly Thr Lys Val Glu Ile Lys
465                 470                 475                 480

Arg

<210> SEQ ID NO 181
<211> LENGTH: 475
<212> TYPE: PRT
<213> ORGANISM: Artificial Sequence
<220> FEATURE:
<223> OTHER INFORMATION: DMS1576 with C-terminal K-044-085 DAB
      ((TGLDSP)x4) amino acid sequence identified using
      molecular biology techniques.

<400> SEQUENCE: 181

Glu Val Gln Leu Leu Val Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
                20                  25                  30

Pro Met Met Trp Val Arg Gln Ala Pro Gly Lys Gly Leu Glu Trp Val
            35                  40                  45

Ser Glu Ile Ser Pro Ser Gly Ser Asn Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110
```

```
Thr Val Ser Ser Ala Ser Thr His Thr Cys Pro Pro Cys Pro Ala Pro
        115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys Thr Gly Leu Asp Ser Pro Thr Gly Leu
            340                 345                 350

Asp Ser Pro Thr Gly Leu Asp Ser Pro Thr Gly Leu Asp Ser Pro Asp
        355                 360                 365

Ile Gln Met Thr Gln Ser Pro Ser Ser Leu Ser Ala Ser Val Gly Asp
    370                 375                 380

Arg Val Thr Ile Thr Cys Arg Ala Ser Gln Trp Ile Gly Pro Glu Leu
385                 390                 395                 400

Lys Trp Tyr Gln Gln Lys Pro Gly Lys Ala Pro Lys Leu Leu Ile Tyr
                405                 410                 415

His Gly Ser Ile Leu Gln Ser Gly Val Pro Ser Arg Phe Ser Gly Ser
            420                 425                 430

Gly Ser Gly Thr Asp Phe Thr Leu Thr Ile Ser Ser Leu Gln Pro Glu
        435                 440                 445

Asp Phe Ala Thr Tyr Tyr Cys Gln Gln Tyr Met Tyr Tyr Pro His Thr
    450                 455                 460

Phe Gly Gln Gly Thr Lys Val Glu Ile Lys Arg
465                 470                 475

<210> SEQ ID NO 182
<211> LENGTH: 497
<212> TYPE: PRT
<213> ORGANISM: Artificial Sequence
<220> FEATURE:
<223> OTHER INFORMATION: DOM15-26-597 DAB N-((TGLDSP)x4) & C-terminal
      K-044-085 DAB ((TGLDSP)x4) amino acid sequence
      identified using molecular biology techniques.
```

<400> SEQUENCE: 182

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Thr Gly Leu Asp Ser Pro Thr Gly Leu Asp Ser Pro
        115                 120                 125

Thr Gly Leu Asp Ser Pro Thr Gly Leu Asp Ser Pro Thr His Thr Cys
130                 135                 140

Pro Pro Cys Pro Ala Pro Glu Leu Leu Gly Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Asn Ser Thr Tyr Arg Val Val Ser Val Leu
    210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Leu Pro Pro Ser
            260                 265                 270

Arg Asp Glu Leu Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
    290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Lys Thr Gly Leu
        355                 360                 365

Asp Ser Pro Thr Gly Leu Asp Ser Pro Thr Gly Leu Asp Ser Pro Thr
    370                 375                 380

Gly Leu Asp Ser Pro Asp Ile Gln Met Thr Gln Ser Pro Ser Ser Leu
385                 390                 395                 400

Ser Ala Ser Val Gly Asp Arg Val Thr Ile Thr Cys Arg Ala Ser Gln

```
                      405                 410                 415
Trp Ile Gly Pro Glu Leu Lys Trp Tyr Gln Gln Lys Pro Gly Lys Ala
                420                 425                 430

Pro Lys Leu Leu Ile Tyr His Gly Ser Ile Leu Gln Ser Gly Val Pro
            435                 440                 445

Ser Arg Phe Ser Gly Ser Gly Ser Gly Thr Asp Phe Thr Leu Thr Ile
        450                 455                 460

Ser Ser Leu Gln Pro Glu Asp Phe Ala Thr Tyr Tyr Cys Gln Gln Tyr
465                 470                 475                 480

Met Tyr Tyr Pro His Thr Phe Gly Gln Gly Thr Lys Val Glu Ile Lys
                485                 490                 495

Arg

<210> SEQ ID NO 183
<211> LENGTH: 491
<212> TYPE: PRT
<213> ORGANISM: Artificial Sequence
<220> FEATURE:
<223> OTHER INFORMATION: DOM15-26-597 DAB N-((TGLDSP)x3 T113P mutation
      Fc) & C-terminal K-044-085 DAB ((TGLDSP)x4) amino acid
      sequence identified using molecular biology techniques.

<400> SEQUENCE: 183

Glu Val Gln Leu Leu Val Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
             20                  25                  30

Pro Met Met Trp Val Arg Gln Ala Pro Gly Lys Gly Leu Glu Trp Val
         35                  40                  45

Ser Glu Ile Ser Pro Ser Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Asp Pro Arg Lys Leu Asp Tyr Trp Gly Gln Gly Thr Leu Val
            100                 105                 110

Thr Val Ser Ser Thr Gly Leu Asp Ser Pro Thr Gly Leu Asp Ser Pro
        115                 120                 125

Thr Gly Leu Asp Ser Pro Thr His Pro Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255
```

Glu Pro Gln Val Tyr Thr Leu Pro Pro Ser Arg Asp Glu Leu Thr Lys
                260                 265                 270

Asn Gln Val Ser Leu Thr Cys Leu Val Lys Gly Phe Tyr Pro Ser Asp
            275                 280                 285

Ile Ala Val Glu Trp Glu Ser Asn Gly Gln Pro Glu Asn Asn Tyr Lys
        290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Thr Gly Leu Asp Ser Pro Thr Gly Leu
        355                 360                 365

Asp Ser Pro Thr Gly Leu Asp Ser Pro Thr Gly Leu Asp Ser Pro Asp
370                 375                 380

Ile Gln Met Thr Gln Ser Pro Ser Ser Leu Ser Ala Ser Val Gly Asp
385                 390                 395                 400

Arg Val Thr Ile Thr Cys Arg Ala Ser Gln Trp Ile Gly Pro Glu Leu
                405                 410                 415

Lys Trp Tyr Gln Gln Lys Pro Gly Lys Ala Pro Lys Leu Leu Ile Tyr
            420                 425                 430

His Gly Ser Ile Leu Gln Ser Gly Val Pro Ser Arg Phe Ser Gly Ser
        435                 440                 445

Gly Ser Gly Thr Asp Phe Thr Leu Thr Ile Ser Ser Leu Gln Pro Glu
450                 455                 460

Asp Phe Ala Thr Tyr Tyr Cys Gln Gln Tyr Met Tyr Tyr Pro His Thr
465                 470                 475                 480

Phe Gly Gln Gly Thr Lys Val Glu Ile Lys Arg
                485                 490

<210> SEQ ID NO 184
<211> LENGTH: 497
<212> TYPE: PRT
<213> ORGANISM: Artificial Sequence
<220> FEATURE:
<223> OTHER INFORMATION: DOM15-26-597 DAB N-((TGLDSP)x4 T113P mutation
      Fc) & C-terminal K-044-085 DAB ((TGLDSP)x4) amino acid
      sequence identified using molecular biology techniques.

<400> SEQUENCE: 184

Glu Val Gln Leu Leu Val Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
                20                  25                  30

Pro Met Met Trp Val Arg Gln Ala Pro Gly Lys Gly Leu Glu Trp Val
            35                  40                  45

Ser Glu Ile Ser Pro Ser Gly Ser Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Thr Gly Leu Asp Ser Pro Thr Gly Leu Asp Ser Pro

```
                    115                 120                 125
Thr Gly Leu Asp Ser Pro Thr Gly Leu Asp Ser Pro Thr His Pro Cys
        130                 135                 140
Pro Pro Cys Pro Ala Pro Glu Leu Leu Gly Gly Pro Ser Val Phe Leu
145                 150                 155                 160
Phe Pro Pro Lys Pro Lys Asp Thr Leu Met Ile Ser Arg Thr Pro Glu
                165                 170                 175
Val Thr Cys Val Val Val Asp Val Ser His Glu Asp Pro Glu Val Lys
            180                 185                 190
Phe Asn Trp Tyr Val Asp Gly Val Glu Val His Asn Ala Lys Thr Lys
                195                 200                 205
Pro Arg Glu Glu Gln Tyr Asn Ser Thr Tyr Arg Val Val Ser Val Leu
        210                 215                 220
Thr Val Leu His Gln Asp Trp Leu Asn Gly Lys Glu Tyr Lys Cys Lys
225                 230                 235                 240
Val Ser Asn Lys Ala Leu Pro Ala Pro Ile Glu Lys Thr Ile Ser Lys
                245                 250                 255
Ala Lys Gly Gln Pro Arg Glu Pro Gln Val Tyr Thr Leu Pro Pro Ser
            260                 265                 270
Arg Asp Glu Leu Thr Lys Asn Gln Val Ser Leu Thr Cys Leu Val Lys
                275                 280                 285
Gly Phe Tyr Pro Ser Asp Ile Ala Val Glu Trp Glu Ser Asn Gly Gln
        290                 295                 300
Pro Glu Asn Asn Tyr Lys Thr Thr Pro Pro Val Leu Asp Ser Asp Gly
305                 310                 315                 320
Ser Phe Phe Leu Tyr Ser Lys Leu Thr Val Asp Lys Ser Arg Trp Gln
                325                 330                 335
Gln Gly Asn Val Phe Ser Cys Ser Val Met His Glu Ala Leu His Asn
            340                 345                 350
His Tyr Thr Gln Lys Ser Leu Ser Leu Ser Pro Gly Lys Thr Gly Leu
                355                 360                 365
Asp Ser Pro Thr Gly Leu Asp Ser Pro Thr Gly Leu Asp Ser Pro Thr
        370                 375                 380
Gly Leu Asp Ser Pro Asp Ile Gln Met Thr Gln Ser Pro Ser Ser Leu
385                 390                 395                 400
Ser Ala Ser Val Gly Asp Arg Val Thr Ile Thr Cys Arg Ala Ser Gln
                405                 410                 415
Trp Ile Gly Pro Glu Leu Lys Trp Tyr Gln Gln Lys Pro Gly Lys Ala
            420                 425                 430
Pro Lys Leu Leu Ile Tyr His Gly Ser Ile Leu Gln Ser Gly Val Pro
                435                 440                 445
Ser Arg Phe Ser Gly Ser Gly Ser Gly Thr Asp Phe Thr Leu Thr Ile
        450                 455                 460
Ser Ser Leu Gln Pro Glu Asp Phe Ala Thr Tyr Tyr Cys Gln Gln Tyr
465                 470                 475                 480
Met Tyr Pro His Thr Phe Gly Gln Gly Thr Lys Val Glu Ile Lys
                485                 490                 495
Arg

<210> SEQ ID NO 185
<211> LENGTH: 480
<212> TYPE: PRT
<213> ORGANISM: Artificial Sequence
<220> FEATURE:
```

<223> OTHER INFORMATION: DOM15-26-597 DAB N-(VEPKSSDK linker) &
C-terminal K-044-085 DAB minus C-term R ((TGLDSP)x4) Codon
optimised amino acid sequence identified
using molecular biology techniques.

<400> SEQUENCE: 185

```
Glu Val Gln Leu Leu Val Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro

```
Ser Ala Ser Val Gly Asp Arg Val Thr Ile Thr Cys Arg Ala Ser Gln
385                 390                 395                 400

Trp Ile Gly Pro Glu Leu Lys Trp Tyr Gln Gln Lys Pro Gly Lys Ala
                405                 410                 415

Pro Lys Leu Leu Ile Tyr His Gly Ser Ile Leu Gln Ser Gly Val Pro
                420                 425                 430

Ser Arg Phe Ser Gly Ser Gly Ser Gly Thr Asp Phe Thr Leu Thr Ile
            435                 440                 445

Ser Ser Leu Gln Pro Glu Asp Phe Ala Thr Tyr Tyr Cys Gln Gln Tyr
        450                 455                 460

Met Tyr Tyr Pro His Thr Phe Gly Gln Gly Thr Lys Val Glu Ile Lys
465                 470                 475                 480

<210> SEQ ID NO 186
<211> LENGTH: 482
<212> TYPE: PRT
<213> ORGANISM: Artificial Sequence
<220> FEATURE:
<223> OTHER INFORMATION: DOM15-26-597 DAB N-(VEPKSSDK linker) &
      C-terminal K-044-085 DAB + A ((TGLDSP)x4) Codon optimised
      amino acid sequence identified
      using molecular biology techniques.

<400> SEQUENCE: 186

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
            35                  40                  45

Ser Glu Ile Ser Pro Ser Gly Ser Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Val Glu Pro Lys Ser Ser Asp Lys Thr His Thr Cys
        115                 120                 125

Pro Pro Cys Pro Ala Pro Glu Leu Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255
```

-continued

```
Arg Asp Glu Leu Thr Lys Asn Gln Val Ser Leu Thr Cys Leu Val Lys
            260                 265                 270
Gly Phe Tyr Pro Ser Asp Ile Ala Val Glu Trp Glu Ser Asn Gly Gln
        275                 280                 285
Pro Glu Asn Asn Tyr Lys Thr Thr Pro Pro Val Leu Asp Ser Asp Gly
    290                 295                 300
Ser Phe Phe Leu Tyr Ser Lys Leu Thr Val Asp Lys Ser Arg Trp Gln
305                 310                 315                 320
Gln Gly Asn Val Phe Ser Cys Ser Val Met His Glu Ala Leu His Asn
                325                 330                 335
His Tyr Thr Gln Lys Ser Leu Ser Leu Ser Pro Gly Lys Thr Gly Leu
            340                 345                 350
Asp Ser Pro Thr Gly Leu Asp Ser Pro Thr Gly Leu Asp Ser Pro Thr
        355                 360                 365
Gly Leu Asp Ser Pro Asp Ile Gln Met Thr Gln Ser Pro Ser Ser Leu
    370                 375                 380
Ser Ala Ser Val Gly Asp Arg Val Thr Ile Thr Cys Arg Ala Ser Gln
385                 390                 395                 400
Trp Ile Gly Pro Glu Leu Lys Trp Tyr Gln Gln Lys Pro Gly Lys Ala
                405                 410                 415
Pro Lys Leu Leu Ile Tyr His Gly Ser Ile Leu Gln Ser Gly Val Pro
            420                 425                 430
Ser Arg Phe Ser Gly Ser Gly Ser Gly Thr Asp Phe Thr Leu Thr Ile
        435                 440                 445
Ser Ser Leu Gln Pro Glu Asp Phe Ala Thr Tyr Tyr Cys Gln Gln Tyr
    450                 455                 460
Met Tyr Tyr Pro His Thr Phe Gly Gln Gly Thr Lys Val Glu Ile Lys
465                 470                 475                 480
Arg Ala

<210> SEQ ID NO 187
<211> LENGTH: 484
<212> TYPE: PRT
<213> ORGANISM: Artificial Sequence
<220> FEATURE:
<223> OTHER INFORMATION: DOM15-26-597 DAB N-(VEPKSSDK linker) &
      C-terminal K-044-085 DAB +AAA ((TGLDSP)x4) Codon optimised
      amino acid sequence identified
      using molecular biology techniques.

<400> SEQUENCE: 187

Glu Val Gln Leu Leu Val Ser Gly Gly Gly Leu Val Gln Pro Gly Gly
  1               5                  10                  15
Ser Leu Arg Leu Ser Cys Ala Ala Ser Gly Phe Thr Phe Lys Ala Tyr
             20                  25                  30
Pro Met Met Trp Val Arg Gln Ala Pro Gly Lys Gly Leu Glu Trp Val
         35                  40                  45
Ser Glu Ile Ser Pro Ser Gly Asn Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Pro Arg Lys Leu Asp Tyr Trp Gly Gln Gly Thr Leu Val
            100                 105                 110
Thr Val Ser Ser Val Glu Pro Lys Ser Ser Asp Lys Thr His Thr Cys
```

```
                115                 120                 125
Pro Pro Cys Pro Ala Pro Glu Leu Leu Gly Gly Pro Ser Val Phe Leu
130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
                180                 185                 190

Pro Arg Glu Glu Gln Tyr Asn Ser Thr Tyr Arg Val Val Ser Val Leu
                195                 200                 205

Thr Val Leu His Gln Asp Trp Leu Asn Gly Lys Glu Tyr Lys Cys Lys
                210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Asp Glu Leu Thr Lys Asn Gln Val Ser Leu Thr Cys Leu Val Lys
                260                 265                 270

Gly Phe Tyr Pro Ser Asp Ile Ala Val Glu Trp Glu Ser Asn Gly Gln
                275                 280                 285

Pro Glu Asn Asn Tyr Lys Thr Thr Pro Pro Val Leu Asp Ser Asp Gly
290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys Thr Gly Leu
                340                 345                 350

Asp Ser Pro Thr Gly Leu Asp Ser Pro Thr Gly Leu Asp Ser Pro Thr
                355                 360                 365

Gly Leu Asp Ser Pro Asp Ile Gln Met Thr Gln Ser Pro Ser Ser Leu
370                 375                 380

Ser Ala Ser Val Gly Asp Arg Val Thr Ile Thr Cys Arg Ala Ser Gln
385                 390                 395                 400

Trp Ile Gly Pro Glu Leu Lys Trp Tyr Gln Gln Lys Pro Gly Lys Ala
                405                 410                 415

Pro Lys Leu Leu Ile Tyr His Gly Ser Ile Leu Gln Ser Gly Val Pro
                420                 425                 430

Ser Arg Phe Ser Gly Ser Gly Ser Gly Thr Asp Phe Thr Leu Thr Ile
                435                 440                 445

Ser Ser Leu Gln Pro Glu Asp Phe Ala Thr Tyr Tyr Cys Gln Gln Tyr
                450                 455                 460

Met Tyr Tyr Pro His Thr Phe Gly Gln Gly Thr Lys Val Glu Ile Lys
465                 470                 475                 480

Arg Ala Ala Ala

<210> SEQ ID NO 188
<211> LENGTH: 482
<212> TYPE: PRT
<213> ORGANISM: Artificial Sequence
<220> FEATURE:
<223> OTHER INFORMATION: DOM15-26-597 DAB N-(VEPKSSDK linker) &
      C-terminal K-044-085 DAB +T ((TGLDSP)x4) Codon optimised
      amino acid sequence identified
``` using molecular biology techniques.

<400> SEQUENCE: 188

| Glu | Val | Gln | Leu | Leu | Val | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

Ser Leu Arg Leu Ser Cys Ala Ala Ser Gly Phe Thr Phe Lys Ala Tyr
            20              25              30

Pro Met Met Trp Val Arg Gln Ala Pro Gly Lys Gly Leu Glu Trp Val
            35              40              45

Ser Glu Ile Ser Pro Ser Gly Ser Asn Thr Tyr Tyr Ala Asp Ser Val
 50                     55              60

Lys Gly Arg Phe Thr Ile Ser Arg Asp Asn Ser Lys Asn Thr Leu Tyr
65                  70              75              80

Leu Gln Met Asn Ser Leu Arg Ala Glu Asp Thr Ala Val Tyr Tyr Cys
            85              90              95

Ala Lys Asp Pro Arg Lys Leu Asp Tyr Trp Gly Gln Gly Thr Leu Val
            100            105           110

Thr Val Ser Ser Val Glu Pro Lys Ser Ser Asp Lys Thr His Thr Cys
            115            120           125

Pro Pro Cys Pro Ala Pro Glu Leu Leu Gly Gly Pro Ser Val Phe Leu
            130            135           140

Phe Pro Pro Lys Pro Lys Asp Thr Leu Met Ile Ser Arg Thr Pro Glu
145                  150            155           160

Val Thr Cys Val Val Val Asp Val Ser His Glu Asp Pro Glu Val Lys
            165            170           175

Phe Asn Trp Tyr Val Asp Gly Val Glu Val His Asn Ala Lys Thr Lys
            180            185           190

Pro Arg Glu Glu Gln Tyr Asn Ser Thr Tyr Arg Val Val Ser Val Leu
            195            200           205

Thr Val Leu His Gln Asp Trp Leu Asn Gly Lys Glu Tyr Lys Cys Lys
        210            215           220

Val Ser Asn Lys Ala Leu Pro Ala Pro Ile Glu Lys Thr Ile Ser Lys
225                  230            235           240

Ala Lys Gly Gln Pro Arg Glu Pro Gln Val Tyr Thr Leu Pro Pro Ser
            245            250           255

Arg Asp Glu Leu Thr Lys Asn Gln Val Ser Leu Thr Cys Leu Val Lys
            260            265           270

Gly Phe Tyr Pro Ser Asp Ile Ala Val Glu Trp Glu Ser Asn Gly Gln
            275            280           285

Pro Glu Asn Asn Tyr Lys Thr Thr Pro Pro Val Leu Asp Ser Asp Gly
            290            295           300

Ser Phe Phe Leu Tyr Ser Lys Leu Thr Val Asp Lys Ser Arg Trp Gln
305                  310            315           320

Gln Gly Asn Val Phe Ser Cys Ser Val Met His Glu Ala Leu His Asn
            325            330           335

His Tyr Thr Gln Lys Ser Leu Ser Leu Ser Pro Gly Lys Thr Gly Leu
            340            345           350

Asp Ser Pro Thr Gly Leu Asp Ser Pro Thr Gly Leu Asp Ser Pro Thr
            355            360           365

Gly Leu Asp Ser Pro Asp Ile Gln Met Thr Gln Ser Pro Ser Ser Leu
            370            375           380

Ser Ala Ser Val Gly Asp Arg Val Thr Ile Thr Cys Arg Ala Ser Gln
385                  390            395           400

```
Trp Ile Gly Pro Glu Leu Lys Trp Tyr Gln Gln Lys Pro Gly Lys Ala
                405                 410                 415

Pro Lys Leu Leu Ile Tyr His Gly Ser Ile Leu Gln Ser Gly Val Pro
            420                 425                 430

Ser Arg Phe Ser Gly Ser Gly Ser Gly Thr Asp Phe Thr Leu Thr Ile
        435                 440                 445

Ser Ser Leu Gln Pro Glu Asp Phe Ala Thr Tyr Tyr Cys Gln Gln Tyr
    450                 455                 460

Met Tyr Tyr Pro His Thr Phe Gly Gln Gly Thr Lys Val Glu Ile Lys
465                 470                 475                 480

Arg Thr

<210> SEQ ID NO 189
<211> LENGTH: 474
<212> TYPE: PRT
<213> ORGANISM: Artificial Sequence
<220> FEATURE:
<223> OTHER INFORMATION: DMS1576 with C-terminal K-044-085 DAB minus
      C-term R ((TGLDSP)x4) Codon optimised amino acid sequence
      identified using molecular biology techniques.

<400> SEQUENCE: 189

Glu Val Gln Leu Leu Val Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Ala Ser Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Ser Leu Thr Cys Leu Val Lys Gly Phe Tyr Pro Ser Asp
            260                 265                 270
```

```
Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys Thr Gly Leu Asp Ser Pro Thr Gly Leu
            340                 345                 350

Asp Ser Pro Thr Gly Leu Asp Ser Pro Thr Gly Leu Asp Ser Pro Asp
            355                 360                 365

Ile Gln Met Thr Gln Ser Pro Ser Ser Leu Ser Ala Ser Val Gly Asp
        370                 375                 380

Arg Val Thr Ile Thr Cys Arg Ala Ser Gln Trp Ile Gly Pro Glu Leu
385                 390                 395                 400

Lys Trp Tyr Gln Gln Lys Pro Gly Lys Ala Pro Lys Leu Leu Ile Tyr
                405                 410                 415

His Gly Ser Ile Leu Gln Ser Gly Val Pro Ser Arg Phe Ser Gly Ser
            420                 425                 430

Gly Ser Gly Thr Asp Phe Thr Leu Thr Ile Ser Ser Leu Gln Pro Glu
        435                 440                 445

Asp Phe Ala Thr Tyr Tyr Cys Gln Gln Tyr Met Tyr Tyr Pro His Thr
    450                 455                 460

Phe Gly Gln Gly Thr Lys Val Glu Ile Lys
465                 470

<210> SEQ ID NO 190
<211> LENGTH: 476
<212> TYPE: PRT
<213> ORGANISM: Artificial Sequence
<220> FEATURE:
<223> OTHER INFORMATION: DMS1576 with C-terminal K-044-085 DAB +A
      ((TGLDSP)x4) Codon optimised amino acid sequence
      identified using molecular biology techniques.

<400> SEQUENCE: 190

Glu Val Gln Leu Leu Val Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Ala Ser Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140
```

Asp Thr Leu Met Ile Ser Arg Thr Pro Glu Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys Thr Gly Leu Asp Ser Pro Thr Gly Leu
            340                 345                 350

Asp Ser Pro Thr Gly Leu Asp Ser Pro Thr Gly Leu Asp Ser Pro Asp
        355                 360                 365

Ile Gln Met Thr Gln Ser Pro Ser Ser Leu Ser Ala Ser Val Gly Asp
    370                 375                 380

Arg Val Thr Ile Thr Cys Arg Ala Ser Gln Trp Ile Gly Pro Glu Leu
385                 390                 395                 400

Lys Trp Tyr Gln Gln Lys Pro Gly Lys Ala Pro Lys Leu Leu Ile Tyr
                405                 410                 415

His Gly Ser Ile Leu Gln Ser Gly Val Pro Ser Arg Phe Ser Gly Ser
            420                 425                 430

Gly Ser Gly Thr Asp Phe Thr Leu Thr Ile Ser Ser Leu Gln Pro Glu
        435                 440                 445

Asp Phe Ala Thr Tyr Tyr Cys Gln Gln Tyr Met Tyr Tyr Pro His Thr
450                 455                 460

Phe Gly Gln Gly Thr Lys Val Glu Ile Lys Arg Ala
465                 470                 475

<210> SEQ ID NO 191
<211> LENGTH: 478
<212> TYPE: PRT
<213> ORGANISM: Artificial Sequence
<220> FEATURE:
<223> OTHER INFORMATION: DMS1576 with C-terminal K-044-085 DAB +AAA
    ((TGLDSP)x4) Codon optimised amino acid sequence
    identified using molecular biology techniques.

<400> SEQUENCE: 191

Glu Val Gln Leu Leu Val Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr

```
            20                  25                  30
Pro Met Met Trp Val Arg Gln Ala Pro Gly Lys Gly Leu Glu Trp Val
        35                  40                  45
Ser Glu Ile Ser Pro Ser Gly Ser Asn Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Pro Arg Lys Leu Asp Tyr Trp Gly Gln Gly Thr Leu Val
                100                 105                 110
Thr Val Ser Ser Ala Ser Thr His Thr Cys Pro Pro Cys Pro Ala Pro
                115                 120                 125
Glu Leu Leu Gly Gly Pro Ser Val Phe Leu Phe Pro Pro Lys Pro Lys
                130                 135                 140
Asp Thr Leu Met Ile Ser Arg Thr Pro Glu Val Thr Cys Val Val Val
145                 150                 155                 160
Asp Val Ser His Glu Asp Pro Glu Val Lys Phe Asn Trp Tyr Val Asp
                165                 170                 175
Gly Val Glu Val His Asn Ala Lys Thr Lys Pro Arg Glu Glu Gln Tyr
                180                 185                 190
Asn Ser Thr Tyr Arg Val Val Ser Val Leu Thr Val Leu His Gln Asp
                195                 200                 205
Trp Leu Asn Gly Lys Glu Tyr Lys Cys Lys Val Ser Asn Lys Ala Leu
                210                 215                 220
Pro Ala Pro Ile Glu Lys Thr Ile Ser Lys Ala Lys Gly Gln Pro Arg
225                 230                 235                 240
Glu Pro Gln Val Tyr Thr Leu Pro Pro Ser Arg Asp Glu Leu Thr Lys
                245                 250                 255
Asn Gln Val Ser Leu Thr Cys Leu Val Lys Gly Phe Tyr Pro Ser Asp
                260                 265                 270
Ile Ala Val Glu Trp Glu Ser Asn Gly Gln Pro Glu Asn Asn Tyr Lys
                275                 280                 285
Thr Thr Pro Pro Val Leu Asp Ser Asp Gly Ser Phe Phe Leu Tyr Ser
                290                 295                 300
Lys Leu Thr Val Asp Lys Ser Arg Trp Gln Gln Gly Asn Val Phe Ser
305                 310                 315                 320
Cys Ser Val Met His Glu Ala Leu His Asn His Tyr Thr Gln Lys Ser
                325                 330                 335
Leu Ser Leu Ser Pro Gly Lys Thr Gly Leu Asp Ser Pro Thr Gly Leu
                340                 345                 350
Asp Ser Pro Thr Gly Leu Asp Ser Pro Thr Gly Leu Asp Ser Pro Asp
                355                 360                 365
Ile Gln Met Thr Gln Ser Pro Ser Ser Leu Ser Ala Ser Val Gly Asp
                370                 375                 380
Arg Val Thr Ile Thr Cys Arg Ala Ser Gln Trp Ile Gly Pro Glu Leu
385                 390                 395                 400
Lys Trp Tyr Gln Gln Lys Pro Gly Lys Ala Pro Lys Leu Leu Ile Tyr
                405                 410                 415
His Gly Ser Ile Leu Gln Ser Gly Val Pro Ser Arg Phe Ser Gly Ser
                420                 425                 430
Gly Ser Gly Thr Asp Phe Thr Leu Thr Ile Ser Ser Leu Gln Pro Glu
                435                 440                 445
```

```
Asp Phe Ala Thr Tyr Tyr Cys Gln Gln Tyr Met Tyr Tyr Pro His Thr
            450                 455                 460

Phe Gly Gln Gly Thr Lys Val Glu Ile Lys Arg Ala Ala Ala
465                 470                 475

<210> SEQ ID NO 192
<211> LENGTH: 476
<212> TYPE: PRT
<213> ORGANISM: Artificial Sequence
<220> FEATURE:
<223> OTHER INFORMATION: DMS1576 with C-terminal K-044-085 DAB +T
      ((TGLDSP)x4) Codon optimised amino acid sequence
      identified using molecular biology techniques.

<400> SEQUENCE: 192

Glu Val Gln Leu Leu Val Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
             20                  25                  30

Pro Met Met Trp Val Arg Gln Ala Pro Gly Lys Gly Leu Glu Trp Val
         35                  40                  45

Ser Glu Ile Ser Pro Ser Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Lys Leu Asp Tyr Trp Gly Gln Gly Thr Leu Val
            100                 105                 110

Thr Val Ser Ser Ala Ser Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320
```

```
Cys Ser Val Met His Glu Ala Leu His Asn His Tyr Thr Gln Lys Ser
            325                 330                 335

Leu Ser Leu Ser Pro Gly Lys Thr Gly Leu Asp Ser Pro Thr Gly Leu
        340                 345                 350

Asp Ser Pro Thr Gly Leu Asp Ser Pro Thr Gly Leu Asp Ser Pro Asp
        355                 360                 365

Ile Gln Met Thr Gln Ser Pro Ser Ser Leu Ser Ala Ser Val Gly Asp
    370                 375                 380

Arg Val Thr Ile Thr Cys Arg Ala Ser Gln Trp Ile Gly Pro Glu Leu
385                 390                 395                 400

Lys Trp Tyr Gln Gln Lys Pro Gly Lys Ala Pro Lys Leu Leu Ile Tyr
            405                 410                 415

His Gly Ser Ile Leu Gln Ser Gly Val Pro Ser Arg Phe Ser Gly Ser
            420                 425                 430

Gly Ser Gly Thr Asp Phe Thr Leu Thr Ile Ser Ser Leu Gln Pro Glu
        435                 440                 445

Asp Phe Ala Thr Tyr Tyr Cys Gln Gln Tyr Met Tyr Tyr Pro His Thr
    450                 455                 460

Phe Gly Gln Gly Thr Lys Val Glu Ile Lys Arg Thr
465                 470                 475

<210> SEQ ID NO 193
<211> LENGTH: 231
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 193

Gln Ala Ser Ser Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
            85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
            165                 170                 175

Thr Thr Pro Pro Val Leu Asp Ser Asp Gly Ser Phe Phe Leu Tyr Ser
        180                 185                 190

Lys Leu Thr Val Asp Lys Ser Arg Trp Gln Gln Gly Asn Val Phe Ser
    195                 200                 205
```

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 194
<211> LENGTH: 9
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 194

Ala Ser Thr His Thr Cys Pro Pro Cys
1               5

<210> SEQ ID NO 195
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 195

Thr His Thr Cys Pro Pro Cys
1               5

<210> SEQ ID NO 196
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 196

Thr Ala Thr Cys Pro Pro Cys
1               5

<210> SEQ ID NO 197
<211> LENGTH: 8
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 197

Gly Ser Thr Val Ala Ala Pro Ser
1               5

<210> SEQ ID NO 198
<211> LENGTH: 8
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 198

Thr Val Ala Ala Pro Ser Gly Ser
1               5

<210> SEQ ID NO 199

```
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 199

Gly Ser Thr Val Ala Ala Pro Ser Gly Ser
1               5                   10

<210> SEQ ID NO 200
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 200

Gly Gly Gly Gly Ser
1               5

<210> SEQ ID NO 201
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 201

Thr Val Ala Ala Pro Ser
1               5

<210> SEQ ID NO 202
<211> LENGTH: 8
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 202

Thr Val Ala Ala Pro Ser Gly Ser
1               5

<210> SEQ ID NO 203
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 203

Pro Ala Val Pro Pro Pro
1               5

<210> SEQ ID NO 204
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 204
```

```
Thr Val Ser Asp Val Pro
1               5

<210> SEQ ID NO 205
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 205

Thr Gly Leu Asp Ser Pro
1               5

<210> SEQ ID NO 206
<211> LENGTH: 16
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 206

Asp Glu Thr Tyr Val Pro Lys Glu Phe Asn Ala Glu Thr Phe Gly Ser
1               5                   10                  15

<210> SEQ ID NO 207
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 207

Asp Glu Thr Tyr Val Pro Lys Glu Phe Asn Ala Glu Thr Phe
1               5                   10

<210> SEQ ID NO 208
<211> LENGTH: 23
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 208

Glu Val Asp Glu Thr Tyr Val Pro Lys Glu Phe Asn Ala Glu Thr Phe
1               5                   10                  15

Thr Phe His Ala Asp Gly Ser
            20

<210> SEQ ID NO 209
<211> LENGTH: 21
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 209

Glu Val Asp Glu Thr Tyr Val Pro Lys Glu Phe Asn Ala Glu Thr Phe
1               5                   10                  15

Thr Phe His Ala Asp
            20
```

```
<210> SEQ ID NO 210
<211> LENGTH: 13
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 210

Asp Asp Asn Pro Asn Leu Pro Arg Leu Val Arg Pro Glu
 1               5                  10

<210> SEQ ID NO 211
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 211

Asp Glu Met Pro Ala Asp Leu Pro Ser Leu Ala Ala Asp Phe
 1               5                  10

<210> SEQ ID NO 212
<211> LENGTH: 19
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 212

His Lys Asp Asp Asn Pro Asn Leu Pro Arg Leu Val Arg Pro Glu Val
 1               5                  10                  15

Asp Val Met

<210> SEQ ID NO 213
<211> LENGTH: 21
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 213

Glu Asn Asp Glu Met Pro Ala Asp Leu Pro Ser Leu Ala Ala Asp Phe
 1               5                  10                  15

Val Glu Ser Lys Asp
                20

<210> SEQ ID NO 214
<211> LENGTH: 4
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 214

Ala Ser Thr Lys
 1

<210> SEQ ID NO 215
<211> LENGTH: 5
<212> TYPE: PRT
```

```
<213> ORGANISM: Artificial Sequence
<220> FEATURE:
<223> OTHER INFORMATION: Amino acid sequence identified using molecular
      biology techniques.

<400> SEQUENCE: 215

Ala Ser Thr Lys Gly
1               5

<210> SEQ ID NO 216
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 216

Ala Ser Thr Lys Gly Pro
1               5

<210> SEQ ID NO 217
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 217

Gly Ser Thr Val Ala Ala Pro Ser Gly Ser
1               5                   10

<210> SEQ ID NO 218
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 218

Ala Ser Thr His Pro
1               5

<210> SEQ ID NO 219
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: (5)..(5)
<223> OTHER INFORMATION: Residue at position 5 is (Ser)n, wherein n
      represents an integer independently selected from 0 or 1.
<220> FEATURE:
<221> NAME/KEY: VARIANT
<222> LOCATION: (6)..(6)
<223> OTHER INFORMATION: Residue Xaa at position 6 may be present or
      absent, and if present, represents an amino acid extension of 1
      to 8 amino acid residues.

<400> SEQUENCE: 219

Val Thr Val Ser Ser Xaa
1               5

<210> SEQ ID NO 220
```

```
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: (4)..(5)
<223> OTHER INFORMATION: Residues at positions 4 and 5 are (Lys)p(Arg)q,
      wherein p and q each represent 0 or 1 such that when p represents
      1 q may be 0 or 1 and such that when p represents 0, q also
      represents 0.
<220> FEATURE:
<221> NAME/KEY: VARIANT
<222> LOCATION: (6)..(6)
<223> OTHER INFORMATION: Residue Xaa at position 6 may be present or
      absent, and if present represents an amino acid extension of 1 to
      8 amino acid residues.

<400> SEQUENCE: 220

Val Glu Ile Lys Arg Xaa
1               5
```